(12) United States Patent
Van Wagenen et al.

(10) Patent No.: US 6,211,244 B1
(45) Date of Patent: *Apr. 3, 2001

(54) CALCIUM RECEPTOR-ACTIVE COMPOUNDS

(75) Inventors: Bradford C. Van Wagenen; Scott T. Moe, both of Salt Lake City; Manuel F. Balandrin, Sandy; Eric G. DelMar; Edward F. Nemeth, both of Salt Lake City, all of UT (US)

(73) Assignee: NPS Pharmaceuticals, Inc., Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/546,998

(22) Filed: Oct. 23, 1995

(51) Int. Cl.$^7$ .................. A61K 31/135; A01N 33/02; C07C 209/48

(52) U.S. Cl. .................. 514/649; 564/182; 564/271; 564/374; 536/23.5

(58) Field of Search .................. 564/374, 182, 564/271; 514/649; 536/23.5

(56) References Cited

U.S. PATENT DOCUMENTS

| | | | |
|---|---|---|---|
| 2,276,618 | 3/1942 | Kulz et al. | 260/520.8 |
| 2,930,731 | 3/1960 | Heinzelmann et al. | 167/52 |
| 2,949,359 | 8/1960 | Blout et al. | 96/66 |
| 3,202,711 | 8/1965 | Fruhstorfer et al. | 260/570 |
| 3,262,977 | 7/1966 | Harsanyi et al. | 260/570 |
| 3,493,662 | 2/1970 | Duerr et al. | 424/330 |
| 3,536,712 | 10/1970 | Keck et al. | 260/253 |
| 3,689,524 | 9/1972 | Jack et al. | 260/471 A |
| 3,842,067 | 10/1974 | Sarantakis | 260/112.5 |
| 3,862,925 | 1/1975 | Sarantakis | 260/112.5 |
| 3,972,859 | 8/1976 | Fujino et al. | 260/112.5 |
| 4,000,197 | 12/1976 | Barfknecht et al. | 260/570.8 R |
| 4,014,937 | 3/1977 | Richardson | 260/570.8 R |
| 4,098,890 | 7/1978 | Molloy | 424/248.4 |
| 4,105,602 | 8/1978 | Colescott et al. | 260/8 |
| 4,242,355 | 12/1980 | Nedelec et al. | 424/275 |
| 4,289,787 | 9/1981 | Molloy et al. | 424/329 |
| 4,360,511 | 11/1982 | Baldwin et al. | 424/1.5 |
| 4,391,826 | 7/1983 | Mills et al. | 424/324 |
| 4,487,965 | 12/1984 | Himmele et al. | 564/454 |
| 4,587,253 | 5/1986 | Halczenko et al. | 514/289 |
| 4,591,605 | 5/1986 | Ray | 514/579 |
| 4,608,391 | 8/1986 | Ginos et al. | 514/654 |

(List continued on next page.)

FOREIGN PATENT DOCUMENTS

| | | |
|---|---|---|
| 621300 | 12/1962 | (BE) . |
| 1065857 | 11/1992 | (CH) . |
| 217009 | 1/1984 | (CS) . |
| 1231690 | 1/1967 | (DE) . |
| 2541184 | 4/1976 | (DE) . |
| 2825961 | 3/1980 | (DE) . |
| 0009702 | 9/1979 | (EP) . |
| 0005848 | 12/1979 | (EP) . |
| 0007204 | 1/1980 | (EP) . |
| 0015505 | 9/1980 | (EP) . |
| 0023385 | 2/1981 | (EP) . |
| 0 44 158 A1 | 1/1982 | (EP) . |
| 0101069 | 8/1983 | (EP) . |
| 0092787 | 11/1983 | (EP) . |
| 0200101 | 12/1986 | (EP) . |
| 0253327 | 1/1988 | (EP) . |
| 0270376 | 7/1988 | (EP) . |
| 0289287 | 11/1988 | (EP) . |
| 0309100 | 3/1989 | (EP) . |
| 0395357 | 10/1990 | (EP) . |
| 0408284 | 1/1991 | (EP) . |
| 0455510 | 3/1991 | (EP) . |
| 0224163 | 10/1991 | (EP) . |
| 0508307 | 10/1992 | (EP) . |

(List continued on next page.)

OTHER PUBLICATIONS

Fox et al;Journal of Bone and Mineral Research;8:S181, abstract 260;Suppl. 1, Aug. 1993.
Majewski et al;Canadian J.Chem;73;1616–1626, 1995.
Hashimoto et al;Synlett;961–962, Sep. 1995.
Majewski et al;Tetrahedron:Asymmetry;vol. 6;No. 8;pp 1837–1840, 1995.
Polniaszek et al;J.Am.Chem.Soc;111;4859–4863, 1989.
Kametani et al;J.Chem.Soc:Perkin Trans1;579–581, 1977.
Polniaszek et al;Tetrahedron Letters;vol. 31;No. 6; pp797–800, 1990.
Merck Index;;Eleventh Ed;#2993;p.2997, 1989.
Walker, et al., J. Med. Chem., 9(4), 624–30 (1966),"Synthesis of Varied Heterocyclic and Substituted Aryl Alkyl Secondary Amines, Related Schiff Bases, and Amides".
Burke, et al., J. Org. Chem. 28, 1098–1100 (1963), "Mono–1,3–benzoxazines from Hydroquinone".
West, et al., J. Am. Pharm. Assoc. 46, 58–61 (1957), "A pharmacological Study of a Series of Aralkylamines".
Anderson and Santi, "Phenylalanyl Transfer Ribonucleic Acid Synthase from *Escherichia coli* B. Potent Inhibition by Analogues of N–Benzyl–2–phenylethylamine," *J. Med. Chem.* 19:1270–1275 (1976).
Arjona et al., "Sterochemistry of the reduction of the imino group. IV. Sterochemistry of the reduction of N–(1–phenylethyl)–1–alkyl–1–arylmethanimines," *An. Quim. Ser. C* 81(1):23–29 (1985).

(List continued on next page.)

Primary Examiner—Gary Geist
Assistant Examiner—Sreeni Padmanabhan

(57) ABSTRACT

The present invention features compounds able to modulate one or more activities of an inorganic ion receptor and methods for treating diseases or disorders by modulating inorganic ion receptor activity. Preferably, the compound can mimic or block the effect of extracellular $Ca^{2+}$ on a calcium receptor.

46 Claims, 104 Drawing Sheets

U.S. PATENT DOCUMENTS

| | | | |
|---|---|---|---|
| 4,609,494 | 9/1986 | Baldwin et al. | 544/250 |
| 4,647,446 | 3/1987 | Sargent et al. | 424/1.1 |
| 4,661,635 | 4/1987 | Carson | 564/374 |
| 4,675,321 | 6/1987 | Baldwin et al. | 514/274 |
| 4,677,101 | 6/1987 | Claremon et al. | 514/215 |
| 4,769,483 | 9/1988 | Lombardi et al. | 560/19 |
| 4,797,411 | 1/1989 | Crugnola et al. | 514/357 |
| 4,808,718 | 2/1989 | Hartman et al. | 546/14 |
| 4,839,369 | 6/1989 | Youssefyeh et al. | 514/314 |
| 4,916,145 | 4/1990 | Tilley et al. | 514/357 |
| 4,925,664 | 5/1990 | Jackson et al. | 424/537 |
| 4,925,873 | 5/1990 | Friedhoff et al. | 514/469 |
| 4,967,003 | 10/1990 | Rentzea et al. | 564/381 |
| 4,988,730 | 1/1991 | Korbonits et al. | 514/466 |
| 5,001,251 | 3/1991 | MacManus et al. | 558/255 |
| 5,011,834 | 4/1991 | Weber et al. | 514/212 |
| 5,021,599 | 6/1991 | Beer et al. | 556/142 |
| 5,030,576 | 7/1991 | Dull et al. | 435/69.7 |
| 5,034,514 | 7/1991 | Nitecki et al. | 530/390 |
| 5,053,337 | 10/1991 | Weinshank et al. | 435/240.2 |
| 5,064,657 | 11/1991 | Jackson et al. | 424/537 |
| 5,073,648 | 12/1991 | Hagishita et al. | 564/374 |
| 5,075,338 | 12/1991 | Knoll et al. | 514/634 |
| 5,082,837 | 1/1992 | Palfreyman | 514/183 |
| 5,334,628 | 8/1994 | Maeda et al. | 514/311 |
| 5,403,861 | 4/1995 | Goldin et al. | 514/634 |
| 5,688,938 | 11/1997 | Brown et al. | 536/23.5 |
| 5,763,569 | 6/1998 | Brown et al. | 530/324 |

FOREIGN PATENT DOCUMENTS

| | | |
|---|---|---|
| 0443606 | 5/1995 | (EP) . |
| 1109924 | 4/1968 | (GB) . |
| 1448437 | 7/1974 | (GB) . |
| 1464209 | 9/1977 | (GB) . |
| 2113089 | 11/1982 | (GB) . |
| 2213818 | 8/1989 | (GB) . |
| 1079091 | 9/1997 | (GB) . |
| 53-90272 | 8/1978 | (JP) . |
| 59-50358 | 3/1984 | (JP) . |
| 2200658 | 8/1990 | (JP) . |
| 8204052 | 11/1982 | (WO) . |
| 8906135 | 7/1989 | (WO) . |
| 8909834 | 10/1989 | (WO) . |
| 9100853 | 1/1991 | (WO) . |
| 9109594 | 7/1991 | (WO) . |
| 9207829 | 5/1992 | (WO) . |
| 9214709 | 9/1992 | (WO) . |
| 9304373 | 4/1993 | (WO) . |
| 9310073 | 5/1993 | (WO) . |
| 9315044 | 5/1993 | (WO) . |
| 9313052 | 8/1993 | (WO) . |
| 9418959 | 9/1994 | (WO) . |
| 9511221 | 4/1995 | (WO) . |
| 9518134 | 7/1995 | (WO) . |
| WO 9518134 | 7/1995 | (WO) . |
| 9521815 | 8/1995 | (WO) . |

OTHER PUBLICATIONS

Barney et al., "A Convenient Synthesis of Hindered Amines and α–Trifluoromethylamines from Ketones," *Tetrahedron Letters* 31:5547–5550 (1990).

Batra and Alenfall, "Effects of Diverse Categories of Drugs on Human Colon Tumour Cell Proliferation," *Anticancer Research* 11:1221–1224 (1991).

Becalski et al., "Catalytic asymmetric hydrogenation of imines. Use of rhodium(I)/phosphine comploexes and characterization of rhodium(I)/imine complexes," *Chemical Abstracts* 116:558 at Abstract No. 14742U (1992).

Bertz et al., "Asymmetric Induction with Amidocuprates," *J. Org. Chem.* 51:4953–4949 (1986).

Boyd et al., "Dynamic Sterochemistry of Imines and Derivatives. Part 18. Photosynthesis and Photoracemization of Optically Active Oxaziridines," *J. Chem. Soc. Perkin Trans. I* 4:849–855 (1985).

Bringmann et al., "The Enantioselective Synthesis of Optically Active, Benzene Nucleus–Substituted 1–Phenylethylamines from the Corresponding Acetophenones," *Leibigs Ann.Chem.* 5:795–805 (1990).

Bringmann et al., "Enantiomerically Pure N–Boc Protected β–Keto–65 –Amino Acid Esters from Simple Keto Precursors: A Novel, Stereocontrolled Approach to Statine Derivatives with Any Desired Configuration," *Synlet Letters* pp. 253–255 (1990).

Brown et al., "A Comparison of the Effects of Divalent and Trivalent Cations on Parathyroid Hormone Release, 3',5'–Cyclic–Adenosine Monophosphate Accumulation, and the Levels of Inositol Phosphates in Bovine Parathyroid Cells," *Endocrinology* 127:1064–1071 (1990).

Brown et al., "Cloning and characterization of an extracellular $Ca^{2+}$ sensing receptor from bovine parathryoid," *Nature* 366:575–580 (1993).

Brown, "Extracellular $Ca^{2+}$ Sensing, Regulation of Parathyroid Cell Function and Role of $Ca^{2+}$ and Other Ions as Extracellular (First) Messengers," *Physiological Reviews* 71:371–411 (1991).

Brown et al., "High Extracellular $Ca^{2+}$ and $Mg^{2+}$ Stimulate Accumulation of Inositol Phosphates in Bovine Parathyroid Cells," *FEBS Letters* 218:113–118 (1987).

Brown et al., "Neomycin Mimics the Effects of High Extracellular Calcium Concentrations on Parathyroid Function in Dispersed Bovine Parathyroid Cells," *Endocrinology* 128:3047–3054 (1991).

Brown et al., "Polyarginine, Polylysine, and Protamine Mimic the Effects of High Extracellular Calcium Concentrations on Dispersed Bovine Parathyroid Cells," *Journal of Bone and Mineral Research* 6:1217–1225 (1991).

Capuano et al., "Characterization of the Human Calcium Receptor Gene," *Journal of Bone and Mineral Research* 9(1):S145 at abstract No. 98 (1994).

*Chemical Abstracts Formula Index*, vol. 110 p. 537F (1989).

*Chemical Abstracts Formula Index*, vol. 110 p. 1793F (1989).

Chen et al., "Injection of Bovine Parathyroid Poly(A)+ RNA into Xenopus Oocytes Confers Sensitivity to High Extracellular Calcium," *Journal of Bone and Mineral Research* 9:293–300 (1994).

Chen and Brown, "The Diltiazem Analog TA–3090 Mimics the Actions of High Extracellular $Ca^{2+}$ on Parathyroid Function in Dispersed Bovine Parathyroid Cells," *Journal of Bone and Mineral Research* 5:581–587 (1990).

Clifton et al., "Arylethanolamines derived from salicylamide with alpha– and beta–adrenoceptor blocking activities. Preparation of labetalol, its enantiomers and related salicylamides," *J. Med. Chem.* 25:670–679 (1982).

Danks, "Reaction of Hydride Transfer Reducing Agents with (1–Heterodiene) Tricarbonyliron(0) Complexes and the Synthesis of Saturated Amines and Alcohols," *Tetrahedron Letters* 35:4177–4178 (1994).

Davies and Ichihara, "Asymmetric Synthesis of R–β–Amino Butanoic Acid and S–β–Tyrosine: Homochiral Lithium Amide Equivalents for Michael Additions to α,β–Unsaturated Esters," *Tetrahedron Asymmetry* 2:183–186 (1991).

De Feo et al., "Natriuretic Peptide Receptors Regulate Endothelin Synthesis and Release From Parathyroid Cells," *Proc. Natl. Acad. Sci. USA* 88:6496–6500 (1991).

Fox et al., "A First Generation Calcimimetic Compound (NPS R–568) That Acts on the Parathyroid Cell Calcium Receptor: A Novel Therapeutic Approach for Hyperparathyroidism," *Journal of Bone and Mineral Research* 8(1):S181 at abstract No. 260 (1993).

Fox et al., "NPS R–568 Acts on Calcium Receptors to Inhibit Parathyroid Hormone and Stimulate Calcitonin Secretion: A Novel Therapeutic Approach for Hyperparathyroidisum," *J. American Society of Nephrology* 4:719 at abstract No. 120P (1993).

Fox et al., "NPS R–568 Inhibits Parathyroid Hormone Secretion and Stimulates Calcitonin Secretion in Hyperparathyroid Rats with Chronic Renal Failure," *J. American Society of Nephrology* 4:719 at abstract No. 69P (1993).

Fox et al., "Parathyroid Gland Calcium Receptor Gene Expression is Unaffected by Chronic Renal Failure or Low Dietary Calcium in Rats," *J. Am. Soc. Nephrology* 5:879 at abstract No. 90P (1994).

Fox et al., "Physiology Relevant PTH Levels are Anabolic on Bone in Ovariectomized Rats," *Bone* 16(Supplement):194S at abstract No. 434 (1995).

Fox et al., "Prevention of Hypocalcemia Prolongs the Plasma Parathyroid Hormone and Calcitonin Responses to the Calcimimetic Compound NPS R–568 in Rats," *Journal of Bone and Mineral Research* 9(1):S409 at abstract No. C396 (1994).

Fraser et al., "Substitution α to the Nitrogen in Dibenzylamine via Carbanion Intermediates," *Can. J. Chem.* 51:1109–1115 (1973).

Freifelder, "Selective Hydrogenolysis. Dehalogenation in the Presence of N–Benzyl Linkage," *J. Org. Chem.* 31(11):3875–3877 (1966).

Fuji et al., "Endothelin as an Autocrine Factor in the Regulation of Parathyroid Cells," *Proc. Natl. Acad. Sci. USA* 88:4235–4239 (1991).

Fuleihan et al., "Effects of the Lectin Concanavalin–A on the Regulation of Second Messengers and Parathyroid Hormone Release by Extracellular $Ca^{2+}$ in Bovine Parathyroid Cells," *Endocrinology* 128:2931–2936 (1991).

Fuleihan and Brown, "Effect on the Lectin Concanavalin–A on Calcium–Regulated Adenosine 3', 5'–Monophosphate Accumulation in Bovine Parathyroid Cells," *Endocrinology* 126:1996–2002 (1990).

Garrett et al., "Cloning and Expression of a G–Protein––Coupled Calcium Receptor From a Human Parathyroid Adenoma," *Journal of Bone and Mineral Research* 8(Supplement 1):S148 at abstract No. 125 (1993).

Garrett et al., "Expression of the Parathyroid Calcium Receptor Gene in C–Cells," *Journal of Bone and Mineral Research* 9(1):S409 at abstract No. C398 (1994).

Gracheva et al., "Stereodirection of Ketimine Reduction Reactions," *Zhural Organicheskoi Khimii* 9(6):1235–1239 (1973).

Gracheva et al., "The Stereoselectivity of the Reactions of Schiff Bases with Organomagnesium Compounds," *Zhural Organicheskoi Khimii* 10(3):577–561 (1974).

Grethe et al., "Syntheses in the Isoquinoline Series. Synthesis of 2,3–Dihydro–4(1H)–isoquinolones," *J. Org. Chem.* 33(2):491–494 (1968).

Hammerland et al., "Mechanism of Action of the Calcimimetic Compounds NPS R–467 and NPS R–568 in Xenopus Oocytes Expressing a Bovine Parathyroid Cell Calcium Receptor," *Journal of Bone and Mineral Research* 8(Supplement 1):S133 at abstract No. 65 (1993).

Harootunian et al., "Effect of Calcitonin and Extracellular Calcium on Cytosolic Levels of Cyclic AMP and $Ca^{2+}$ in Rabbit Osteoclasts," *Journal of Bone and Mineral Research* 9(1):S246 at abstract No. B66 (1994).

Hashimoto et al., "Highly Diastereoselective Addition of Organometallic Reagents to Chiral Imines Derived from 1–(2–Methoxyphenyl)ethylamine," *Synlett Letters* pp. 961–962 (1995).

Hawkins et al., "The Effects of High Extracellular $Ca^{2+}$ and $Mg^{2+}$ Concentrations on the Levels of Inositol 1,3,4,5–Tetrakisphosphate in Bovine Parathyroid Cells," *Endocrinology* 124:838–844 (1989).

Heath et al., "Inhibition of Human Parathyroid Hormone Secretion In Vivo by NPS R–568, a Calcimimetic Drug that Targets the Parathyroid Cell–Surface Calcium Receptor," *Bone* 16(Supplement):85S at abstract No. 23 (1995).

Hiroi et al., "A Highly Efficient and Recyclable Chiral Director for Asymmetric Synthesis of Sulfoxides," *Chemistry Letters* pp. 1595–1598 (1980).

Hiroi et al., "Studies on Chiral Organo–Sulfur Compounds. I. Asymmetric Synthesis of Sulfoxides with Optically Active o–Aminoalkylphenol Derivatives," *Chem. Pharm. Bull.* 31:3471–3485 (1983).

Höltje and Maurhofer, "Conformational Analysis on Calcium Channel Active Diphenylalkylamines, Diphenylbutylpiperidines, Phenylalkylamines, and Perhexiline," *Quant. Struct.–Act. Relat.* 8:259–265 (1989).

Hu et al., "Lithium hydride elimination in the reactions of organolithium compounds with imines: synthesis of secondary amines with branched groups," *C.R. Acad. Sci. Paris Ser. C* 284(4):195–198 (1977).

Hung et al., "Coupling of the Porcine Calcitonin Receptor to Cytosolic $Ca^{2+}$ and cAMP Levels in Xenopus Oocytes," *Journal of Bone and Mineral Research* 9(1):S410 at abstract No. C400 (1994).

Hutton et al., "Organic Reagents for the Precipitation of Nitrate Ion. Part I. N–Substituted 1–napthylmethylamines," *J. Chem. Soc. (A)* 11:1573–1579 (1966).

Ikegami and Yamada, "Chemistry of Sodium Borohydride and Diborane. II. Reduction of Schiff Bases with Diborane in Tetrahydrofuran," *Chem. Pharm. Bull.* 14(12):1389–1399 (1966).

Jasys et al., "The Total Synthesis of Argiotoxins 636, 659 and 673," *Tetrahedron Letters* 29:6223–6226 (1988).

Joshi and Mehrotra, "Reductive Coupling In Substituted Imines with Aluminium–Amalgam in Moist Ether," *Nat. Acad. Sci. Letters (India)* 3:268–272 (1980).

Juaristi et al., "Use of N,N'–Dimethylpropyleneurea (DMPU) as Solvent in the Efficient Preparation of Enantiomerically Pure Secondary Amines," *Synthesis* pp. 1243–1246 (1993).

Kametani et al., "Studies on the Synthesis of Heterocyclic Compounds. Part 687. Asymmetric Synthesis of Salsolidine," *J. Chem. Soc. Perkin Trans. 1* pp. 579–581 (1977).

Kang et al., "Rhodium(I)–catalysed Asymmetric Hydrogenation of Imines," *J. Chem. Soc. Chem. Commun.* pp. 1466–1467 (1988).

Katritzky et al., "Convenient Preparations of Imines and Symmetrical Secondary Amines Possessing Primary or Secondary Alkyl Groups," *Synthesis* 9:703–708 (1991).

Katz et al., "Structure–Function Relationships for the Effects of Various Aminoglycoside Antibotics on Dispersed Bovine Parathyroid Cells," *Endocrinology* 131:903–910 (1992).

Kienzle et al., "1,5–Dihydroimidazoquinazolinones as blood platelet aggregation inhibitors," *Eur. J. Med. Chem.—Chem. Ther.* 17:547–556 (1982).

Kifor and Brown, "Relationship between Diacylglycerol Levels and Extracellular $Ca^{2+}$ in Dispersed Bovine Parathyroid Cells," *Endocrinology* 123:2723–2729 (1988).

Koenig et al., "Polyamines Mediate Androgenic Stimulation of Clacum Fluxes and Membrane Transport in Rat Heart Myocytes," *Circulation Research* 64:415–426 (1989).

Komeyoshi and Kudo, "Optically active amines and their manufacture, intermediates and uses," *Chemical Abstracts* 121:1060 at Abstract No. 230462Y (1994).

Kozlov et al., "Reductive animation of 1–acetylcyclohexene by nitriles," *Vestsi Akad. Navuk BSSR, Ser. Khim. Navuk* pp. 55–58 (1977).

Langlois et al., "Asymmetric synthesis of amines by hydrosilylation of imines catalyzed by a chiral complex of rhodium," *Tetrahedron Lett.* 49:4865–4868 (1973).

Lensink and De Vries, "Diastereoselective hydrogenation and kinetic resolution of imines using rhodium/diphosphine catalyzed hydrogenation," *Tetrahedron: Asymmetry* 4:215–222 (1993).

Lensink and de Vries, "Improving Enantioselectivity by Using a Mono–Sulphonated Diphosphine as Ligand for Homogenous Imine Hydrogenation," *Tetrahedron:Assymetry* 3(2):235–238 (1992).

Leszkovzky et al., "The Pharmacology of Diphenylalkyl Derivatives," *Acta Physiologica Academiae Scientiarum Hungaricae Tomus* 29:283–297 (1966).

Levine, *Pharmacology: Drug Actions and Reactions*, Little Brown and Company, Inc. pp. 192–196 (1990).

Lopez–Barneo and Armstrong, "Depolarizing Response of Rat Parathyroid Cells to Divalent Cations," *J. Gen. Physiol.* 82:269–294 (1983).

Majewski and MacKinnon, "Enantioselective deprotonation of protected 4–hydroxycyclohexanones," *Can. J. Chem.* 72:1699–1704 (1994).

Mattson et al., "An Improved Method for Reductive Alkylation of Amines Using Titanium(IV) Isopropoxide and Sodium Cyanoborohydride," *J. Org. Chem.* 55:2552–2554 (1990).

Merck Index, 11th Edition, Monograph No. 8699, pp. 420, 1379 (1989).

Merck Index, 11th Edition, Monograph No. 3916, p. 623 (1989).

Merrifield, "Solid Phase Peptide Synthesis. I. The Synthesis of a Tetrapeptide," *J. Amer. Chem. Society* 85:2149–2154 (1963).

Mithal et al., "Highly Purified Sheep C–Cells Express an Extracellular $Ca^{2+}$ Receptor Similar to that Present in Parathyroid," *Journal of Bone and Mineral Research* 9(1):S282 at abstract No. B209 (1994).

Mori et al., "Formic Acid Reduction. XI. Reduction of Schiff Bases," *Chem. Pharm. Bull.* 19:1722–1727 (1971).

Muff et al., "Regulation of Hormone Secretion and Cytosolic $Ca^{2+}$ by Extracellular $Ca^{2+}$ in Parathyroid Cells and C–Cell: Role of Voltage–Senstive $Ca^{2+}$ Channels," *Archives of Biochemistry and Biophysics* 265:128–135 (1988).

Nason et al., "Synthesis of Neurotoxic Nephlla Spider Venoms: NSTX–3 and JSTX–3," *Tetrahedron Letters* 30:2337–2340 (1989).

Nemeth, "$Ca^{2+}$ Receptor–Dependent Regulation of Cellular Functions," *NIPS* 10:1–5 (1995) Check 1–15.

Nemeth and Scarpa, "Cystolic $Ca^{2+}$ and the regulation of secretion in parathyroid cells," *FEBS Letters* 203(1):15–19 (1986).

Nemeth, "Evidence for the Presence of a Novel $Ca^{2+}$–Binding Protein ($Ca^{2+}$ Receptor) on the Surface of Parathyroid Cells," *Calcium–Binding Proteins in Health and Disease*, Norman et al. editors, Academic Press, Inc., San Diego, pp. 36–38 (1987).

Nemeth and Scarpa, "Rapid Mobilization of Cellular $Ca^{2+}$ in Bocine Parathyroid Cells Evoked by Extracellular Divalent Cations—Evidence for a Cell Surface Calcium Receptor," *J. Biol. Chem.* 262(11):5188–5196 (1987).

Nemeth and Scarpa, "Receptor–Dependent Mobilization of Cellular $Ca^{2+}$ and the Regulation of Hormone Secretion in Parathyroid Cells," *Calcium Regulation and Bone Metabolism: Basic and Clinical Aspects* 9:167–171 (1987).

Nemeth, "Regulation of cystolic calcium by extracellular divalent cations in C–cells and parathyroid cells," *Cell Calcium* 11:323–327 (1990).

Nemeth et al., "Screening of compounds with potential action against calcium receptors and their use in therapy of disorders of calcium metabolism," *Chemical Abstracts* 122(1):P1057y (1995).

Nemeth and Scarpa, "Spermine Evokes the Rapid Mobilization of Cellular $Ca^{2+}$ in Parathyroid Cells," *Calcium–Binding Proteins in Health and Disease,* Normal et al. editors, Academic Press, Inc., San Diego, pp. 33–35 (1987).

Nemeth and Carafoli, "The role of extracellular calcium in the regulation of intracellular calcium and cell function," *Cell Calcium* 11:319–321 (1990).

Neuvonen and Pihlaja, "Studies on the Benzoxazine Series. Part 3—Preparation and $^{13}C$ NMR Structural Study of γ Effects of Some N–Substituted 3,4–Dihydro–2H–1,3–benzoxazines," *Magnetic Resonance in Chemistry* 28:239–245 (1990).

Opie, "Calcium Channel Antagonists Part V: Second–Generation Agents," *Cardiovascular Drugs and Therapy* 2:191–203 (1988).

Paulsen–Sorman et al., "Cytochrome P–455 nm Complex Formation in the Metabolism of Phenylalkylamines. 8. Stereoselectivity in Metabolic Intermediary Complex Formation with a Series of Chiral 2–Substituted 1–Phenyl–2–aminoethanes," *J. Med. Chem.* 27:342–346 (1984).

Polniaszek and Dillard, "Diastereoselective Addition of Organometallic Reagents to Chiral Immune Ions: Synthesis of (S)–(+)–Cryptostyline I," *Tetrahedron Letters* 31:797–800 (1990).

Racke et al., "Functional expression of the parathyroid cell calcium receptor in Xenopus oocytes," *FEBS Letters* 333(1, 2):132–136 (1993).

Racke et al., "Functional Expression of the Parathyroid Cell Calcium Receptor in Xenopus Oocytes," *Journal of Bone and Mineral Research* Supplement 1, 6:S118 at abstract No. 141 (1991).

Rai and Singh, "Synthesis and reduction of ketimines," *Indian J. Chem. Sect. B* 14B:377–378 (1976).

Rogers et al., "Calcium Receptor Expression in the Parathyroid Glands of Vitamin D–Deficient Rats is not Regulated by Plasma Caclium and 1,25(OH)$_2$D$_3$," *Journal of Bone and Mineral Research* 9(1):S409 at abstract No. C392 (1994).

Rogers et al., "Localization of Calcium Receptor mRNA in Rat Thyroid and Parathyroid Glands Using In Situ Hybridization Histochemistry," *Journal of Bone and Mineral Research* 9(1):S409 at abstract No. C390 (1994).

Rogers et al., "The Calcimimetic Compound NPS467 Reduces Plasma Calcium in a Dose–Dependent and Stero–Specific Manner," *Journal of Bone and Mineral Research* 8(Supplement 1):S180 at abstract No. 254 (1993).

Schäfer et al., "Polyamine Toxins from Spiders and Wasps," *The Alkaloids* 45:1–125 (1994).

Schwartz and Hu, "Synthesis of Hindered Secondary Amines via Grignard Reagent Addition to Ketonitrones," *Tetrahedron Letters* 13:1689–1692 (1992).

Seely et al., "The Calcium Channel Blocker Diltiazem Lowers Serum Parathyroid Hormone Levels in Vivo and in Vitro," *Journal of Clinical Endocrinology and Metabolism* 68(6):1007–1012 (1989).

Shoback and Chen, "Injection of Poly (A)$^+$ RNA from Bovine Parathyroid Tissue into Xenopus Oocytes Confers Sensitivity to Extracellular Calcium," *Journal of Bone and Mineral Research* 6(Supplement 1):S135 at abstract No. 207 (1991).

Standridge et al., "Phenylalkylamines with Potential Psychotherapeutic Utility. 2. Nuclear Substituted 2–Amino–1–phenylbutanes," *J. Med. Chem.* 23:154–162 (1980).

Standridge et al., "Phenylalkylamines with Potential Psychotherapeutic Utility. 1. 2–Amino–1–(2, 5–dimethoxy–4–methylphenyl) butane," *J. Med. Chem.* 19:1400–1404 (1976).

Steffey and Nemeth, "Extracellular Calcium–Sensing Mechanisms on Osteoclasts and Parathyroid Cells are Pharmacologically Distinct," *Journal of Bone and Mineral Research* 8(Supplement 11):S384 at at abstract No. 1071 (1993).

Steffey et al., "Calcimimetics: Structurally and Mechanistically Novel Compounds that Inhibit Hormone Secretion From Parathyroid Cells," *Journal of Bone and Mineral Research* 8(Supplement 1):S175 at abstract No. 236 (1993).

Triggle et al., "Ca$^{2+}$ Channel Ligands: Structure–Function Relationships of the 1,4–Dihydropyridines," *Medicinal Research Reviews* 9(2):123–180 (1989).

Van Dijk and Moed, "Synthesis of β–Phenylethyloamine Derivatives X$^{1*}$ N–(Hydroxy– and Methoxy–Aralkyl) Derivatives," *Recl. Trav. Chim. Pays–Bas* 92:1281–1297 (1973).

Van Niel and Pandit, "NADH Models XXI. Steroselective Reduction of Chiral Imines with Hantzsch Ester," *Tetrahedron* 41:6065–6011 (1985).

Wang and Bäckvall, "Ruthenium–catalysed Transfer Hydrogenation of Imines by Propan–2–ol," *J. Chem. Soc. Commun.* pp. 980–982 (1992).

Witkop "Nonenzymatic Methods for the Preferential and Selective Cleavage and Modification of Proteins," *Advances in Protein Chemistry,* Anfinsen et al. editors, Academic Press, Inc., New York, 16:221–321 (1961).

Yamaguchi et al., "Asymmetric Reduction with Chiral Reagents from Lithium Aluminum Hydride and (S)–(–)–N–(o–Substituted benzyl)–α–phenylethylamines," *J. Org. Chem.* 42:1578–1581 (1977).

Zaidi, "'Calcium Receptors' on Eukaryotic Cells with Special Reference to the Osteoclast," *Bioscience Reports* 10:493–507 (1990).

Zaidi et al., "Intracellular calcium in the control of osteoclast function. II. Paradoxical elevation of cytosolic free calcium by verapamil," *Biochemical and Biophysical Research Communications* 167:807–812 (1990).

Anderson and Santi, "Phenylalanyl Transfer Ribonucleic Acid Synthetase from *Escherichia coli* B. Potent Inhibition by Analogues of N–Benzyl–2–phenylethylamine," *J. Med. Chem.* 19:1270–1275 (1976).

Langlois et al., "Asymmetric synthesis of amines by hydrosilyation of imines catalyzed by a chiral complex of rhodium," *Tetrahedron Lett.* 49:4865–4868 (1973).

Larsson et al., "Paradoxical effects of K$^+$ and D–600 on parathyroid hormone secretion and cytoplasmic Ca$^{2+}$ in normal bovine and pathological human parathyroid cells," *Biochimica et Biophysica Acta* 847:263–269 (1985).

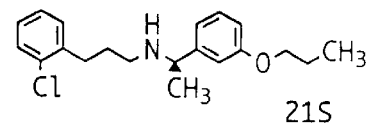
21S
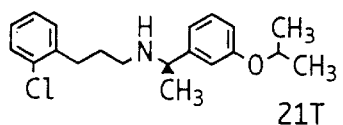
21T
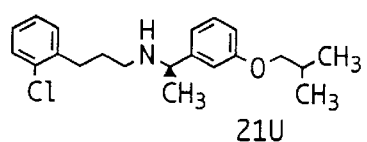
21U
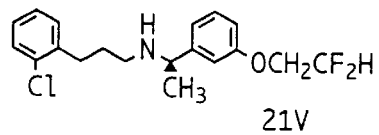
21V
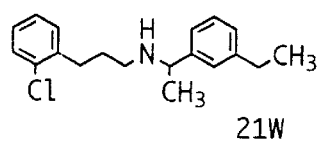
21W
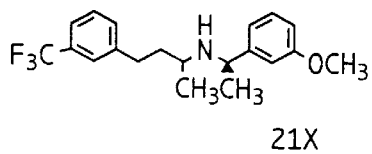
21X
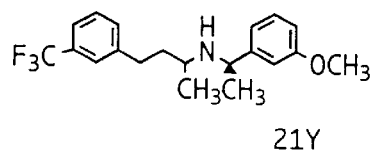
21Y
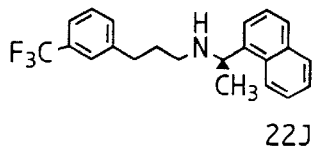
22J
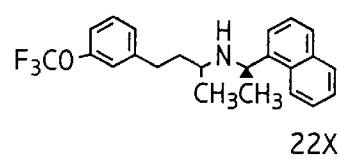
22X
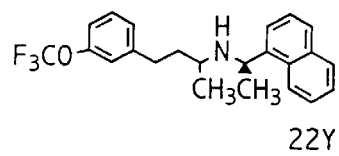
22Y
FIG. 1o.

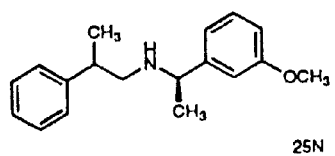
25N
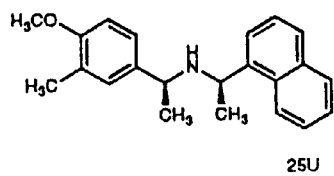
25U
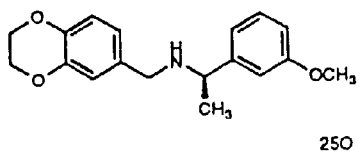
25O
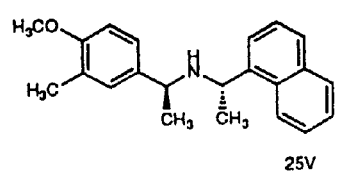
25V
25P
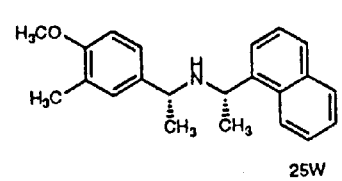
25W
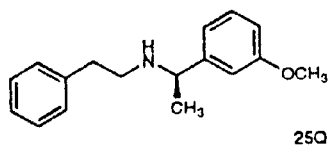
25Q
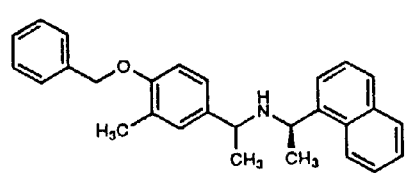
25X
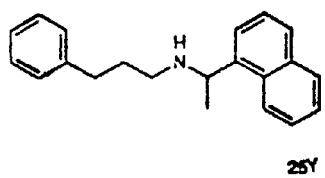
25Y
FIG. *1*r.

NPS R-467 · HCl mp 157.4-158 °C; [α]$_D^{20}$ +41.7° (c 6.11, CHCl$_3$); UV $_{max}$ (EtOH) 276 (ε 1900), sh 282 nm (ε 1700); $^1$H NMR (CDCl$_3$) δ 1.83 (3H, d, J=7, C-CH$_3$), 2.29 (2H, q, J=8), 2.51 (2H, q, J=6), 2.65 (2H, br m), 3.87 (3H, s, -OCH$_3$), 4.11 (1H, br q, CH), 6.91 (1H, dd, J=8, J=2), 7.05-7.07 (3H, m), 7.11-7.21 (3H, m), 7.27-7.32 (2H, m) 9.8 (1H, br s), 10.2 (1H, br s); $^{13}$C NMR (CDCl$_3$) δ 20.3, 27.0, 32.3, 44.9, 55.3, 58.8, 111.8, 115.3, 119.7, 125.8, 127.9 (2C), 128.1 (2C), 130.0, 137.2, 139.6, 161.1; GC/EI-MS (t$_R$=9.03 min), m/z (rel. int.) 269 (M$^+$, 17), 254 (100), 164 (8), 135 (50), 121 (8), 105 (7), 91 (23), 77 (7); HR-EI-MS observed (M$^+$) m/z 269.1796, C$_{18}$H$_{23}$NO required 269.1780.

NPS R-568 · HCl mp 188.188.5 °C; [α]$_D^{20}$ +37.8° (c 6.80, CHCl$_3$); UV $_{max}$ (EtOH) 274 (ε 2200), sh 282 nm (ε 1900); $^1$H NMR (CDCl$_3$) δ1.85 (3H, d, J=7, C-CH$_3$), 2.24 (2H, q, J=8), 2.66 (2H, q, J=7), 2.68 (2H, br q, J=7), 3.87 (3H, s, -OCH$_3$), 4.15 (1H, br t, J=7, CH), 6.90 (1H, dd, J=8, J=2), 7.06-7.15 (4H, m), 7.23-7.32 (3H, m), 9.85 (1H, br s), 10.2 (1H, br s); $^{13}$C NMR (CDCl$_3$) δ20.2, 25.2, 30.0, 44.7, 55.6, 58.6, 112.0, 115.3, 119.7, 126.5, 127.4, 129.1, 129.9, 130.0, 133.4, 137.1, 137.2, 160.0; GC/EI-MS ($t_R$=9.93 min), m/z (rel. int.) 303 (M$^+$,2), 288 (100), 268 (17), 196 (4), 164 (8), 135 (56), 126 (21), 103 (9); 91 (7), 77 (7); HR-EI-MS observed (M$^+$) m/z 303.1403, C$_{18}$H$_{22}$ClNO required 303.1390.

VARIAN 300 MHz $^1$H-NMR SPECTRAL ASSIGNMENT OF:

9C HYDROCHLORIDE

NMR SPECTRA ARE OF THE HCl SALT. RESONANCES FROM 0-5 PPM ARE IN 1% MeOD/CDCl$_3$ (5mg/mL). RESONANCES FROM 5-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.85 | d | J=6.8 | aliph-CH$_3$ |
| 1H | 4.05 | d | J=13.2 | -CH$_2$- |
| 1H | 4.16 | d | J=13.4 | -CH$_2$- |
| 1H | 5.06 | q | J=7.0 | aliph-CH- |
| 8H | 7.21-7.47 | m | n.a. | |
| 1H | 7.54 | d | J=8.8 | |
| 2H | 7.65-7.73 | m | n.a. | |
| 2H | 7.89 | d | J=7.8 | |
| 1H | 8.43 | d | J=7.2 | |
| 1H | 10.47 | bs | n.a. | aliph-NH$_2$+ |
| 1H | 10.84 | bs | n.a. | aliph-NH$_2$+ |

VARIAN 75 MHz $^{13}$C-NMR SPECTRAL ASSIGNMENT OF:

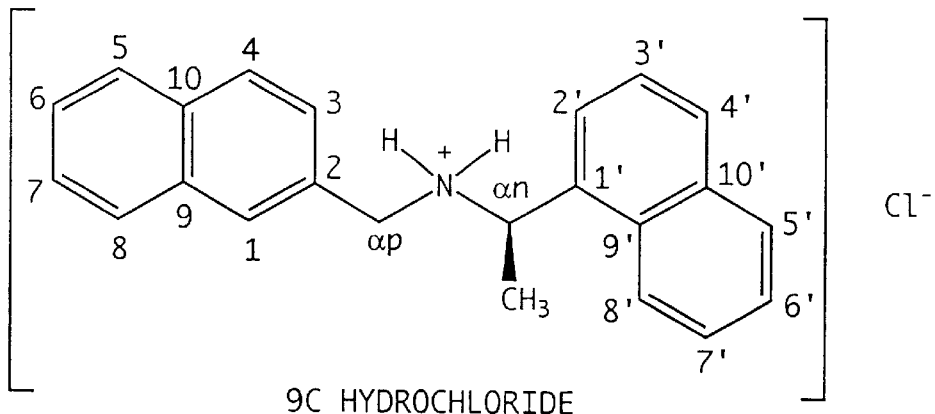

9C HYDROCHLORIDE

NMR SPECTRA ARE OF THE HCl SALT IN CDCl$_3$ (60 mg/mL).

| δ(PPM) | MULTIPLICITY | ASSIGNMENT |
|---|---|---|
| 21.18 | CH$_3$ | aliph-CH$_3$ |
| 48.5 | CH$_2$ | -CH$_2$- |
| 51.46 | CH | -CH- |
| 121.42 | CH | RIGHT SIDE |
| 125.21 | CH | RIGHT SIDE |
| 125.99 | CH | LEFT SIDE |
| 126.04 | CH | RIGHT SIDE |
| 126.15 | CH | RIGHT SIDE |
| 126.63 | CH | LEFT SIDE |
| 126.69 | CH | LEFT SIDE |
| 126.91 | Q | LEFT SIDE |
| 127.37 | CH | RIGHT SIDE |
| 127.45 | CH | LEFT SIDE |
| 127.93 | CH | LEFT SIDE |
| 128.52 | CH | LEFT SIDE |
| 129.04 | CH | LEFT SIDE |
| 129.24 | CH | RIGHT SIDE |
| 130.32 | Q | RIGHT SIDE |
| 130.83 | CH | RIGHT SIDE |
| 132.23 | Q | RIGHT SIDE |
| 132.59 | Q | LEFT SIDE |
| 133.15 | Q | LEFT SIDE |
| 133.66 | Q | RIGHT SIDE |

FIG. 97.

VARIAN 300 MHz $^1$H-NMR SPECTRAL ASSIGNMENT OF:

9R HYDROCHLORIDE

NMR SPECTRA ARE OF THE HCl SALT. RESONANCES FROM 0-5 PPM ARE IN 1% MeOD/CDCl$_3$ (5mg/mL). RESONANCES FROM 5-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.97 | d | J=6.8 | aliph-CH$_3$ |
| 3H | 2.03 | d | J=6.8 | aliph-CH$_3$ |
| 1H | 4.17 | q | J=6.9 | aliph-CH- |
| 1H | 4.81 | q | J=6.9 | aliph-CH- |
| 2H | 6.77-6.85 | m | n.a. | |
| 1H | 7.14 | bs | n.a. | |
| 4H | 7.33-7.52 | m | n.a. | |
| 6H | 7.74-7.94 | m | n.a. | |
| 1H | 8.69 | bs | n.a. | |
| 1H | 10.82 | bs | n.a. | aliph-NH$_2$+ |
| 1H | 10.89 | bs | n.a. | aliph-NH$_2$+ |

VARIAN 75 MHz $^{13}$C-NMR SPECTRAL ASSIGNMENT OF:

9R HYDROCHLORIDE

NMR SPECTRA ARE OF THE HCl SALT IN CDCl$_3$ (60 mg/mL).

| δ(PPM) | MULTIPLICITY | ASSIGNMENT |
|---|---|---|
| 20.83 | CH$_3$ | aliph-CH$_3$ |
| 21.87 | CH$_2$ | aliph-CH$_3$ |
| 51.37 | CH | -CH$_2$- |
| 57.27 | CH | -CH- |
| | | |
| 121.40 | CH | |
| 124.65 | CH | |
| 125.50 | CH | |
| 125.82 | CH | |
| 126.09 | CH | |
| 126.22 | CH | |
| 126.62 | CH | |
| 127.49 | CH | |
| 128.01 | CH | |
| 128.76 | CH | |
| 129.08 | CH | |
| 129.25 | CH | |
| 130.19 | Q | |
| 132.74 | Q | |
| 132.78 | Q | |
| 132.95 | Q | |
| 133.27 | Q | |
| 133.53 | Q | |

VARIAN 300 MHz $^1$H-NMR SPECTRAL ASSIGNMENT OF:

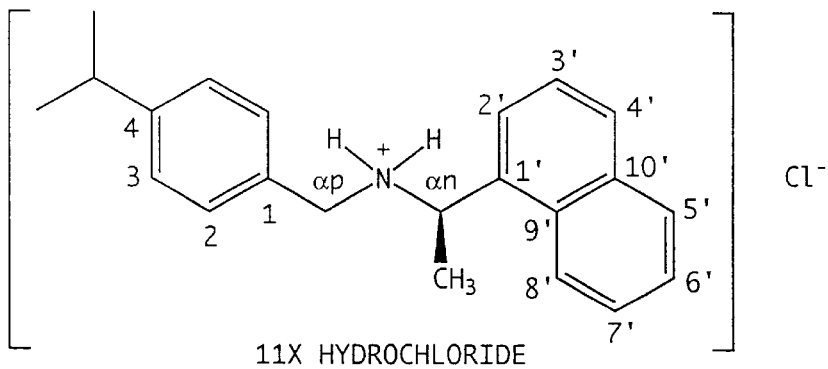

11X HYDROCHLORIDE

NMR SPECTRA ARE OF THE HCl SALT. RESONANCES FROM 0-5 PPM ARE IN 1% MeOD/CDCl$_3$ (5mg/mL). RESONANCES FROM 5-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 6H | 1.17 | d | J=7.1 | -CH(CH$_3$)$_2$ |
| 3H | 1.86 | d | J=6.8 | aliph-CH$_3$ |
| 1H | 2.84 | p | J=7.0 | -CH(CH$_3$)$_2$ |
| 1H | 3.88 | d | J=13.3 | -CH2- |
| 1H | 3.97 | d | J=13.3 | -CH2- |
| 1H | 5.02 | q | J=6.8 | aliph-CH- |
| 1H | 7.03 | d | J=8.1 | 3 |
| 1H | 7.17 | d | J=8.1 | 2 |
| 3H | 7.40-7.54 | m | n.a. | |
| 1H | 7.68 | dd | J$_1$=J$_2$=7.9 | 3' |
| 1H | 7.89 | d | J=8.3 | 4' OR 5' |
| 1H | 7.91 | d | J=8.1 | 4' OR 5' |
| 1H | 8.41 | d | J=7.1 | 2' |
| 1H | 10.38 | bs | n.a. | aliph-NH$_2$+ |
| 1H | 10.77 | bs | n.a. | aliph-NH$_2$+ |

FIG. 100.

VARIAN 75 MHz $^{13}$C-NMR SPECTRAL ASSIGNMENT OF:

11X HYDROCHLORIDE

NMR SPECTRA ARE OF THE HCl SALT IN CDCl$_3$ (60 mg/mL).

| δ(PPM) | MULTIPLICITY | ASSIGNMENT |
|---|---|---|
| 21.33 | CH$_3$ | aliph-CH$_3$ |
| 23.58 | CH$_3$ | -CH(CH$_3$)$_2$ |
| 33.66 | CH | arom-CH |
| 48.27 | CH$_2$ | -CH$_2$- |
| 51.52 | CH | aliph-CH- |
| | | |
| 121.57 | CH | |
| --- | --- | |
| --- | --- | |
| 125.17 | CH | |
| 125.94 | CH | |
| 126.05 | CH | |
| 126.65 | CH | |
| 127.05 | Q | |
| 129.10 | CH | |
| 130.02 | CH | |
| 130.39 | Q | |
| 130.90 | CH | |
| 132.43 | Q | |
| 133.71 | Q | |
| 149.84 | Q | |

VARIAN 300 MHz $^1$H-NMR SPECTRAL ASSIGNMENT OF:

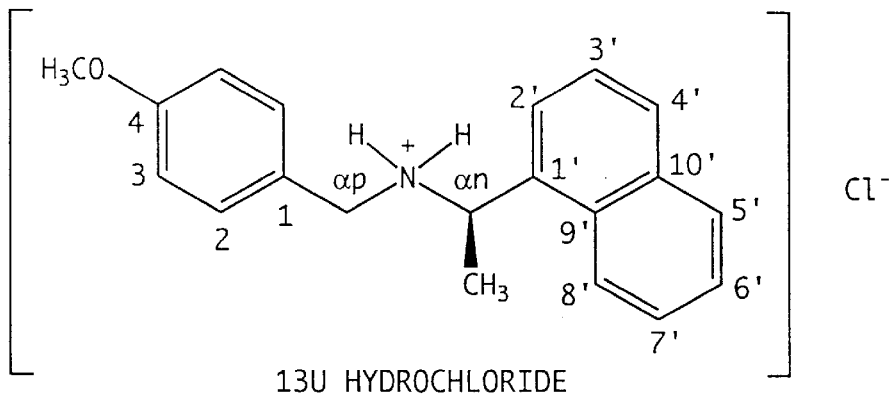

13U HYDROCHLORIDE

NMR SPECTRA ARE OF THE HCl SALT. RESONANCES FROM 0-5 PPM ARE IN 1% MeOD/CDCl$_3$ (5mg/mL). RESONANCES FROM 5-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.92 | d | J=6.6 | aliph-CH$_3$ |
| 3H | 3.64 | s | n.a. | -OCH$_3$ |
| 1H | 3.85 | d | J=13.4 | -CH$_2$- |
| 1H | 3.93 | d | J=13.5 | -CH$_2$- |
| 1H | 5.04 | q | J=6.9 | aliph-CH- |
| 2H | 6.72 (6.71 calc) | d | J=8.3 | 3 |
| 2H | 7.21 (7.10 calc) | d | J=8.0 | 2 |
| 2H | 7.47-7.55 | m | n.a. | |
| 1H | 7.60 | d | J=8.3 | |
| 1H | 7.69 | dd | J=7.9/7.5 | 3' |
| 1H | 7.90 | d | J=7.9 | 4' OR 5' |
| 1H | 7.92 | d | J=7.7 | 4' OR 5' |
| 1H | 8.42 | d | J=7.3 | 2' |
| 1H | 10.35 | bs | n.a. | aliph-NH$_2$+ |
| 1H | 10.73 | bs | n.a. | aliph-NH$_2$+ |

FIG. 102.

VARIAN 75 MHz $^{13}$C-NMR SPECTRAL ASSIGNMENT OF:

13U HYDROCHLORIDE

NMR SPECTRA ARE OF THE HCI SALT IN CDCl$_3$ (60 mg/mL).

| δ(PPM) | MULTIPLICITY | ASSIGNMENT |
| --- | --- | --- |
| 21.16 | CH$_3$ | aliph-CH$_3$ |
| 47.86 | CH$_2$ | -CH$_2$- |
| 51.28 | CH | -CH- |
| 54.94 | CH$_3$ | O-CH$_3$ |
| 113.82 | CH | 3' |
| 121.47 | CH | |
| 121.58 | Q | LEFT SIDE arom-C-CH$_2$NH$_2$ |
| --- | --- | |
| 125.03 | CH | |
| 125.91 | CH | |
| 125.94 | CH | |
| 126.68 | CH | |
| 129.06 | CH | |
| --- | --- | |
| 130.25 | Q | |
| --- | --- | |
| --- | --- | |
| 132.27 | CH | 2' |
| 133.63 | Q | NH$_2$-CH$_2$-C-naphthyl |
| 159.95 | Q | arom-C-OCH$_3$ |

VARIAN 300 MHz ¹H-NMR SPECTRAL ASSIGNMENT OF:

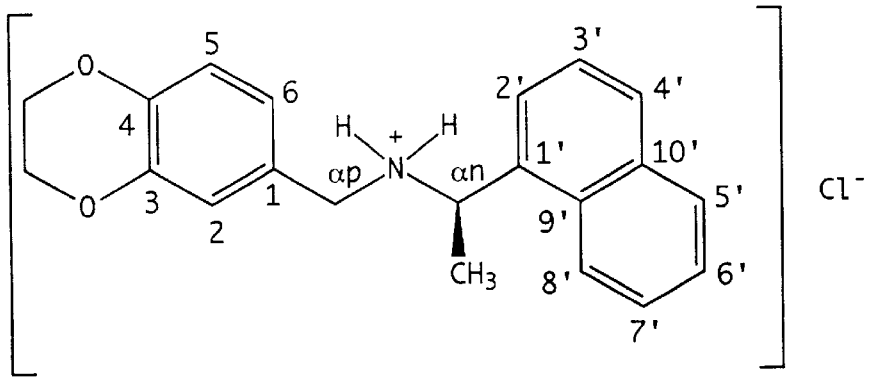

13X HYDROCHLORIDE

NMR SPECTRA ARE OF THE HCl SALT. RESONANCES FROM 0-5 PPM
ARE IN 1% MeOD/CDCl₃ (5mg/mL). RESONANCES FROM 5-12 PPM
ARE IN CDCl₃ (60mg/mL).

| # OF H's | δ(PPM) | MULTIPLICITY | COUPLING (Hz) | ASSIGNMENT |
|---|---|---|---|---|
| 3H | 1.91 | d | J=6.7 | aliph-$CH_3$ |
| 1H | 3.75 | d | J=13.3 | -$CH_2$- |
| 1H | 3.91 | d | J=13.3 | -$CH_2$- |
| 4H | 4.10 | m | n.a. | -O-$CH_2CH_2$-O- |
| 1H | 5.03 | q | J=7.0 | aliph-CH- |
| 3H | 6.70-6.80 | m | n.a. | |
| 4H | 7.47-7.56 | m | n.a. | |
| 1H | 7.66 | dd | $J_1=J_2=8.1$ | 3' |
| 1H | 7.90 | d | J=7.4 | 4' OR 5' |
| 1H | 7.91 | d | J=7.4 | 4' OR 5' |
| 1H | 8.28 | d | J=7.2 | 2' |
| 1H | 10.34 | bs | n.a. | aliph-$NH_2$+ |
| 1H | 10.83 | bs | n.a. | aliph-$NH_2$+ |

FIG. 104.

VARIAN 75 MHz $^{13}$C-NMR SPECTRAL ASSIGNMENT OF:

13X HYDROCHLORIDE

NMR SPECTRA ARE OF THE HCl SALT IN CDCl$_3$ (60 mg/mL).

| δ(PPM) | MULTIPLICITY | ASSIGNMENT |
| --- | --- | --- |
| 20.87 | CH$_3$ | aliph-CH$_3$ |
| 47.87 | CH$_2$ | -CH$_2$- |
| 51.16 | CH | -CH- |
| 63.86 | CH$_2$ | -O-CH$_2$-CH$_2$-O- |
| 64.09 | CH$_2$ | -O-CH$_2$-CH$_2$-O- |
| 117.40 | CH | |
| 119.66 | CH | |
| 121.45 | CH | |
| 122.61 | Q | |
| 123.67 | CH | |
| 124.83 | CH | |
| 125.85 | CH | |
| 125.96 | CH | |
| 126.76 | CH | |
| 129.09 | CH | |
| 129.22 | CH | |
| 130.31 | Q | |
| 132.17 | Q | |
| 133.67 | Q | |
| 143.28 | Q | -O-C-arom |
| 144.17 | Q | -O-C-arom |

VARIAN 300 MHz ¹H-NMR SPECTRAL ASSIGNMENT OF:

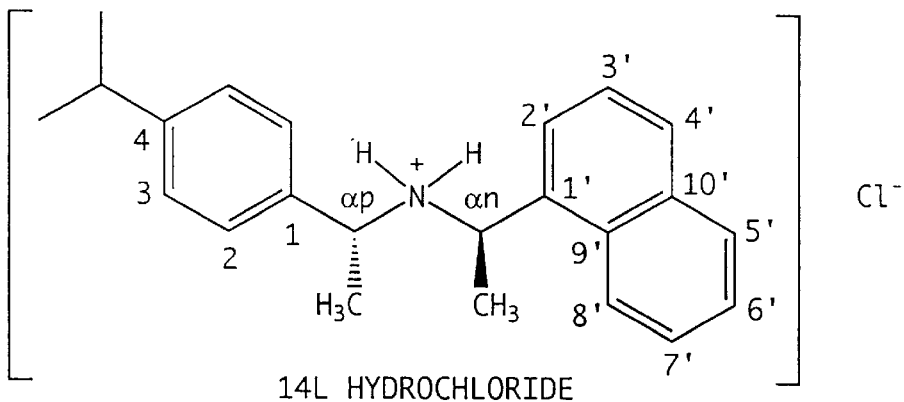

14L HYDROCHLORIDE

NMR SPECTRA ARE OF THE HCl SALT. RESONANCES FROM 0-10 PPM ARE IN 1% MeOD/CDCl₃ (5 mg/mL). RESONANCES FROM 10-12 PPM ARE IN CDCl₃ (60 mg/mL).

| # OF H's | δ(PPM) | MULTIPLICITY | COUPLING (Hz) | ASSIGNMENT |
|---|---|---|---|---|
| 3H | 1.236 | d | J=7.0 | -CH(CH₃)₂ |
| 3H | 1.242 | d | J=6.9 | -CH(CH₃)₂ |
| 3H | 1.84 | d | J=6.8 | aliph-CH₃ |
| 3H | 1.86 | d | J=6.8 | aliph-CH₃ |
| 1H | 2.88 | p | J=6.8 | -CH(CH₃)₂ |
| 1H | 3.97 | bq | J=6.7 | aliph-CH- |
| 1H | 4.77 | bq | J=6.9 | aliph-CH- |
| 1H | 6.95 | d | J=8.2 | H-3' |
| 1H | 7.05 | d | J=8.3 | H-2' |
| 1H | 7.26 | dd | J₁=J₂=7.1 | |
| 1H | 7.48 | dd | J₁=J₂=7.7 | |
| 1H | 7.68 | dd | J₁=J₂=7.7 | |
| 1H | 7.90 | d | J=7.7 | |
| 1H | 7.91 | d | J=7.9 | |
| 1H | 8.24 | bd | J=6.5 | |
| 2H | 10.71 | bs | n.a. | aliph-NH₂+ |

FIG. 106.

VARIAN 300 MHz $^1$H-NMR SPECTRAL ASSIGNMENT OF:

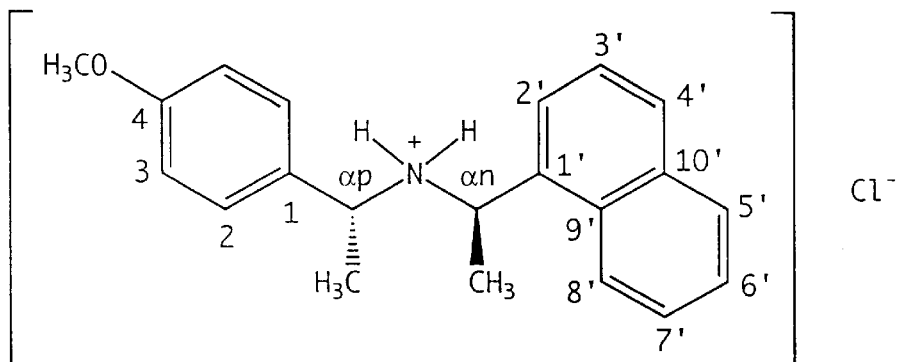

14U HYDROCHLORIDE

NMR SPECTRA ARE OF THE HCl SALT. RESONANCES FROM 0-10 PPM ARE IN 1% MeOD/CDCl$_3$ (5 mg/mL). RESONANCES FROM 10-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.93 | d | J=6.8 | aliph-CH$_3$ |
| 3H | 1.94 | d | J=6.7 | aliph-CH$_3$ |
| 3H | 3.80 | s | n.a. | -OCH$_3$ |
| 1H | 4.01 | q | J=7.0 | aliph-CH- |
| 1H | 4.82 | q | J=6.9 | aliph-CH- |
| 2H | 6.73 | d | J=8.8 | 3 |
| 2H | 7.07 | d | J=8.6 | 2 |
| 1H | 7.15 | bd | J=7.3 | 8' |
| 1H | 7.33 | dd | J$_1$=J$_2$=7.7 | 7' |
| 1H | 7.49 | dd | J$_1$=J$_2$=7.6 | 6' |
| 1H | 7.70 | dd | J$_1$=J$_2$=7.8 | 3' |
| 1H | 7.90 | d | J=8.1 | 4' OR 5' |
| 1H | 7.91 | d | J=8.0 | 4' OR 5' |
| 1H | 8.44 | bd | J=5.4 | 2' |
| 2H | 10.65 | bs | n.a. | aliph-NH$_2$+ |

FIG. 107.

VARIAN 75MHz $^{13}$C-NMR SPECTRAL ASSIGNMENT OF:

14U HYDROCHLORIDE

NMR SPECTRA ARE OF THE HCl SALT IN CDCl$_3$ (60 mg/mL).

| δ(PPM) | MULTIPLICITY | ASSIGNMENT |
|---|---|---|
| 21.11 | CH$_3$ | aliph-CH$_3$ |
| 21.93 | CH$_3$ | aliph-CH$_3$ |
| 51.29 | CH | -CH- |
| 55.30 | CH$_3$ | O-CH$_3$ |
| 56.61 | CH | -CH- |
| 114.30 | CH | 3' |
| 121.77 | CH | |
| --- | --- | |
| 125.38 | CH | |
| 125.91 | CH | |
| 126.17 | CH | |
| 126.40 | CH | |
| 127.88 | Q | |
| 128.96 | CH | |
| 128.99 | CH | |
| 128.79 | CH | |
| 130.22 | Q | |
| --- | --- | |
| 132.88 | Q | |
| 133.70 | Q | |
| 159.97 | Q | arom-C-OCH$_3$ |

VARIAN 300 MHz ¹H-NMR SPECTRAL ASSIGNMENT OF:

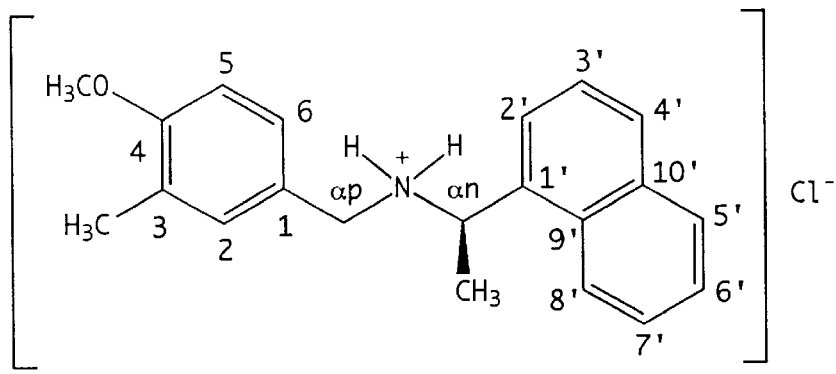

16Q HYDROCHLORIDE

NMR SPECTRA ARE OF THE HCl SALT. RESONANCES FROM 0-5 PPM ARE IN 1% MeOD/CDCl₃ (5 mg/mL). RESONANCES FROM 5-12 PPM ARE IN CDCl₃ (60 mg/mL).

| # OF H's | δ(PPM) | MULTIPLICITY | COUPLING (Hz) | ASSIGNMENT |
|---|---|---|---|---|
| 3H | 1.85 | d | J=6.7 | aliph-CH₃ |
| 3H | 2.01 | s | n.a. | arom-CH₃ |
| 3H | 3.77 | s | n.a. | -OCH₃ |
| 1H | 3.80 | d | J=13.1 | -CH₂- |
| 1H | 3.97 | d | J=13.2 | -CH₂- |
| 1H | 5.00 | q | J=6.7 | aliph-CH- |
| 1H | 6.69 (6.59 calc) | d | J=8.4 | 5 |
| 1H | 6.78 (6.90 calc) | bs | n.a. | 2' |
| 1H | 7.22 (6.88 calc) | bd | J=8.2 | 6' |
| 3H | 7.44-7.57 | m | n.a. | |
| 1H | 7.70 | dd | J=7.6/7.8 | 3' |
| 1H | 7.91 | d | J=8.1 | 4' OR 5' |
| 1H | 7.92 | d | J=8.1 | 4' OR 5' |
| 1H | 8.44 | d | J=7.1 | 2' |
| 1H | 10.35 | bs | n.a. | aliph-NH₂+ |
| 1H | 10.70 | bs | n.a. | aliph-NH₂+ |

FIG. 109.

VARIAN 75 MHz $^{13}$C-NMR SPECTRAL ASSIGNMENT OF:

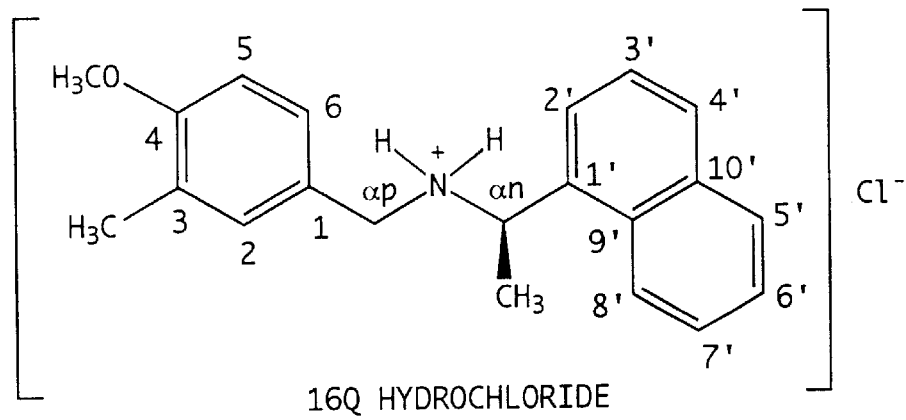

16Q HYDROCHLORIDE

NMR SPECTRA ARE OF THE HCl SALT IN CDCl$_3$ (60 mg/mL).

| δ(PPM) | MULTIPLICITY | ASSIGNMENT |
|---|---|---|
| 15.74 | CH$_3$ | arom-CH$_3$ |
| 22.32 | CH$_3$ | aliph-CH$_3$ |
| 47.85 | CH$_2$ | -CH$_2$- |
| 51.01 | CH | -CH- |
| 55.09 | CH$_3$ | O-CH$_3$ |
| | | |
| 109.81 | CH | 5' |
| 121.56 | CH | RIGHT SIDE |
| 121.01 | Q | LEFT SIDE arom-C-CH$_2$NH$_2$ |
| --- | --- | |
| 125.13 | CH | RIGHT SIDE |
| 125.90 | CH | |
| 126.03 | CH | RIGHT SIDE |
| 126.61 | CH | RIGHT SIDE |
| 129.05 | CH | RIGHT SIDE |
| 129.72 | CH | RIGHT SIDE |
| 130.31 | Q | RIGHT SIDE |
| --- | --- | |
| 132.44 | Q | RIGHT SIDE |
| 133.23 | CH | 6' |
| 133.68 | Q | NH$_2$-CH$_2$-C-naphthyl |
| 158.16 | Q | arom-C-OCH$_3$ |

FIG. 11O.

VARIAN 300 MHz $^1$H-NMR SPECTRAL ASSIGNMENT OF:

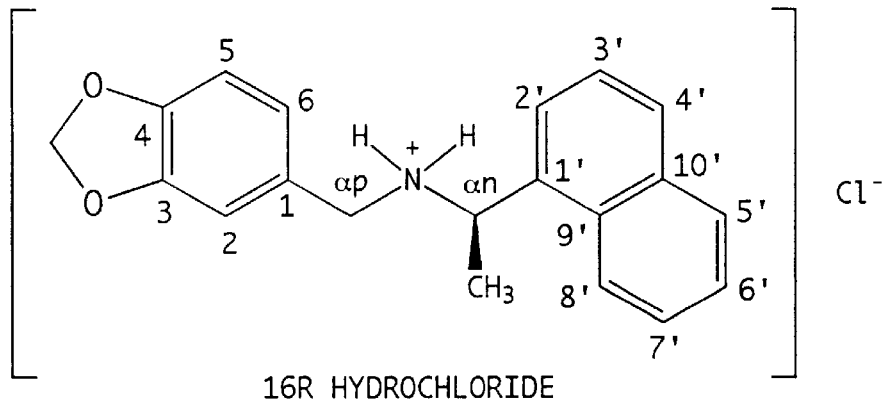

16R HYDROCHLORIDE

NMR SPECTRA ARE OF THE HCl SALT. RESONANCES FROM 0-10 PPM ARE IN 1% MeOD/CDCl$_3$ (5 mg/mL). RESONANCES FROM 10-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.88 | d | J=6.8 | aliph-CH$_3$ |
| 1H | 3.85 | d | J=13.4 | -CH$_2$- |
| 1H | 3.94 | d | J=13.4 | -CH$_2$- |
| 1H | 5.06 | q | J=6.7 | aliph-CH- |
| 2H | 5.90 | dd | J1=2.2; J2=1.4 | -O-CH$_2$-O- |
| 2H | 6.65 | s | n.a. | |
| 1H | 6.85 | s | n.a. | |
| 2H | 7.50-7.58 | m | n.a. | |
| 2H | 7.63-7.70 | m | n.a. | |
| 1H | 7.92 | d | J=8.1 | 4' OR 5' |
| 1H | 7.94 | d | J=9.5 | 4' OR 5' |
| 1H | 8.12 | d | J=6.7 | 2' |
| 1H | 10.37 | bs | n.a. | aliph-NH$_2$+ |
| 1H | 10.80 | bs | n.a. | aliph-NH$_2$+ |

FIG. 111.

VARIAN 75 MHz $^{13}$C-NMR SPECTRAL ASSIGNMENT OF:

16R HYDROCHLORIDE

NMR SPECTRA ARE OF THE HCl SALT IN CDCl$_3$ (60 mg/mL).

| δ(PPM) | MULTIPLICITY | ASSIGNMENT |
|---|---|---|
| 21.20 | CH$_3$ | aliph-CH$_3$ |
| 48.39 | CH$_2$ | -CH$_2$- |
| 51.26 | CH | -CH- |
| 101.16 | CH$_2$ | -O-$\underline{C}$H$_2$-O- |
| 108.19 | CH | |
| 110.11 | CH | |
| 121.25 | CH | |
| 123.18 | Q | |
| 124.13 | CH | |
| 124.21 | CH | |
| 125.49 | CH | |
| 126.05 | CH | |
| 126.89 | CH | |
| 129.03 | CH | |
| 129.88 | CH | |
| 130.22 | Q | |
| 131.93 | Q | |
| 133.63 | Q | |
| 147.77 | Q | -O-$\underline{C}$-arom |
| 148.26 | Q | -O-$\underline{C}$-arom |

VARIAN 300 MHz ¹H-NMR SPECTRAL ASSIGNMENT OF:

16T HYDROCHLORIDE

NMR SPECTRA ARE OF THE HCl SALT. RESONANCES FROM 0-10 PPM ARE IN 1% MeOD/CDCl$_3$ (5 mg/mL). RESONANCES FROM 10-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.89 | d | J=6.6 | aliph-CH$_3$ |
| 3H | 3.80 | s | n.a. | -OCH$_3$ |
| 1H | 3.85 | d | J=13.7 | -CH$_2$- |
| 1H | 3.95 | d | J=13.3 | -CH$_2$- |
| 1H | 5.09 | q | J=6.6 | aliph-CH- |
| 1H | 6.84 | t | J=8.2 | |
| 2H | 7.01-7.08 | m | n.a. | |
| 2H | 7.53-7.56 | m | n.a. | |
| 2H | 7.64-7.72 | m | n.a. | |
| 2H | 7.93 | d | J=7.6 | 4' OR 5' |
| 1H | 8.19 | d | J=7.1 | 2' |
| 1H | 10.41 | bs | n.a. | aliph-NH$_2$+ |
| 1H | 10.82 | bs | n.a. | aliph-NH$_2$+ |

VARIAN 75 MHz $^{13}$C-NMR SPECTRAL ASSIGNMENT OF:

16T HYDROCHLORIDE

NMR SPECTRA ARE OF THE HCl SALT IN CDCl$_3$ (60 mg/mL).

| δ(PPM) | MULTIPLICITY | ASSIGNMENT |
|---|---|---|
| 20.71 | CH$_3$ | aliph-CH$_3$ |
| 47.67 | CH$_2$ | -CH$_2$- |
| 51.47 | CH | -CH- |
| 55.91 | CH$_3$ | O-CH$_3$ |
| 113.12 | CH | |
| 113.13 | CH | |
| 117.99 | CH | |
| 118.24 | CH | |
| 121.30 | CH | |
| 122.22 | Q | |
| 122.31 | Q | |
| 124.61 | CH | |
| 125.76 | CH | |
| 126.16 | CH | |
| 126.92 | CH | |
| 127.00 | CH | |
| 129.17 | CH | |
| 129.47 | CH | |
| 130.29 | Q | |
| 131.92 | Q | |
| 133.73 | Q | |
| 148.21 | Q | |
| 148.35 | Q | |
| 150.01 | Q | |
| 153.29 | Q | |

VARIAN 300 MHz ¹H-NMR SPECTRAL ASSIGNMENT OF:

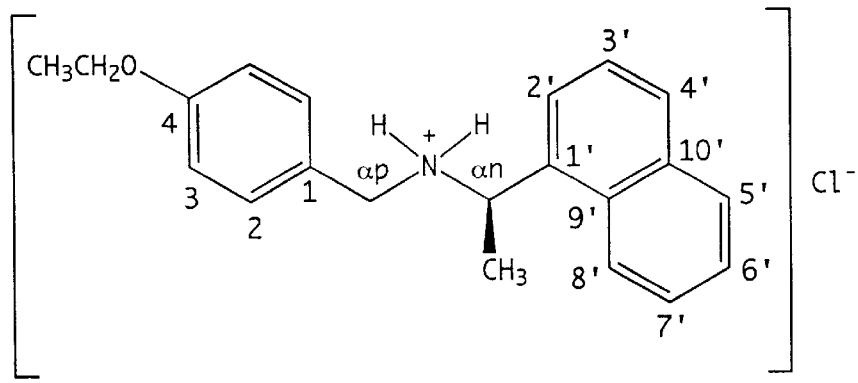

16W HYDROCHLORIDE

NMR SPECTRA ARE OF THE HCl SALT. RESONANCES FROM 0-5 PPM ARE IN 1% MeOD/CDCl₃ (5 mg/mL). RESONANCES FROM 5-12 PPM ARE IN CDCl₃ (60 mg/mL).

| # OF H's | δ(PPM) | MULTIPLICITY | COUPLING (Hz) | ASSIGNMENT |
|---|---|---|---|---|
| 3H | 1.35 | t | J=6.9 | -OCH₂CH₃ |
| 3H | 1.86 | d | J=6.8 | aliph-CH₃ |
| 4H | 3.81-3.96 | m | | -CH₂ AND CH₂ |
| 1H | 5.00 | q | J=6.7 | aliph-CH- |
| 1H | 6.70 | d | J=8.4 | 3 |
| 1H | 7.19 | d | J=8.6 | 2 |
| 2H | 7.44-7.54 | m | n.a. | |
| 1H | 7.58 | d | J=8.3 | |
| 1H | 7.68 | dd | J₁=J₂=7.7 | 3' |
| 1H | 7.89 | d | J=7.7 | 4' OR 5' |
| 1H | 7.91 | d | J=7.7 | 4' OR 5' |
| 1H | 8.42 | d | J=7.0 | 2' |
| 1H | 10.30 | bs | n.a. | aliph-NH₂+ |
| 1H | 10.72 | bs | n.a. | aliph-NH₂+ |

FIG. 115.

VARIAN 75 MHz $^{13}$C-NMR SPECTRAL ASSIGNMENT OF:

16W HYDROCHLORIDE

NMR SPECTRA ARE OF THE HCl SALT IN CDCl$_3$ (60 mg/mL).

| δ(PPM) | MULTIPLICITY | ASSIGNMENT |
|---|---|---|
| 14.51 | CH$_3$ | $\underline{C}$H$_3$-CH$_2$-O- |
| 21.20 | CH$_3$ | aliph-CH$_3$ |
| 47.91 | CH$_2$ | -CH$_2$- |
| 51.27 | CH | -CH- |
| 63.16 | CH$_2$ | CH$_3$-$\underline{C}$H$_2$-O- |
| | | |
| 114.36 | CH | 3' |
| 121.43 | Q | LEFT SIDE arom-$\underline{C}$-CH$_2$NH$_2$ |
| 121.52 | CH | |
| --- | --- | |
| 125.07 | CH | |
| 125.93 | CH | |
| 125.99 | CH | |
| 126.70 | CH | |
| 129.08 | CH | |
| --- | --- | |
| 130.29 | Q | |
| --- | --- | |
| 132.25 | CH | 2' |
| 132.33 | Q | |
| 133.67 | Q | NH$_2$-CH$_2$-$\underline{C}$-naphthyl |
| 159.38 | Q | arom-$\underline{C}$-OCH$_3$ |

VARIAN 300 MHz $^1$H-NMR SPECTRAL ASSIGNMENT OF:

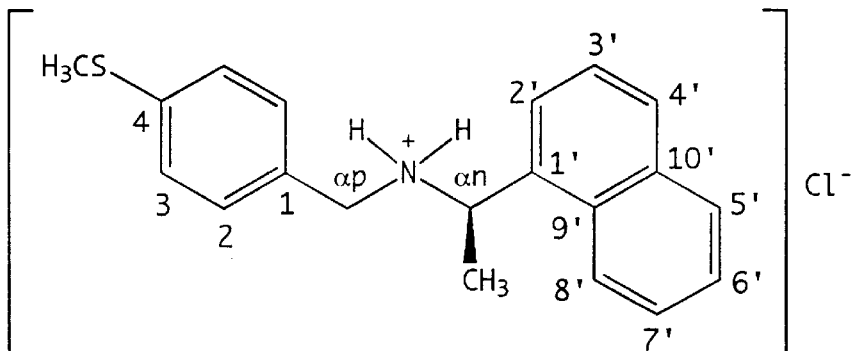

16X HYDROCHLORIDE

NMR SPECTRA ARE OF THE HCl SALT. RESONANCES FROM 0-5 PPM ARE IN 1% MeOD/CDCl$_3$ (5 mg/mL). RESONANCES FROM 5-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.87 | d | J=6.8 | aliph-CH$_3$ |
| 3H | 2.38 | s | n.a. | -SCH$_3$ |
| 1H | 3.82 | d | J=13.4 | -CH$_2$- |
| 1H | 3.91 | d | J=13.2 | -CH$_2$- |
| 1H | 5.04 | q | J=6.6 | aliph-CH- |
| 1H | 7.03 | d | J=8.2 | H-3' |
| 1H | 7.20 | d | J=8.2 | H-2' |
| 2H | 7.45-7.55 | m | n.a. | |
| 1H | 7.59 | d | J=7.9 | |
| 1H | 7.68 | dd | J$_1$=J$_2$=7.4 | 3' |
| 1H | 7.90 | d | J=8.1 | 4' OR 5' |
| 1H | 7.91 | d | J=7.0 | 4' OR 5' |
| 1H | 8.39 | d | J=7.3 | 2' |
| 1H | 10.38 | bs | n.a. | aliph-NH$_2$+ |
| 1H | 10.78 | bs | n.a. | aliph-NH$_2$+ |

FIG. 117.

VARIAN 75 MHz $^{13}$C-NMR SPECTRAL ASSIGNMENT OF:

16X HYDROCHLORIDE

NMR SPECTRA ARE OF THE HCl SALT IN CDCl$_3$ (60 mg/mL).

| δ(PPM) | MULTIPLICITY | ASSIGNMENT |
|---|---|---|
| 14.95 | CH$_3$ | S-CH$_3$ |
| 21.18 | CH$_3$ | aliph-CH$_3$ |
| 48.02 | CH$_2$ | -CH$_2$- |
| 51.57 | CH | -CH- |
| | | |
| 121.44 | CH | |
| 121.10 | CH | |
| --- | --- | |
| 125.81 | CH | |
| 125.95 | Q | |
| 125.99 | CH | |
| 126.77 | CH | |
| 129.12 | CH | |
| 129.20 | CH | |
| 130.30 | Q | |
| --- | --- | |
| 131.29 | CH | |
| 132.16 | CH | 2' |
| 133.67 | Q | NH$_2$-CH$_2$-C-naphthyl |
| 140.18 | Q | arom-C-SCH$_3$ |

VARIAN 300 MHz $^1$H-NMR SPECTRAL ASSIGNMENT OF:

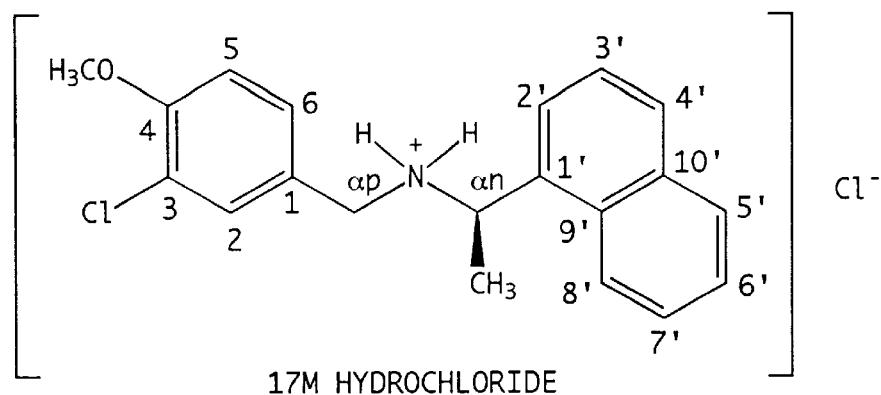

17M HYDROCHLORIDE

NMR SPECTRA ARE OF THE HCl SALT. RESONANCES FROM 0-5 PPM ARE IN 1% MeOD/CDCl$_3$ (5 mg/mL). RESONANCES FROM 5-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.88 | d | J=6.6 | aliph-CH$_3$ |
| 3H | 3.85 | s | n.a. | -OCH$_3$ |
| 1H | 3.82 | d | J=13.1 | -CH$_2$- |
| 1H | 3.95 | d | J=13.2 | -CH$_2$- |
| 1H | 5.03 | q | J=7.0 | aliph-CH- |
| 1H | 6.79 (6.69 calc) | d | J=8.5 | 5 |
| 1H | 7.10 (7.13 calc) | s | n.a. | 2 |
| 1H | 7.33 (7.01 calc) | d | J=8.3 | 6 |
| 2H | 7.48-7.57 | m | n.a. | |
| 1H | 7.62 | d | J=7.7 | |
| 1H | 7.69 | dd | J=7.4/8.1 | 3' |
| 1H | 7.92 | d | J=7.7 | 4' OR 5' |
| 1H | 7.94 | d | J=7.7 | 4' OR 5' |
| 1H | 8.38 | d | J=7.5 | 2' |
| 1H | 10.42 | bs | n.a. | aliph-NH$_2$+ |
| 1H | 10.79 | bs | n.a. | aliph-NH$_2$+ |

FIG. 119.

| | | |
|---|---|---|
| 21.32 | CH3 | aliph-CH3 |
| 47.45 | CH2 | -CH2- |
| 51.47 | CH | -CH- |
| 55.96 | CH3 | O-CH3 |
| 111.88 | CH | 5' |
| 121.27 | CH | |
| 122.27 | Q | |
| 122.65 | Q | |
| 125.14 | CH | |
| 126.01 | CH | |
| 126.14 | CH | |
| 127.05 | CH | |
| 129.21 | CH | |
| 129.35 | CH | |
| 130.30 | Q | |
| 130.69 | CH | |
| 132.09 | Q | |
| 132.71 | CH | 6' |
| 133.76 | Q | NH2-CH2-C-naphthyl |
| 155.52 | Q | arom-C-OCH3 |

VARIAN 300 MHz ¹H-NMR SPECTRAL ASSIGNMENT OF:

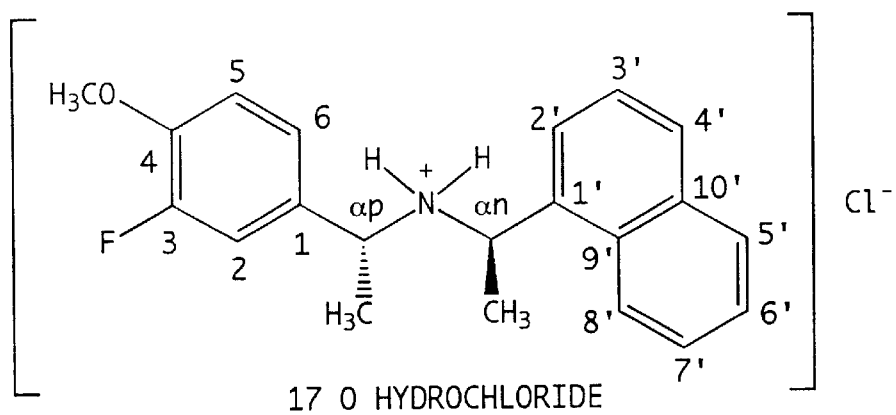

17 0 HYDROCHLORIDE

NMR SPECTRA ARE OF THE HCl SALT. RESONANCES FROM 0-5 PPM ARE IN 1% MeOD/CDCl$_3$ (5 mg/mL). RESONANCES FROM 5-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.86 | d | J=7.0 | aliph-CH$_3$ |
| 3H | 1.99 | d | J=6.8 | aliph-CH$_3$ |
| 3H | 3.87 | s | n.a. | -OCH$_3$ |
| 1H | 3.91 | q | J=7.0 | aliph-CH- |
| 1H | 4.80 | q | J=6.7 | aliph-CH- |
| 1H | 6.79 | dd | J$_1$=J$_2$=8.5 | |
| 1H | 6.89 | dd | J$_1$=12.0 J$_2$=2.0 | |
| 1H | 6.96 | d | J=8.7 | |
| 1H | 7.16 | bd | J=7.14 | 8' |
| 1H | 7.34 | dd | J$_1$=J$_2$=8.3 | 7' |
| 1H | 7.49 | dd | J$_1$=J$_2$=7.2 | 6' |
| 1H | 7.71 | dd | J$_1$=J$_2$=8.1 | 3' |
| 1H | 7.90 | d | J=8.1 | 4' OR 5' |
| 1H | 7.91 | d | J=7.8 | 4' OR 5' |
| 1H | 8.53 | bs | n.a. | 2' |
| 1H | 10.64 | bs | n.a. | aliph-NH$_2$+ |

FIG. 121.

VARIAN 75 MHz $^{13}$C-NMR SPECTRAL ASSIGNMENT OF:

17 O HYDROCHLORIDE

NMR SPECTRA ARE OF THE HCl SALT IN CDCl$_3$ (60 mg/mL).

| | | |
|---|---|---|
| 20.89 | CH$_3$ | aliph-CH$_3$ |
| 21.78 | CH$_3$ | arom-CH$_3$ |
| 51.26 | CH | -CH- |
| 56.12 | CH$_3$ | O-CH$_3$ |
| 56.19 | CH | -CH- |
| 113.44 | CH | |
| 116.27 | CH | |
| 116.52 | CH | |
| 121.31 | CH | |
| 124.39 | CH | |
| 124.43 | CH | |
| 125.24 | CH | |
| 125.97 | CH | |
| 126.03 | CH | |
| 126.45 | CH | |
| 128.35 | Q | |
| 128.43 | Q | |
| 128.98 | CH | |
| 129.10 | CH | |
| 130.05 | Q | |
| 132.45 | Q | |
| 133.61 | Q | |
| 147.96 | Q | |
| 148.10 | Q | |
| 150.26 | Q | |
| 153.55 | Q | |

VARIAN 300 MHz $^1$H-NMR SPECTRAL ASSIGNMENT OF:

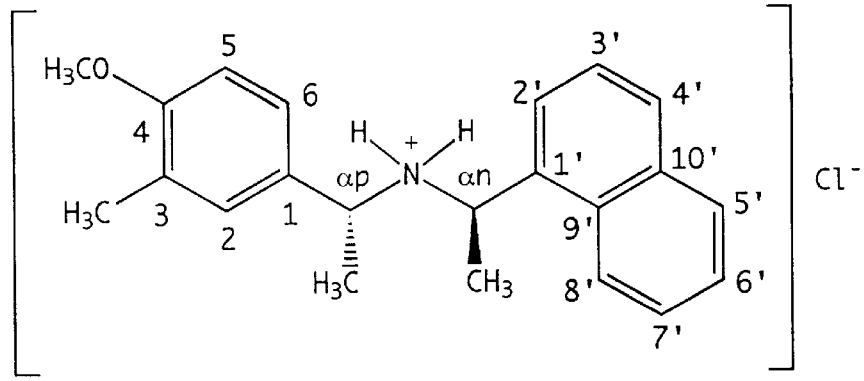

17P HYDROCHLORIDE

NMR SPECTRA ARE OF THE HCl SALT. RESONANCES FROM 0-10 PPM ARE IN 1% MeOD/CDCl$_3$ (5 mg/mL). RESONANCES FROM 10-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.82 | d | J=6.7 | phenyl-CH$_3$ |
| 3H | 1.83 | d | J=6.7 | naphthyl-CH$_3$ |
| 3H | 1.93 | s | n.a. | arom-CH$_3$ |
| 3H | 3.83 | s | n.a. | -OCH$_3$ |
| 1H | 3.90 | q | J=6.9 | phenyl-CH- |
| 1H | 4.74 | q | J=7.0 | naphthyl-CH- |
| 1H | 6.52 | d | J=1.6 | 2 |
| 1H | 6.70 | d | J=8.5 | 5 |
| 1H | 7.03 | dd | J$_1$=8.4, J$_2$=2.2 | 6 |
| 1H | 7.17 | bd | J=9.2 | 8' |
| 1H | 7.34 | dd | J$_1$=J$_2$=8.4 | 7' |
| 1H | 7.51 | dd | J$_1$=J$_2$=8.2 | 6' |
| 1H | 7.68 | dd | J$_1$=J$_2$=7.9 | 3' |
| 1H | 7.91 | d | J=8.0 | 4' OR 5' |
| 1H | 7.92 | d | J=7.8 | 4' OR 5' |
| 1H | 8.21 | bd | J=6.6 | 2' |
| 1H | 8.65 | bs | n.a. | aliph-NH$_2$+ |
| 1H | 10.58 | bs | n.a. | aliph-NH$_2$+ |

FIG. 123.

VARIAN 75 MHz $^{13}$C-NMR SPECTRAL ASSIGNMENT OF:

17P HYDROCHLORIDE

NMR SPECTRA ARE OF THE HCl SALT IN CDCl$_3$ (60 mg/mL).

| δ(PPM) | MULTIPLICITY | ASSIGNMENT |
|---|---|---|
| 15.7 | CH$_3$ | arom-CH$_3$ |
| 20.5 | CH$_3$ | phenyl-CH$_3$ |
| 21.6 | CH$_3$ | naphthyl-CH$_3$ |
| 51.0 | CH | naphthyl-CH- |
| 55.2 | CH$_3$ | O-CH$_3$ |
| 56.3 | CH | phenyl-CH- |
| 110.2 | CH | 5 |
| 121.5 | CH | 8' OR 6' |
| 124.8 | CH | 2' |
| 125.8 | CH | 3' AND 6' |
| 125.8 | CH | 3' AND 6' |
| 126.3 | CH | 7' |
| 126.5 | CH | 8' OR 6' |
| 126.6 | Q | |
| 127.0 | Q | |
| 128.8 | CH | 4' OR 5' |
| 129.0 | CH | 4' OR 5' |
| 130.1 | Q | |
| 130.9 | CH | 2 |
| 132.6 | Q | |
| 133.6 | Q | |
| 158.1 | Q | |

VARIAN 300 MHz $^1$H-NMR SPECTRAL ASSIGNMENT OF:

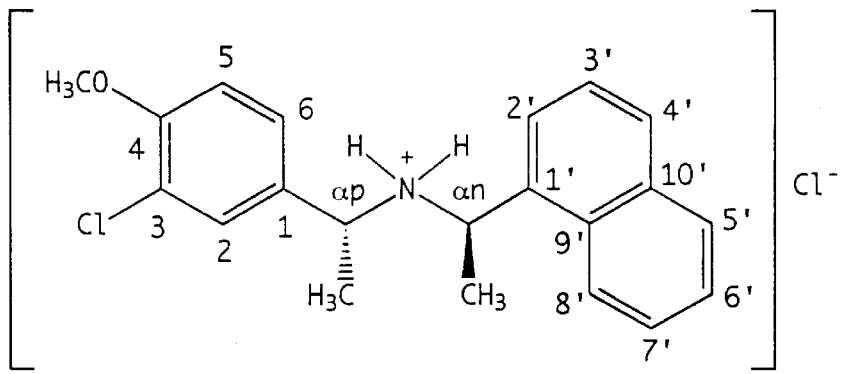

17X HYDROCHLORIDE

NMR SPECTRA ARE OF THE HCl SALT. RESONANCES FROM 0-10 PPM ARE IN 1% MeOD/CDCl$_3$ (5 mg/mL). RESONANCES FROM 10-12 PPM ARE IN CDCl$_3$ (60 mg/mL).

| # OF H's | δ(PPM) | MULTIPLICITY | COUPLING (Hz) | ASSIGNMENT |
|---|---|---|---|---|
| 3H | 1.86 | d | J=7.0 | phenyl-CHC$\underline{H}_3$ |
| 3H | 1.90 | d | J=6.8 | naphthyl-CHC$\underline{H}_3$ |
| 3H | 3.90 | s | n.a. | -OCH$_3$ |
| 1H | 3.91 | q | J=~6.4 | phenyl-C$\underline{H}$CH$_3$ |
| 1H | 4.79 | q | J=6.7 | naphthyl-C$\underline{H}$CH$_3$ |
| 1H | 6.79 | d | J=2.0 | 2 |
| 1H | 6.84 | d | J=8.5 | 5 |
| 1H | 7.19 | bd | J=7.6 | 8' |
| 1H | 7.26 | dd | J$_1$=8.4, J$_2$=1.7 | 6 |
| 1H | 7.38 | dd | J$_1$=J$_2$=7.0 | 7' |
| 1H | 7.52 | dd | J$_1$=J$_2$=8.1 | 6' |
| 1H | 7.69 | dd | J$_1$=J$_2$=8.1 | 3' |
| 1H | 7.92 | d | J=8.2 | 4' OR 5' |
| 1H | 7.94 | d | J=8.1 | 4' OR 5' |
| 1H | 8.30 | bd | J=5.0 | 2' |
| 2H | 10.72 | vbs | n.a. | aliph-NH$_2$+ |

FIG. 126.

VARIAN 75 MHz $^{13}$C-NMR SPECTRAL ASSIGNMENT OF:

17X HYDROCHLORIDE

NMR SPECTRA ARE OF THE HCl SALT IN CDCl$_3$ + 1% MeOD (20 mg/mL).

| δ(PPM) | MULTIPLICITY | ASSIGNMENT |
|---|---|---|
| --- | --- | |
| 20.6 | CH$_3$ | phenyl-CHCH$_3$ |
| 21.7 | CH$_3$ | naphthyl-CHCH$_3$ |
| 51.2 | CH | naphthyl-CHCH$_3$ |
| 55.9 | CH | phenyl-CHCH$_3$ |
| 56.2 | CH$_3$ | O-CH$_3$ |
| 112.4 | CH | 5 |
| 121.2 | CH | 8' |
| 122.5 | Q | |
| 125.1 | CH | 2' |
| 125.9 | CH | 3' |
| 126.2 | CH | 6' |
| 126.8 | CH | 6 OR 7' |
| 127.6 | CH | 6 OR 7' |
| 128.4 | Q | |
| 129.0 | CH | 4' OR 5' |
| 129.3 | CH | 4' OR 5' |
| 130.1 | Q | |
| 130.7 | CH | 2' |
| 132.2 | Q | |
| 133.7 | Q | |
| 155.4 | Q | 3 |

VARIAN 300 MHz ¹H-NMR SPECTRAL ASSIGNMENT OF:

25U HYDROCHLORIDE

NMR SPECTRA ARE OF THE HCl SALT. RESONANCES FROM 0-10 PPM ARE IN 1% MeOD/CDCl₃ (5 mg/mL). RESONANCES FROM 10-12 PPM ARE IN CDCl₃ (60 mg/mL).

| # OF H's | δ(PPM) | MULTIPLICITY | COUPLING (Hz) | ASSIGNMENT |
|---|---|---|---|---|
| 3H | 1.74 | d | J=6.7 | aliph-CH3 |
| 3H | 1.90 | d | J=6.0 | aliph-CH3 |
| 3H | 2.23 | s | n.a. | arom-CH3 |
| 3H | 3.88 | s | n.a. | -OCH3 |
| 1H | 4.25 | bq | J=7.3 | -CH- |
| 1H | 4.90 | bq | J=6.5 | -CH- |
| 1H | 6.87 | d | J=8.4 | |
| 1H | 7.17 | bs | n.a. | |
| 1H? | 7.20-7.27 | m | n.a. | |
| 2H? | 7.35-7.46 | m | n.a. | |
| 1H | 7.50 | dd | J1=J2=8.1 | |
| 1H | 7.59 | dd | J1=J2=7.9 | |
| 1H | 7.87 | d | J=6.7 | |
| 1H | 7.89 | d | J=6.6 | |
| 1H | 8.02 | d | J=7.0 | |
| 1H | 8.97 | bs | n.a. | -NH2+- |
| 1H | 10.83 | bs | n.a. | -NH2+- |

| | | | | |
|---|---|---|---|---|
| 9H | 1.92 | bs | n.a. | phenyl-CH$_3$ |
| | | | | naphthyl-CH$_3$ |
| | | | | arom-CH$_3$ |
| 3H | 3.83 | s | n.a. | -OCH$_3$ |
| 1H | 3.95 | bq | J=6.0 | phenyl-CH- |
| 1H | 4.79 | bq | J=5.5 | naphthyl-CH- |
| 1H | 6.57 | bs | n.a. | 2 |
| 1H | 6.71 | d | J=8.2 | 5 |
| 2H | 7.10-7.17 | m | n.a. | |
| 1H | 7.30-7.35 | m | n.a. | |
| 1H | 7.50 | dd | J$_1$=J$_2$=7.7 | 6' |
| 1H | 7.70 | dd | J$_1$=J$_2$=7.3 | 3' |
| 1H | 7.91 | d | J=7.8 | 4'  5' |
| 1H | 7.92 | d | J=8.0 | 4'  5' |
| 1H | 8.39 | bd | J=2.8? | 2' |
| 1H | 8.63 | bs | n.a. | aliph-NH$_2$+ |
| 1H | 10.59 | bs | n.a. | aliph-NH$_2$+ |

VARIAN 75 MHz $^{13}$C-NMR SPECTRAL ASSIGNMENT OF:

25V HYDROCHLORIDE

NMR SPECTRA ARE OF THE HCl SALT IN CDCl$_3$ + 1% MeOD (20 mg/mL).

| δ(PPM) | MULTIPLICITY | ASSIGNMENT |
|---|---|---|
| 15.8 | CH3 | arom-CH3 |
| 20.97 | CH3 | aliph-CH3 |
| 22.0 | CH3 | aliph-CH3 |
| 51.2 | CH | -CH- |
| 55.4 | CH3 | -OCH3 |
| 56.6 | CH | -CH- |
| 110.3 | ? | |
| 121.8 | CH | |
| 125.5 | CH | |
| 125.8 | CH | |
| 126.2 | CH | |
| 126.3 | CH | |
| 126.9 | CH | |
| 127.0 | Q | |
| 127.2 | CH | |
| 128.8 | Q | |
| 128.9 | ? | |
| 130.3 | Q | |
| 131.2 | CH | |
| 133.0 | Q | |
| 133.7 | Q | |
| 158.1 | Q | |

VARIAN 300 MHz ¹H-NMR SPECTRAL ASSIGNMENT OF:

25W HYDROCHLORIDE

NMR SPECTRA ARE OF THE HCl SALT. RESONANCES FROM 0-10 PPM ARE IN 1% MeOD/CDCl₃ (5 mg/mL). RESONANCES FROM 10-12 PPM ARE IN CDCl₃ (60 mg/mL).

| # OF H's | δ(PPM) | MULTIPLICITY | COUPLING (Hz) | ASSIGNMENT |
|---|---|---|---|---|
| 3H | 1.74 | d | J=6.1 | aliph-CH3 |
| 3H | 1.89 | d | J=6.0 | aliph-CH3 |
| 3H | 2.24 | s | n.a. | arom-CH3 |
| 3H | 3.89 | s | n.a. | -OCH3 |
| 1H | 4.27 | bq | J=6.2 | -CH- |
| 1H | 4.92 | bq | J=5.1 | -CH- |
| 1H | 6.89 | d | J=7.7 | |
| 1H | 7.18 | bs | n.a. | |
| 1H | 7.26 | bd | J=7.9 | |
| 2H? | 7.36-7.47 | m | n.a. | |
| 1H | 7.51 | dd | J1=J2=7.6 | |
| 1H | 7.61 | dd | J1=J2=7.5 | |
| 1H | 7.88 | d | J=8.0 | |
| 1H | 7.90 | d | J=7.5 | |
| 1H | 7.99 | d | J=6.9 | |
| 1H | 9.10 | bs | n.a. | -NH2+- |
| 1H | 10.67 | bs | n.a. | -NH2+- |

CALCIUM RECEPTOR-ACTIVE COMPOUNDS

FIELD OF THE INVENTION

This invention relates to the design, development, composition and use of compounds able to modulate one or more inorganic ion receptor activities.

BACKGROUND OF THE INVENTION

Certain cells in the body respond not only to chemical signals, but also to ions such as extracellular calcium ions ($Ca^{2+}$). Changes in the concentration of extracellular $Ca^{2+}$ (referred to herein as "[$Ca^{2+}$]") alter the functional responses of these cells. One such specialized cell is the parathyroid cell which secretes parathyroid hormone (PTH). PTH is the principal endocrine factor regulating $Ca^{2+}$ homeostasis in the blood and extracellular fluids.

PTH, by acting on bone and kidney cells, increases the level of $Ca^{2+}$ in the blood. This increase in [$Ca^{2+}$] then acts as a negative feedback signal, depressing PTH secretion. The reciprocal relationship between [$Ca^{2+}$] and PTH secretion forms the essential mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in [$Ca^{2+}$] has been confirmed. Brown et al., 366 *Nature* 574, 1993. In parathyroid cells, this protein acts as a receptor for extracellular $Ca^{2+}$ ("the calcium receptor"), and detects changes in [$Ca^{2+}$] and to initiate a functional cellular response, PTH secretion.

Extracellular $Ca^{2+}$ can exert effects on different cell functions, reviewed in Nemeth et al., 11 *Cell Calcium* 319, 1990. The role of extracellular $Ca^{2+}$ in parafollicular (C-cells) and parathyroid cells is discussed in Nemeth, 11 *Cell Calcium* 323, 1990. These cells have been shown to express similar $Ca^{2+}$ receptor. Brown et al., 366 *Nature* 574, 1993; Mithal et al., 9 Suppl. 1 *J. Bone and Mineral Res.* s282, 1994; Rogers et al., 9 Suppl. 1 *J. Bone and Mineral Res.* s409, 1994; Garrett et al., 9 Suppl. 1 *J. Bone and Mineral Res.* s409, 1994. The role of extracellular $Ca^{2+}$ on bone osteoclasts is discussed by Zaidi, 10 *Bioscience Reports* 493, 1990. In addition keratinocytes, juxtaglomerular cells, trophoblasts, pancreatic beta cells and fat/adipose cells all respond to increases in extracellular calcium which likely reflects activation of calcium receptors of these cells.

The ability of various compounds to mimic extra-cellular $Ca^{2+}$ in vitro is discussed by Nemeth et al., (spermine and spermidine) in "Calcium-Binding Proteins in Health and Disease," 1987, Academic Press, Inc., pp. 33–35; Brown et al., (e.g., neomycin) 128 *Endocrinolocy* 3047, 1991; Chen et al., (diltiazem and its analog, TA-3090) 5 *J. Bone and Mineral Res.* 581, 1990; and Zaidi et al., (verapamil) 167 *Biochem. Biophys. Res. Commun.* 807, 1990. Nemeth et al., PCT/US93/01642, International Publication Number WO 94/18959, and Nemeth et al., PCT/US92/07175, International Publication Number WO 93/04373, describe various compounds which can modulate the effect of an inorganic ion on a cell having an inorganic ion receptor.

The references provided in the background are not admitted to be prior art.

SUMMARY OF THE INVENTION

The present invention features compounds able to modulate one or more activities of an inorganic ion receptor and methods for treating diseases or disorders by modulating inorganic ion receptor activity. Preferred compounds can mimic or block the effect of extracellular calcium on a cell surface calcium receptor.

Diseases or disorders which can be treated by modulating inorganic ion receptor activity include one or more of the following types: (1) those characterized by abnormal inorganic ion homeostasis, preferably calcium homeostasis; (2) those characterized by an abnormal amount of an extracellular or intracellular messenger whose production can be affected by inorganic ion receptor activity, preferably calcium receptor activity; (3) those characterized by an abnormal effect (e.g., a different effect in kind or magnitude) of an intracellular or extracellular messenger which can itself be ameliorated by inorganic ion receptor activity, preferably calcium receptor activity; and (4) other diseases or disorders in which modulation of inorganic ion receptor activity, preferably calcium receptor activity will exert a beneficial effect, for example, in diseases or disorders where the production of an intracellular or extracellular messenger stimulated by receptor activity compensates for an abnormal amount of a different messenger. Examples of extracellular messengers whose secretion and/or effect can be affected by modulating inorganic ion receptor activity include inorganic ions, hormones, neurotransmitters, growth factors, and chemokines. Examples of intracellular messengers include cAMP, cGMP, IP3, and diacylglycerol.

Thus, a compound of this invention preferably modulates calcium receptor activity and is used in the treatment of diseases or disorders which can be affected by modulating one or more activities of a calcium receptor. Calcium receptor proteins enable certain specialized cells to respond to changes in extracellular $Ca^{2+}$ concentration. For example, extracellular $Ca^{2+}$ inhibits the secretion of parathyroid hormone from parathyroid cells, inhibits bone resorption by osteoclasts, and stimulates secretion of calcitonin from C-cells.

In a preferred embodiment, the compound is used to treat a disease or disorder characterized by abnormal bone and mineral homeostasis, more preferably calcium homeostasis. Extracellular $Ca^{2+}$ is under tight homeostatic control and controls various processes such as blood clotting, nerve and muscle excitability, and proper bone formation. Abnormal calcium homeostasis is characterized by one or more of the following activities: (1) an abnormal increase or decrease in serum calcium; (2) an abnormal increase or decrease in urinary excretion of calcium; (3) an abnormal increase or decrease in bone calcium levels, for example, as assessed by bone mineral density measurements; (4) an abnormal absorption of dietary calcium; (5) an abnormal increase or decrease in the production and/or release of messengers which affect serum calcium levels such as parathyroid hormone and calcitonin; and (6) an abnormal change in the response elicited by messengers which affect serum calcium levels. The abnormal increase or decrease in these different aspects of calcium homeostasis is relative to that occurring in the general population and is generally associated with a disease or disorder.

Diseases and disorders characterized by abnormal calcium homeostasis can be due to different cellular defects such as a defective calcium receptor activity, a defective number of calcium receptors, or a defective intracellular protein acted on by a calcium receptor. For example, in parathyroid cells, the calcium receptor is coupled to the $G_i$ protein which in turn inhibits cyclic AMP production. Defects in $G_i$ protein can affect its ability to inhibit cyclic AMP production.

Thus, a first aspect the invention features an inorganic ion receptor modulating compound having the formula:

STRUCTURE I

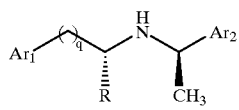

where $Ar_1$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, acetoxy, $N(CH_3)_2$, phenyl, phenoxy, benzyl, benzyloxy, α,α-dimethylbenzyl, $NO_2$, CHO, $CH_3CH(OH)$, acetyl, ethylene dioxy;

$Ar_2$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, and acetoxy;

q is 0, 1, 2, or 3; and

R is either H, or lower alkyl;

and pharmaceutically salts and complexes thereof.

Compounds of this invention have preferred stereochemistry. The $CH_3$ shown in Structure I is at a chiral center and provides an a-(R)-methyl structure. When R is $CH_3$, the R shown in Structure I is also at chiral center which provides an (R)-methyl structure. Thus, when R is $CH_3$, the Structure I compound has (R,R) stereochemistry.

Inorganic ion receptor activities are those processes brought about as a result of inorganic ion receptor activation. Such processes include the production of molecules which can act as intracellular or extracellular messengers.

Inorganic ion receptor-modulating compound include ionomimetics, ionolytics, calcimimetics, and calcilytics. Ionomimetics are compounds which bind to an inorganic ion receptor and mimic (i.e., evoke or potentiate) the effects of an inorganic ion at an inorganic ion receptor. Preferably, the compound affects one or more calcium receptor activities. Calcimimetics are ionomimetics which effects one or more calcium receptor activities and bind to a calcium receptor.

Ionolytics are compounds which bind to an inorganic ion receptor and block (i.e., inhibit or diminish) one or more activities caused by an inorganic ion at an inorganic ion receptor. Preferably, the compound affects one or more calcium receptor activities. Calcilytics are ionolytics which block one or more calcium receptor activities evoked by extracellular calcium and bind to a calcium receptor.

Ionomimetics and ionolytics may bind at the same receptor site as the native inorganic ion ligand binds or can bind at a different site (e.g., allosteric site). For example, NPS R-467 binding to a calcium receptor results in calcium receptor activity and, thus, NPS R-467 is classified as a calcimimetic. However, NPS R-467 binds to the calcium receptor at a different site (i.e., an allosteric site) than extracellular calcium.

A measure of a compounds effectiveness can be determined by calculating the $EC_{50}$ or $IC_{50}$ for that compound. The $EC_{50}$, is the concentration of a compound which causes a half maximal mimicking effect. The $IC_{50}$ is the concentration of compound which causes a half-maximal blocking effect. $EC_{50}$ and $IC_{50}$ for compounds at a calcium receptor can be determined by assaying one or more of the activities of extracellular calcium at a calcium receptor. Examples of assays for measuring $EC_{50}$, and $IC_{50}$ are described Nemeth et al., PCT/US93/01642, International Publication Number WO 94/18959, and Nemeth et al., PCT/US92/07175, International Publication Number WO 93/04373, (both of these publications are hereby incorporated by reference here) and below. Such assays include oocyte expression assays and measuring increases in intracellular calcium ion concentration ($[Ca^{2+}]_i$) due to calcium receptor activity. Preferably, such assays measure the release or inhibition of a particular hormone associated with activity of a calcium receptor.

An inorganic ion receptor-modulating compound preferably selectively targets inorganic ion receptor activity in a particular cell. For example, selective targeting of a calcium receptor activity is achieved by a compound exerting a greater effect on a calcium receptor activity in one cell type than at another cell type for a given concentration of compound. Preferably, the differential effect is 10-fold or greater as measured in vivo or in vitro. More preferably, the differential effect is measured in vivo and the compound concentration is measured as the plasma concentration or extracellular fluid concentration and the measured effect is the production of extracellular messengers such as plasma calcitonin, parathyroid hormone, or plasma calcium. For example, in a preferred embodiment, the compound selectively targets PTH secretion over calcitonin secretion.

Preferably, the compound is either a calcimimetic or calcilytic having an $EC_{50}$ or $IC_{50}$ at a calcium receptor of less than or equal to 5 μM, and even more preferably less than or equal to 1 μM, 100 nmolar, 10 nmolar, or 1 nmolar using one of the assays described below. More preferably, the assay measures intracellular $Ca^{2+}$ in HEK 293 cells transformed with nucleic acid expressing the human parathyroid calcium receptor and loaded with fura-2. Lower $EC_{50}$'s or $IC_{50}$'s are advantageous since they allow lower concentrations of compounds to be used in vivo or in vitro. The discovery of compounds with low $EC_{50}$'s and $IC_{50}$'s enables the design and synthesis of additional compounds having similar or improved potency, effectiveness, and/or selectivity.

Another aspect of the present invention features an inorganic ion receptor modulating compound having the formula:

STRUCTURE II

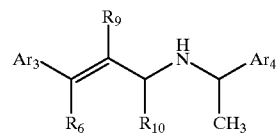

where $Ar_3$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, acetoxy, benzyl, benzyloxy, α,α-dimethylbenzyl, $NO_2$, CHO, $CH_3CH(OH)$, $N(CH_3)_2$, acetyl, ethylene dioxy.

$Ar_4$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, and acetoxy;

$R_8$ is either hydrogen or phenyl;

$R_9$ is either hydrogen or methyl; and $R_{10}$ is either hydrogen, methyl, or phenyl; or pharmaceutically acceptable salts and complexes thereof.

Another aspect of the present invention features an inorganic ion receptor modulating compound having the formula:

STRUCTURE III

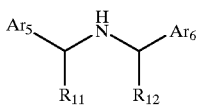

where $Ar_5$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, acetoxy, benzyl, benzyloxy, α,α-dimethylbenzyl, $NO_2$, CHO, $CH_3CH(OH)$, acetyl, ethylene dioxy, —CH=CH-phenyl;

$Ar_6$ is either naphthyl or phenyl optionally substituted with 0 to 5 substituents each independently selected from the group consisting of, acetyl, lower alkyl, halogen, lower alkoxy, lower thioalkyl, methylene dioxy, lower haloalkyl, lower haloalkoxy, OH, $CH_2OH$, $CONH_2$, CN, carbomethoxy, $OCH_2C(O)C_2H_5$ and acetoxy;

$R_{11}$ is hydrogen or methyl; and $R_{12}$ is hydrogen or methyl.

Another aspect of the present invention features a pharmaceutical composition made up of an inorganic ion receptor-modulating compound described herein and a physiologically acceptable carrier. A "pharmacological composition" refers to a composition in a form suitable for administration into a mammal, preferably a human. Preferably, the pharmaceutical composition contains a sufficient amount of a calcium receptor modulating compound in a proper pharmaceutical form to exert a therapeutic effect on a human.

Considerations concerning forms suitable for administration are known in the art and include toxic effects, solubility, route of administration, and maintaining activity. For example, pharmacological compositions injected into the blood stream should be soluble.

Pharmaceutical compositions can also be formulated as pharmaceutically acceptable salts (e.g., acid addition salts) and complexes thereof. The preparation of such salts can facilitate the pharmacological use of a compound by altering its physical characteristics without preventing it from exerting a physiological effect.

Another aspect the present invention features a method for treating a patient by modulating inorganic ion receptor activity using inorganic ion receptor modulating compounds described herein. The method involves administering to the patient a pharmaceutical composition containing a therapeutically effective amount of an inorganic ion receptor-modulating compound. In a preferred embodiment, the disease or disorder is treated by modulating calcium receptor activity by administering to the patient a therapeutically effective amount of a calcium receptor-modulating compound.

Inorganic ion receptor-modulating compounds, and compositions containing the compounds, can be used to treat patients. A "patient" refers to a mammal in which modulation of an inorganic ion receptor will have a beneficial effect. Patients in need of treatment involving modulation of inorganic ion receptors can be identified using standard techniques known to those in the medical profession.

Preferably, a patient is a human having a disease or disorder characterized by one more of the following: (1) abnormal inorganic ion homeostasis, more preferably abnormal calcium homeostasis; (2) an abnormal level of a messenger whose production or secretion is affected by inorganic ion receptor activity, more preferably affected by calcium receptor activity; and (3) an abnormal level or activity of a messenger whose function is affected by inorganic ion receptor activity, more preferably affected by calcium receptor activity.

Diseases characterized by abnormal calcium homeostasis include hyperparathyroidism, osteoporosis and other bone and mineral-related disorders, and the like (as described, e.g., in standard medical text books, such as "Harrison's Principles of Internal Medicine"). Such diseases are treated using calcium receptor-modulating compounds which mimic or block one or more of the effects of extracellular $Ca^{2+}$ on a calcium receptor and, thereby, directly or indirectly affect the levels of proteins or other compounds in the body of the patient.

By "therapeutically effective amount" is meant an amount of a compound which relieves to some extent one or more symptoms of the disease or disorder in the patient; or returns to normal either partially or completely one or more physiological or biochemical parameters associated with or causative of the disease or disorder.

In a preferred embodiment, the patient has a disease or disorder characterized by an abnormal level of one or more calcium receptor-regulated components and the compound is active on a calcium receptor of a cell selected from the group consisting of: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, platelet, vascular smooth muscle cell, cardiac atrial cell, gastrin-secreting cell, glucagon-secreting cell, kidney mesangial cell, mammary cell, beta cell, fat/adipose cell, immune cell, GI tract cell, skin cell, adrenal cell, pituitary cell, hypothalamic cell and cell of the subfornical organ.

More preferably, the cells are chosen from the group consisting of: parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell and cell of the subfornical organ.

In a preferred embodiment, the compound is a calcimimetic acting on a parathyroid cell calcium receptor and reduces the level of parathyroid hormone in the serum of the patient. More preferably, the level is reduced to a degree sufficient to cause a decrease in plasma $Ca^{2+}$. Most preferably, the parathyroid hormone level is reduced to that present in a normal individual.

In another preferred embodiment, the compound is a calcilytic acting on a parathyroid cell calcium receptor and increases the level of parathyroid hormone in the serum of the patient. More preferably, the level is increased to a degree sufficient to cause an increase in bone mineral density of a patient.

Patients in need of such treatments can be identified by standard medical techniques, such as blood or urine analysis. For example, by detecting a deficiency of protein whose production or secretion is affected by changes in inorganic ion concentrations, or by detecting abnormal levels of inorganic ions or hormones which effect inorganic ion homeostasis.

Various examples are used throughout the application. These examples are not intended in any way to limit the invention.

Other features and advantages of the invention will be apparent from the following figures, detailed description of the invention, examples, and the claims.

DESCRIPTION OF THE PREFERRED EMBODIMENTS

Figure 1A:
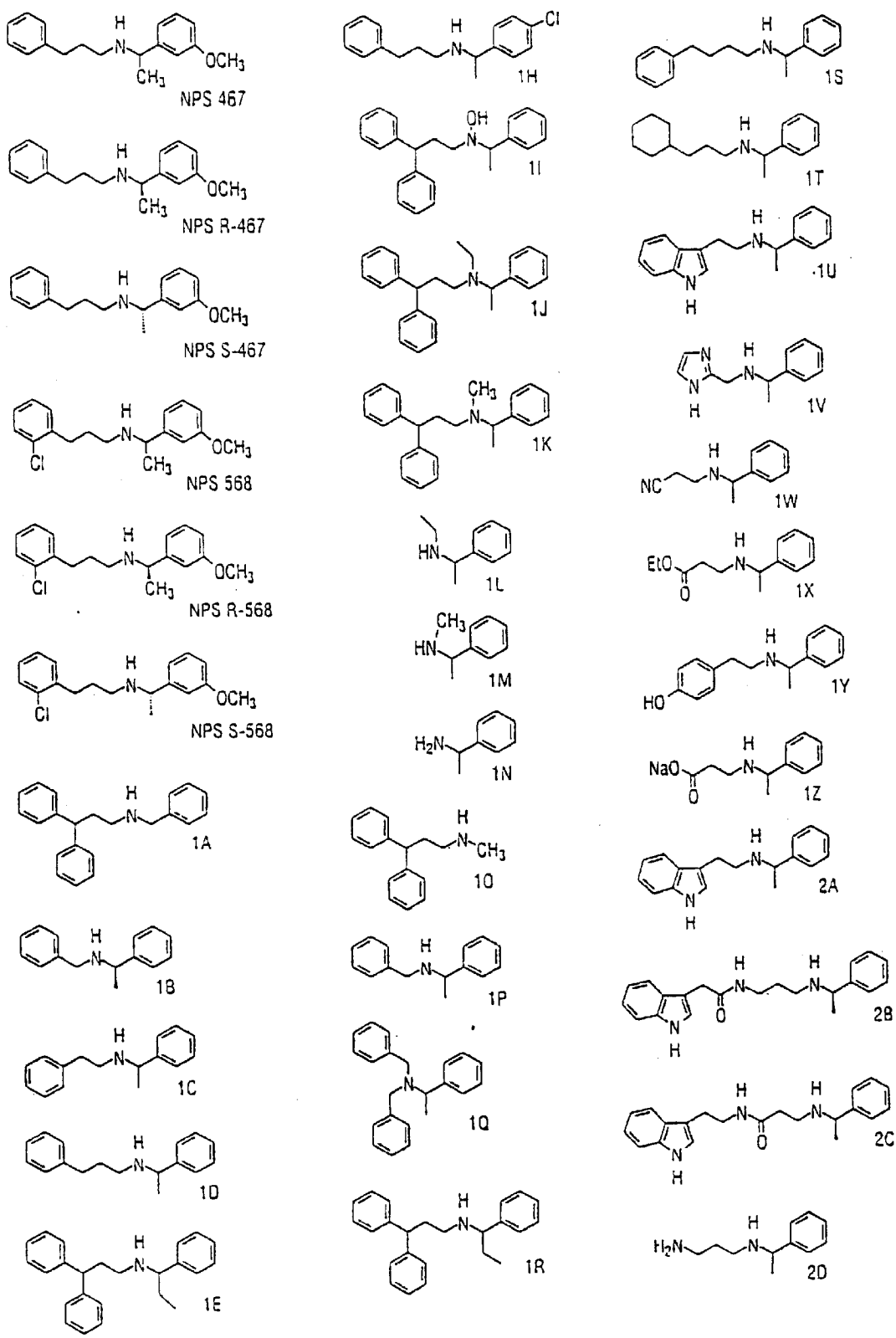
FIGS. 1a–1r, show the chemical structures of different compounds.

The present invention features compounds able to modulate one or more inorganic ion receptor activities, preferably the compound can mimic or block an effect of an extracellular ion on a cell having an inorganic ion receptor, more preferably the extracellular ion is $Ca^{2+}$ and the effect is on a cell having a calcium receptor. Publications concerned with the calcium activity, calcium receptor and/or calcium receptor modulating compounds include the following: Brown et al., *Nature* 366: 574, 1993; Nemeth et al., PCT/US93/01642, International Publication Number WO 94/18959; Nemeth et al., PCT/US92/07175, International Publication Number WO 93/04373; Shoback and Chen, *J. Bone Mineral Res.* 9: 293 (1994); and Racke et al., *FEBS Lett.* 333: 132, (1993). These publications are not admitted to be prior art to the claimed invention.

I. CALCIUM RECEPTORS

Calcium receptors are present on different cell types and can have different activities in different cell types. The pharmacological effects of the following cells, in response to calcium, is consistent with the presence of a calcium receptor: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, platelet, vascular smooth muscle cell, cardiac atrial cell, gastrin-secreting cell, glucagon-secreting cell, kidney mesangial cell, mammary cell, beta cell, fat/adipose cell, immune cell, GI tract cell, skin cell, adrenal cell, pituitary cell, hypothalamic cell and cell of the subfornical organ. In addition, the presence of calcium receptors on parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell and cell of the subfornical organ, has been confirmed by physical data.

The calcium receptor on these different cell types may be different. It is also possible that a cell can have more than one type of calcium receptor. Comparison of calcium receptor activities and amino acid sequences from different cells indicate that distinct calcium receptor types exist. For example, calcium receptors can respond to a variety of di- and trivalent cations. The parathyroid calcium receptor responds to calcium and $Gd^{3+}$, while osteoclasts respond to divalent cations such as calcium, but do not respond to $Gd^{3+}$. Thus, the parathyroid calcium receptor is pharmacologically distinct from the calcium receptor on the osteoclast.

On the other hand, the nucleic acid sequences encoding calcium receptors present in parathyroid cells and C-cells indicate that these receptors have a very similar amino acid structure. Nevertheless, calcimimetic compounds exhibit differential pharmacology and regulate different activities at parathyroid cells and C-cells. Thus, pharmacological properties of calcium receptors may vary significantly depending upon the cell type or organ in which they are expressed even though the calcium receptors may have similar or even identical structures.

Calcium receptors, in general, have a low affinity for extracellular $Ca^{2+}$ (apparent $K_d$ generally greater than about 0.5 mM). Calcium receptors may include a free or bound effector mechanism as defined by Cooper, Bloom and Roth, "The Biochemical Basis of Neuropharmacology", Ch. 4, and are thus distinct from intracellular calcium receptors, e.g., calmodulin and the troponins.

Calcium receptors respond to changes in extracellular calcium levels. The exact changes depend on the particular receptor and cell line containing the receptor. For example, the in vitro effect of calcium on the calcium receptor in a parathyroid cell includes the following:

1. An increase in internal calcium. The increase is due to the influx of external calcium and/or to mobilization of internal calcium. Characteristics of the increase in internal calcium include the following:

(a) A rapid (time to peak <5 seconds) and transient increase in $[Ca^{2+}]_i$ that is refractory to inhibition by 1 $\mu$M $La^{3+}$ or 1 $\mu$M $Gd^{3+}$ and is abolished by pretreatment with ionomycin (in the absence of extracellular $Ca^{2+}$);

(b) The increase is not inhibited by dihydropyridines;

(c) The transient increase is abolished by pretreatment for 10 minutes with 10 mM sodium fluoride;

(d) The transient increase is diminished by pretreatment with an activator of protein kinase C (PKC), such as phorbol myristate acetate (PMA), mezerein or (−)-indolactam V. The overall effect of the protein kinase C activator is to shift the concentration-response curve of calcium to the right without affecting the maximal response; and (e) Pretreatment with pertussis toxin (100 ng/ml for >4 hours) does not affect the increase.

2. A rapid (<30 seconds) increase in the formation of inositol-1,4,5-triphosphate or diacylglycerol. Pretreatment with pertussis toxin (100 ng/ml for >4 hours) does not affect this increase;

3. The inhibition of dopamine- and isoproterenol-stimulated cyclic AMP formation. This effect is blocked by pretreatment with pertussis toxin (100 ng/ml for >4 hours); and 4. The inhibition of PTH secretion. Pretreatment with pertussis toxin (100 ng/ml for >4 hours) does not affect the inhibition in PTH secretion.

Using techniques known in the art, the effect of calcium on other calcium receptors in different cells can be readily determined. Such effects may be similar in regard to the increase in internal calcium observed in parathyroid cells. However, the effect is expected to differ in other aspects, such as causing or inhibiting the release of a hormone other than parathyroid hormone.

II. INORGANIC ION RECEPTOR MODULATING COMPOUNDS

Inorganic ion receptor modulating compounds modulate one or more inorganic ion receptor activities. Preferred calcium receptor modulating compounds are calcimimetics and calcilytics. Inorganic ion receptor modulating compounds can be identified by screening compounds which are modelled after a compound shown to have a particular activity (i.e., a lead compound).

A preferred method of measuring calcium receptor activity is to measure changes in $[Ca^{2+}]_i$. Changes in $[Ca^{2+}]_i$ can be measured using different techniques such by using HEK 293 cells transduced with nucleic acid expressing the human parathyroid calcium receptor and loaded with fura-2; and by measuring an increase in $Cl^-$ current in a Xenopus oocyte injected with nucleic acid coding for a calcium receptor. (See Nemeth et al., PCT/US93/01642, International Publication Number WO 94/18959.) For example, poly(A)$^+$ mRNA can be obtained from cells expressing a calcium receptor, such as a parathyroid cell, bone osteoclast, juxtaglomerular kidney cell, proximal tubule kidney cell, distal tubule kidney cell, cell of the thick ascending limb of Henle's loop and/or collecting duct, keratinocyte in the epidermis, parafollicular cell in the thyroid (C-cell), intestinal cell, central nervous cell, peripheral nervous system cell, platelet, vascular smooth muscle cell, cardiac atrial cell, gastrin-secreting cell, glucagon-secreting cell, kidney mesangial cell, mammary cell, beta cell, fat/adipose cell, immune cell, and GI tract cell. Preferably, the nucleic acid is from a parathyroid cell, C-cell, or osteoclast. More preferably, the nucleic acid encodes a calcium receptor and is present on a plasmid or vector.

In preferred embodiments the calcium receptor modulating compound is a calcimimetic which inhibits bone resorption in vivo by an osteoclast; inhibits bone resorption in vitro by an osteoclast; stimulates calcitonin secretion in vitro or in vivo from a c-cell; inhibits parathyroid hormone secretion from a parathyroid cell in vitro and decreases PTH secretion in vivo; elevates calcitonin levels in vivo; or blocks osteoclastic bone resorption in vitro and inhibits bone resorption in vivo.

In another preferred embodiment the calcium receptor modulating compound is a calcilytic which evokes the secretion of parathyroid hormone from parathyroid cells in vitro and elevates the level of parathyroid hormone in vivo.

Preferably, the compound selectively targets inorganic ion receptor activity, more preferably calcium receptor activity, in a particular cell. By "selectively" is meant that the compound exerts a greater effect on inorganic ion receptor activity in one cell type than at another cell type for a given concentration of compound. Preferably, the differential effect is 10-fold or greater. Preferably, the concentration refers to blood plasma concentration and the measured effect is the production of extracellular messengers such as plasma calcitonin, parathyroid hormone or plasma calcium. For example, in a preferred embodiment, the compound selectively targets PTH secretion over calcitonin secretion.

In another preferred embodiment, the compound has an $EC_{50}$ or $IC_{50}$ less than or equal to 5 µM at one or more, but not all cells chosen from the group consisting of: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, platelet, vascular smooth muscle cell, cardiac atrial cell, gastrin-secreting cell, glucagon-secreting cell, kidney mesangial cell, mammary cell, beta cell, fat/adipose cell, immune cell, GI tract cell, skin cell, adrenal cell, pituitary cell, hypothalamic cell and cell of the subfornical organ. More preferably, the cells are chosen from the group consisting of parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell and cell of the subfornical organ. The presence of a calcium receptor in this group of cells has been confirmed by physical data such as in situ hybridization and antibody staining.

Preferably, inorganic ion receptor modulating compounds mimic or block the effects of an extracellular ion on a cell having an inorganic ion receptor, such that the compounds achieve a therapeutic effect. Inorganic ion receptor modulating compounds may have the same, or different, effects on cells having different types of inorganic ion receptor morphology (e.g., such as cells having normal inorganic ion receptors, a normal number of inorganic ion receptor, an abnormal inorganic ion receptor, and an abnormal number of inorganic ion receptors).

Calcium receptor modulating compounds preferably mimic or block all of the effects of extracellular ion in a cell having a calcium receptor. However, calcimimetics need not possess all the biological activities of extracellular $Ca^{2+}$. Similarly, calcilytics need not block all of the activities caused by extracellular calcium. Additionally, different calcimimetics and different calcilytics do not need to bind to the same site on the calcium receptor as does extracellular $Ca^{2+}$ to exert their effects.

Inorganic modulating compounds need not effect inorganic receptor activity to the same extent or in exactly the same manner as the natural ligand. For example, a calcimimetic may effect calcium receptor activity to a different extent, to a different duration, by binding to a different binding site, or by having a different affinity, compared to calcium acting at a calcium receptor.

A. Calcimimetics

1. Structure I Compounds

Structure I compounds able to modulate calcium receptor activity have the following formula:

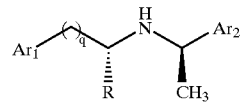

where, $Ar_1$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, acetoxy, $N(CH_3)_2$, phenyl, phenoxy, benzyl, benzyloxy, α,α-dimethylbenzyl, $NO_2$, CHO, $CH_3CH(OH)$, acetyl, ethylene dioxy, preferably each substituent is independently selected from the group consisting of, $CH_3$, $CH_3O$, $CH_3CH_2O$, methylene dioxy, Br, Cl, F, I, $CF_3$, $CHF_2$, $CH_2F$, $CF_3O$, $CF_3CH_2O$, $CH_3S$, OH, $CH_2OH$, $CONH_2$, CN, $NO_2$, $CH_3CH_2$, propyl, isopropyl, butyl, isobutyl, t-butyl, and acetoxy. More preferably, $Ar_1$ is either a naphthyl or a phenyl having 1–5 substituents each independently selected from the group consisting of isopropyl, $CH_3O$, $CH_3S$, $CF_3O$, I, Cl, F, $CF_3$, and $CH_3$, more preferably $CF_3O$, I, Cl, F, and $CF_3$;

$Ar_2$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, and acetoxy, preferably each substituent is independently selected from the group consisting of, $CH_3$, $CH_3O$, $CH_3CH_2O$, methylene dioxy, Br, Cl, F, I, $CF_3$, $CHF_2$, $CH_2F$, $CF_3O$, $CF_3CH_2O$, $CH_3S$, OH, $CH_2OH$, $CONH_2$, CN, $NO_2$, $CH_3CH_2$, propyl, isopropyl, butyl, isobutyl, t-butyl, and acetoxy. More preferably, $Ar_2$ is either a naphthyl or a phenyl having 1–5 substituents each independently selected from the group consisting of isopropyl, $CH_3O$, $CH_3S$, $CF_3O$, I, Cl, F, $CF_3$, and $CH_3$, more preferably $CF_3O$, I, Cl, F, $CH_3O$, and $CF_3$.

q is 0, 1, 2, or 3; and

R is either H, or $CH_3$;

and pharmaceutically salts and complexes thereof.

"Lower alkyl" refers to a saturated hydrocarbon having 1–4 carbons, preferably 1–3 carbon atoms, which may be straight chain or branched.

"Lower alkoxy" refers to "O-lower alkyl". Where "O" is an oxygen joined to a lower alkyl.

"Lower thioalkyl" refers to "S-lower alkyl". Where "S" is a sulfur joined to a lower alkyl.

"Lower haloalkyl" refers to a lower alkyl substituted with at least one halogen. Preferably, only the terminal carbon of the lower haloalkyl is substituted with a halogen and 1 to 3 halogens are present. More preferably, the lower haloalkyl contains 1 carbon. Preferably, the halogen substitutions are either Cl or F.

"Lower haloalkoxy" refers to "O-lower haloalkyl". Where "O" is an oxygen joined to a lower haloalkyl.

a. $Ar_1$ and $Ar_2$ are Both Optionally Substituted Phenyls

In a preferred embodiment both $Ar_1$ and $Ar_2$ are optionally substituted phenyls and the compound has following formula:

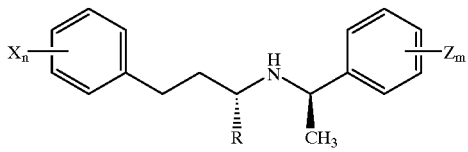

where R is hydrogen or methyl m and n are each independently 0, 1, 2, 3, 4, or 5;

each X is independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, acetoxy, $N(CH_3)_2$, phenyl, phenoxy, benzyl, benzyloxy, α,α-dimethylbenzyl, $NO_2$, CHO, $CH_3CH$ (OH), acetyl, ethylene dioxy. Preferably each X is independently selected from the group consisting of, $CH_3$, $CH_3O$, $CH_3CH_2O$, methylene dioxy, Br, Cl, F, I, $CF_3$, $CHF_2$, $CH_2F$, $CF_3O$, $CF_3CH_2O$, $CH_3S$, OH, $CH_2OH$, $CONH_2$, CN, $NO_2$, $CH_3CH_2$, propyl, isopropyl, butyl, isobutyl, t-butyl, and acetoxy. More preferably, each X is independently selected from the group consisting of isopropyl, $CH_3O$, $CH_3S$, $CF_3O$, I, Cl, F, $CF_3$, and $CH_3$, more preferably $CF_3O$, I, Cl, F, and $CF_3$;

each Z is independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, and acetoxy. Preferably each Z is independently selected from the group consisting of, $CH_3$, $CH_3O$, $CH_3CH_2O$, methylene dioxy, Br, Cl, F, I, $CF_3$, $CHF_2$, $CH_2F$, $CF_3O$, $CF_3CH_2O$, $CH_3S$, OH, $CH_2OH$, $CONH_2$, CN, $CH_3CH_2$, propyl, isopropyl, butyl, isobutyl, t-butyl, and acetoxy. More preferably, each Z is independently selected from the group consisting of, isopropyl, $CH_3O$, $CH_3S$, $CF_3O$, $CF_3$, I, Cl, F, and $CH_3$.

In a more preferred embodiment, at least one of the Z substituents is in the meta position. More preferably, the compound has the follow formula:

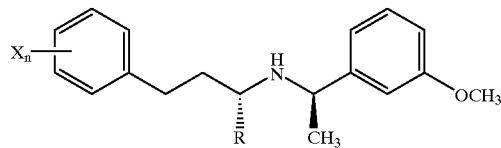

where R is either hydrogen or methyl;

m is 0, 1, 2, 3, 4, or 5, preferably 1 or 2;

and each X is independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, acetoxy, $N(CH_3)_2$, phenyl, phenoxy, benzyl, benzyloxy, α,α-dimethylbenzyl, $NO_2$, CHO, $CH_3CH(OH)$, acetyl, ethylene dioxy, preferably each substituent is independently selected from the group consisting of, $CH_3$, $CH_3O$, $CH_3CH_2O$, methylene dioxy, Br, Cl, F, I, $CF_3$, $CHF_2$, $CH_2F$, $CF_3O$, $CF_3CH_2O$, $CH_3S$, OH, $CH_2OH$, $CONH_2$, CN, $NO_2$, $CH_3CH_2$, propyl, isopropyl, butyl, isobutyl, t-butyl, and acetoxy, more preferably, isopropyl, $CH_3O$, $CH_3S$, $CF_3O$, $CF_3$, I, Cl, F, and $CH_3$.

More preferably, the compound has the formula:

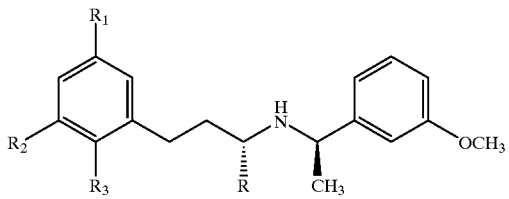

where R is either hydrogen or methyl;

$R_1$ is either halogen or hydrogen, preferably $R_1$ is either F, or hydrogen;

$R_2$ is either hydrogen, halogen, lower alkyl, lower haloalkyl, or lower haloalkoxy, preferably, $R_2$ is either hydrogen, $CF_3$, $CH_3$, $OCF_3$, or F, and $R_3$ is either hydrogen, halogen, or alkoxy, preferably, $R_3$ is either Cl, F, hydrogen, or methoxy, more preferably methoxy.

In alternative more preferred combinations; at least two of $R_1$, $R_2$, and $R_3$ is halogen, preferably F and R is hydrogen or $CH_3$; R is hydrogen or $CH_3$, $R_2$ is either lower haloalkyl, or lower haloalkoxy, preferably $OCF_3$ or $CF_3$, and $R_1$ and $R_3$ is hydrogen; and R is $CH_3$, $R_3$ is halogen, preferably Cl, $R_1$ is either halogen or hydrogen, preferably F or hydrogen, and $R_2$ is either hydrogen, lower alkyl, lower haloalkyl, or lower haloalkoxy, preferably, hydrogen, $CF_3$, $CH_3$, $OCF_3$, or F.

b. $Ar_1$ is Naphthyl and q is 0

In another preferred embodiment, $Ar_2$ is naphthyl, q is 0, and the compound has the formula:

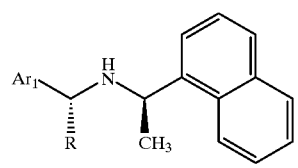

where $Ar_1$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, $CH_2OH$, $CONH_2$, CN, acetoxy, N(CH$_3$)$_2$, phenyl, phenoxy, benzyl, benzyloxy, α,α-dimethylbenzyl, NO$_2$, CHO, CH$_3$CH (OH), acetyl, ethylene dioxy, preferably each substituent is independently selected from the group consisting of, CH$_3$, CH$_3$O, CH$_3$CH$_2$O, methylene dioxy, Br, Cl, F, I, CF$_3$, CHF$_2$, CH$_2$F, CF$_3$O, CF$_3$CH$_2$O, CH$_3$S, OH, CH$_2$OH, CONH$_2$, CN, NO$_2$, CH$_3$CH$_2$, propyl, isopropyl, butyl, isobutyl, t-butyl, and acetoxy. More preferably, Ar$_1$ is either a naphthyl or a phenyl having 1–5 substituents each independently selected from the group consisting of isopropyl, CH$_3$O, CH$_3$S, CF$_3$, CF$_3$O, I, Cl, F, and CH$_3$ More preferably, Ar$_1$ is an optional substituted phenyl where the compound has the formula:

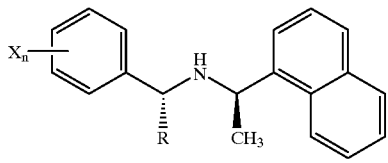

where X$_n$ represents the optional substituents for the optionally substituted phenyl as described above (with the preferred substituents and number of substituents as described above).

Even more preferably the compound has the formula:

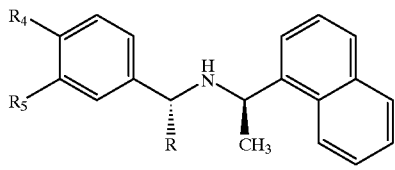

where R is either CH$_3$ or hydrogen;

R$_4$ is either lower alkyl, halogen, or alkoxy, preferably isopropyl, chlorine, or methoxy; and R$_5$ is either hydrogen, lower alkyl, or halogen, preferably methyl, CH$_3$, Br, or Cl.

c. Ar$_2$ is Naphthyl and q is 2

In another preferred embodiment, Ar$_1$ is a substituted phenyl, Ar$_2$ is naphthyl, q is 2 and the compound has the formula:

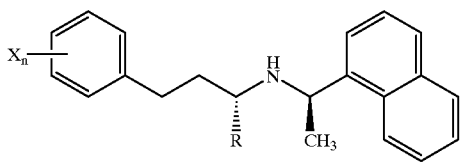

where R is either hydrogen or CH$_3$;

n is 0, 1, 2, 3, 4, or 5, preferably 1 or 2; and each X is independently selected from the group consisting of, lower alkyl, halogen, lower alkoxy, lower thioalkyl, methylene dioxy, lower haloalkyl, lower haloalkoxy, OH, CH$_2$OH, CONH$_2$, CN, acetoxy, N(CH$_3$)$_2$, phenyl, phenoxy, benzyl, benzyloxy, α,α-dimethylbenzyl, NO$_2$, CHO, CH$_3$CH (OH), acetyl, ethylene dioxy, preferably each substituent is independently selected from the group consisting of, CH$_3$, CH$_3$O, CH$_3$CH$_2$O, methylene dioxy, Br, Cl, F, I, CF$_3$, CHF$_2$, CH$_2$F, CF$_3$O, CF$_3$CH$_2$O, CH$_3$S, OH, CH$_2$OH, CONH$_2$, CN, NO$_2$, CH$_3$CH$_2$, propyl, isopropyl, butyl, isobutyl, t-butyl, and acetoxy, more preferably, isopropyl, CH$_3$O, CH$_3$S, CF$_3$O, CF$_3$, I, Cl, F, and CH$_3$.

More preferably, the compound has the formula:

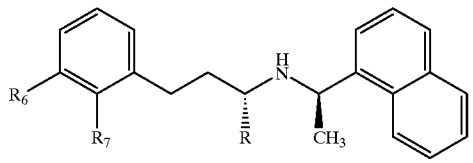

where R$_6$ is either is either hydrogen, lower haloalkyl, or lower haloalkoxy, preferably hydrogen, OCF$_3$ or CF$_3$; and R$_7$ is either halogen or hydrogen, preferably chlorine or hydrogen.

In other embodiments R, R$_6$ and R$_7$ are as described above (with the preferred substituents as described above), provided that when both R and R$_6$ are hydrogen, R$_7$ is not Cl; and R is CH$_3$, and R$_6$ and R$_7$ is as described above (with the preferred substituents as described above).

2. Structure II Compounds

Structure II compounds have the formula:

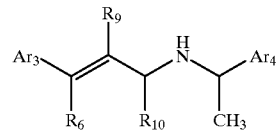

where Ar$_3$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, CH$_2$OH, CONH$_2$, CN, acetoxy, benzyl, benzyloxy, α,α-dimethylbenzyl, NO$_2$, CHO, CH$_3$CH(OH), N(CH$_3$)$_2$, acetyl, ethylene dioxy, preferably N(CH$_3$)$_2$, lower alkoxy, or lower alkyl;

Ar$_4$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, CH$_2$OH, CONH$_2$, CN, and acetoxy, preferably lower alkoxy, more preferably methoxy;

R$_8$ is either hydrogen or phenyl, preferably hydrogen;

R$_9$ is either hydrogen or methyl; and

R$_{10}$ is either hydrogen, methyl, or phenyl, more preferably when R$_{10}$ is methyl the chiral carbon it is attached to is the (R) stereoisomer.

Preferably, the α-methyl in Structure II is an (R)-α-methyl.

3. Structure III Compounds Structure III compounds have the formula:

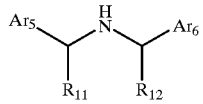

where Ar$_5$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, CH$_2$OH, CONH$_2$, CN, acetoxy, benzyl, benzyloxy, α,α-dimethylbenzyl, NO$_2$, CHO, CH$_3$CH(OH), acetyl, ethylene dioxy, —CH=CH-phenyl, preferably, lower alkyl, phenoxy, —CH=CH-phenyl, dimethylbenzyl, methoxy, methylene, or ethylene;

Ar$_6$ is either naphthyl or phenyl optionally substituted with 0 to 5 substituents each independently selected from the group consisting of, acetyl, lower alkyl, halogen, lower alkoxy, lower thioalkyl, methylene dioxy, lower haloalkyl, lower haloalkoxy, OH, CH$_2$OH, CONH$_2$, CN, carbomethoxy, OCH$_2$C(O)C$_2$H$_5$ and acetoxy, preferably methoxy, lower alkyl, phenyl, halogen, CF$_3$, CN, carbomethoxy or, OCH$_2$C(O)C$_2$H$_5$;

R$_{11}$ is hydrogen or methyl, preferably when R$_{11}$ is methyl the carbon to which it is attached is an (R) stereoisomer; and R$_{12}$ is hydrogen or methyl, preferably when R$_{12}$ is methyl the carbon to which it is attached is an (R) stereoisomer.

4. Calcimimetic Activity

The ability of compounds to mimic the activity of Ca$^{2+}$ at calcium receptors can be determined using procedures known in the art and described by Nemeth et al., PCT/US93/01642, International Publication Number WO 94/18959. For example, calcimimetics possess one or more and preferably all of the following activities when tested on parathyroid cells in vitro:

1. The compound causes a rapid (time to peak <5 seconds) and transient increase in intracellular calcium concentration that is refractory to inhibition by 1 $\mu$M La$^{3+}$ or 1 $\mu$M Gd$^{3+}$. The increase in [Ca$^{2+}$]$_i$ persists in the absence of extracellular Ca$^{2+}$, but is abolished by pretreatment with ionomycin (in the absence of extracellular Ca$^{2+}$);

2. The compound potentiates increases in [Ca$^{2+}$] elicited by submaximal concentrations of extracellular Ca$^{2+}$;

3. The increase in [Ca$^{2+}$]$_i$ elicited by extracellular Ca$^{2+}$ is not inhibited by dihydropyridines;

4. The transient increase in [Ca$^{2+}$]$_i$ caused by the compound is abolished by pretreatment for 10 minutes with 10 mM sodium fluoride;

5. The transient increase in [Ca$^{2+}$]$_i$ caused by the compound is diminished by pretreatment with an activator of protein kinase C (PKC), such as phorbol myristate acetate (PMA), mezerein or (−)-indolactam V. The overall effect of the protein kinase C activator is to shift the concentration-response curve of the compound to the right without affecting the maximal response;

6. The compound causes a rapid (<30 seconds) increase in the formation of inositol-1,4,5-triphosphate and/or diacylglycerol;

7. The compound inhibits dopamine- or isoproterenol-stimulated cyclic AMP formation;

8. The compound inhibits PTH secretion;

9. Pretreatment with pertussis toxin (100 ng/ml for >4 hours) blocks the inhibitory effect of the compound on cyclic AMP formation, but does not effect increases in [Ca$^{2+}$]$_i$, inositol-1,4,5-triphosphate, or diacylglycerol, nor decreases in PTH secretion;

10. The compound elicits increases in Cl$^-$ current in Xenopus oocytes injected with poly(A)$^+$-enriched mRNA from bovine or human parathyroid cells, but is without effect in Xenopus oocytes injected with water, or liver mRNA; and 11. Similarly, using a cloned calcium receptor from a parathyroid cell, the compound will elicit a response in Xenopus oocytes injected with the specific cDNA or mRNA encoding the receptor.

Different calcium activities can be measured using available techniques. (See, Nemeth et al., PCT/US93/01642, International Publication Number WO 94/18959.) Parallel definitions of compounds mimicking Ca$^{2+}$ activity on other calcium responsive cell, preferably at a calcium receptor, are evident from the examples provided herein and Nemeth et al., PCT/US93/01642, International Publication Number WO 94/18959.

Preferably, the compound as measured by the bioassays described herein, or by Nemeth et al., PCT/US93/01642, International Publication Number WO 94/18959, has one or more, more preferably all of the following activities: evokes a transient increase in internal calcium, having a duration of less that 30 seconds (preferably by mobilizing internal calcium); evokes a rapid increase in [Ca$^{2+}$]$_i$, occurring within thirty seconds; evokes a sustained increase (greater than thirty seconds) in [Ca$^{2+}$]$_i$ (preferably by causing an influx of external calcium); evokes an increase in inositol-1,4,5-triphosphate or diacylglycerol levels, preferably within less than 60 seconds; and inhibits dopamine- or isoproterenol-stimulated cyclic AMP formation.

The transient increase in [Ca$^{2+}$]$_i$ is preferably abolished by pretreatment of the cell for ten minutes with 10 mM sodium fluoride, or the transient increase is diminished by brief pretreatment (not more than ten minutes) of the cell with an activator of protein kinase C, preferably, phorbol myristate acetate (PMA), mezerein or (−) indolactam V.

C. Calcilytics

The ability of a compound to block the activity of extracellular calcium at a calcium receptor can be determined using standard techniques based on the present disclosure. (See, also Nemeth et al., PCT/US93/01642, International Publication Number WO 94/18959.) For example, compounds which block the effect of extracellular calcium, when used in reference to a parathyroid cell, possess one or more, and preferably all of the following characteristics when tested on parathyroid cells in vitro:

1. The compound blocks, either partially or completely, the ability of increased concentrations of extracellular Ca$^{2+}$ to:
    (a) increase [Ca$^{2+}$]$_i$,
    (b) mobilize intracellular Ca$^{2+}$,
    (c) increase the formation of inositol-1,4,5-triphosphate,
    (d) decrease dopamine- or isoproterenol-stimulated cyclic AMP formation, and
    (e) inhibit PTH secretion;

2. The compound blocks increases in Cl$^-$ current in Xenopus oocytes injected with poly(A)$^+$-mRNA from bovine or human parathyroid cells elicited by extracellular Ca$^{2+}$ or calcimimetic compounds, but not in Xenopus oocytes injected with water or liver mRNA;

3. Similarly, using a cloned calcium receptor from a parathyroid cell, the compound will block a response in Xenopus oocytes injected with the specific cDNA, mRNA or cRNA encoding the calcium receptor, elicited by extracellular Ca$^{2+}$ or a calcimimetic compound.

Parallel definitions of compounds blocking Ca$^{2+}$ activity on a calcium responsive cell, preferably at a calcium receptor, are evident from the examples provided herein and Nemeth et al., PCT/US93/01642, International Publication Number WO 94/18959.

III. TREATMENT OF DISEASES OR DISORDERS

Diseases or disorders which can be treated by modulating calcium receptor activity are known in the art. For example, diseases or disorders which can be treated by modulating calcium receptor activity can be identified based on the functional responses of cells regulated by calcium receptor activity. Functional responses of cells regulated by calcium receptor are know in the art, including PTH secretion by parathyroid cells, calcitonin secretion by C-cells, and bone resorption by osteoclasts.

Such functional responses are associated with different diseases or disorders. For example, hyperparathyroidism results in elevated levels of PTH in the plasma. Decreasing the plasma levels of PTH offers an effective means of treating hyperparathyroidism. Likewise, increasing plasma levels of calcitonin is associated with an inhibition of bone resorption. Inhibiting bone resorption is an effective treatment for osteoporosis. Thus, modulation of calcium receptor activity can be used to treat diseases such as hyperparathyroidism, and osteoporosis.

Those compounds modulating inorganic ion receptor activity, preferably calcium receptor activity, can be used to confer beneficial effects to patients suffering from a variety of diseases or disorders. For example, osteoporosis is an age-related disorder characterized by loss of bone mass and increased risk of bone fracture. Compounds can be used to block osteoclastic bone resorption either directly (e.g., an osteoclast ionomimetic compound) or indirectly by increasing endogenous calcitonin levels (e.g., a C-cell calcimimetic). Alternatively, a calcilytic active on the parathyroid cell calcium receptor will increase circulating levels of parathyroid hormone, stimulating bone formation. All three of these approaches will result in beneficial effects to patients suffering from osteoporosis.

In addition, it is known that intermittent low dosing with PTH results in an anabolic effect on bone mass and appropriate bone remodeling. Thus, compounds and dosing regimens evoking transient increases in parathyroid hormone (e.g., intermittent dosing with a parathyroid cell ionolytic) can increase bone mass in patients suffering from osteoporosis.

Additional diseases or disorders can be identified by identifying additional cellular functional responses, associated with a disease or disorder, which are regulated by calcium receptor activity. Diseases or disorder which can be treated by modulating other inorganic ion receptors can be identified in an analogous manner.

The inorganic ion receptor-modulating compounds of the present invention can exert an affect at an inorganic ion receptor causing one or more cellular effects ultimately producing a therapeutic effect. Calcium receptor-modulating compounds of the present invention can exert an effect on calcium receptor causing one or more cellular effects ultimately producing a therapeutic effect. Different diseases can be treated by the present invention by targeting cells having a calcium receptor.

For example, primary hyperparathyroidism (HPT) is characterized by hypercalcemia and abnormal elevated levels of circulating PTH. A defect associated with the major type of HPT is a diminished sensitivity of parathyroid cells to negative feedback regulation by extracellular $Ca^{2+}$. Thus, in tissue from patients with primary HPT, the "set-point" for extracellular $Ca^{2+}$ is shifted to the right so that higher than normal concentrations of extracellular $Ca^{2+}$ are required to depress PTH secretion. Moreover, in primary HPT, even high concentrations of extracellular $Ca^{2+}$ often depress PTH secretion only partially. In secondary (uremic) HPT, a similar increase in the set-point for extracellular $Ca^{2+}$ is observed even though the degree to which $Ca^{2+}$ suppresses PTH secretion is normal. The changes in PTH secretion are paralleled by changes in $[Ca^{2+}]_i$: the set-point for extracellular $Ca^{2+}$-induced increases in $[Ca^{2+}]_i$ is shifted to the right and the magnitude of such increases is reduced.

Patients suffering from secondary HPT may also have renal osteodystrophy. Calcimimetics appear to be useful for treating both abnormal PTH secretion and osteodystrophy in such patients.

Compounds that mimic the action of extracellular $Ca^{2+}$ are beneficial in the long-term management of both primary and secondary HPT. Such compounds provide the added impetus required to suppress PTH secretion which the hypercalcemic condition alone cannot achieve and, thereby, help to relieve the hypercalcemic condition. Compounds with greater efficacy than extracellular $Ca^{2+}$ may overcome the apparent nonsuppressible component of PTH secretion which is particularly troublesome in the major form of primary HPT caused by adenoma of the parathyroid gland. Alternatively or additionally, such compounds can depress synthesis of PTH, as prolonged hypercalcemia has been shown to depress the levels of preproPTH mRNA in bovine and human adenomatous parathyroid tissue. Prolonged hypercalcemia also depresses parathyroid cell proliferation in vitro, so calcimimetics can also be effective in limiting the parathyroid cell hyperplasia characteristic of secondary HPT.

Cells other than parathyroid cells can respond directly to physiological changes in the concentration of extracellular $Ca^{2+}$. For example, calcitonin secretion from parafollicular cells in the thyroid (C-cells) is regulated by changes in the concentration of extracellular $Ca^{2+}$.

Isolated osteoclasts respond to increases in the concentration of extracellular $Ca^{2+}$ with corresponding increases in $[Ca^{2+}]$ that arise partly from the mobilization of intracellular $Ca^{2+}$. Increases in $[Ca^{2+}]_i$ in osteoclasts are associated with the inhibition of bone resorption. Release of alkaline phosphatase from bone-forming osteoblasts is directly stimulated by calcium.

Renin secretion from juxtaglomerular cells in the kidney, like PTH secretion, is depressed by increased concentrations of extracellular $Ca^{2+}$. Extracellular $Ca^{2+}$ causes the mobilization of intracellular $Ca^{2+}$ in these cells. Other kidney cells respond to calcium as follows: elevated $Ca^{2+}$ inhibits formation of $1,25(OH)_2$-vitamin D by proximal tubule cells, stimulates production of calcium-binding protein in distal tubule cells, and inhibits tubular reabsorption of $Ca^{2+}$ and $Mg^{2+}$ and the action of vasopressin on the thick ascending limb of Henle's loop (MTAL), reduces vasopressin action in the cortical collecting duct cells, and affects vascular smooth muscle cells in blood vessels of the renal glomerulus.

Calcium also promotes the differentiation of intestinal goblet cells, mammary cells, and skin cells; inhibits atrial natriuretic peptide secretion from cardiac atria; reduces cAMP accumulation in platelets; alters gastrin and glucagon secretion; acts on vascular smooth muscle cells to modify cell secretion of vasoactive factors; and affects cells of the central nervous system and peripheral nervous system.

Thus, there are sufficient indications to suggest that $Ca^{2+}$, in addition to its ubiquitous role as an intracellular signal, also functions as an extracellular signal to regulate the responses of certain specialized cells. Compounds of this invention can be used in the treatment of diseases or disorders associated with disrupted $Ca^{2+}$ responses in these cells.

Specific diseases and disorders which might be treated or prevented, based upon the affected cells, also include those of the central nervous system such as seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); gut motility disorders such as diarrhea, and spastic colon; GI ulcer diseases; GI diseases with excessive calcium absorption such as sarcoidosis; and autoimmune diseases and organ transplant rejection.

While calcium receptor-modulating compounds of the present invention will typically be used in therapy for human patients, they may also be used to treat similar or identical diseases in other warm-blooded animal species such as other primates, farm animals such as swine, cattle, and poultry; and sports animals and pets such as horses, dogs and cats.

IV. ADMINISTRATION

The different compounds described by the present invention can be used to treat different diseases or disorders by modulating inorganic ion receptor activity, preferably calcium receptor activity. The compounds of the invention can be formulated for a variety of modes of administration, including systemic and topical or localized administration. Techniques and formulations generally may be found in *Remington's Pharmaceutical Sciences,* Mack Publishing Co., Easton, Pa. Administration of ionomimetics and ionolytics is discussed by Nemeth et al., PCT/US93/01642, International Publication Number WO 94/18959.

Suitable dosage forms, in part, depend upon the use or the route of entry, for example oral, transdermal, or by injection. Such dosage forms should allow the compound to reach a target cell whether the target cell is present in a multicellular host or in culture. For example, pharmacological compounds or compositions injected into the blood stream should be soluble. Other factors are known in the art, and include considerations such as toxicity and dosage form which retard the compound or composition from exerting its effect.

Compounds can also be formulated as pharmaceutically acceptable salts (e.g., acid addition salts) and complexes thereof. Pharmaceutically acceptable salts are non-toxic salts at the concentration at which they are administered. The preparation of such salts can facilitate the pharmacological use by altering the physical characteristic of the compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, hydrochloride, maleate, phosphate, sulfamate, acetate, citrate, lactate, tartrate, methanesulfonate, ethanesulfonate, benzenesulfonate, p-toluenesulfonate, cyclohexylsulfamate and quinate. (See e.g., PCT/US92/03736, hereby incorporated by reference herein.) Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of a compound is dissolved in a suitable solvent, such as an aqueous or aqueous-alcohol solution, containing the appropriate acid and then isolated by evaporating the solution. In another example, a salt is prepared by reacting the free base and acid in an organic solvent.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

For systemic administration, oral administration is preferred. Alternatively, injection may be used, e.g., intramuscular, intravenous, intraperitoneal, and subcutaneous. For injection, the compounds of the invention are formulated in liquid solutions, preferably in physiologically compatible buffers such as Hank's solution or Ringer's solution. In addition, the compounds may be formulated in solid form and redissolved or suspended immediately prior to use. Lyophilized forms can also be produced.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be through nasal sprays, for example, or using suppositories. For oral administration, the compounds can be formulated into conventional oral administration dosage forms such as capsules, tablets, and liquid preparations.

For topical administration, the compounds of the invention can be formulated into ointments, salves, gels, or creams, as is generally known in the art.

The amounts of various compounds of this invention to be administered can be determined by standard procedures. Generally, a therapeutically effective amount is between about 1 nmole and 3 $\mu$mole of the compound, preferably 0.1 nmole and 1 $\mu$mole depending on its $EC_{50}$ or $IC_{50}$ and on the age and size of the patient, and the disease or disorder associated with the patient. Generally, it is an amount between about 0.1 and 50 mg/kg, preferably 0.01 and 20 mg/kg of the animal to be treated.

V. EXAMPLES

Examples are provided below illustrating different aspects and embodiments of the present invention. These examples are not intended to limit the claimed invention.

Example 1

Cloning of Human Parathyroid Calcium Receptor From a Human Parathyroid Gland Adenoma Tumor This example describes the cloning of a human parathyroid calcium receptor from a human parathyroid gland adenoma tumor using pBoPCaR1 as a hybridization probe (See, Nemeth et al., PCT/US93/01642, International Publication Number WO 94/18959). The probe was used to identify nucleic acid encoding human parathyroid gland calcium receptor by cross-hybridization at reduced stringency.

Messenger RNA was prepared from a human parathyroid gland adenoma tumor removed from a 39-year-old Caucasian male diagnosed with primary hyperparathyroidism. Northern blot analysis of this mRNA using pBoPCaR1 as a hybridization probe identified calcium receptor transcripts of about 5 Kb and about 4 Kb. A cDNA library was constructed from the mRNA. Double-stranded cDNA larger than 3 Kbp were size-selected on an agarose gel and ligated into the cloning vector lambda ZapII. Five hundred thousand primary recombinant phage were screened with the 5.2 Kbp cDNA insert of pBoPCaR1 as a hybridization probe. The pBoPCaR1 insert was labeled by random-primed synthesis using [$^{32}$P]-dCTP to a specific activity of $1\times10^9$ cpm/μg.

Library screening was performed at a hybridization stringency of 400 mM Na$^+$, 50% formamide at a temperature of 38° C. Plaque lift filters were hybridized at a probe concentration of 500,000 cpm/ml for 20 hours. Following hybridization, filters were washed in 1 x SSC at 40° C. for 1 hr.

The primary screen identified about 250 positive clones identified by hybridization to pBoPCaR1. Seven of these clones were taken through secondary and tertiary screens to isolate single clones that hybridized to the pBoPCaR1 probe. These seven clones were analyzed by restriction enzyme mapping and Southern blot analysis. Three of the clones contained cDNA inserts of about 5 Kbp and appear to be full-length clones corresponding to the 5 Kb mRNA. Two of the clones contain cDNA inserts of about 4 Kbp and appear to be full-length clones corresponding to the 4 Kb mRNA.

Restriction enzyme mapping of the two different sized inserts indicate that they share regions of sequence similarity in their 5' ends, but diverge in their 3' end sequences. DNA sequence analyses indicate that the smaller insert may result from alternative polyadenylation upstream of the polyadenylation site used in the larger insert.

Representative cDNA inserts for both size classes were subcloned into the plasmid vector pBluescript SK. Linearization followed by in vitro transcription using T7 RNA polymerase produced cRNA transcripts. The cRNA transcripts were injected into Xenopus oocytes (150 ng/μl RNA; 50 nl/oocyte) for functional analysis. Following incubation periods of 2–4 days, the oocytes were assayed for the presence of functional calcium receptors. Both clone types gave rise to functional calcium receptors as assessed by the stimulation of calcium-activated chloride currents upon addition of appropriate calcium receptor agonists. Known calcium receptor agonists, including NPS R-467 and NPS R-568 (see, Nemeth et al., PCT/US93/01642, International Publication Number WO 94/18959), activated the oocyte-expressed receptor at about the same concentrations known to be effective for the native parathyroid cell receptor. Thus, both clones encode a functional, human parathyroid cell calcium receptor.

Plasmids were prepared by subcloning each size class of insert into pbluescript thereby producing pHuPCaR 5.2 and pHuCaR 4.0. The nucleic acid sequence, and amino acid sequence, of the inserts are shown in SEQ. ID. Nos. 1 and 2.

Several differences were observed between the nucleic acid sequences of the two cDNA inserts. Sequence analyses of the two cDNA inserts indicate the existence of at least two sequence variants differing in the 3' untranslated region and which may result from alternative polyadenylation. In addition, sequence variation exists at the 5' end of the inserts. These distinct sequences correspond to untranslated regions and may have arisen due to alternative transcriptional initiation and/or splicing.

Three additional sites of sequence variation are observed within the coding regions of cDNA clones pHuPCaR5.2 and pHuPCaR4.0 (see SEQ. ID. NOs. 1 and 2) demonstrating that these cDNA clones encode distinct proteins. Sequence analysis of the human CaR gene indicates that the additional 30 base pairs of DNA in cDNA clone pHuPCaR5.2, as compared to the pHuPCaR 4.0 cDNA clone, results from alternative mRNA splicing. The alternative mRNA splicing is predicted to insert 10 additional amino acids into the CaR polypeptide encoded by the pHuPCaR5.2 cDNA at a site between aa#536 and aa#537 in polypeptide encoded by pHuPCaR4.0 cDNA. In addition, pHuPCaR4.0 encodes glutamine (Gln) at aa#925 and glycine (Gly) at position 990 whereas pHuPCaR5.2 encodes arg (Arg) at both equivalent positions. The human CaR gene encodes for Gln and Arg, respectively, at these positions. The difference between the pHuPCaR4.0 cDNA compared to human DNA appears to represent a true sequence polymorphism within the human population while the single base change in pHuPCaR5.2 probably reflects a mutation which occurred during its cloning. Both cDNAs encode functional calcium receptors as demonstrated by the ability of Xenopus oocytes injected with cRNA prepared from these cDNA clones to respond to 10 mM extracellular calcium as ascertained by Cl– conductance. However, it is possible that these two receptor isoforms are functionally and/or pharmacologically distinct.

Example 2

Selection of Stable Recombinant Cells Expressing the Calcium Receptor

Clonal cell lines that stably express the two human and the bovine calcium receptors have been isolated. Calcium receptor cDNAs were subcloned in two different, commercially available expression vectors; pMSG (obtained from Pharmacia) and Cep4B (obtained from Invitrogen). The first vector contains the selectable marker gene for xanthine-guanine phosphoribosyltransferase (gpt) allowing stably transfected cells to overcome the blockade of the purine biosynthetic pathway imposed by addition of 2 μg/ml aminopterin and 25 μg/ml mycophenolic acid. The second vector encodes a gene conferring resistance to the antibiotic hygromycin (used at 200 μg/ml). HuPCaR 5.2 and HuPCaR 4.0 cDNAs (SEQ. ID. NOs. 1 and 2, respectively) were removed from the parent bluescript plasmid with Not I and Hind III restriction enzymes and then either ligated directly into Not I+Hind III digested Cep4B or treated with the klenow fragment of DNA polymerase prior to blunt-end ligation into Sma I digested pMSG.

The pMSG subclone containing the HuPCaR 5.2 insert was transfected into CHO cells as discussed above. Selection has resulted in 20 resistant clones which are being characterized. The Cep4B subclone containing the HuPCaR 5.2 insert was transfected into HEK 293 cells as described above. Selection with hygromycin resulted in a pool of stable clones. Clones expressing the HuPCaR 4.0 receptor isoform were prepared similarly.

Cells obtained from the pool of hygromycin selected HEK 293 cells transfected with Cep4B containing the HuPCaR 5.2 insert were plated on collagen coated Aklar squares which had been placed into individual wells of 12-well tissue culture plates. Two to six days later, medium was removed and the cells washed with balanced salt solution and 1 ml of buffer containing 1 μM fura2-AM, 1 mM $CaCl_2$ and 0.1% BSA and 1 mM $CaCl_2$. Measurements of fluorescence in response to calcium receptor agonists were performed at 37° C. in a spectrofluorimeter using excitation and emission wavelengths of 340 and 510 nm, respectively. For signal calibration, Fmax was determined after addition of ionomycin (40 μM) and the apparent Fmin was determined by addition of 0.3 M EGTA, 2.5 M Tris-HCl; pH 10. Robust increases in $[Ca^{2+}]_i$ were observed in response to the addition of the following calcium receptor agonists: $Ca^{2+}$ (10 mM), $Mg^{2+}$ (20 mM) and NPS R-467. Control cells expressing functional substance K receptors did not respond to these calcimimetic compounds.

Additional clonal isolates of HEK 293 cells transfected with pHuPCaR4.0 sequence were obtained. These were tested for responsiveness to calcimimetics as described above except that the cells were tested while in suspension.

Example 3

Using Fura-2 Loaded Parathyroid cells To Measure to Calcium Receptor Activity This section describes procedures used to obtain parathyroid cells from calves and humans, and to use the parathyroid cells to measure calcium receptor activity.

Parathyroid glands were obtained from freshly slaughtered calves (12–15 weeks old) at a local abattoir and transported to the laboratory in ice-cold parathyroid cell buffer (PCB) which contains (mM): NaCl, 126; KCl, 4; $MgCk_2$, 1; Na-HEPES, 20; pH 7.4; glucose, 5.6, and variable amounts of $CaCl_2$, e.g., 1.25 mM. Human parathyroid glands, were obtained from patients undergoing surgical removal of parathyroid tissue for primary or uremic hyperparathyroidism (uremic HPT), and were treated similarly to bovine tissue.

Glands were trimmed of excess fat and connective tissue and then minced with fine scissors into cubes approximately 2–3 mm on a side. Dissociated parathyroid cells were prepared by collagenase digestion and then purified by centrifugation in Percoll buffer. The resultant parathyroid cell preparation was essentially devoid of red blood cells, adipocytes, and capillary tissue as assessed by phase contrast microscopy and Sudan black B staining. Dissociated and purified parathyroid cells were present as small clusters containing 5 to 20 cells. Cellular viability, as indexed by exclusion of trypan blue or ethidium bromide, was routinely 95%.

Although cells can be used for experimental purposes at this point, physiological responses (e.g., suppressibility of PTH secretion and resting levels of $[Ca^{2+}]_i$) should be determined after culturing the cells overnight. Primary culture also has the advantage that cells can be labeled with isotopes to near isotopic equilibrium, as is necessary for studies involving measurements of inositol phosphate metabolism.

After purification on Percoll gradients, cells were washed several times in a 1:1 mixture of Ham's F12-Dulbecco's modified Eagle's medium (GIBCO) supplemented with 50 µg/ml streptomycin, 100 U/ml penicillin, 5 µg/ml gentamicin and ITS+. ITS+ is a premixed solution containing insulin, transferrin, selenium, and bovine serum albumin (BSA)-linolenic acid (Collaborative Research, Bedford, Mass.). The cells were then transferred to plastic flasks (75 or 150 $cm^2$; Falcon) and incubated overnight at 37° C. in a humid atmosphere of 5% $CO_2$. No serum is added to these overnight cultures, since its presence allows the cells to attach to the plastic, undergo proliferation, and dedifferentiate. Cells cultured under the above conditions were readily removed from the flasks by decanting, and show the same viability as freshly prepared cells.

Purified parathyroid cells were resuspended in 1.25 mM $CaCl_2$-2% BSA-PCB containing 1 µM fura-2-acetoxymethylester and incubated at 37° C. for 20 minutes. The cells were then pelleted, resuspended in the same buffer, but lacking the ester, and incubated a further 15 minutes at 37° C. The cells were subsequently washed twice with PCB containing 0.5 mM $CaCl_2$ and 0.5% BSA and maintained at room temperature (about 20° C.). Immediately before use, the cells were diluted five-fold with prewarmed 0.5 mM $CaCl_2$-PCB to obtain a final BSA concentration of 0.1%. The concentration of cells in the cuvette used for fluorescence recording was $1–2\times10^6$/ml.

The fluorescence of indicator-loaded cells was measured at 37° C. in a spectrofluorimeter (Biomedical Instrumentation Group, University of Pennsylvania, Philadelphia, Pa.) equipped with a thermostated cuvette holder and magnetic stirrer using excitation and emission wavelengths of 340 and 510 nm, respectively. This fluorescence indicates the level of cytosolic $Ca^{2+}$. Fluorescence signals were calibrated using digitonin (50 µg/ml, final) to obtain maximum fluorescence ($F_{max}$), and EGTA (10 mM, pH 8.3, final) to obtain minimal fluorescence ($F_{min}$), and a dissociation constant of 224 nM. Leakage of dye is dependent on temperature and most occurs within the first 2 minutes after warming the cells in the cuvette. Dye leakage increases only very slowly thereafter. To correct the calibration for dye leakage, cells were placed in the cuvette and stirred at 37° C. for 2–3 minutes. The cell suspension was then removed, the cells pelleted, and the supernatant returned to a clean cuvette. The supernatant was then treated with digitonin and EGTA to estimate dye leakage, which is typically 10–15% of the total $Ca^{2+}$-dependent fluorescent signal. This estimate was subtracted from the apparent $F_{min}$.

Example 4

Using Fura-2 Loaded HEK 293/pHuPCaR4.0 Cells To Measure to Calcium Receptor Activity This section describes procedures used to assay calcium receptor activity using fura-2 loaded HEK 293/pHuPCaR4.0 cells. HEK 293 cells transfected with pHuPCaR4.0 were loaded with fura-2 by incubating the cells in Dulbecco's modified Eagle's media buffered with 20 mM HEPES containing about 5 µM fluo-3/AM for one hour at room temperature. Cell were then rinsed with Hank's balanced salt solution buffered with 20 mM HEPES containing 1 mM $CaCl_2$ and 1 mM $MgCl_2$. Compounds to be tested were then added to the cells and fluorescence was measured (excitation and emission wavelengths of 340 and 510 nm, respectively).

Example 5

Measuring the Ability of Compounds to Modulate Calcium Receptor Activity

The ability of different compounds to modulate calcium receptor activity was assayed by measuring increases in $[Ca^{2+}]_i$ in HEK 293 cells transfected with nucleic acid encoding pHuPCaR4.0 using fura-2 loaded cells or using parathyroid cells loaded with using fura-2 loaded cells. Results of different experiments are summarized in Tables 1.a, 1.b.1, 1.b.2, 1.c., and 2. Tables 1.a, 1.b.1, 1.b.2, and 1.c summarizes the effects of compounds, at different concentrations, on calcium receptor activity assayed as described in Example 4 (i.e., using HEK 293 cells transfected with nucleic acid encoding pHuPCaR4.0, which were loaded with fura-2).

Table 2, summarizes the results of different experiments where the $EC_{50}$ was calculated either parathyroid cells, or HEK 293/pHuPCaR4.0, loaded with fura-2. Cells were loaded with fura-2 and assayed as described in Example 2 (for parathyroid cells) or Example 3 (for HEK 293/pHuPCaR4.0 cells).

TABLE 1.a

Calcimimetic compounds which produce greater than 40% response at 3.3 ng/mL in HEK-293 cells expressing the human calcium receptor.

| Compound Code | % activity at four concentrations (ng/mL) | | | |
|---|---|---|---|---|
| | 3300 | 330 | 33 | 3.3 |
| reference compounds | | | | |
| R-568 | | 95 | 69 | 24 |
| 17P | | 101 | 86 | 54 |
| 17X | | 105 | 93 | 51 |
| 24X | 126 | 109 | 124 | 109 |
| 24Y | 119 | 120 | 127 | 102 |
| 17J | 116 | 118 | 122 | 102 |
| 25A | 122 | 120 | 114 | 92 |
| 17E | 116 | 110 | 110 | 92 |
| 24Z | 138 | 138 | 135 | 90 |
| 14S | 116 | 106 | 105 | 88 |
| 25E | 132 | 129 | 122 | 85 |
| 17G | 125 | 128 | 119 | 77 |
| 14T | 126 | 125 | 117 | 77 |
| 17H | 126 | 124 | 111 | 74 |
| 14O | 119 | 119 | 102 | 74 |
| 25I | 119 | 113 | 114 | 74 |
| 12J | 131 | 130 | 113 | 68 |
| 12I | 115 | 111 | 93 | 68 |
| 25G | 130 | 115 | 99 | 66 |
| 9R | | 108 | 101 | 64 |
| 12F | 118 | 110 | 101 | 63 |
| 12O | 110 | 117 | 94 | 62 |
| 23Z | 129 | 126 | 100 | 61 |
| 17M | | 115 | 99 | 59 |
| 16V | | 114 | 102 | 58 |
| 25O | 126 | 115 | 96 | 57 |
| 25J | 119 | 123 | 105 | 56 |
| 16L | 146 | 138 | 98 | 56 |
| 12N | 115 | 106 | 102 | 55 |
| 16T | | 97 | 88 | 55 |
| 25U | 107 | 107 | 95 | 55 |
| 17P | | 101 | 86 | 54 |
| 16Q | | 110 | 88 | 53 |
| 23E | 137 | 113 | 102 | 53 |
| 17C | 113 | 120 | 99 | 52 |
| 25L | 97 | 97 | 85 | 52 |
| 8Z | | 101 | 97 | 52 |
| 17X | | 105 | 93 | 51 |
| 13R | | 132 | 98 | 51 |
| 17O | | 112 | 96 | 51 |
| 23Q | 122 | 114 | 98 | 51 |
| 16X | | 111 | 96 | 51 |
| 24V | 127 | 98 | 71 | 50 |
| 13O | | 115 | 94 | 50 |
| 17N | | 108 | 86 | 49 |
| 21V | 122 | 116 | 99 | 48 |
| 24M | 132 | 134 | 99 | 48 |
| 13U | | 108 | 79 | 47 |
| 24P | 140 | 138 | 110 | 46 |
| 17Y | 109 | 94 | 79 | 46 |
| 11X | | 100 | 76 | 45 |
| 25H | 115 | 107 | 89 | 45 |
| 22J | | 99 | 71 | 45 |
| 9C | | 104 | 82 | 45 |
| 13S | | 102 | 87 | 45 |
| 10Q | 103 | 100 | 84 | 44 |
| 13P | | 110 | 83 | 44 |
| 8K | | 98 | 81 | 44 |
| 13N | | 114 | 88 | 43 |
| 10N | 106 | 97 | 77 | 43 |
| 12H | 114 | 115 | 94 | 43 |
| 25P | 90 | 81 | 75 | 41 |
| 18A | | 111 | 88 | 40 |
| 14L | | 109 | 78 | 40 |

TABLE 1.b.1

Calcimimetic compounds which produce greater than 40% response at 33 ng/mL in HEK-293 cells expressing the human calcium receptor.

| Compound Code | % activity at four concentrations (ng/mL) | | | |
|---|---|---|---|---|
| | 3300 | 330 | 33 | 3.3 |
| reference compounds | | | | |
| R-568 | | 95 | 69 | 24 |
| 17P | | 101 | 86 | 54 |
| 17X | | 105 | 93 | 51 |
| 12C | 134 | 125 | 98 | 39 |
| 16I | 121 | 117 | 96 | 36 |
| 17D | | 108 | 91 | 38 |
| 17F | | 111 | 90 | 28 |
| 24C | 116 | 113 | 87 | 32 |
| 25K | 124 | 107 | 86 | 35 |
| 13F | 125 | 122 | 85 | 38 |
| 21F | | 109 | 85 | 36 |
| 21S | 132 | 131 | 85 | 24 |
| 10F | | 96 | 84 | 27 |
| 14R | 106 | 107 | 84 | 37 |
| 13G | 111 | 128 | 82 | 29 |
| 14Z | 118 | 103 | 82 | 20 |
| 16N | 122 | 159 | 82 | 8 |
| 8U | 123 | 129 | 82 | 11 |
| 23W | 117 | 97 | 81 | 25 |
| 12G | 139 | 139 | 81 | 35 |
| 15G | | 113 | 80 | 32 |
| 25M | 118 | 100 | 79 | 25 |
| 13V | | 110 | 79 | 33 |
| 14P | 112 | 103 | 78 | 30 |
| 6T | 123 | 129 | 78 | 15 |
| 14Q | | 101 | 78 | 35 |
| 17L | 111 | 104 | 78 | 31 |
| 24K | | 106 | 78 | 30 |
| 24U | 106 | 106 | 78 | 25 |
| 25Q | 116 | 95 | 77 | 20 |
| 8J | | 104 | 77 | 39 |
| 23H | 121 | 114 | 77 | 28 |
| 21C = 4U | 134 | 114 | 76 | 17 |
| 25F | 97 | 85 | 76 | 28 |
| 16R | | 100 | 76 | 25 |
| 17I | 118 | 97 | 76 | 18 |
| 24J | | 103 | 75 | 31 |
| 21O | | 109 | 75 | 37 |
| 24G | 109 | 94 | 75 | 22 |
| 15I | 111 | 93 | 75 | 24 |
| 21D | | 104 | 75 | 17 |
| 20Y | 117 | 95 | 74 | 24 |
| 10P | | 102 | 74 | 8 |
| 23M | 113 | 97 | 74 | 26 |
| 14Y | | 109 | 73 | 17 |
| 17K | 98 | 97 | 73 | 37 |
| 12E | 117 | 121 | 73 | 23 |
| 17Z | | 99 | 73 | 37 |
| 16W | | 102 | 73 | 4 |
| 23K | 106 | 107 | 72 | 24 |
| 25X | 96 | 94 | 72 | 22 |
| 13W | | 109 | 71 | 12 |
| 23P | 125 | 99 | 70 | 22 |
| 18B | 111 | 96 | 69 | 26 |
| 21Y | | 100 | 68 | 36 |
| 17W | | 92 | 67 | 13 |
| 23A | | 103 | 67 | 24 |
| 23G | 127 | 93 | 67 | 13 |
| 13M | | 92 | 66 | 15 |
| 21U | 104 | 104 | 66 | 18 |
| 21R | | 100 | 66 | 15 |
| 10S/10T | | 86 | 65 | 13 |
| 17R | | 98 | 65 | 13 |
| 13X | | 102 | 65 | 13 |
| 4N | | 100 | 65 | 13 |
| 21E | | 94 | 64 | 4 |
| 15J | 80 | 75 | 64 | 13 |
| 22Y | | 114 | 64 | 28 |

TABLE 1.b.1-continued

Calcimimetic compounds which produce greater than 40% response at 33 ng/mL in HEK-293 cells expressing the human calcium receptor.

| Compound Code | % activity at four concentrations (ng/mL) | | | |
|---|---|---|---|---|
| | 3300 | 330 | 33 | 3.3 |
| 21G | | 88 | 63 | 18 |
| 24L | | 105 | 62 | 10 |
| 10V | | 99 | 62 | 8 |
| 10W/10X | | 98 | 61 | 9 |
| 17B | | 92 | 61 | 19 |
| 23Y | 106 | 87 | 61 | 16 |
| 11Y | | 103 | 61 | 20 |

TABLE 1.b.2

Calcimimetic compounds which produce greater than 40% response at 33 ng/mL in HEK-293 cells expressing the human calcium receptor.

| Compound Code | % activity at four concentrations (ng/mL) | | | |
|---|---|---|---|---|
| | 3300 | 330 | 33 | 3.3 |
| reference compounds | | | | |
| R-568 | | 95 | 69 | 24 |
| 17P | | 101 | 86 | 54 |
| 17X | | 105 | 93 | 51 |
| 18C | 99 | 87 | 60 | 18 |
| 23T | 102 | 74 | 60 | 31 |
| 4V | | 93 | 59 | |
| 8G | | 84 | 59 | 6 |
| 23I | | 102 | 58 | 3 |
| 21M | | 102 | 58 | 17 |
| 24O | 137 | 114 | 58 | 8 |
| 3U | | 89 | 57 | |
| 9A | | 82 | 56 | 6 |
| 12M | 98 | 86 | 56 | 11 |
| 12B | 130 | 110 | 56 | 4 |
| 21P | | 92 | 56 | 13 |
| 8T | | 85 | 55 | 13 |
| 10L/10M | | 99 | 55 | 4 |
| 24I | 109 | 84 | 55 | 11 |
| 14N | | 89 | 55 | 15 |
| 23R | 104 | 86 | 54 | 13 |
| 23S | | 97 | 53 | 3 |
| 21T | 133 | 112 | 53 | 3 |
| 10W/10X | | 81 | 53 | 4 |
| 13T | | 90 | 53 | 6 |
| 6R | | 94 | 52 | 7 |
| 20I | | 87 | 52 | 12 |
| 24A | 122 | 85 | 52 | 9 |
| 12D | 128 | 109 | 52 | 5 |
| 6X | | 84 | 52 | 10 |
| 18T | 99 | 74 | 52 | 14 |
| 21X | 119 | 101 | 51 | 2 |
| 23J | 102 | 61 | 51 | 29 |
| 10Z | | 96 | 51 | 5 |
| 16Z | | 88 | 51 | 9 |
| 23N | | 96 | 50 | 2 |
| 16U | | 85 | 50 | 4 |
| 11D | | 96 | 50 | 4 |
| 23X | | 94 | 49 | 1 |
| 17A | | 88 | 49 | 7 |
| 20J | | 80 | 48 | 8 |
| 22X | | 86 | 48 | 10 |
| 23U | | 87 | 48 | 3 |
| 9Z | | 74 | 48 | 4 |
| 16J | 92 | 76 | 47 | 31 |
| 25N | 94 | 73 | 46 | 8 |
| 4P | | 81 | 46 | 8 |

TABLE 1.b.2-continued

Calcimimetic compounds which produce greater than 40% response at 33 ng/mL in HEK-293 cells expressing the human calcium receptor.

| Compound Code | % activity at four concentrations (ng/mL) | | | |
|---|---|---|---|---|
| | 3300 | 330 | 33 | 3.3 |
| 23O | 111 | 79 | 46 | 13 |
| 13Q | | 95 | 46 | 5 |
| 4G | | 83 | 46 | |
| 12Y | | 80 | 46 | 10 |
| 12L | | 88 | 45 | 10 |
| 23F | | 82 | 45 | 5 |
| 11W | | 81 | 44 | 2 |
| 8H | | 88 | 44 | 7 |
| 25V | 89 | 59 | 43 | 26 |
| 25W | 95 | 69 | 42 | 8 |
| 10R | | 82 | 42 | 7 |
| 21N | 124 | 98 | 42 | 4 |
| 8S | | 73 | 42 | 7 |
| 8X | | 75 | 40 | 19 |
| 13E | 123 | 94 | 40 | 2 |

TABLE 1.c

Calcimimetic compounds which produce greater than 40% response at 330 ng/mL in HEK-293 cells expressing the human calcium receptor.

| Compound Code | % activity at four concentrations (ng/mL) | | | |
|---|---|---|---|---|
| | 3300 | 330 | 33 | 3.3 |
| reference compounds | | | | |
| R-568 | | 95 | 69 | 24 |
| 17P | | 101 | 86 | 54 |
| 17X | | 105 | 93 | 51 |
| 7X | | 85 | | |
| 3H | | 84 | | |
| 3L | | 81 | 28 | |
| 16O | 129 | 81 | 21 | 2 |
| 8O/8Q | 124 | 80 | 14 | 0 |
| 14A | 98 | 78 | 10 | 7 |
| 23L | 107 | 77 | 37 | 9 |
| 1T | | 76 | | |
| 7W | | 76 | | |
| 4H | | 77 | 37 | |
| 8D | | 75 | | |
| 5M | | 73 | 21 | |
| 4U | | 72 | | |
| 24E | 94 | 71 | 35 | 6 |
| 16M | 130 | 68 | 11 | 4 |
| 4M | | 68 | 34 | |
| 2S | | 67 | 29 | |
| 17V | 91 | 66 | 27 | -1 |
| 2X | | 66 | 15 | |
| 23D | 91 | 66 | 35 | 13 |
| 4D | | 65 | 32 | |
| 5B/5C | | 65 | 20 | |
| 3M | | 64 | 19 | |
| 16K | 78 | 62 | 36 | 8 |
| 5D | | 62 | 18 | |
| 4P | | 61 | 13 | |
| 24B | 76 | 61 | 34 | 11 |
| 24H | 81 | 60 | 32 | 13 |
| 5L | | 60 | 16 | |
| 2Y | | 59 | 10 | |
| 5G | | 58 | 16 | |
| 3V | | 56 | 14 | |
| 2Q | | 56 | 4 | |
| 14B | 75 | 55 | 11 | 4 |
| 13Z | 93 | 54 | 22 | 5 |

TABLE 1.c-continued

Calcimimetic compounds which produce greater than 40% response at 330 ng/mL in HEK-293 cells expressing the human calcium receptor.

| Compound Code | % activity at four concentrations (ng/mL) | | | |
|---|---|---|---|---|
| | 3300 | 330 | 33 | 3.3 |
| 8A | | 54 | | |
| 24D | 87 | 53 | 34 | 39 |
| 1D | | 53 | | |
| 13I | 85 | 52 | 3 | 1 |
| 3B | | 52 | 15 | |
| 8C | | 51 | | |
| 14H | 112 | 49 | 5 | 5 |
| 7U | | 49 | | |
| 5E | | 48 | 7 | |
| 13H | 88 | 48 | 36 | 12 |
| 13Y | 106 | 47 | 2 | 4 |
| 4J | | 47 | 8 | |
| 14I | 80 | 45 | 11 | 7 |
| 4B | | 45 | 8 | |
| 3D | | 45 | 4 | |
| 3R | | 45 | 2 | |
| 3A | | 41 | 7 | |
| 14J | 55 | 41 | 6 | 5 |
| 4I | | 40 | 9 | |

TABLE 2

Figure 1B:
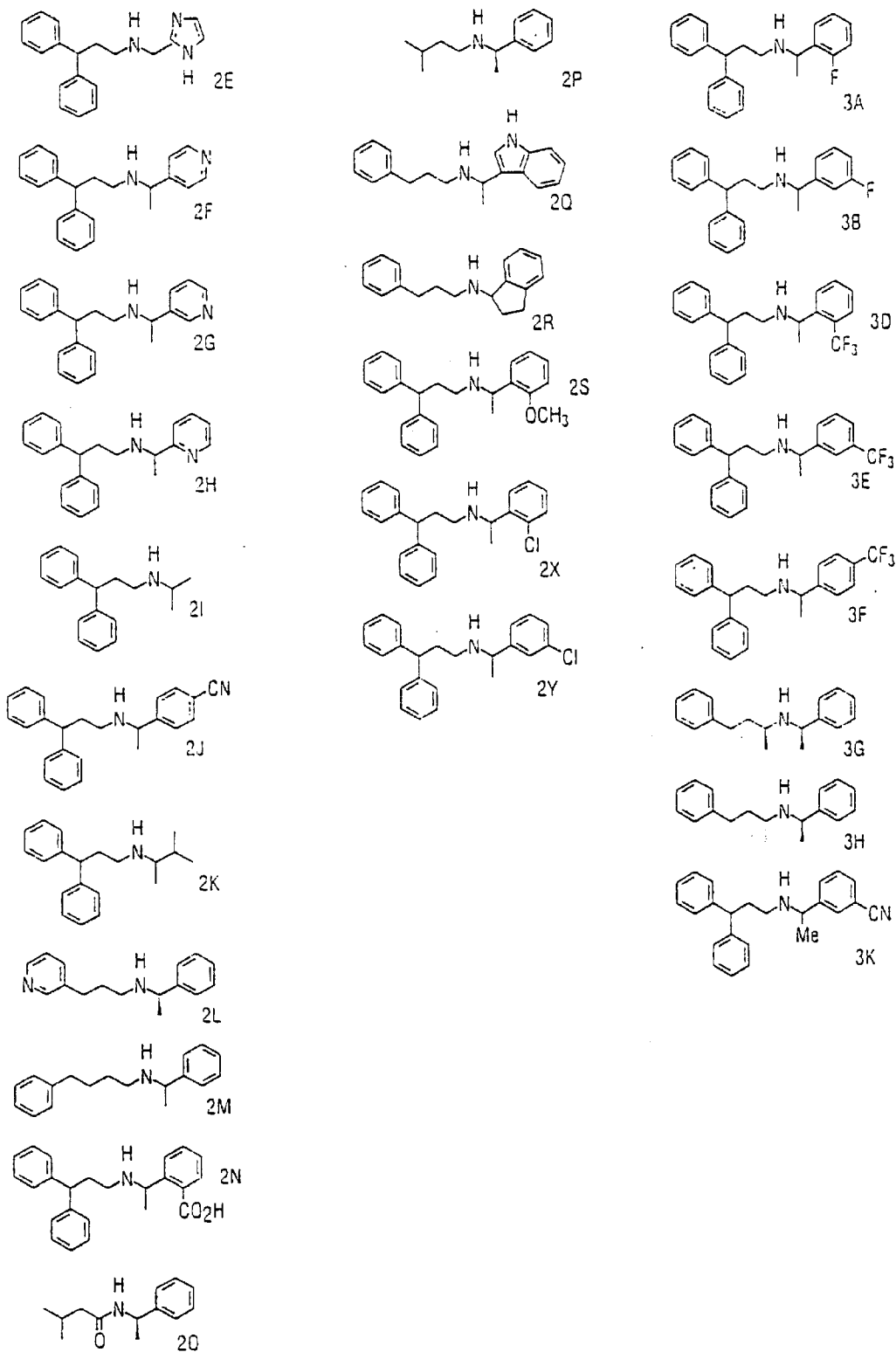
Figure 1C:
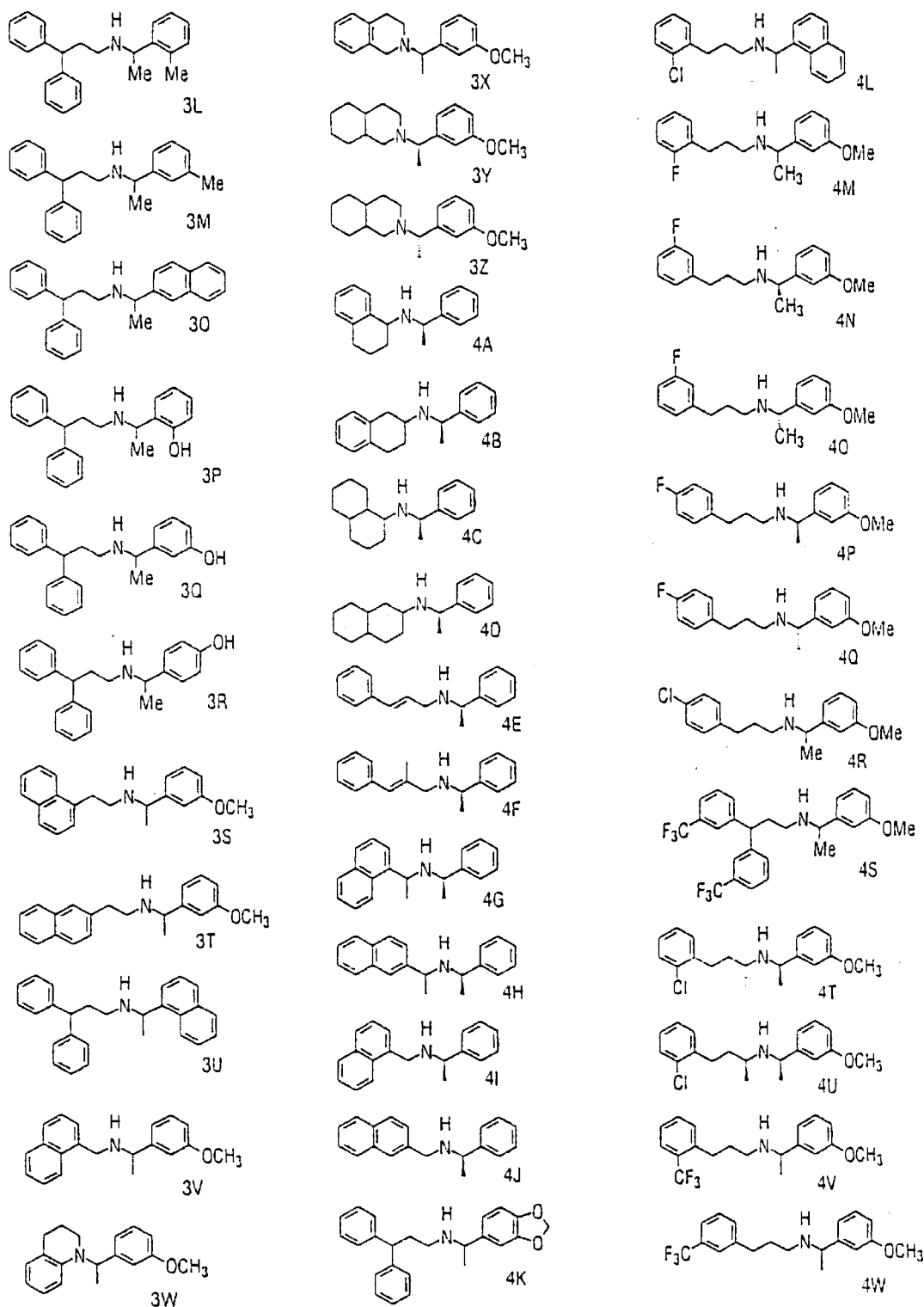
Figure 1D:
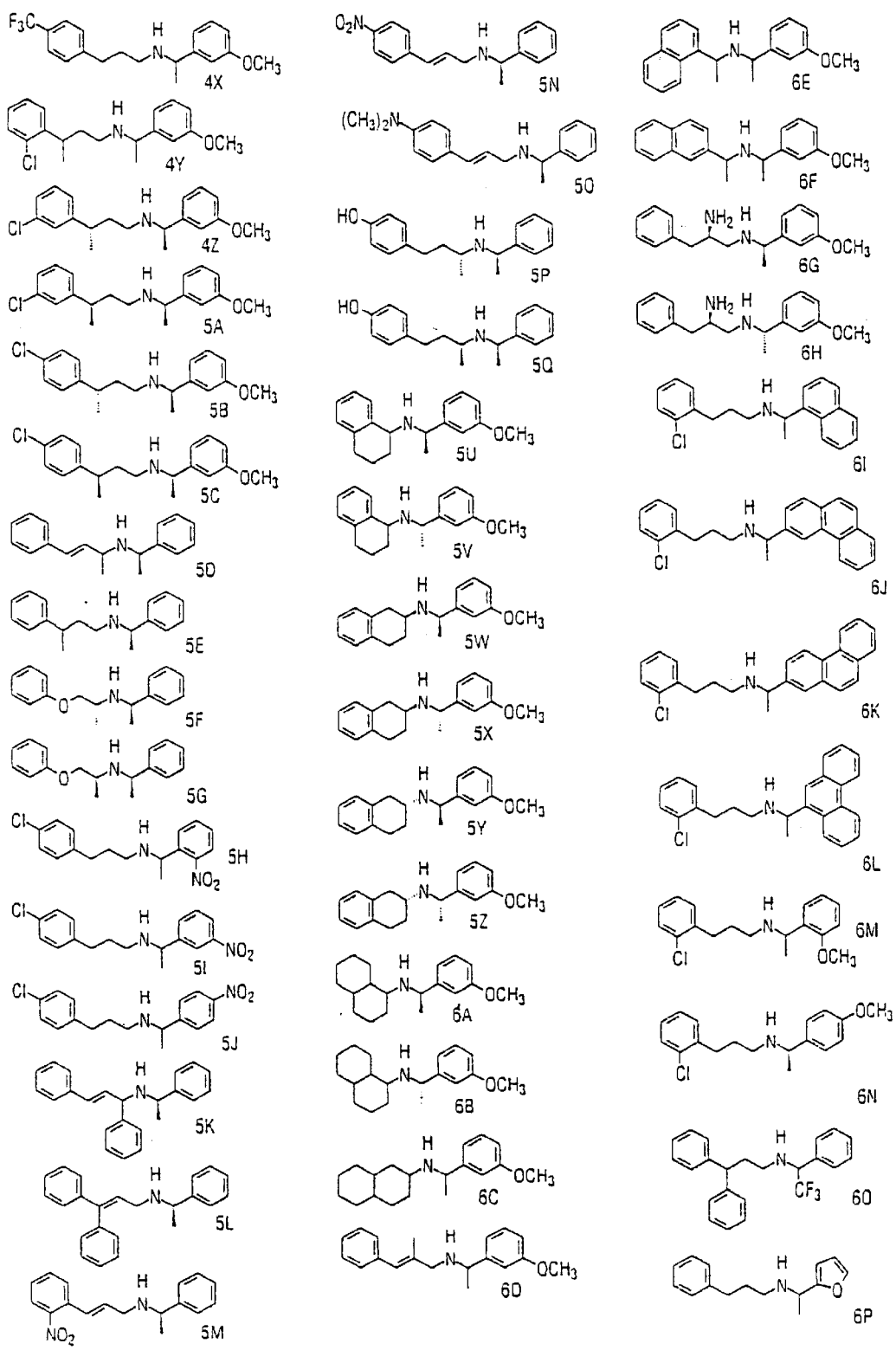
Figure 1E:
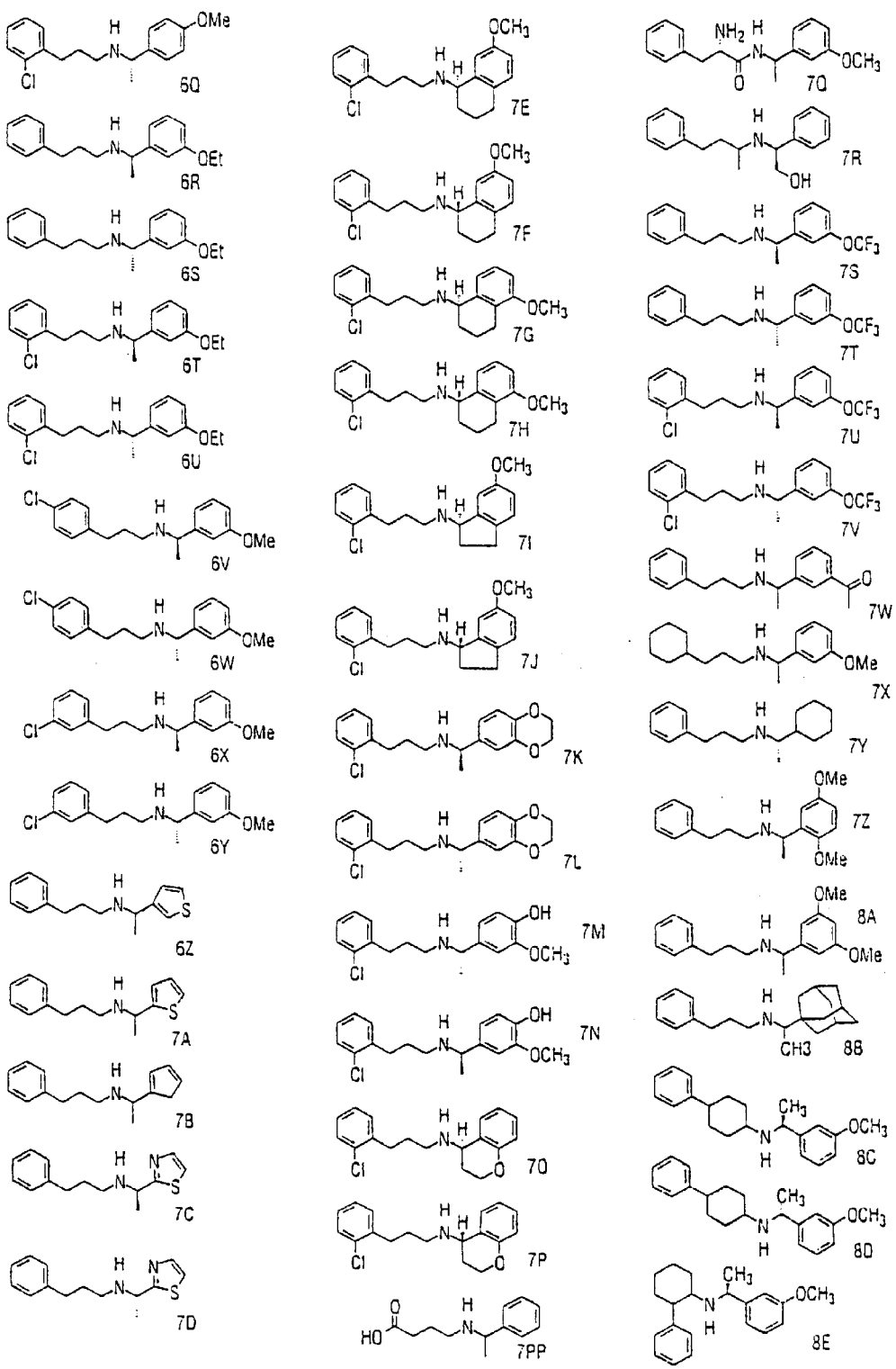
Figure 1F:
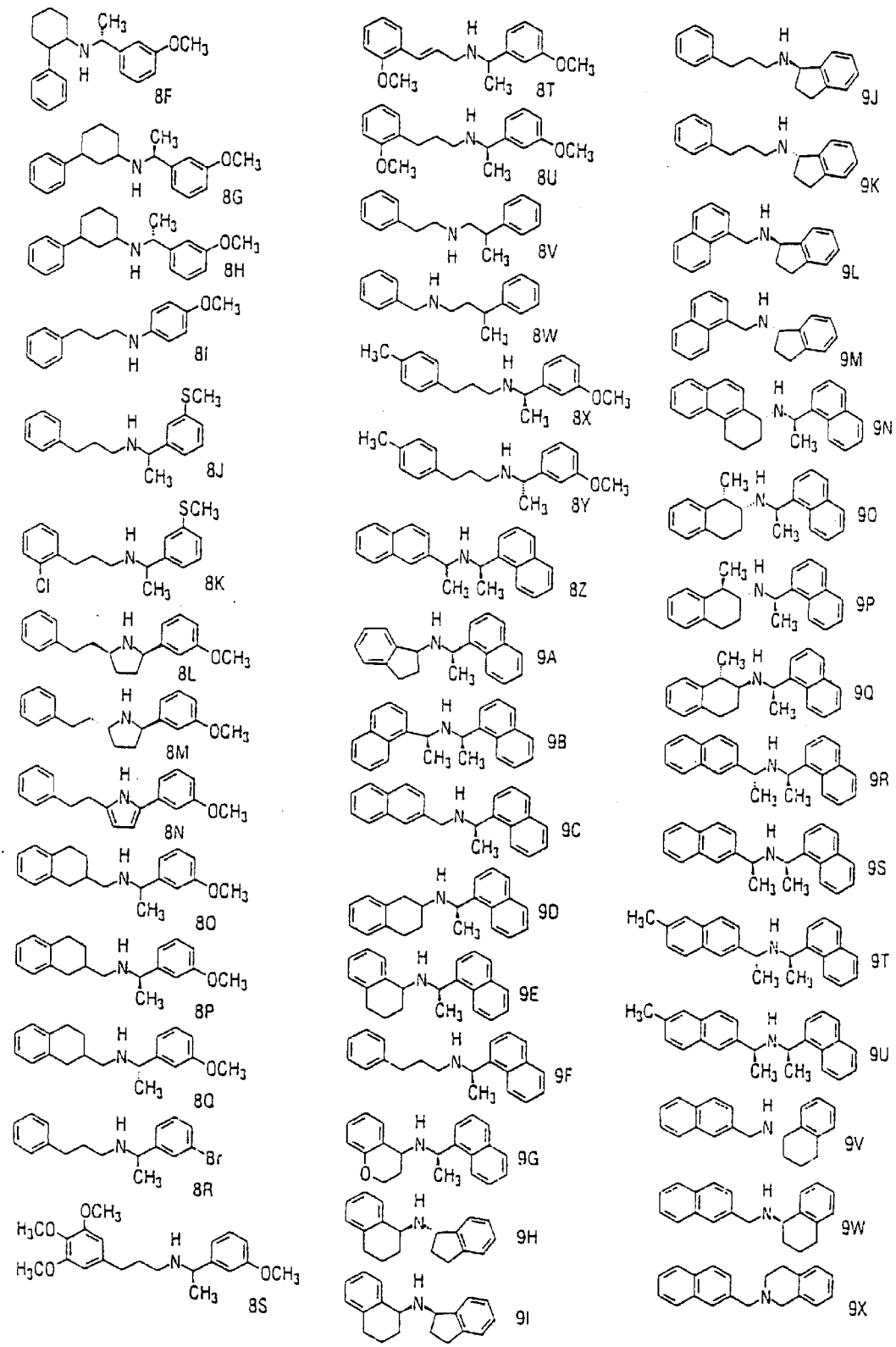
Figure 1G:
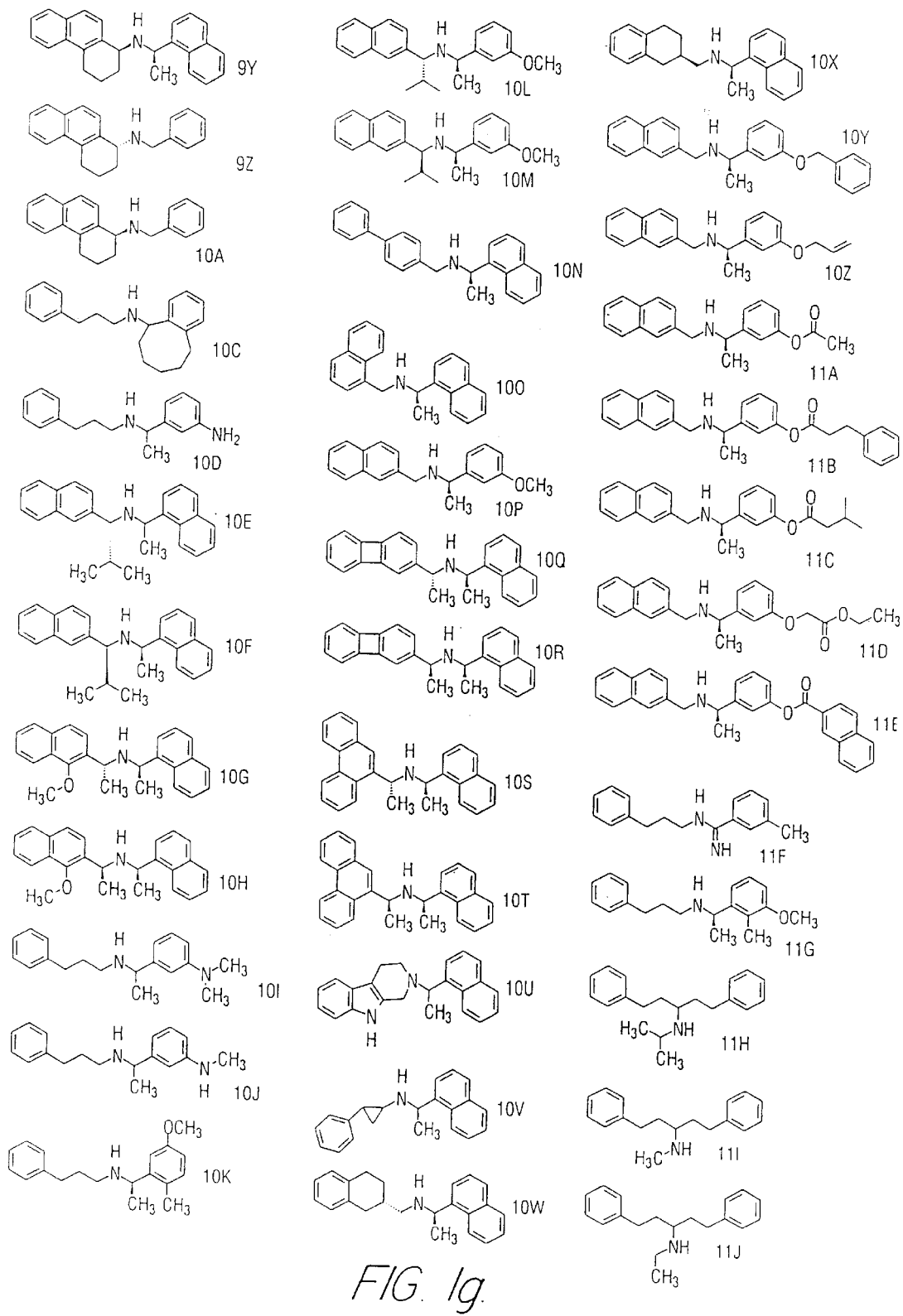
Figure 1H:
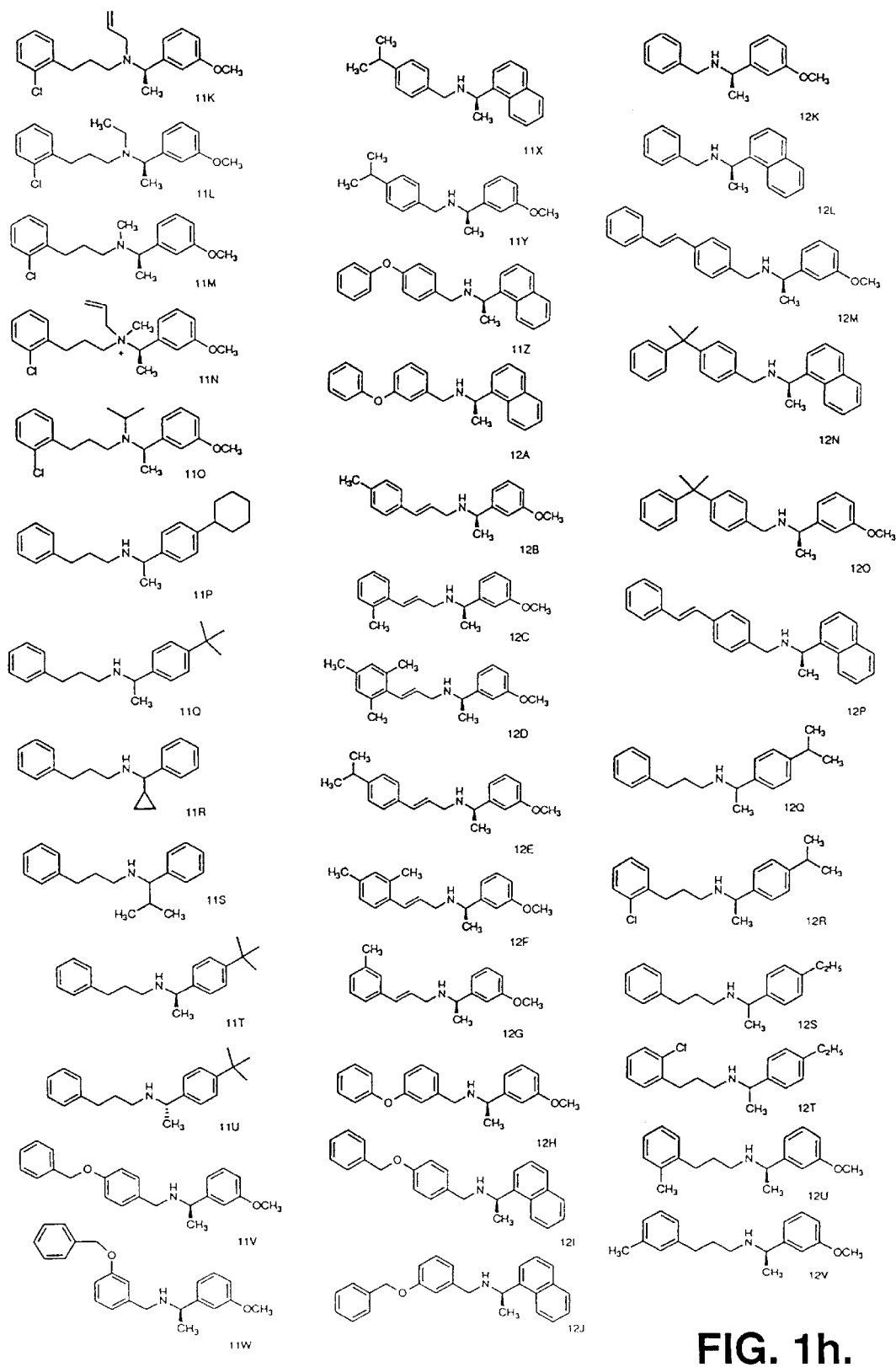
Figure 1I:
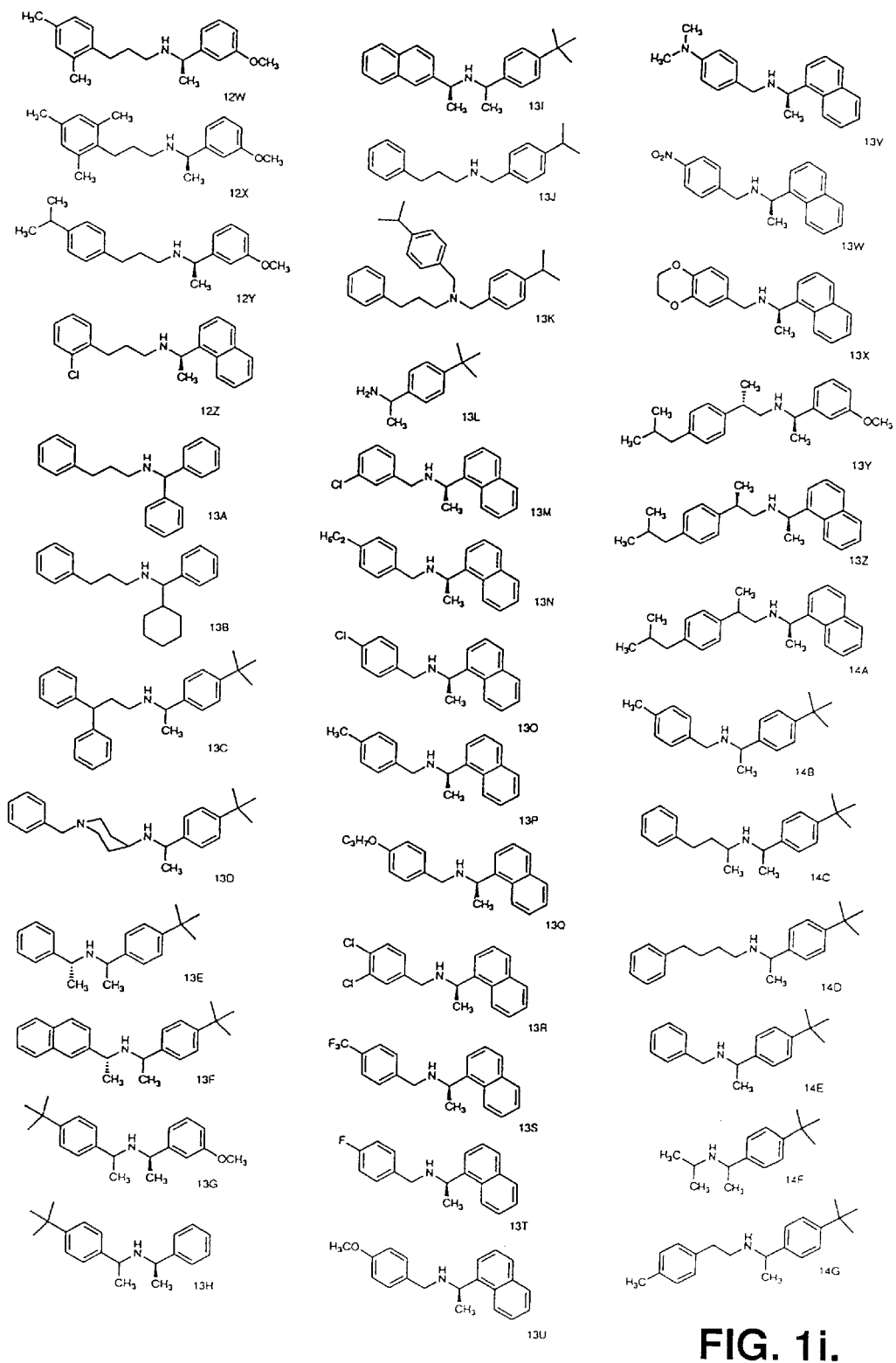
Figure 1J:
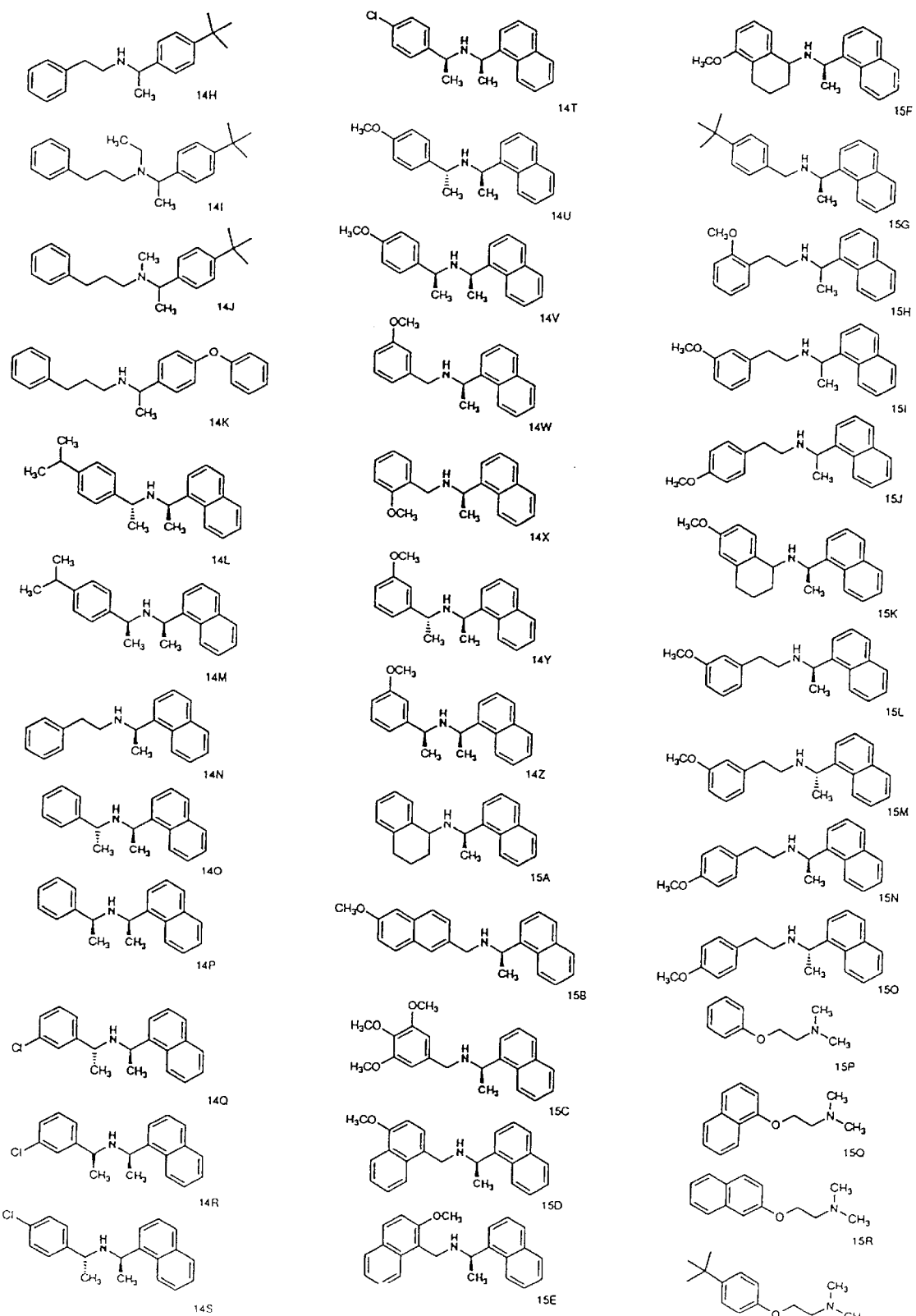
Figure 1K:
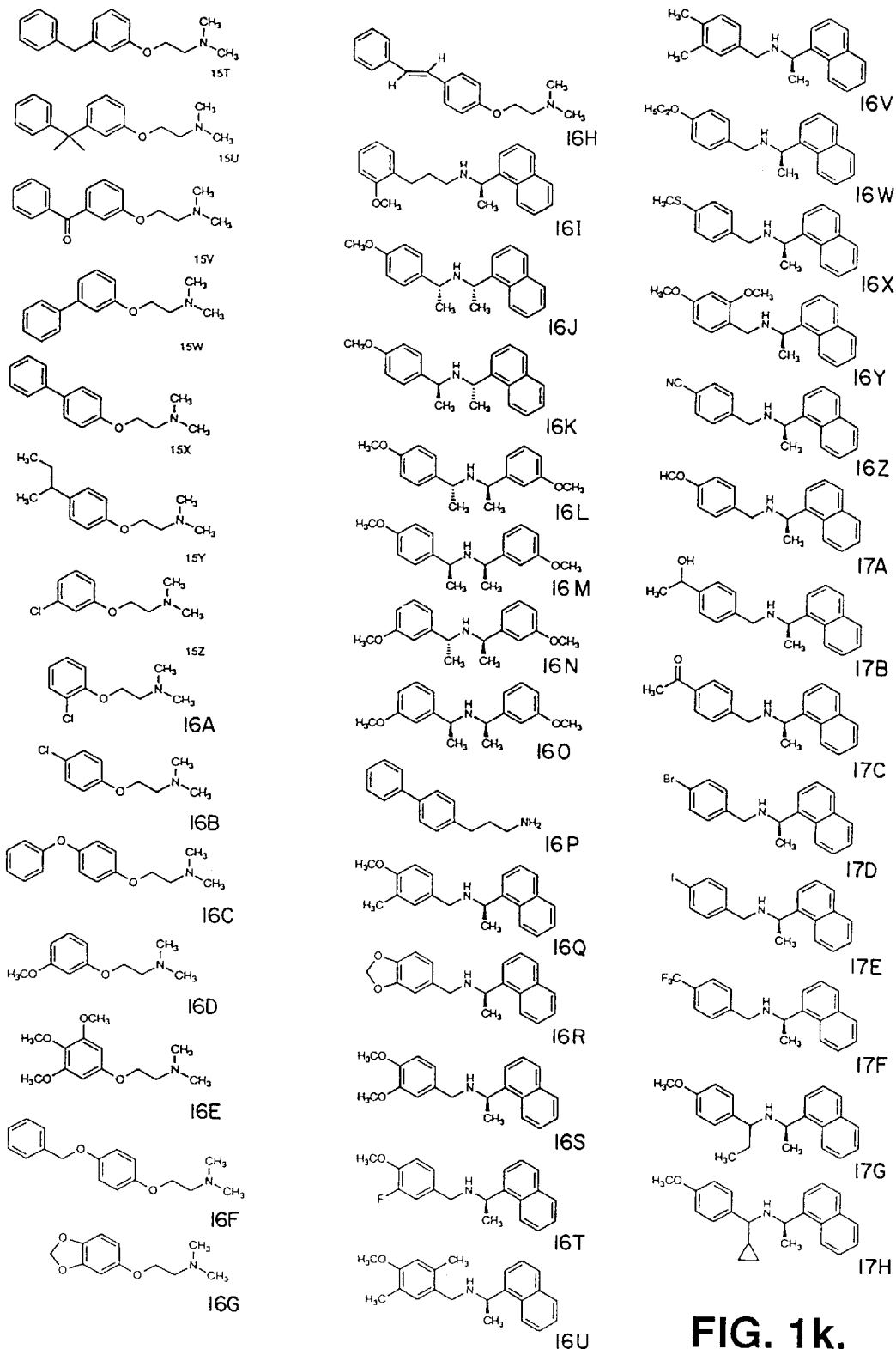
Figure 1I:
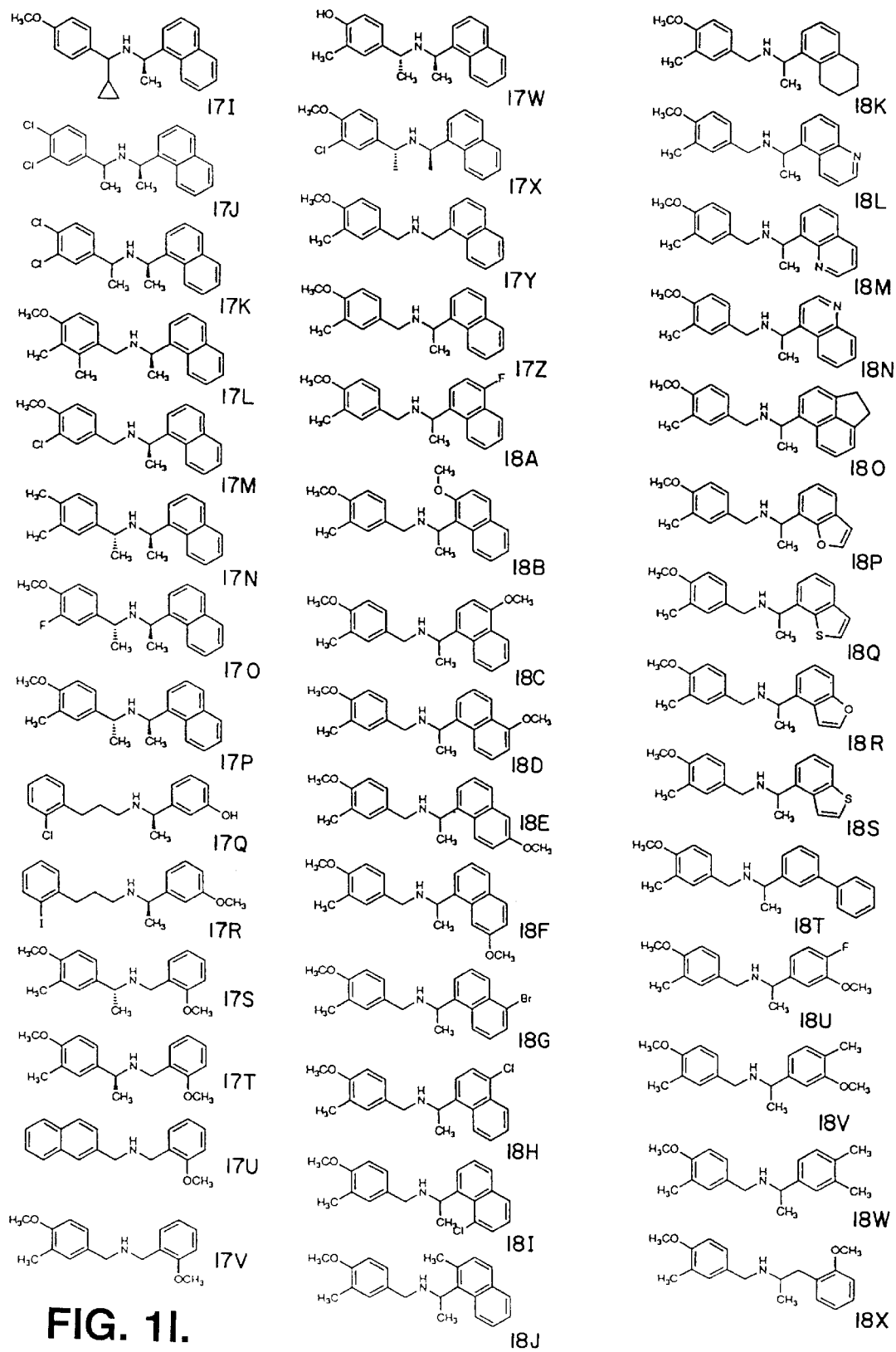
Figure 1M:
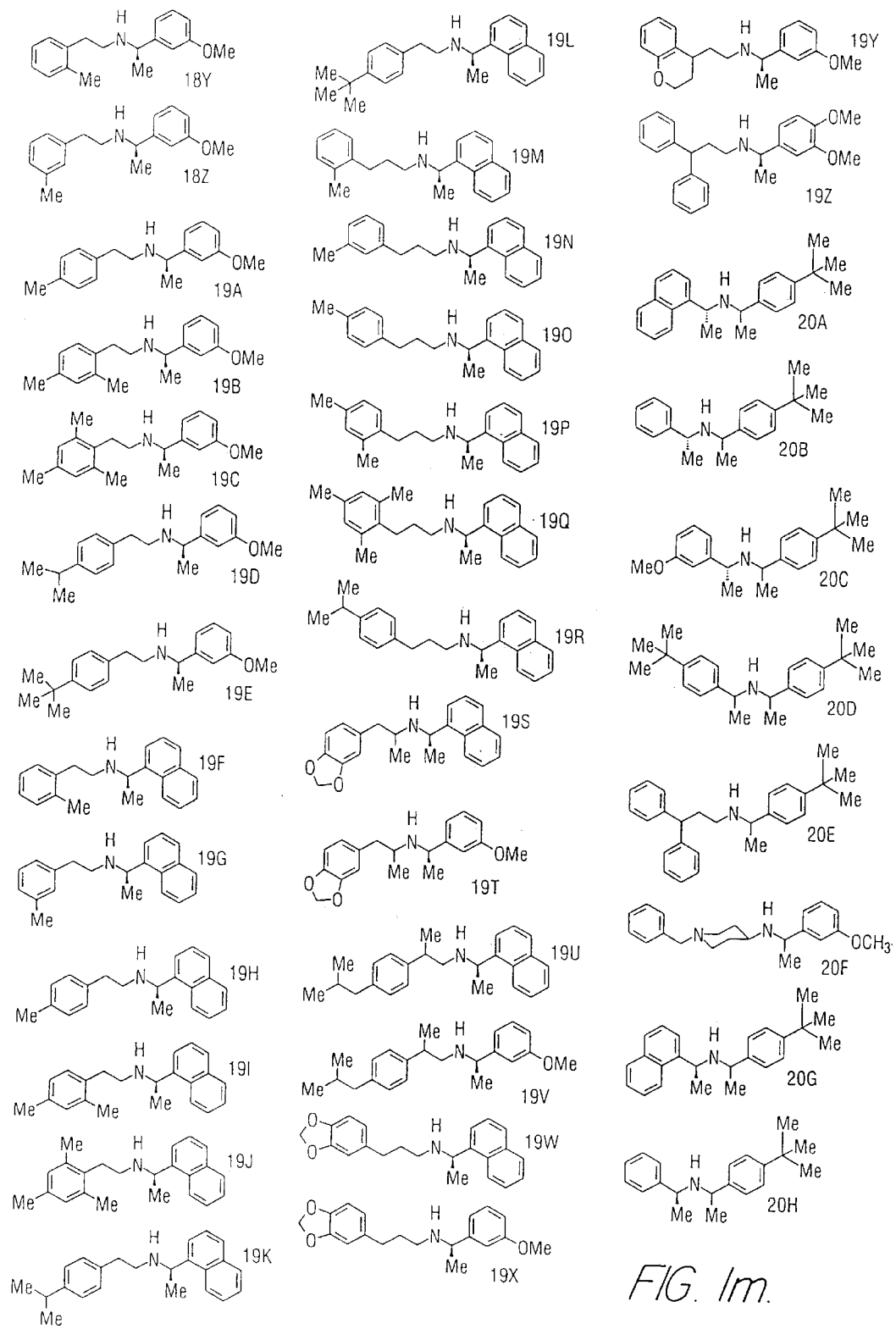
Figure 1N:
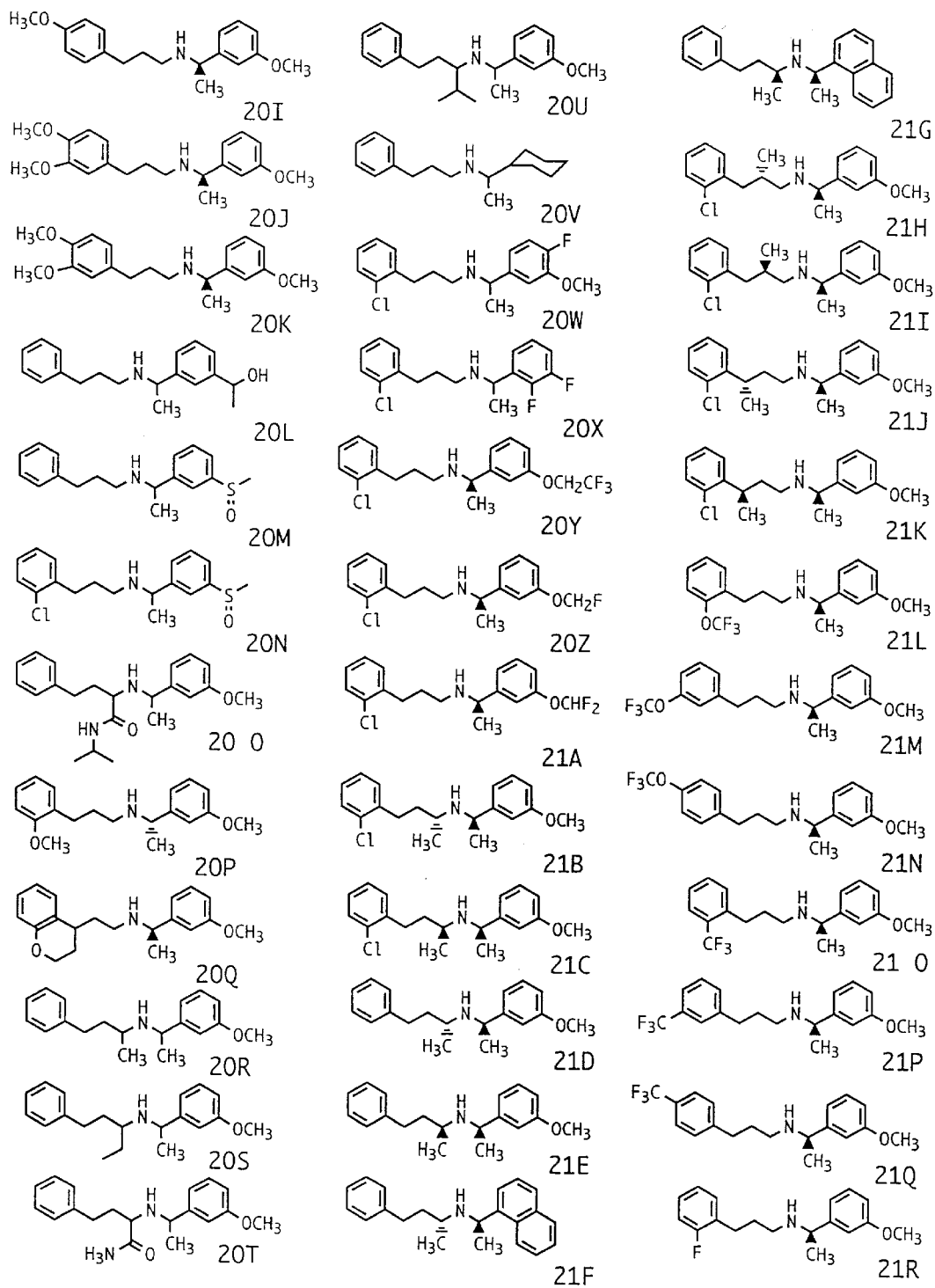
Figure 1P:
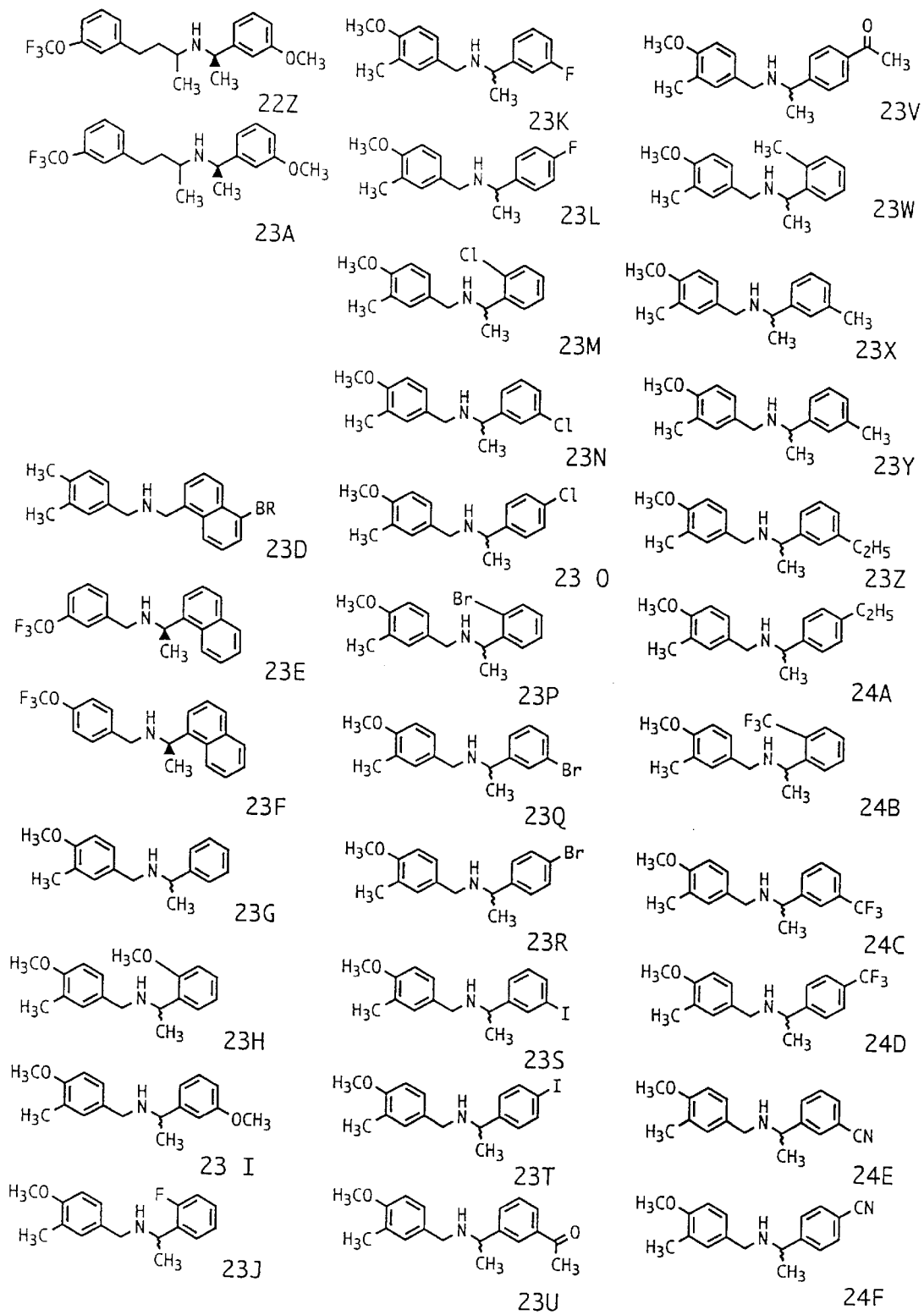
Figure 1Q:
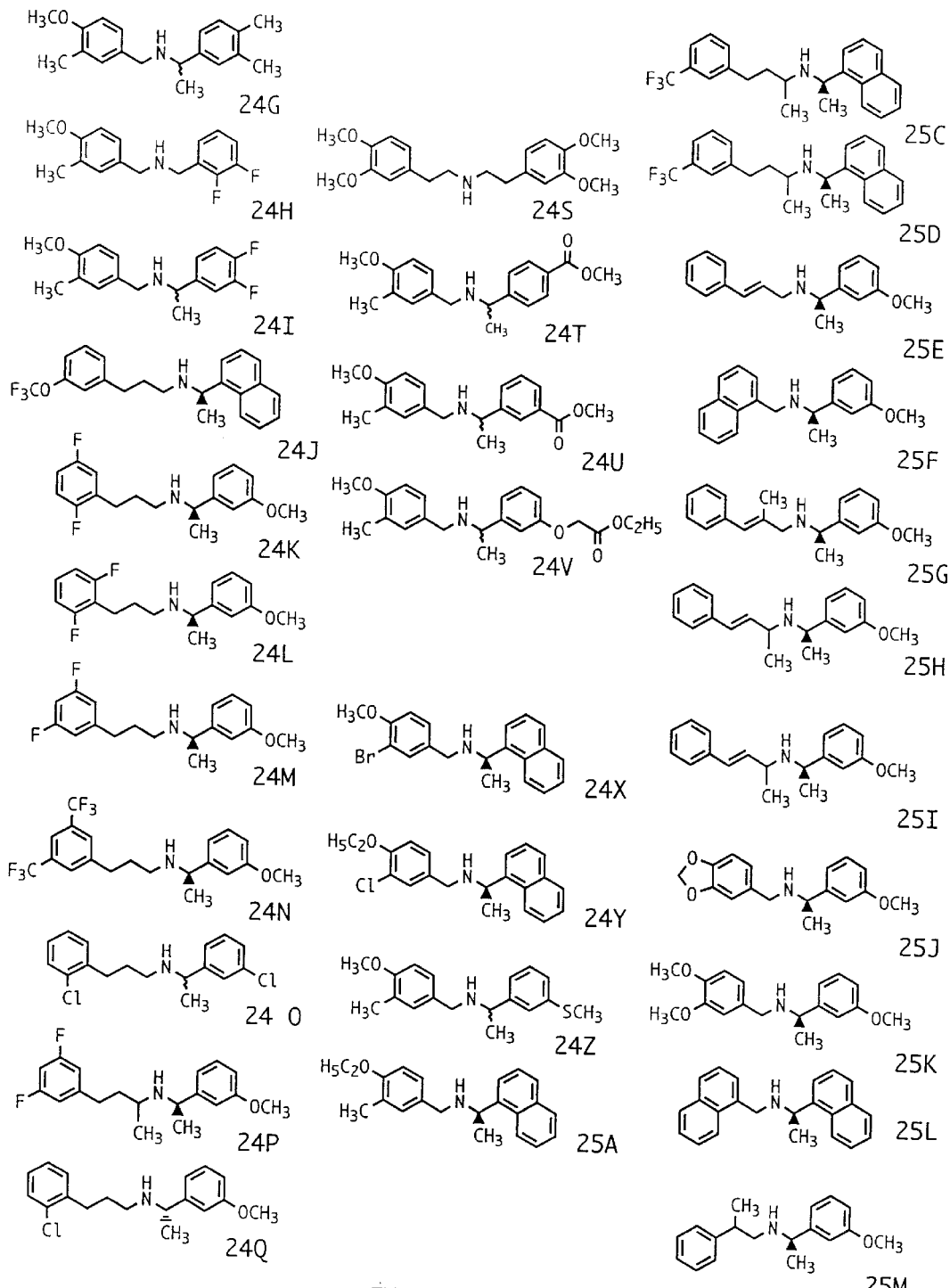
Figure 2:
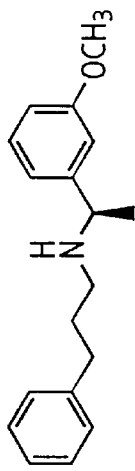
FIGS. 2–131 provided physical data for representative compounds herein described.
Figure 3:
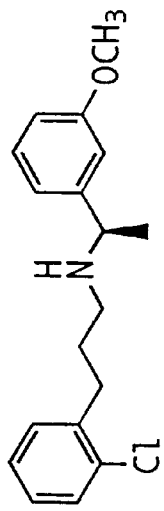
Figure 4:
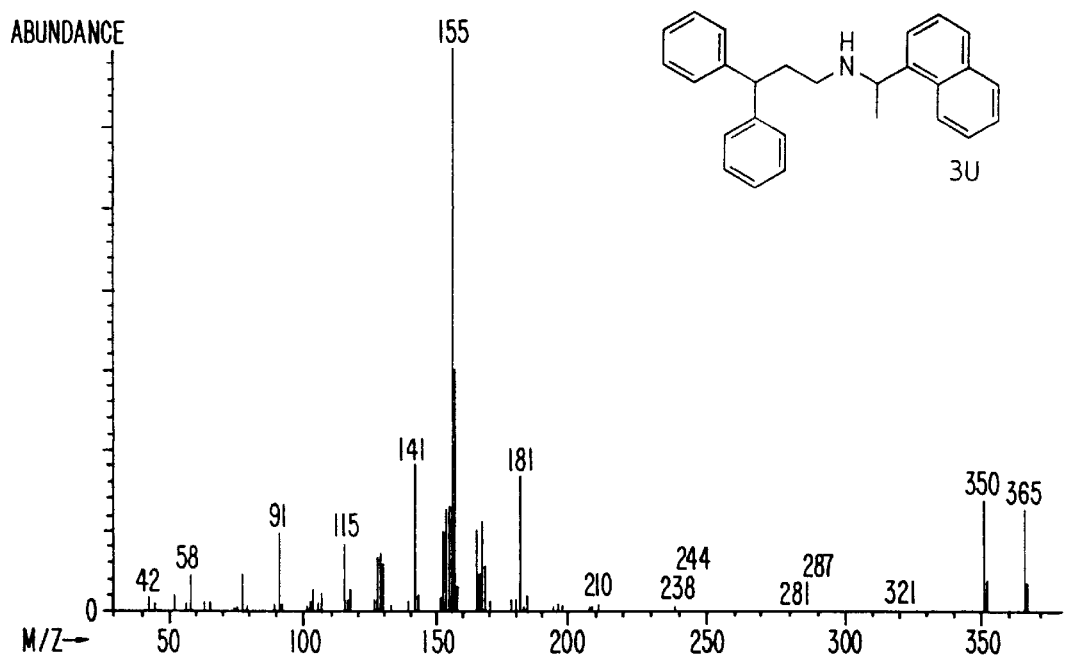
Figure 5:
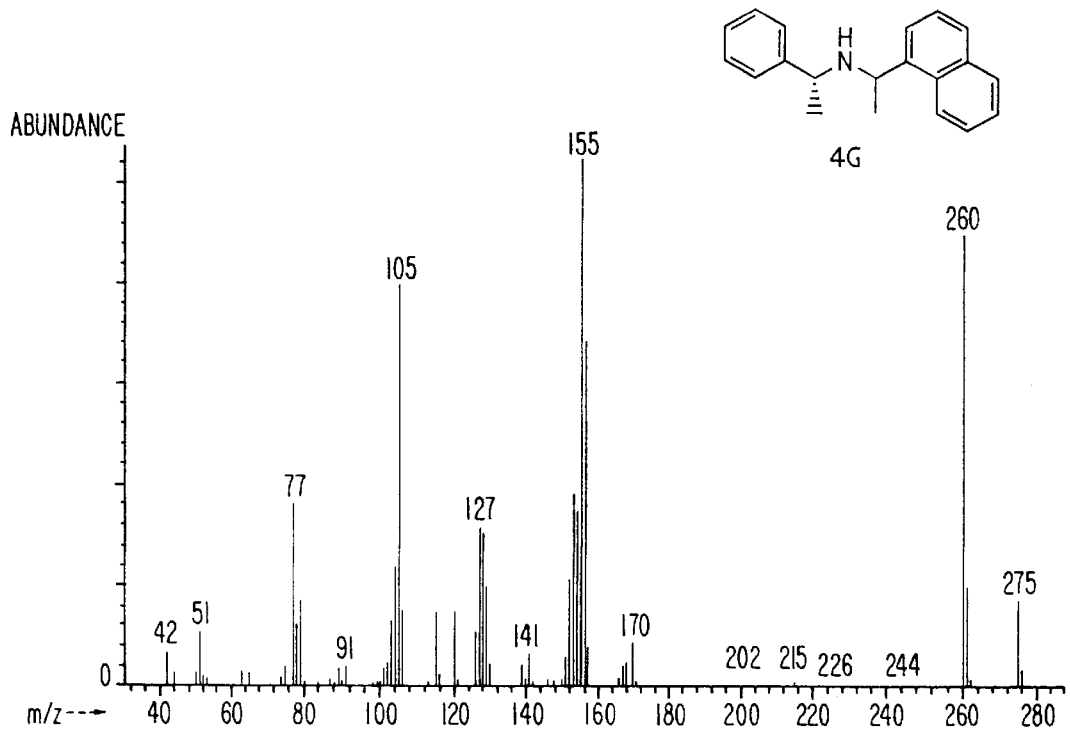
Figure 6:
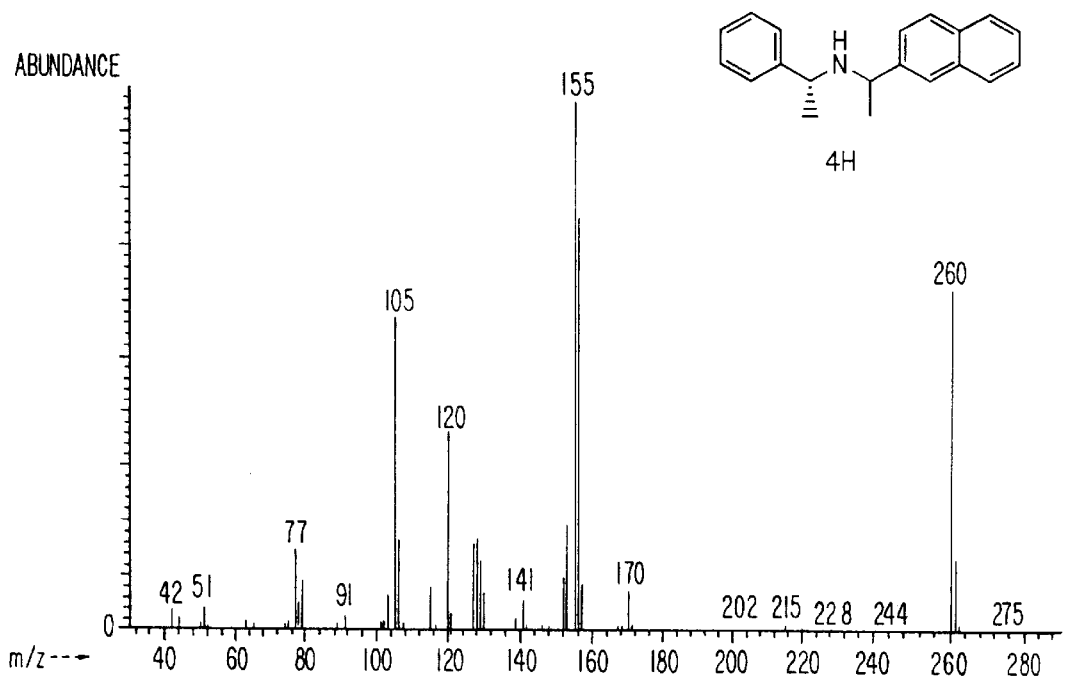
Figure 7:
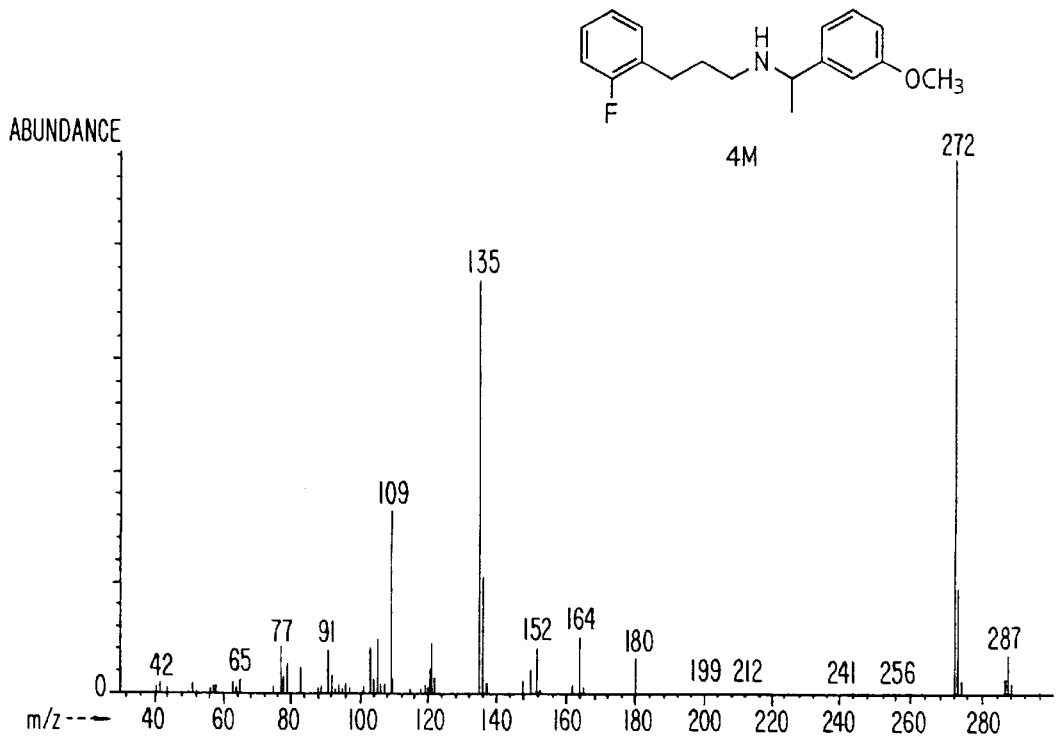
Figure 8:
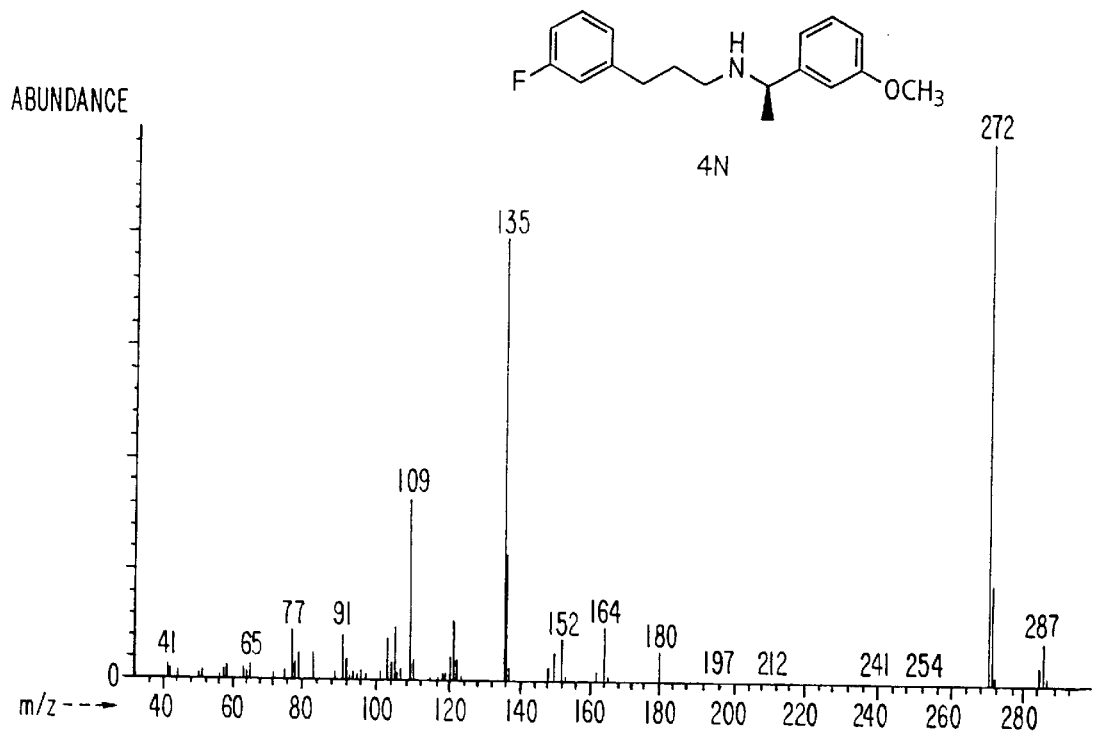
Figure 9:
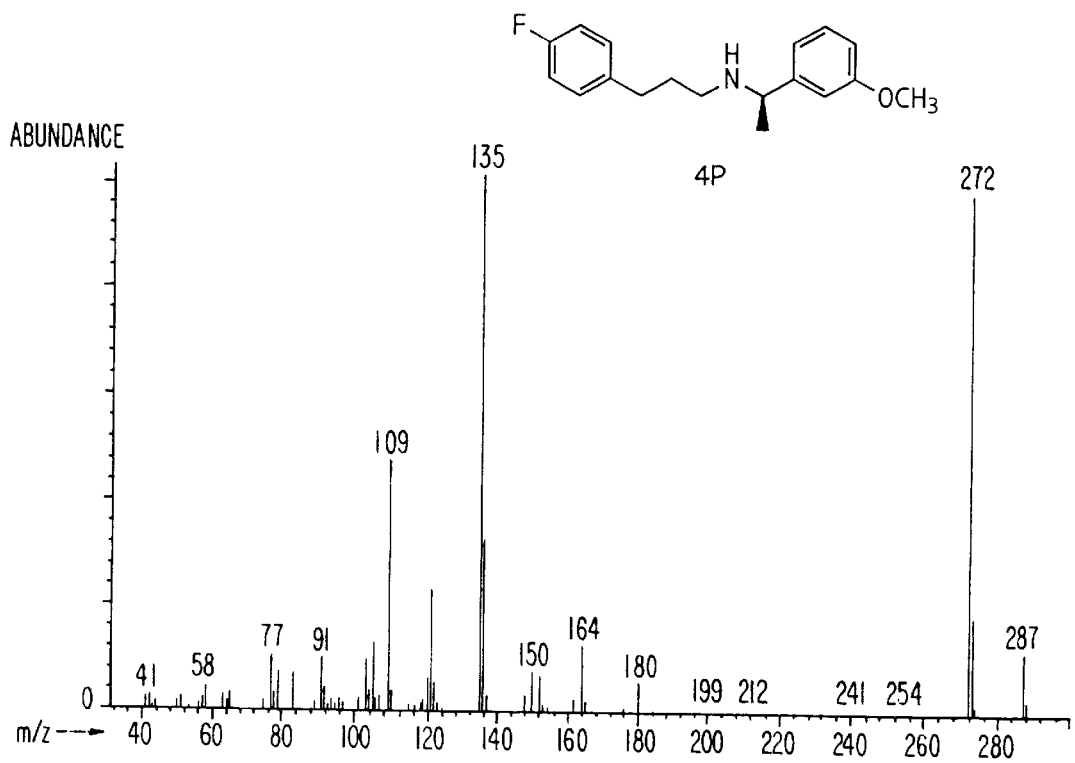
Figure 10:
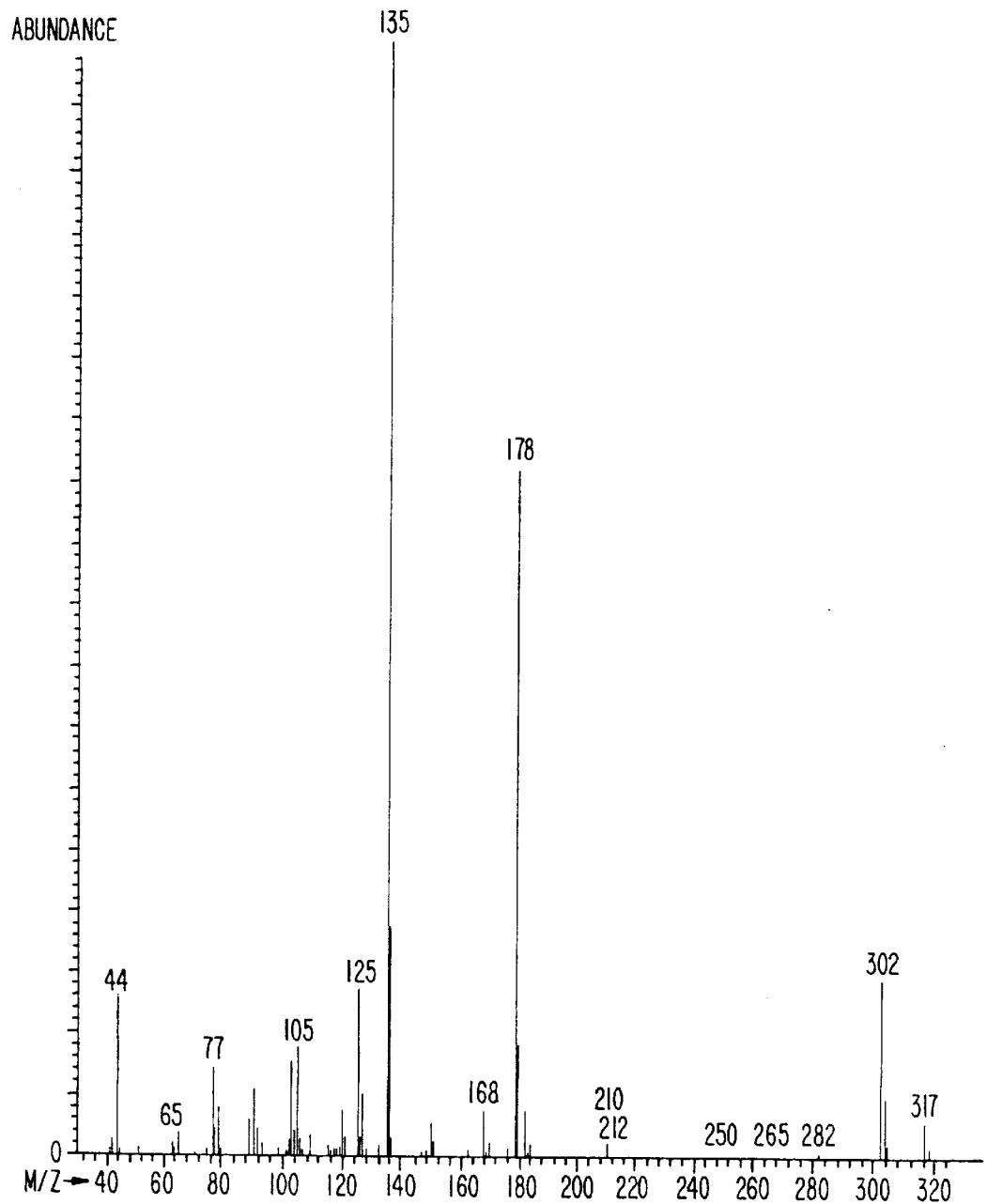
Figure 11:
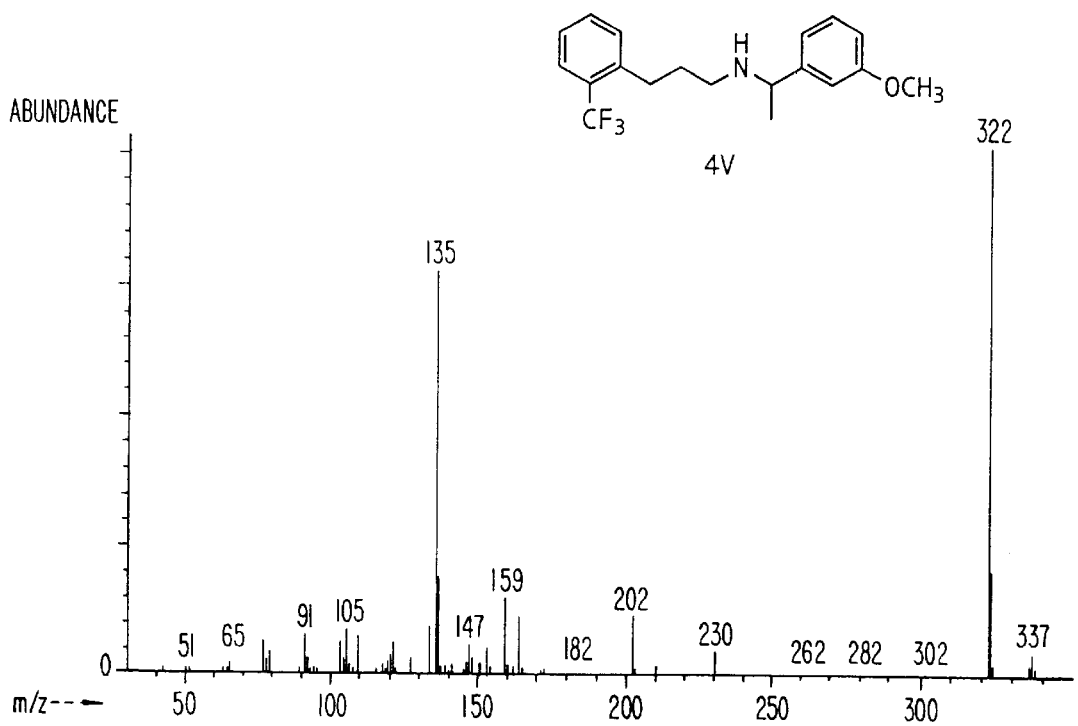
Figure 12:
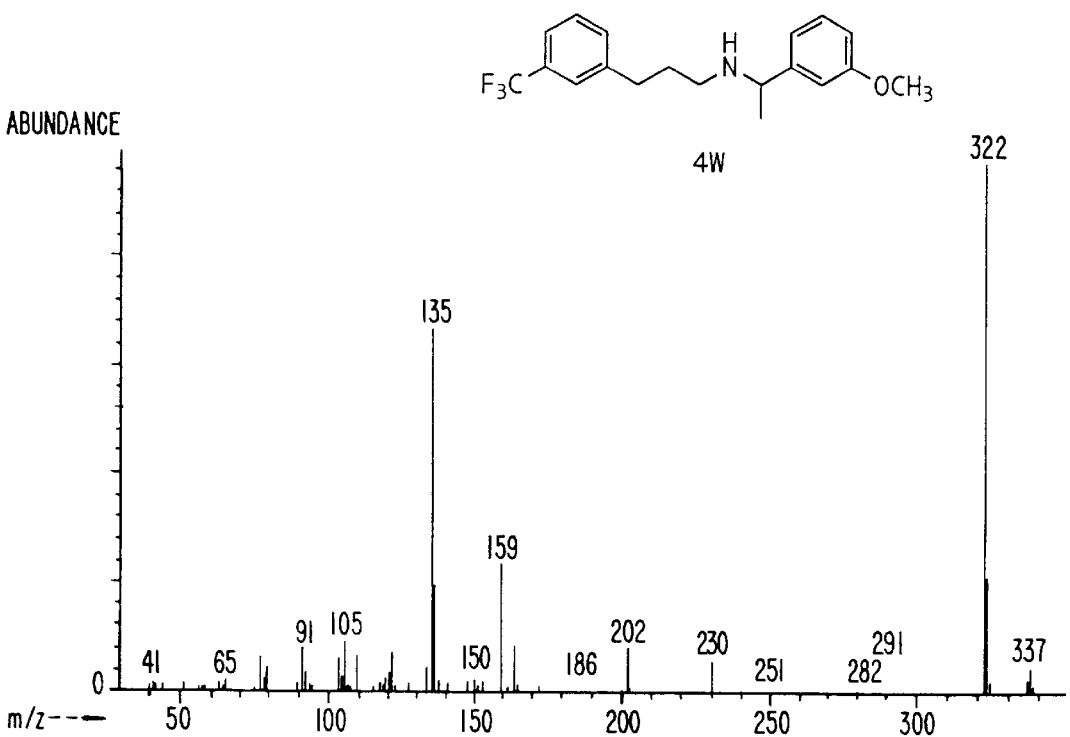
Figure 13:
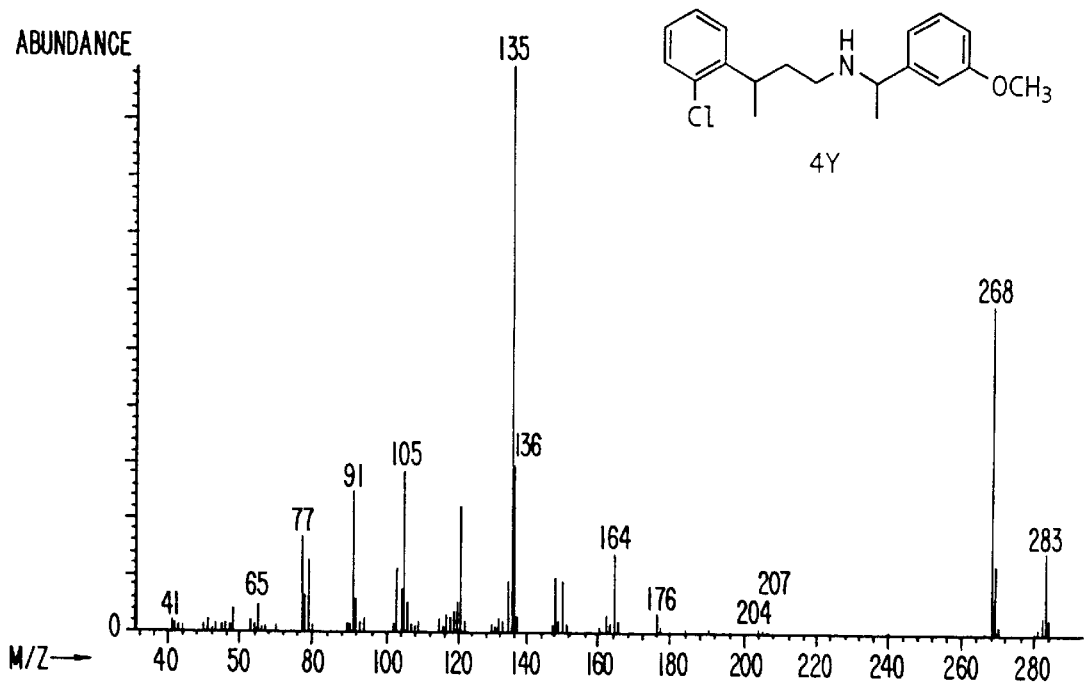
Figure 14:
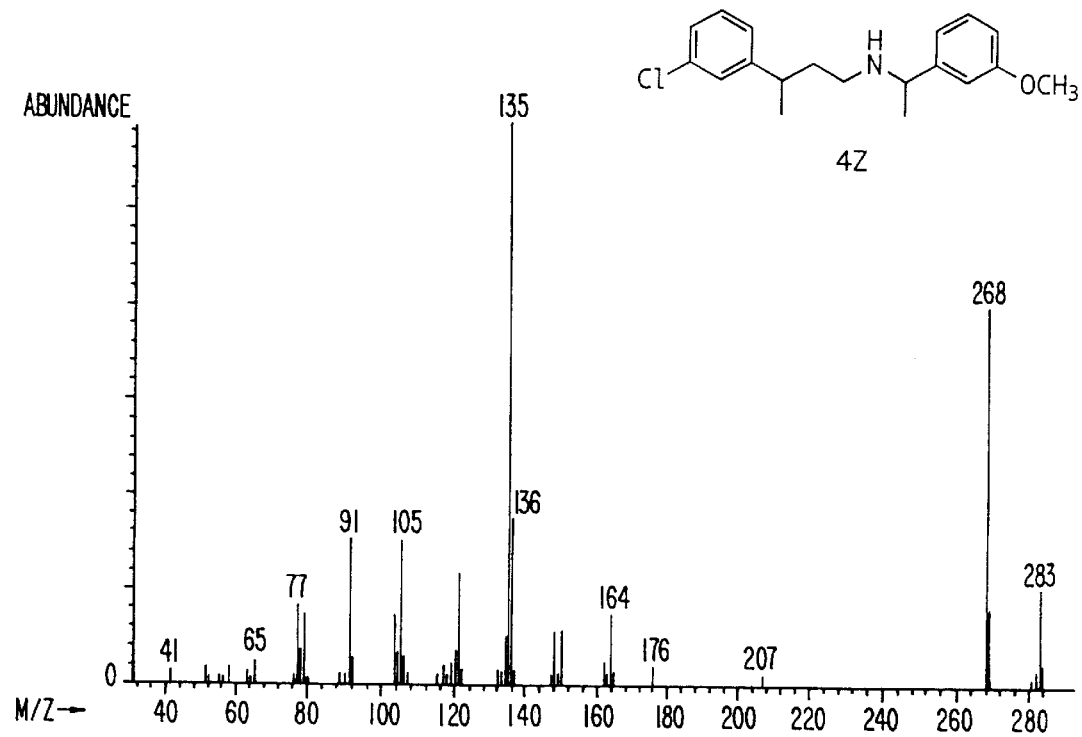
Figure 15:
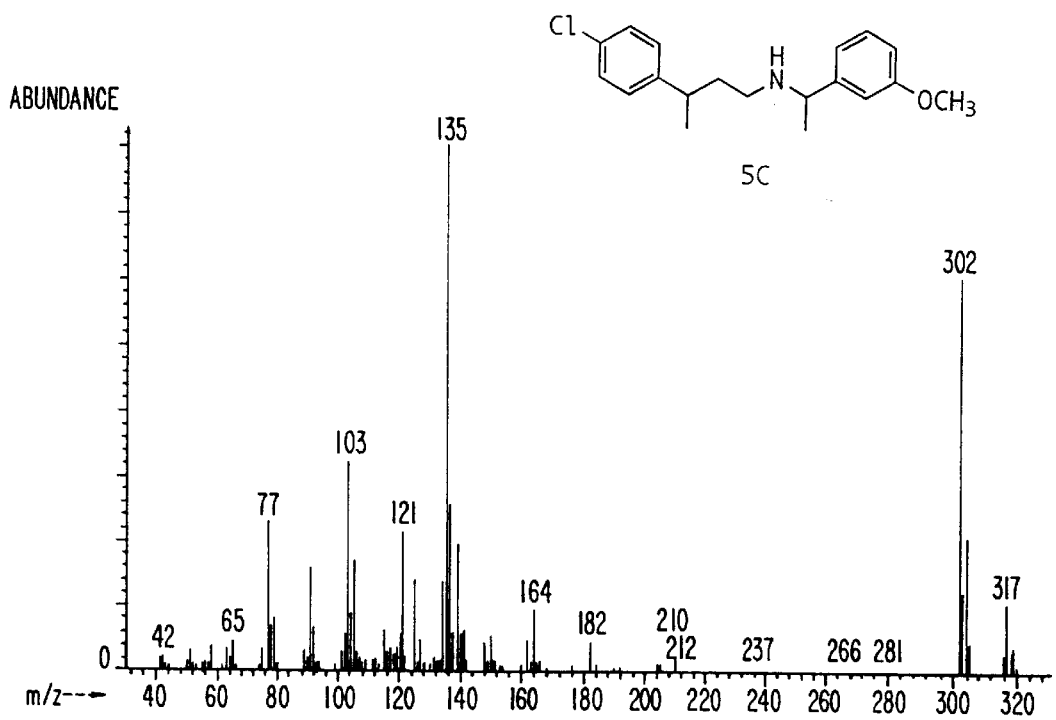
Figure 16:
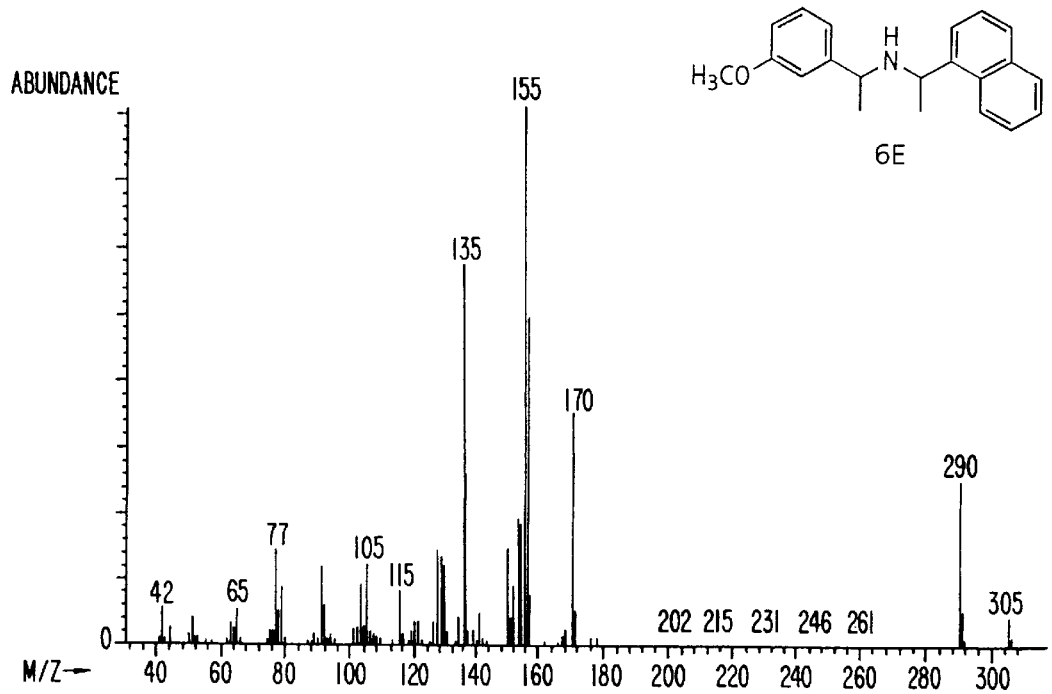
Figure 17:
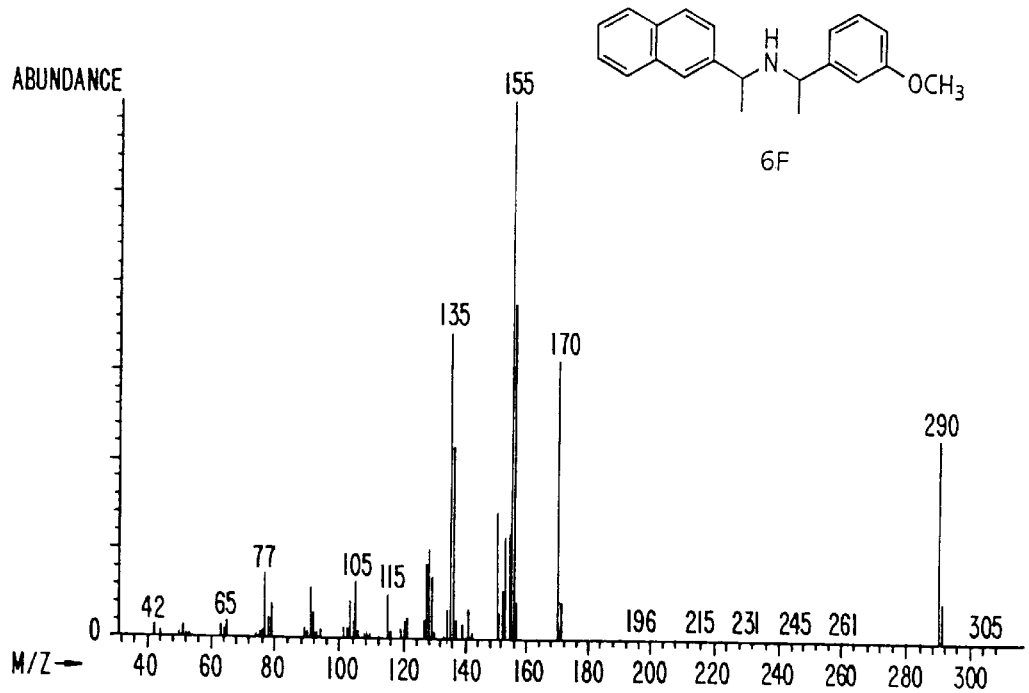
Figure 18:
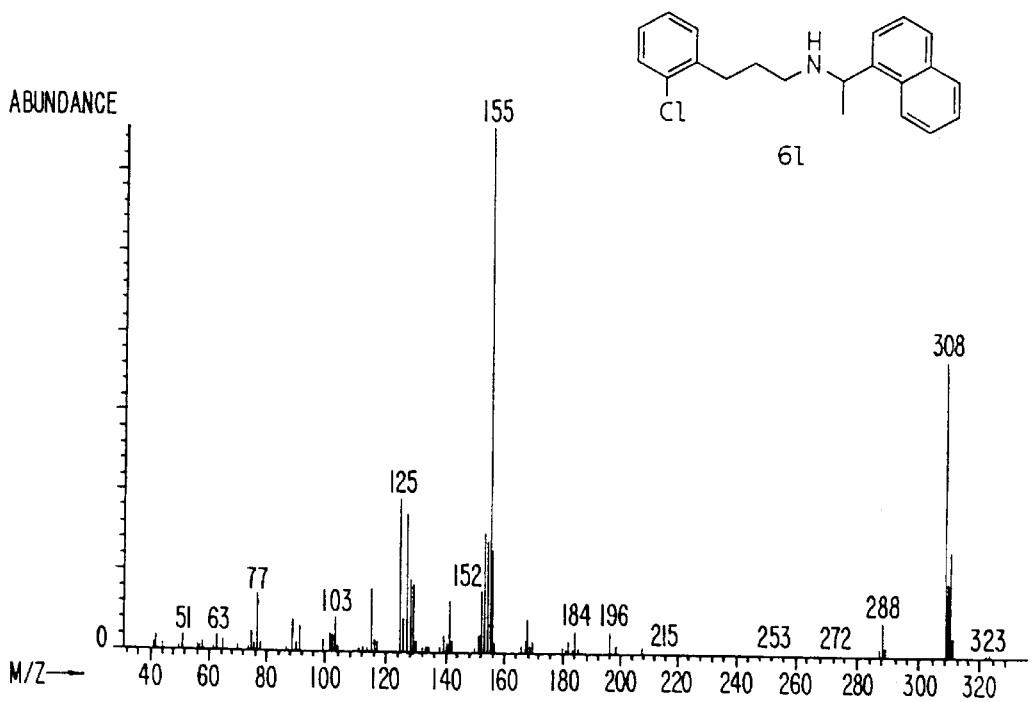
Figure 19:
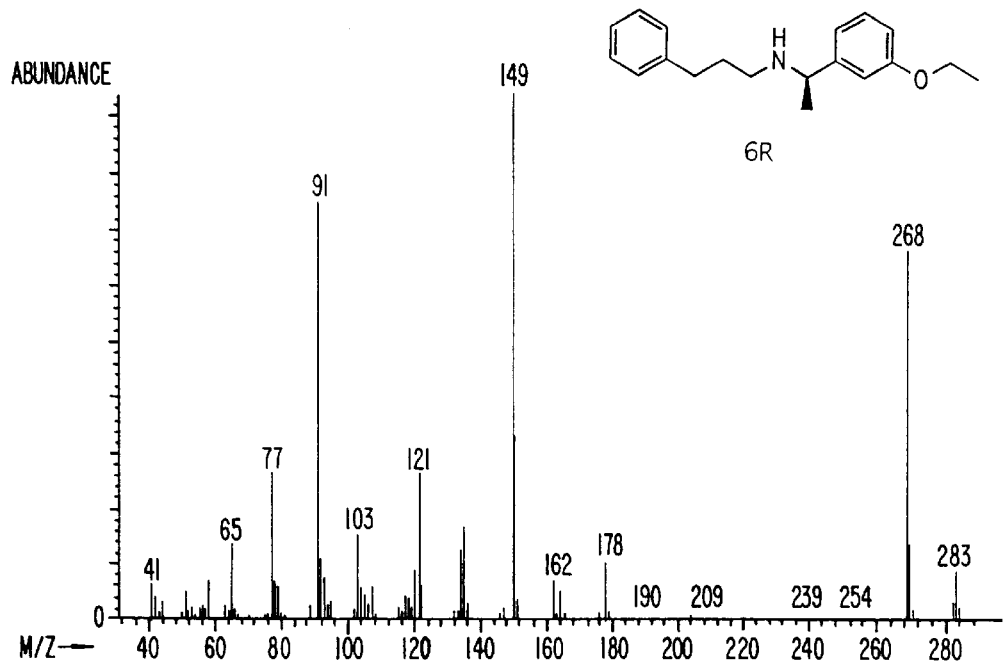
Figure 20:
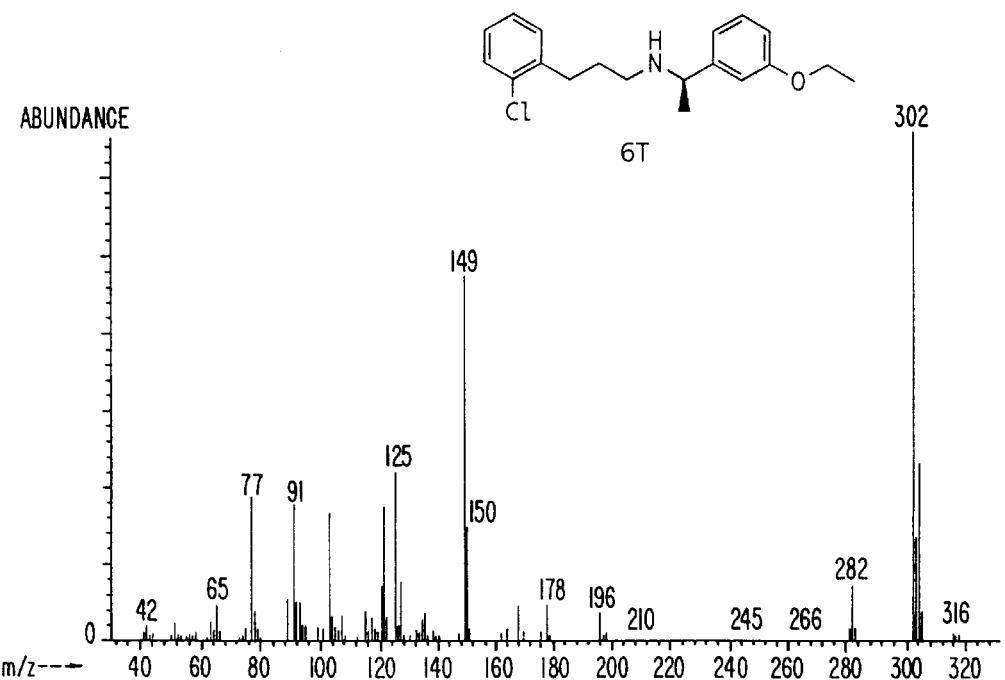
Figure 21:
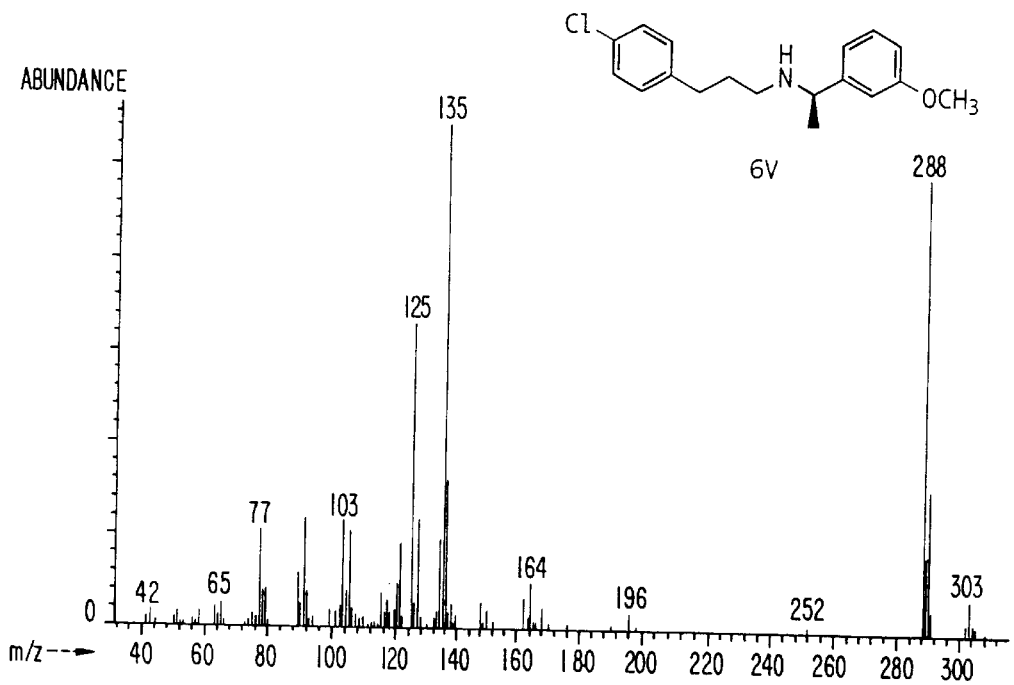
Figure 22:
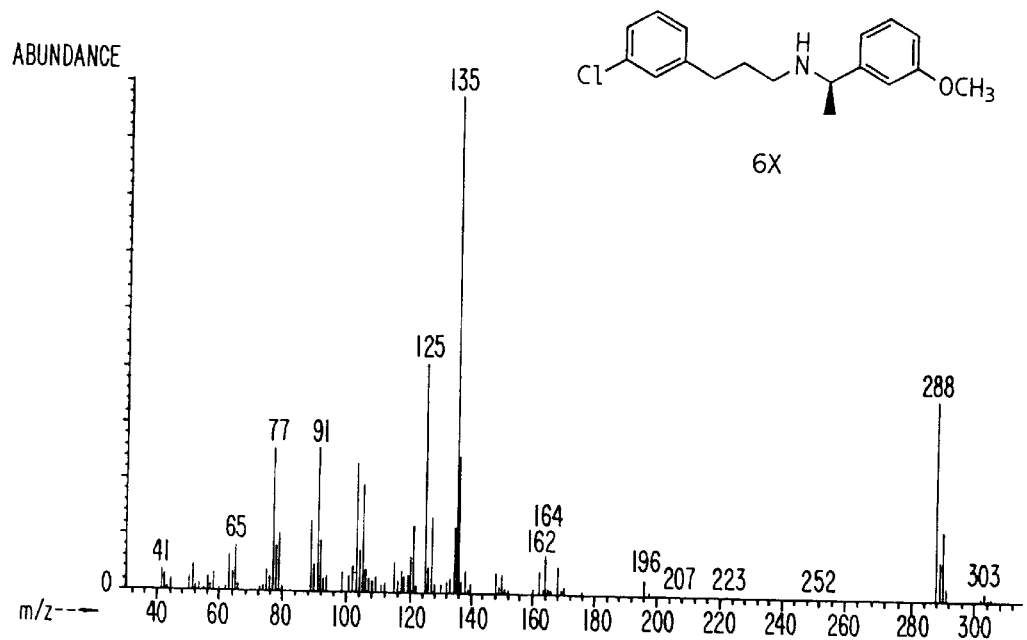
Figure 23:
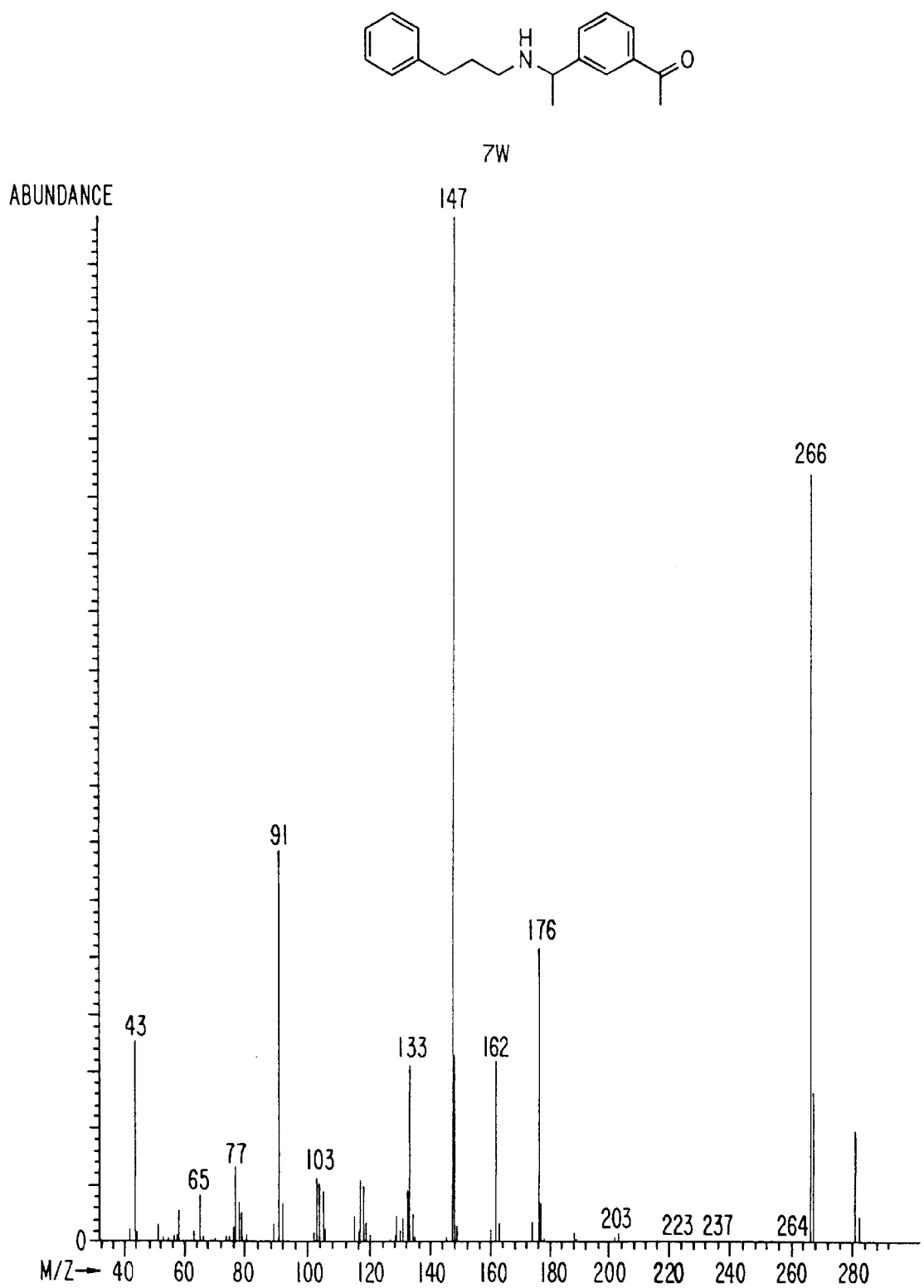
Figure 24:
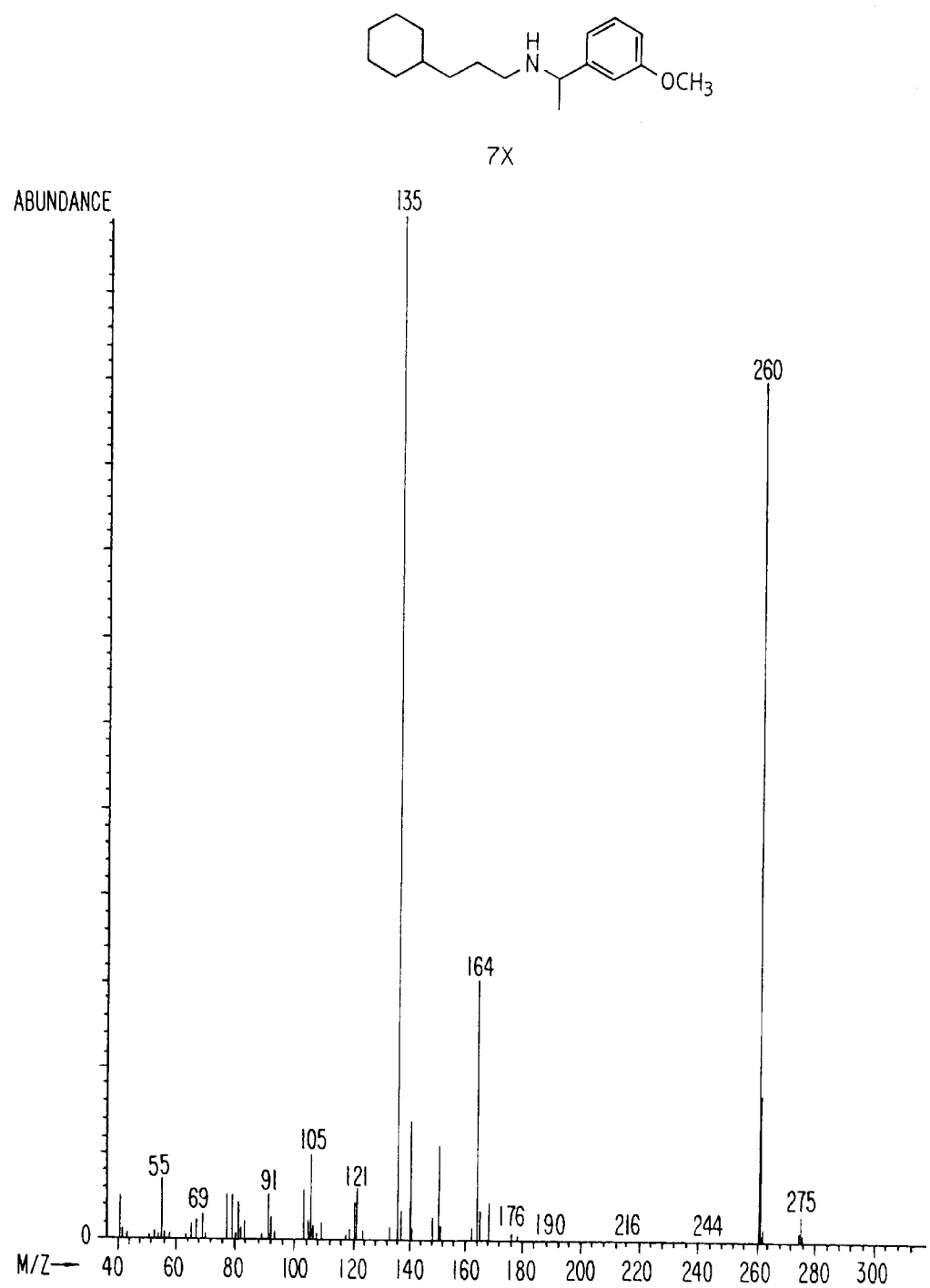
Figure 25:
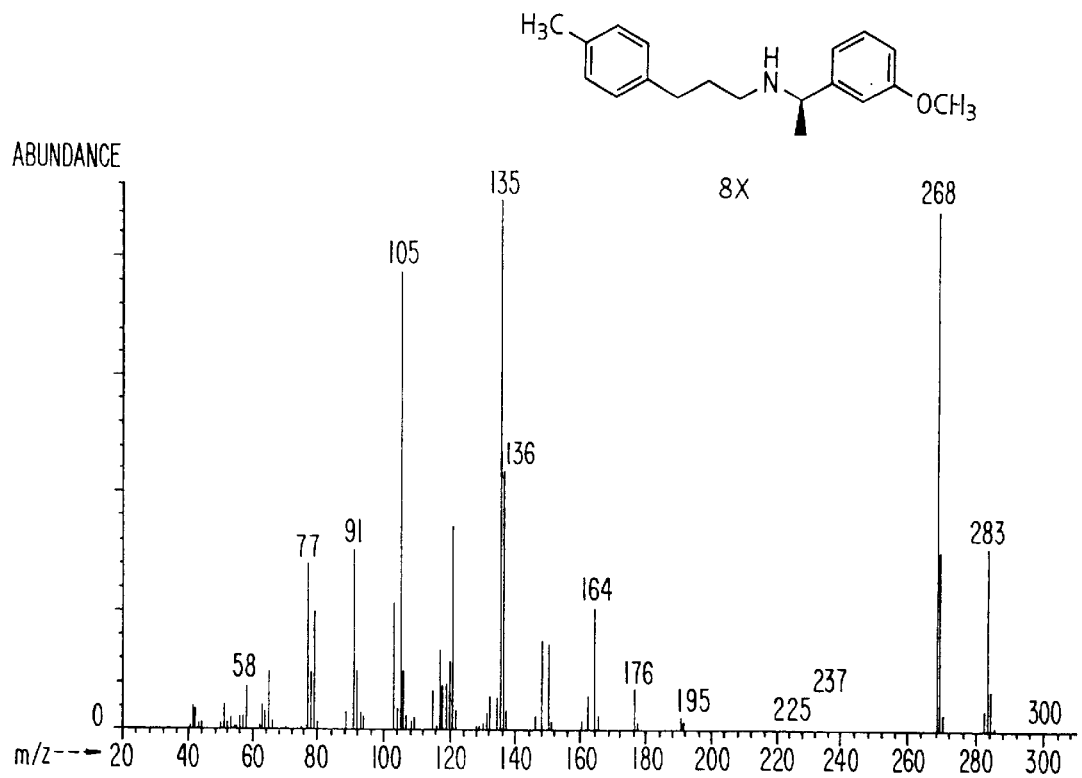
Figure 26:
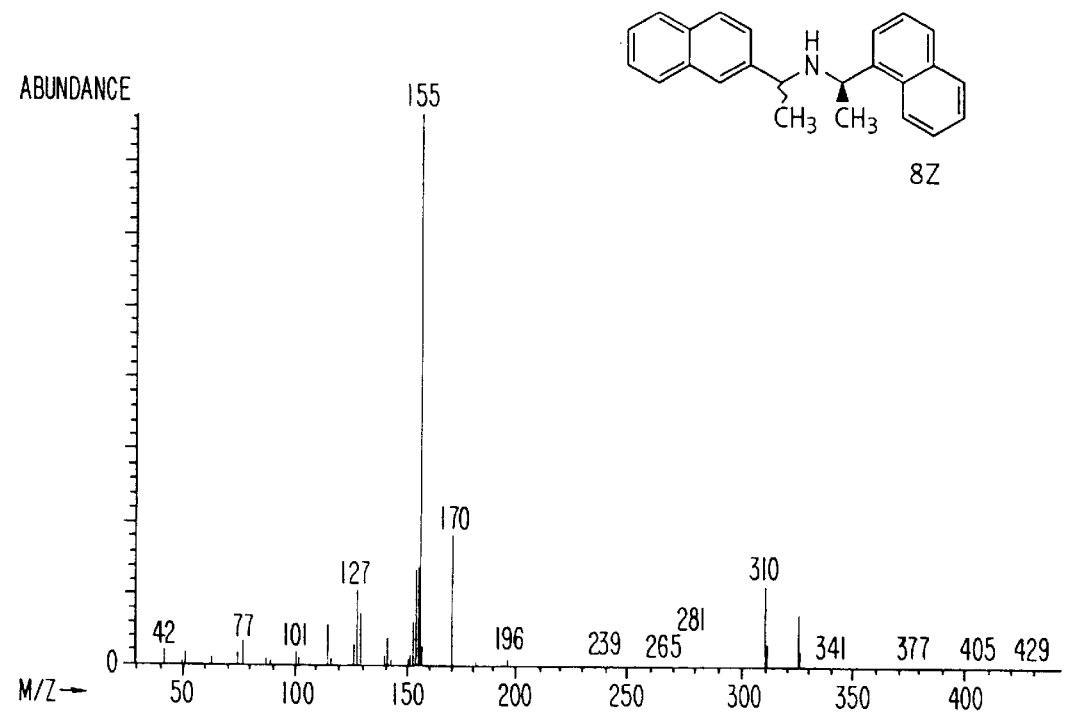
Figure 27:
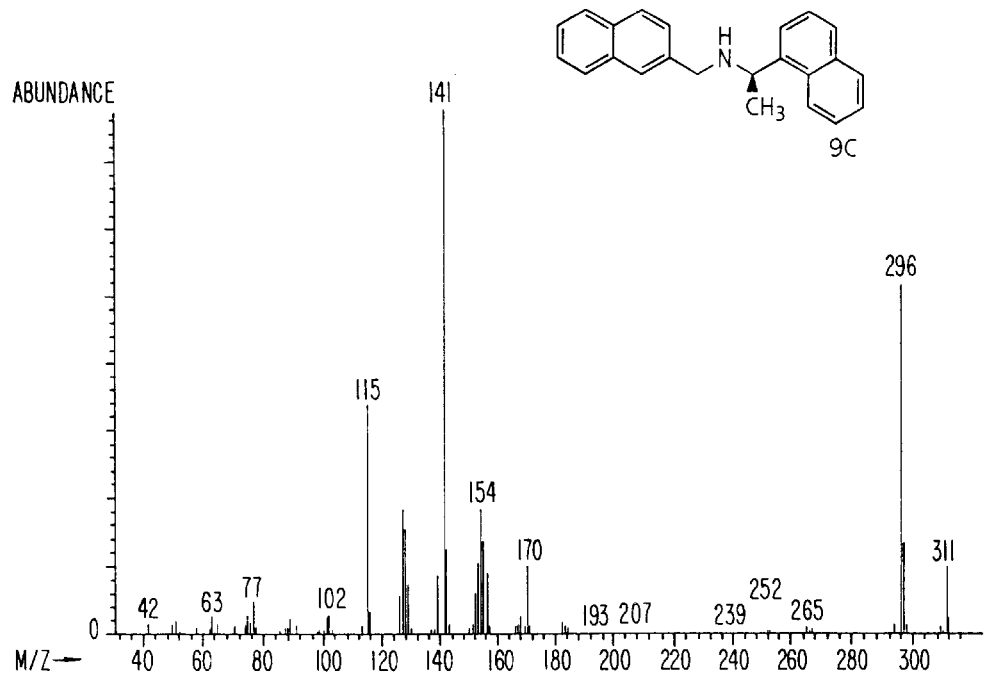
Figure 28:
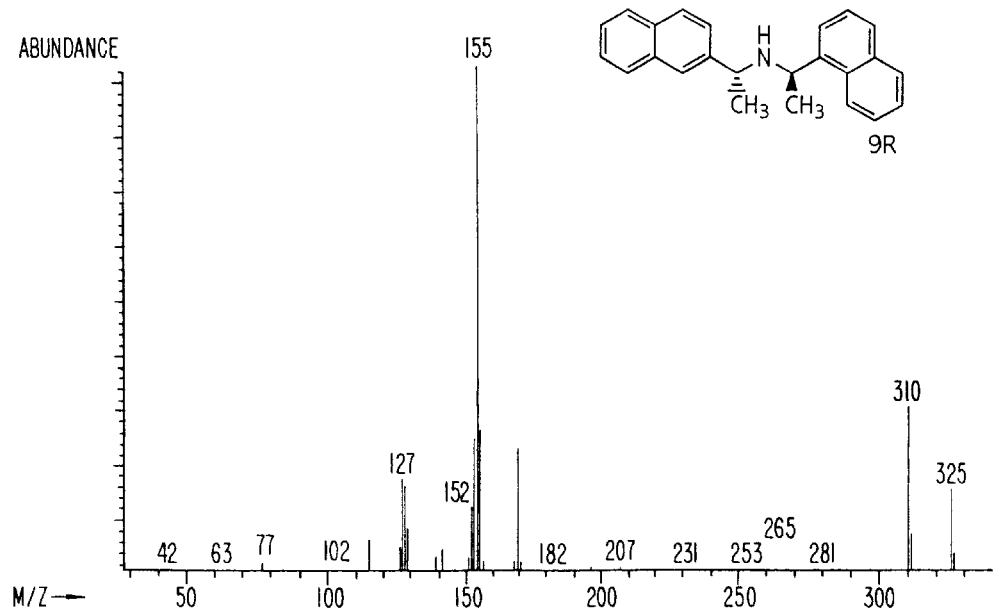
Figure 29:
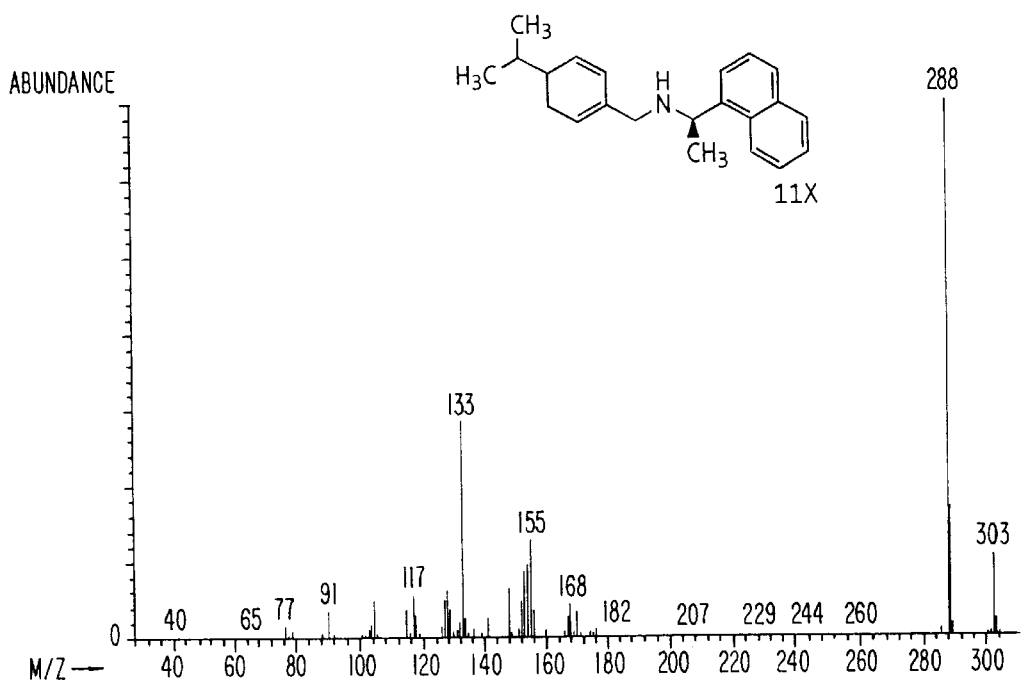
Figure 30:
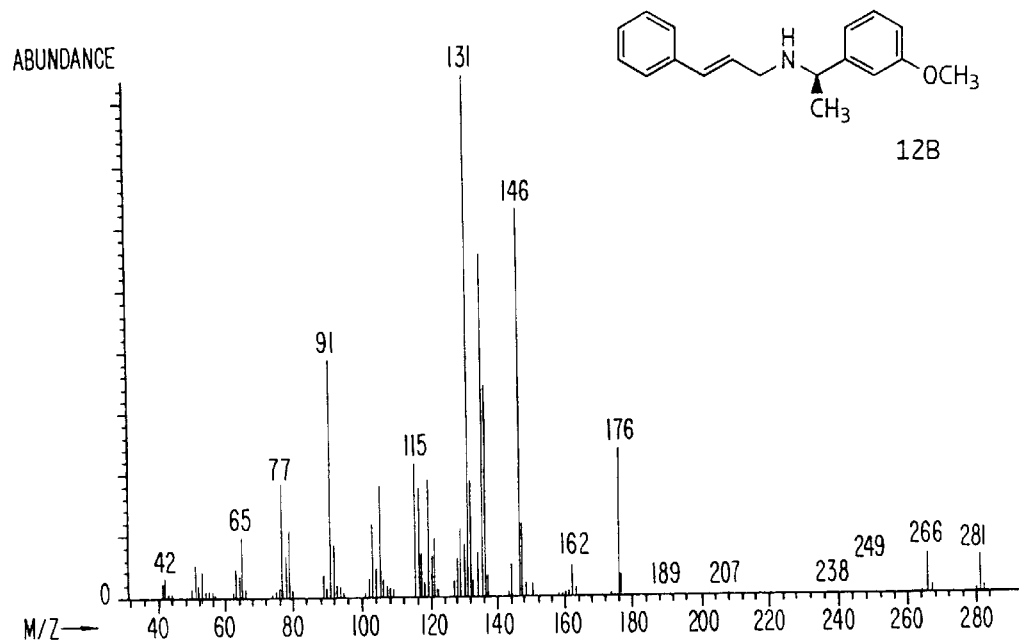
Figure 31:
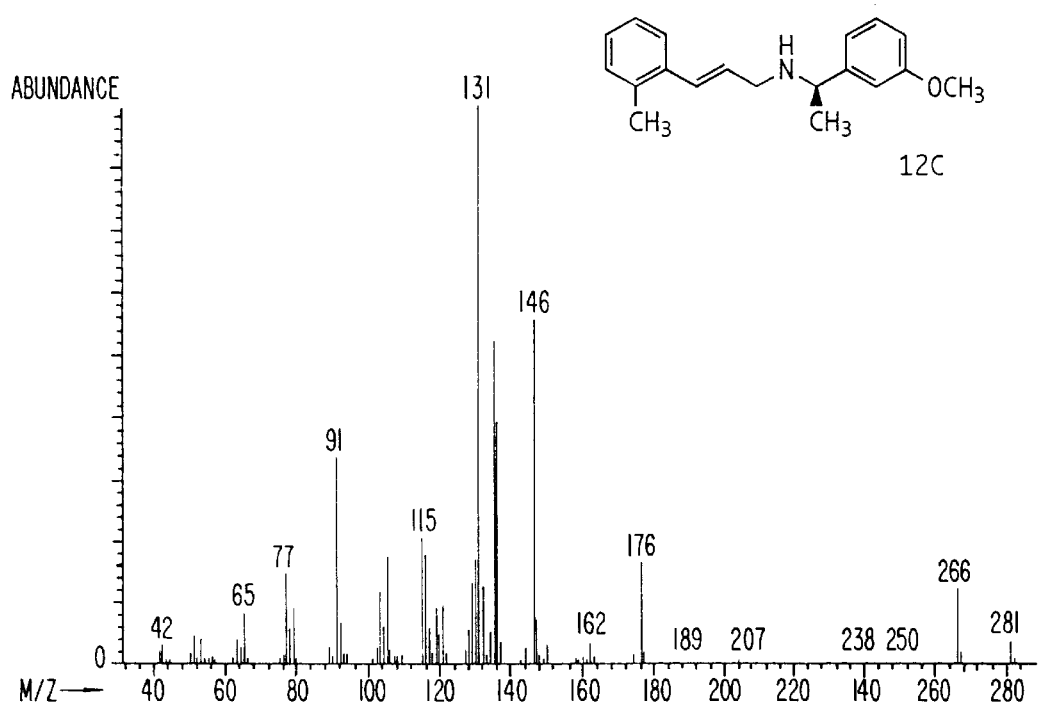
Figure 32:
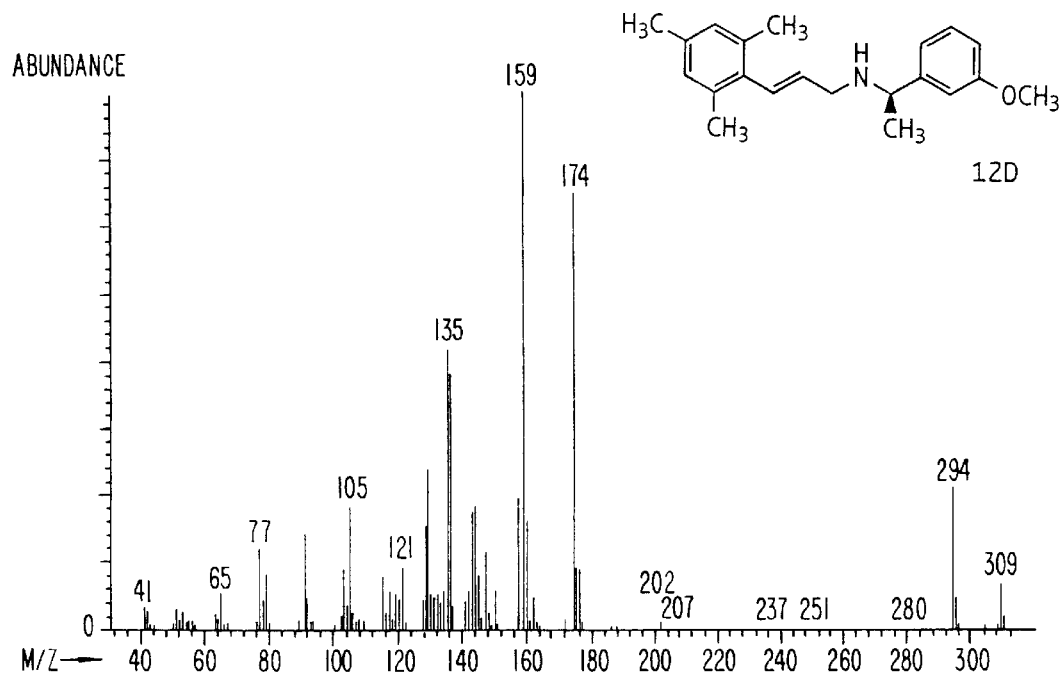
Figure 33:
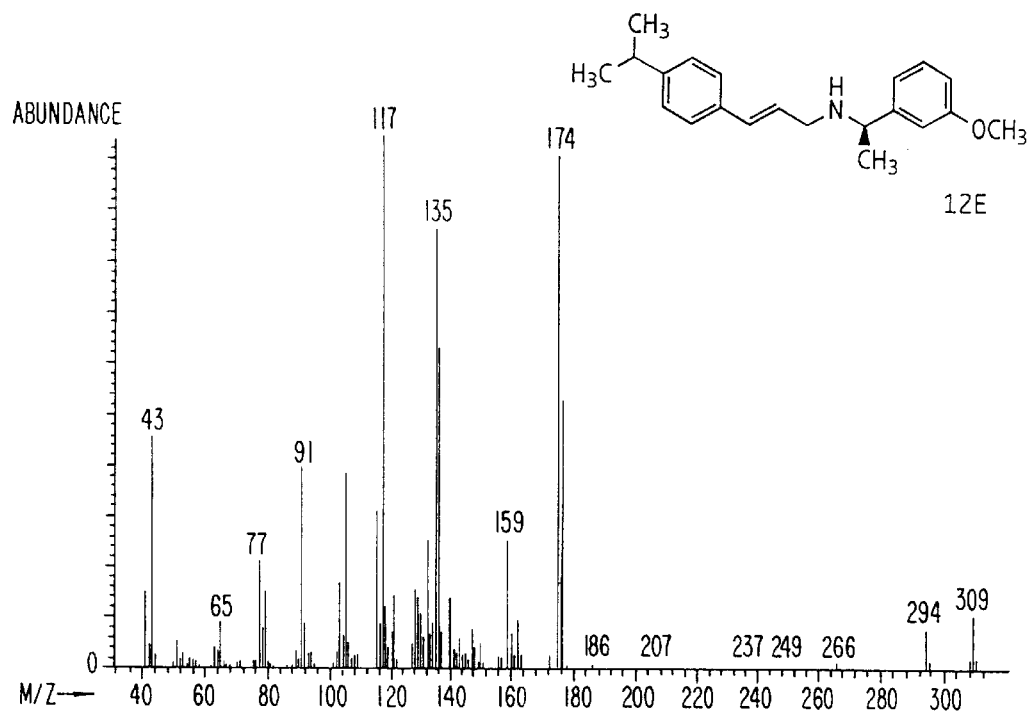
Figure 34:
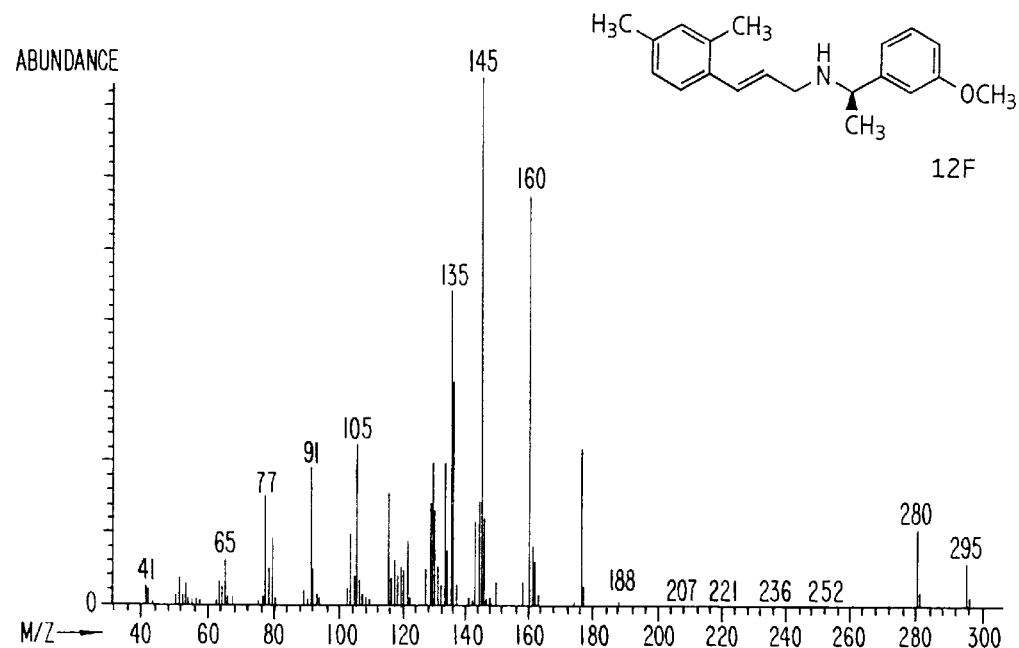
Figure 35:
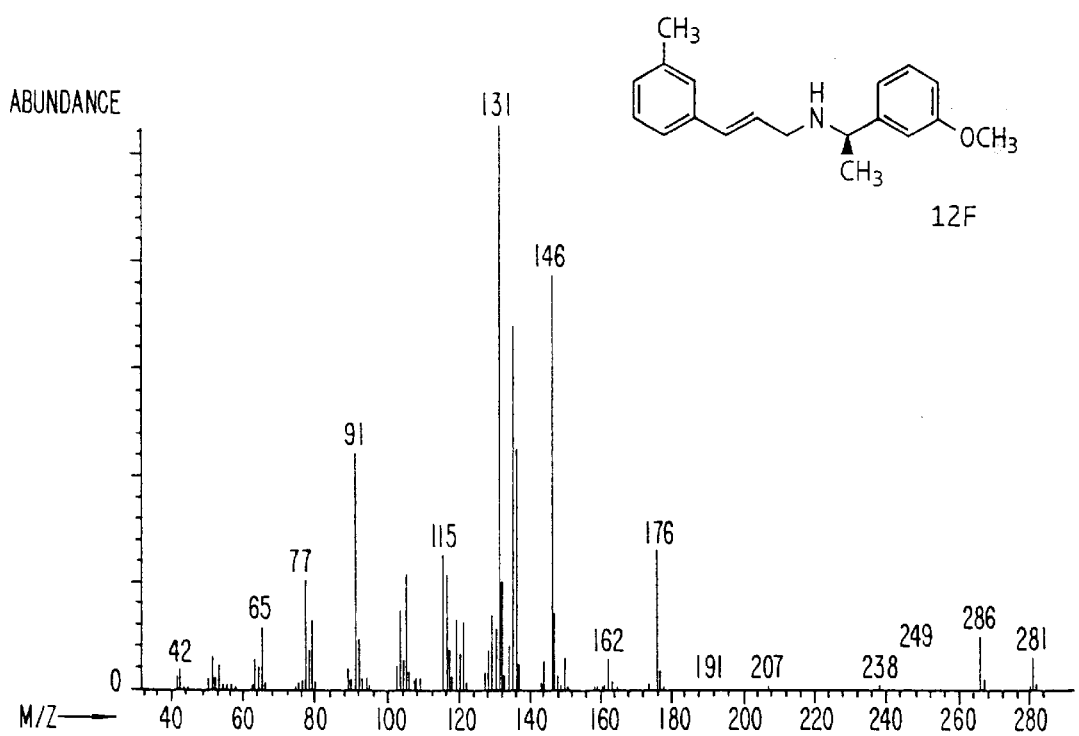
Figure 36:
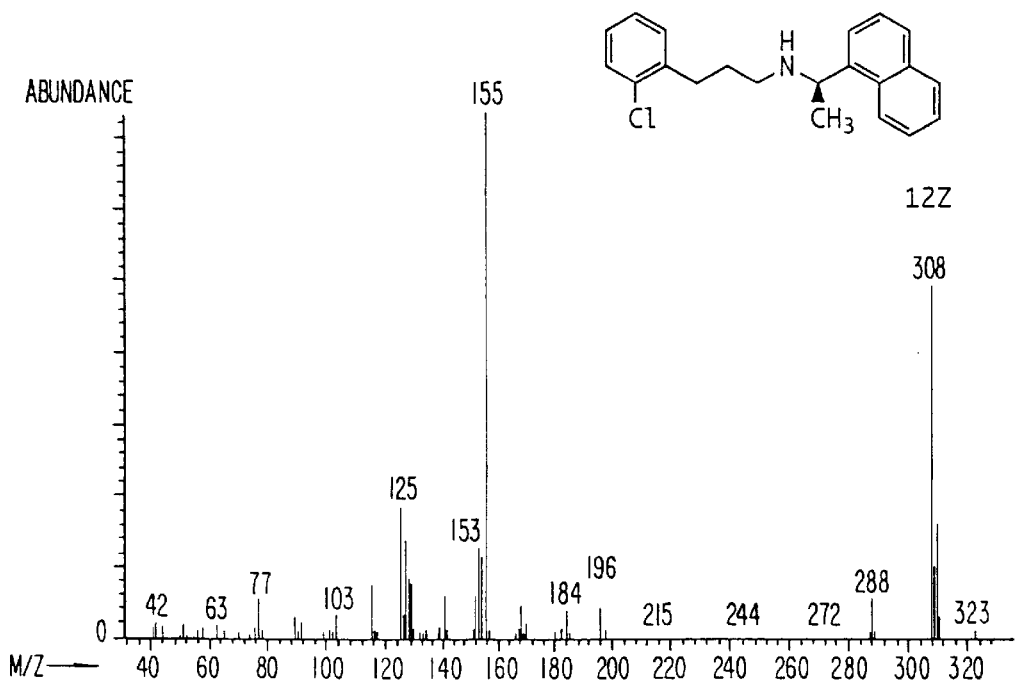
Figure 37:
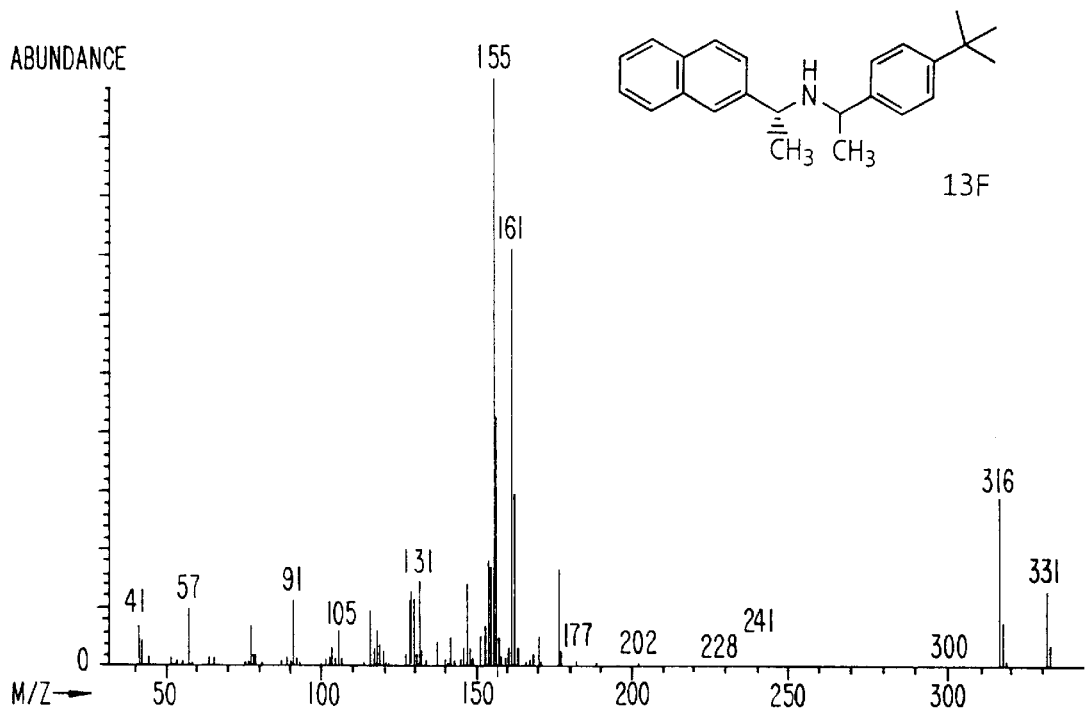
Figure 38:
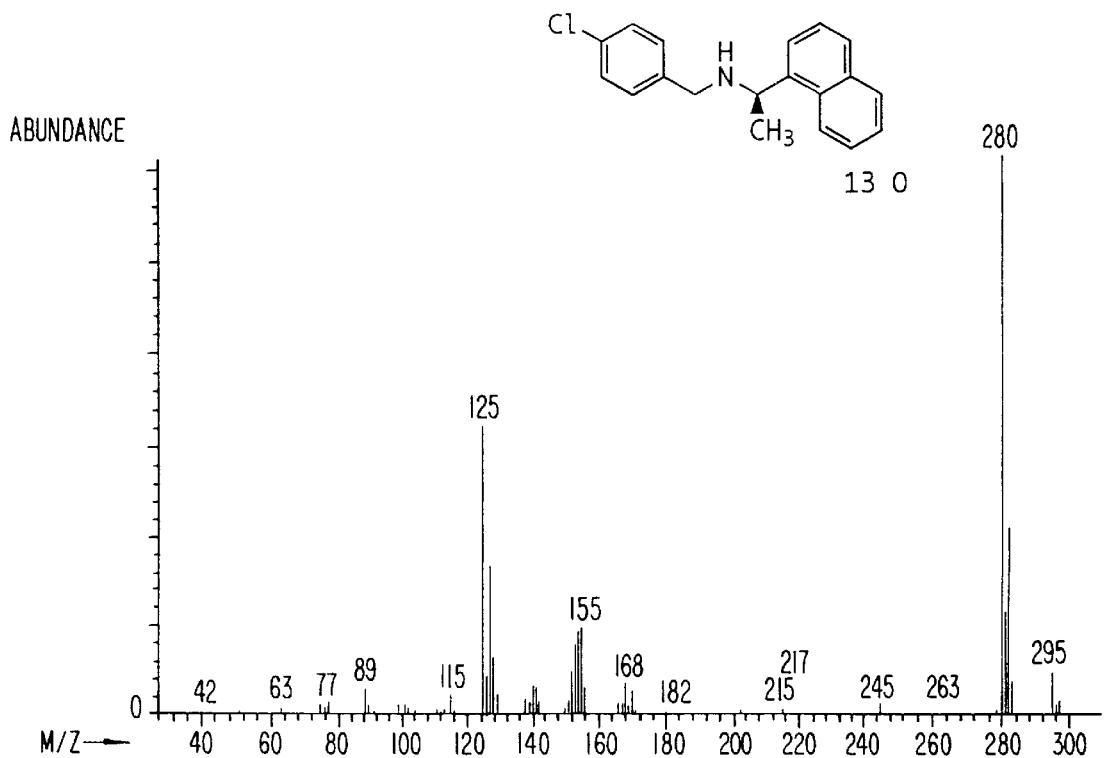
Figure 39:
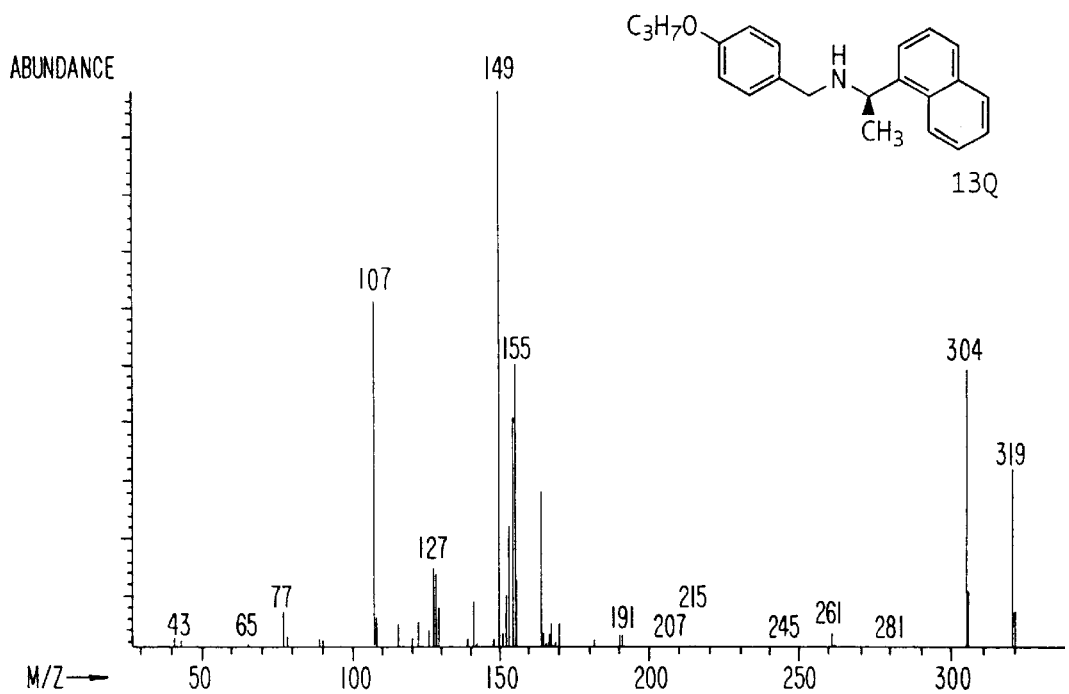
Figure 40:
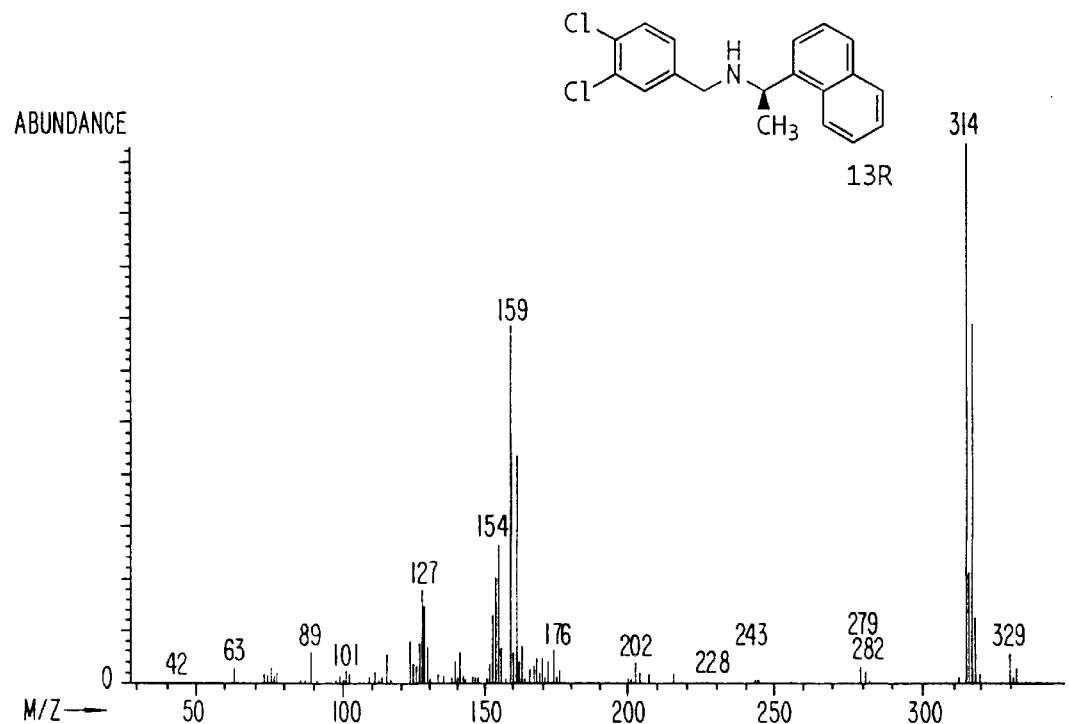
Figure 41:
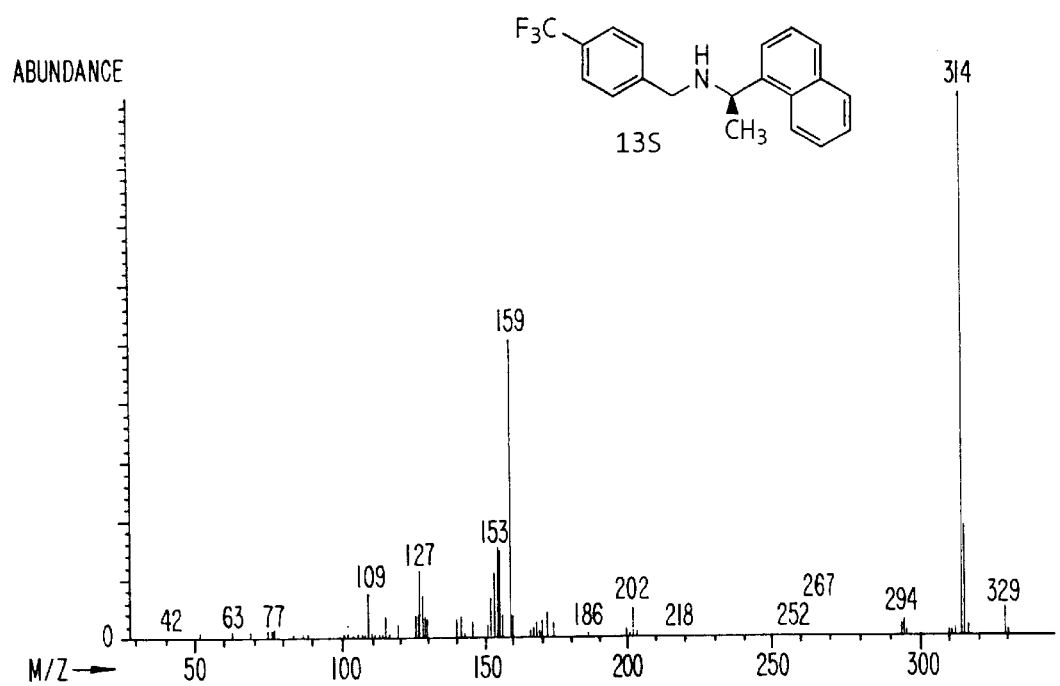
Figure 42:
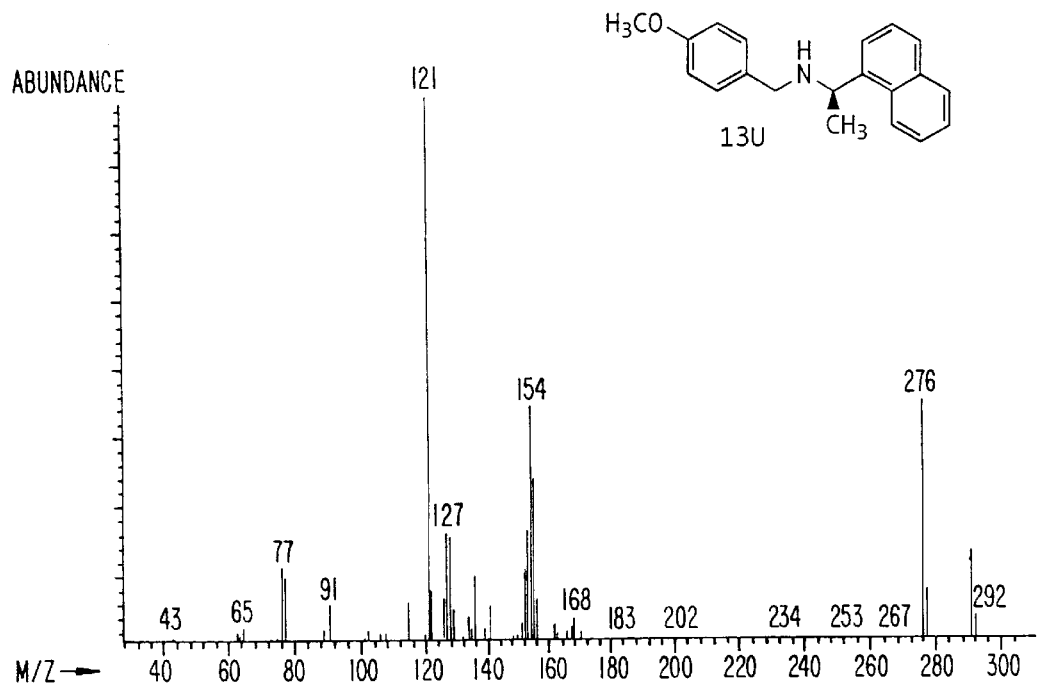
Figure 43:
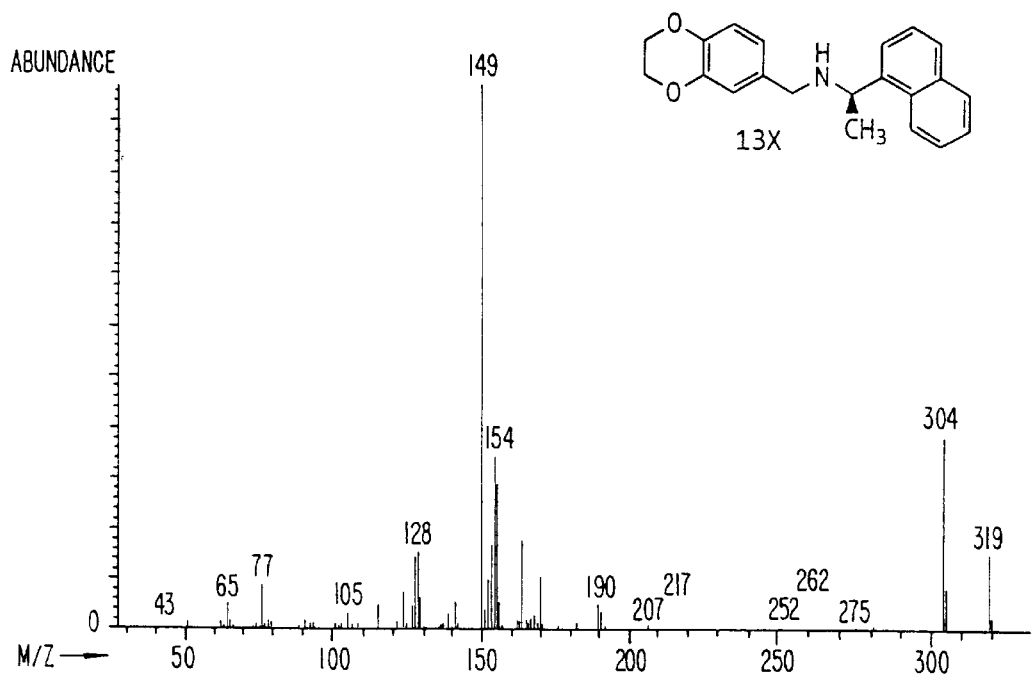
Figure 44:
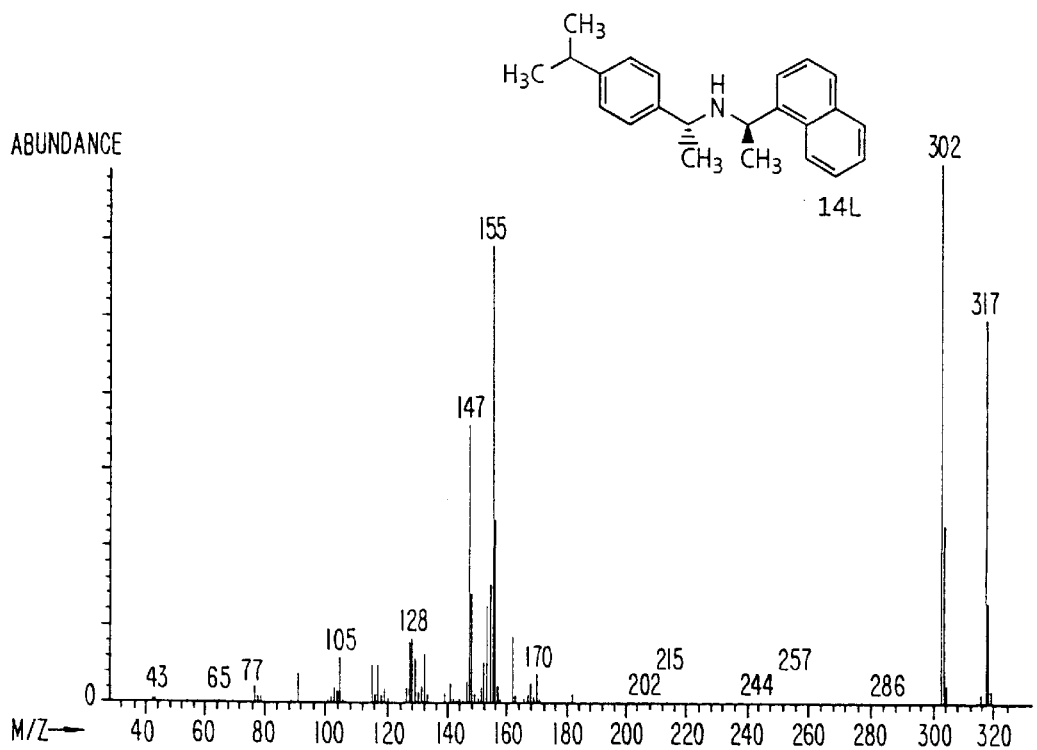
Figure 45:
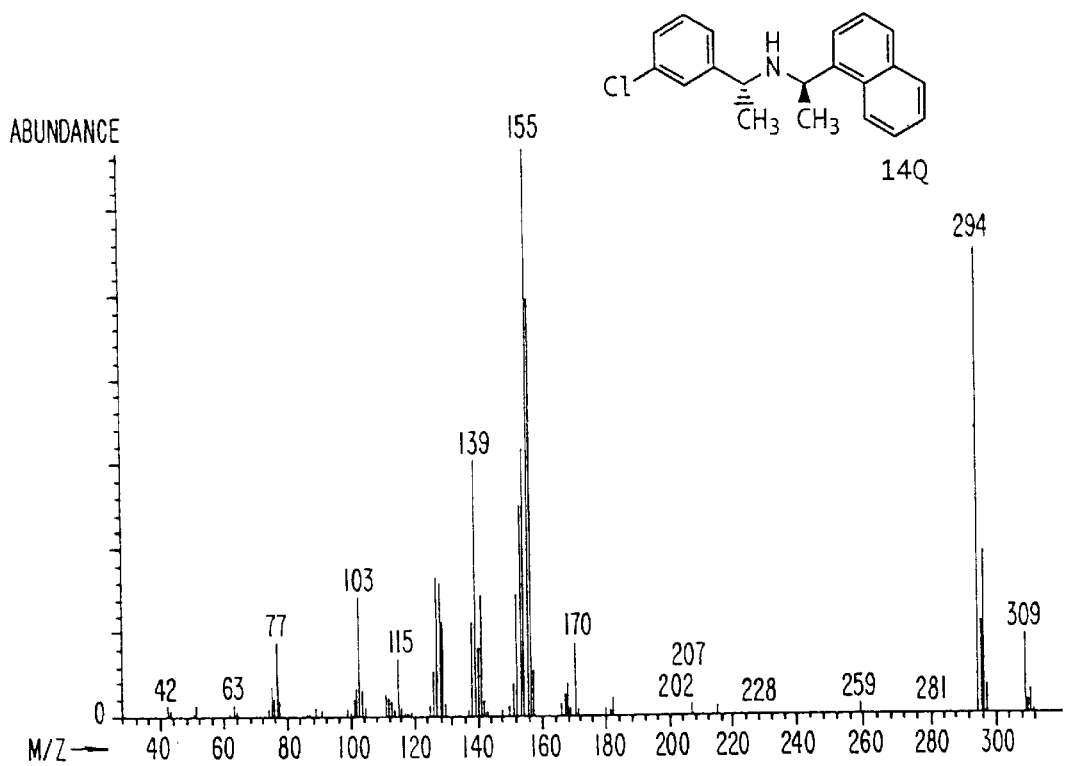
Figure 46:
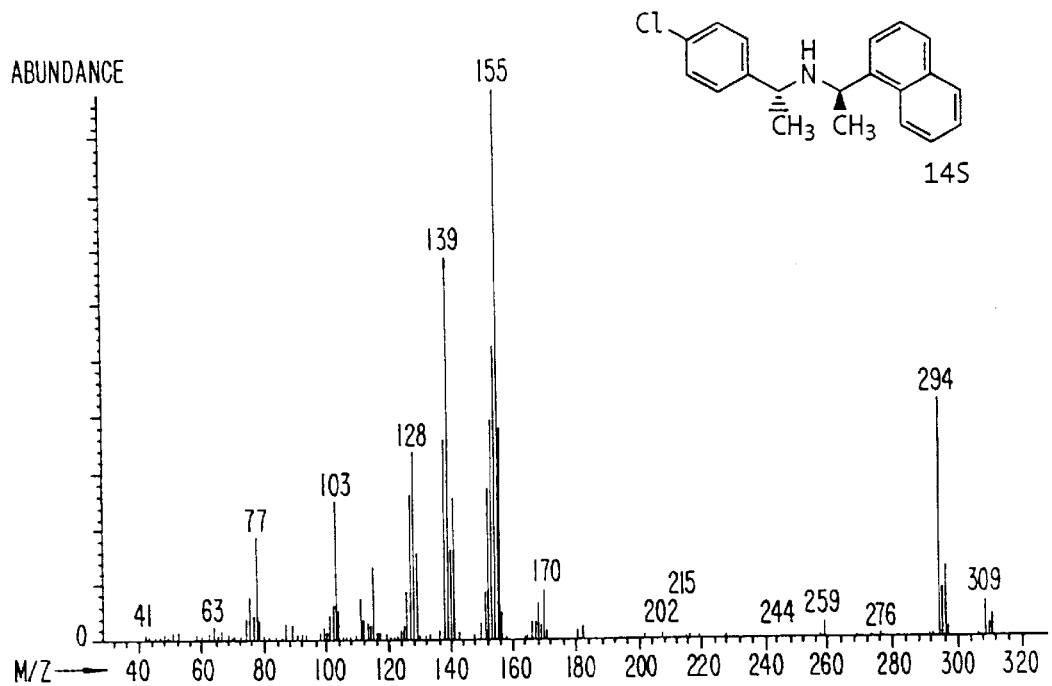
Figure 47:
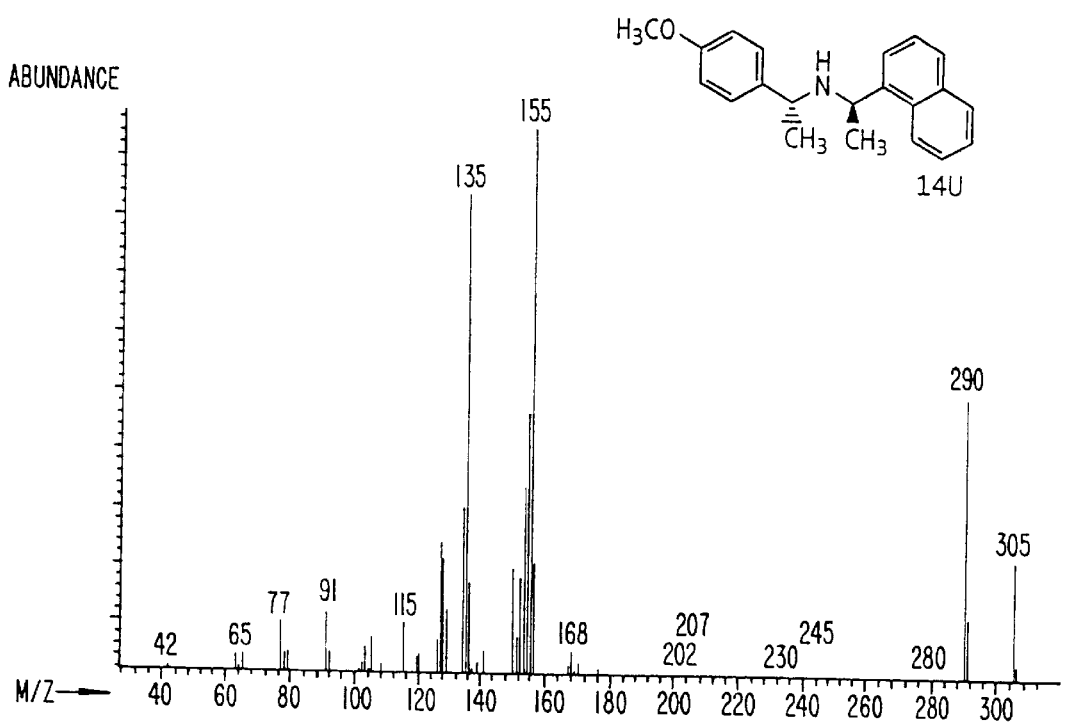
Figure 48:
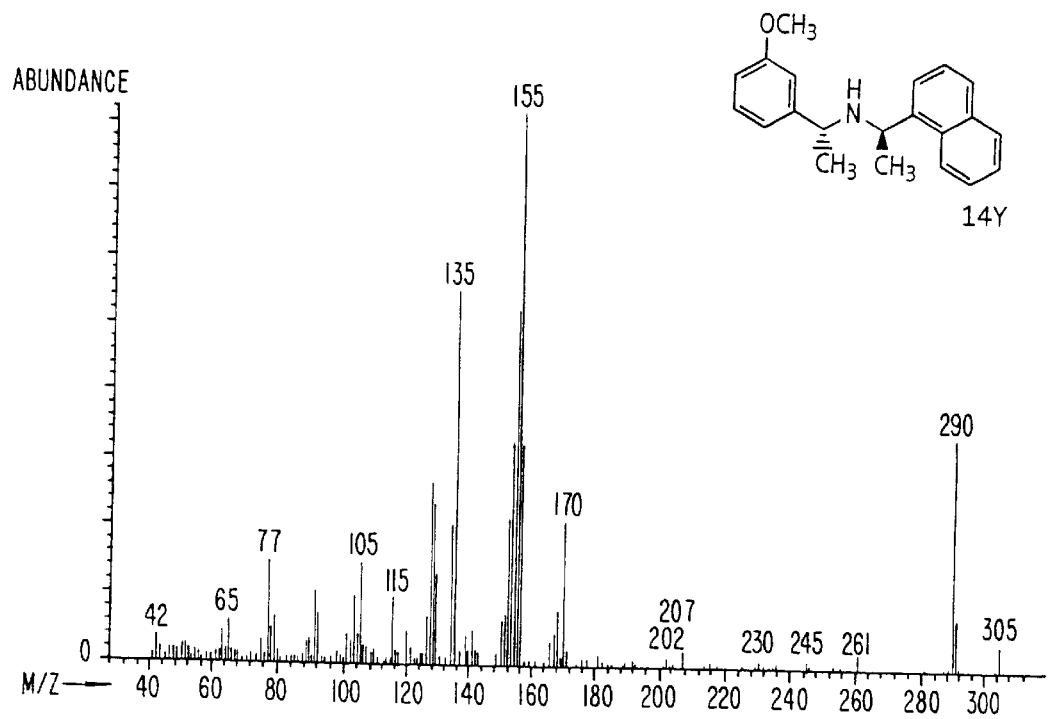
Figure 49:
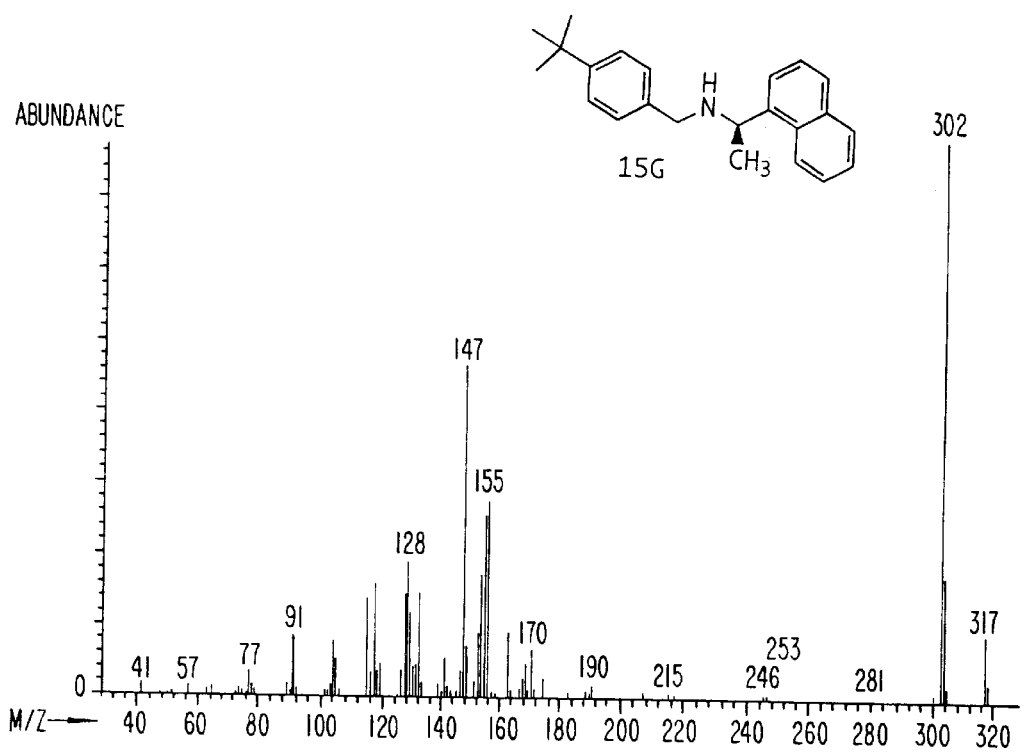
Figure 50:
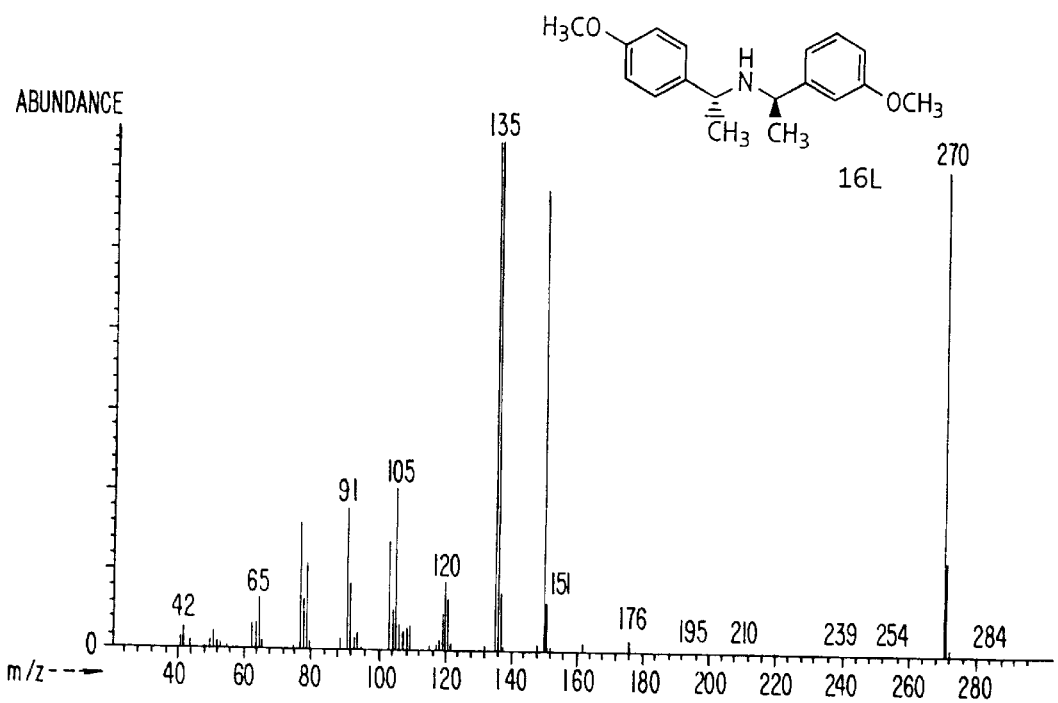
Figure 51:
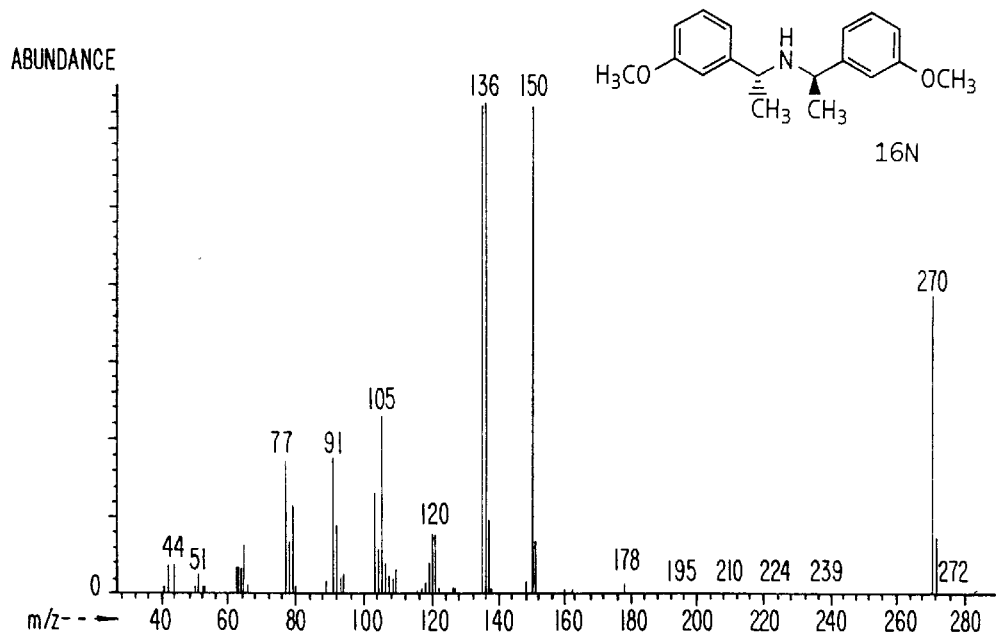
Figure 52:
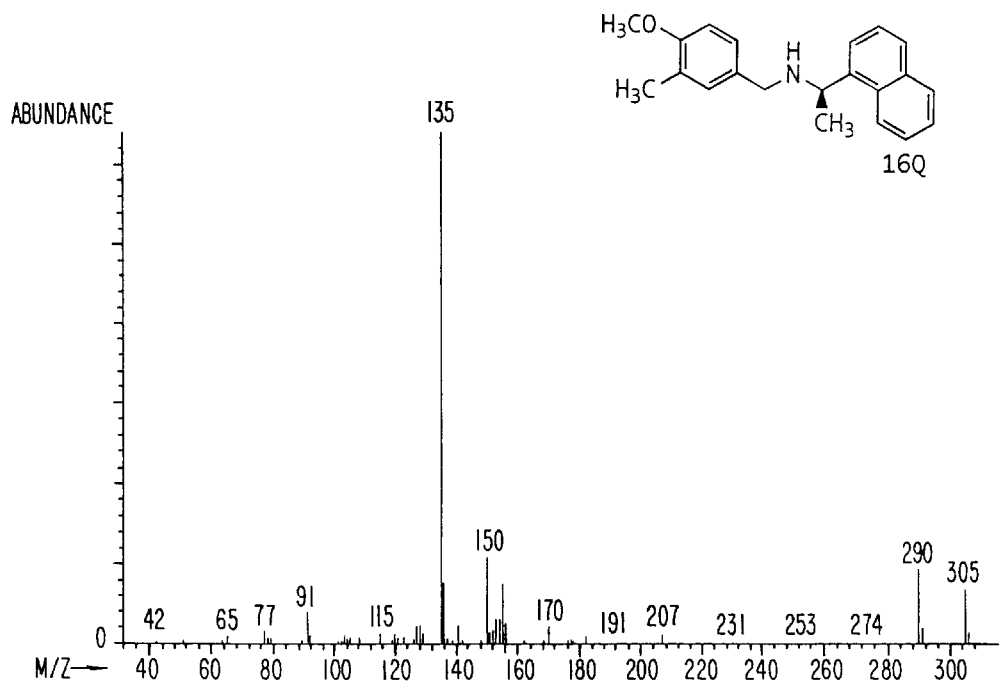
Figure 53:
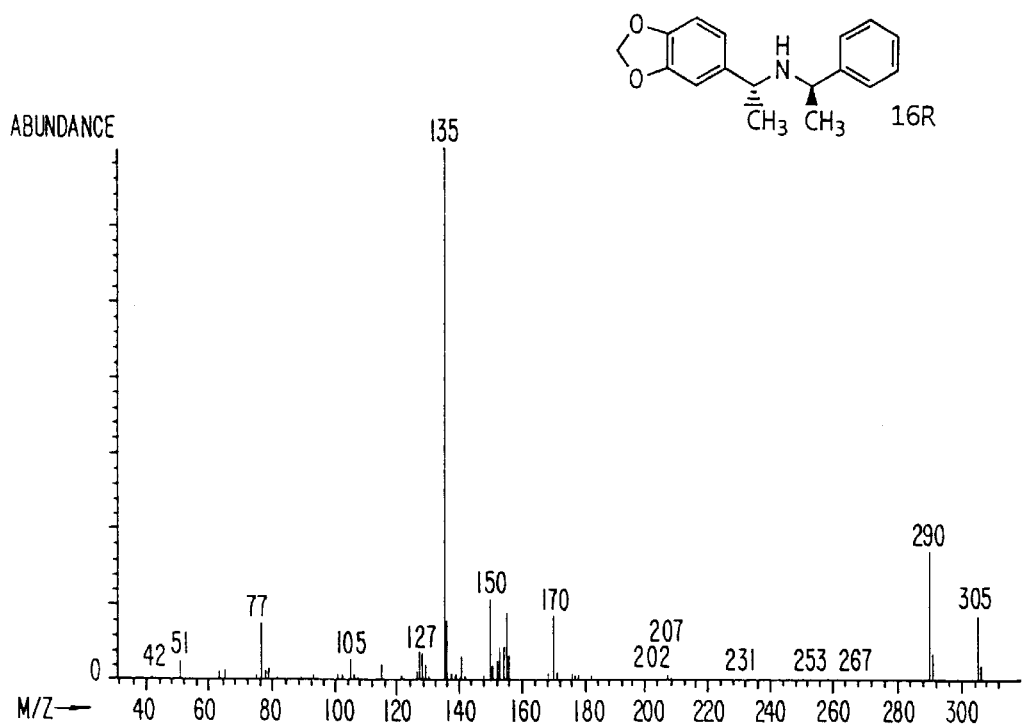
Figure 54:
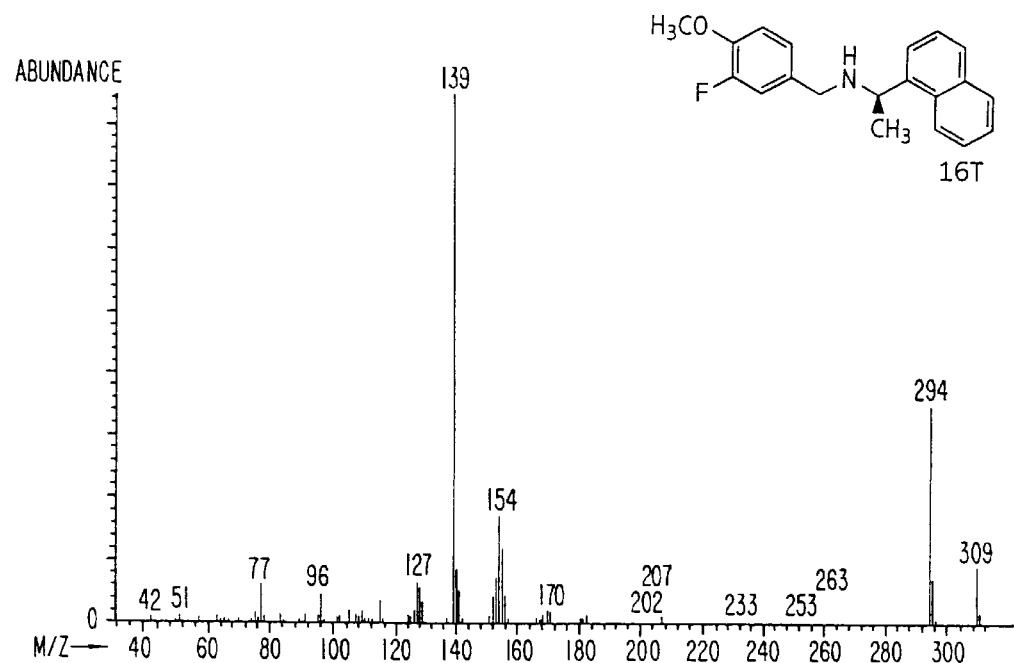
Figure 55:
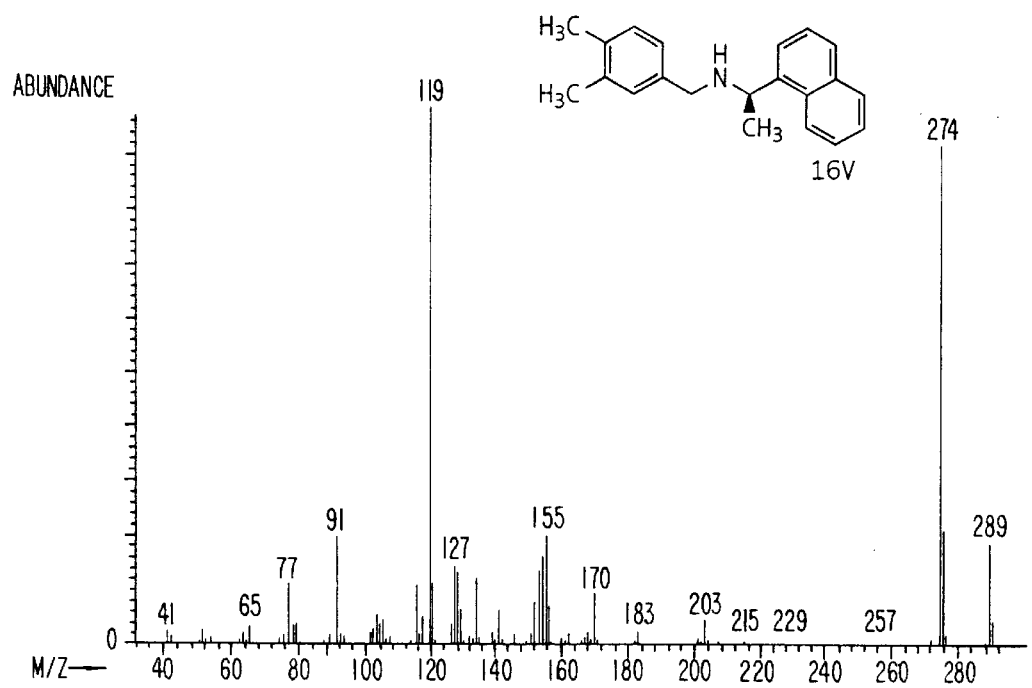
Figure 56:
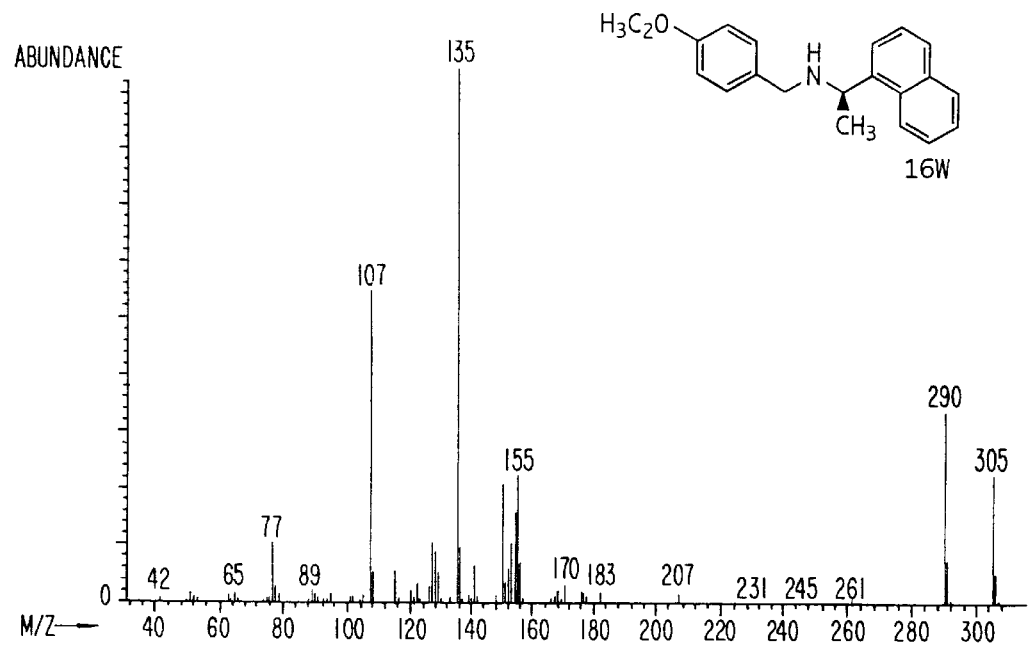
Figure 57:
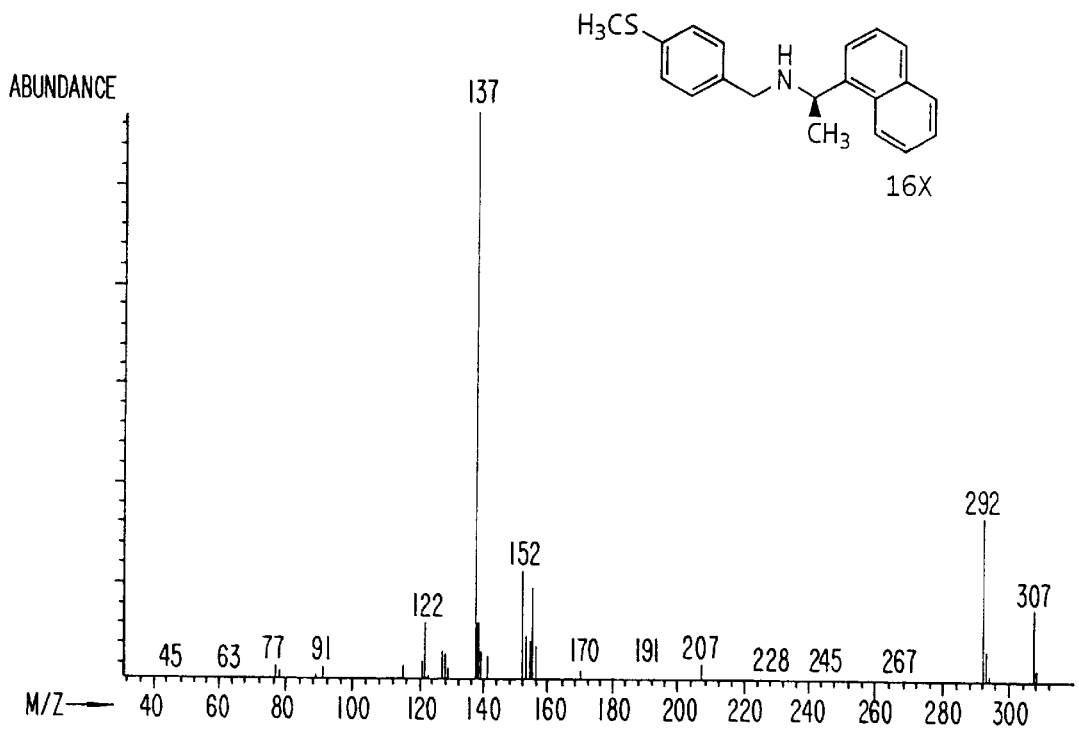
Figure 58:
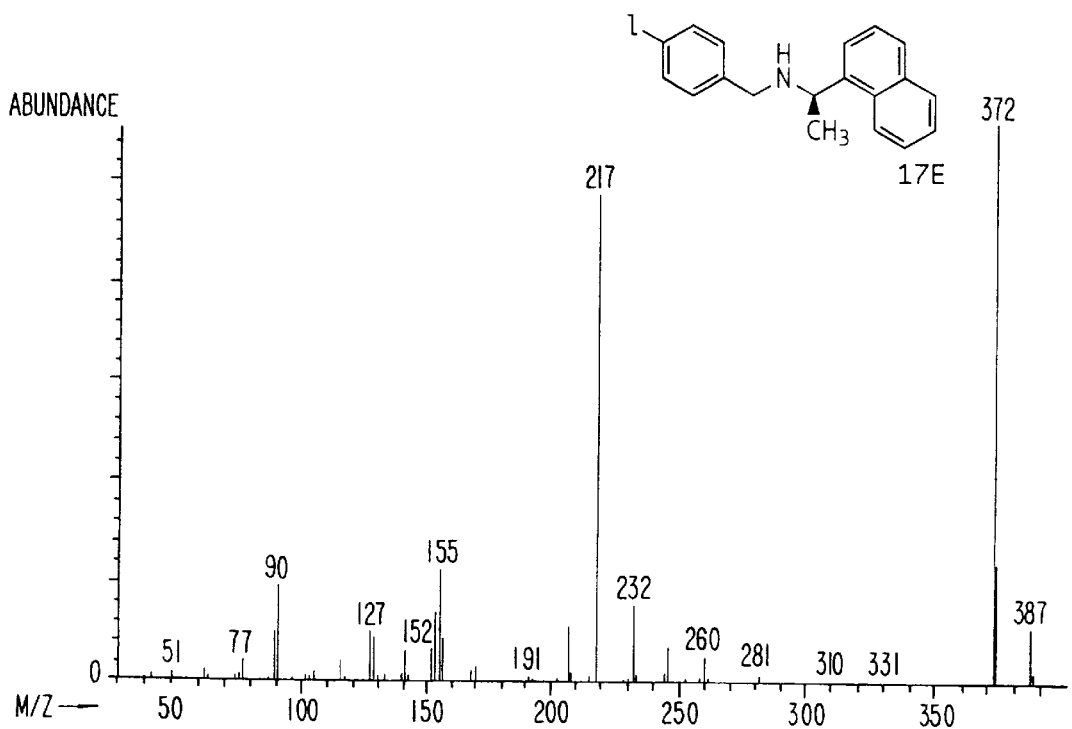
Figures 59, 60:
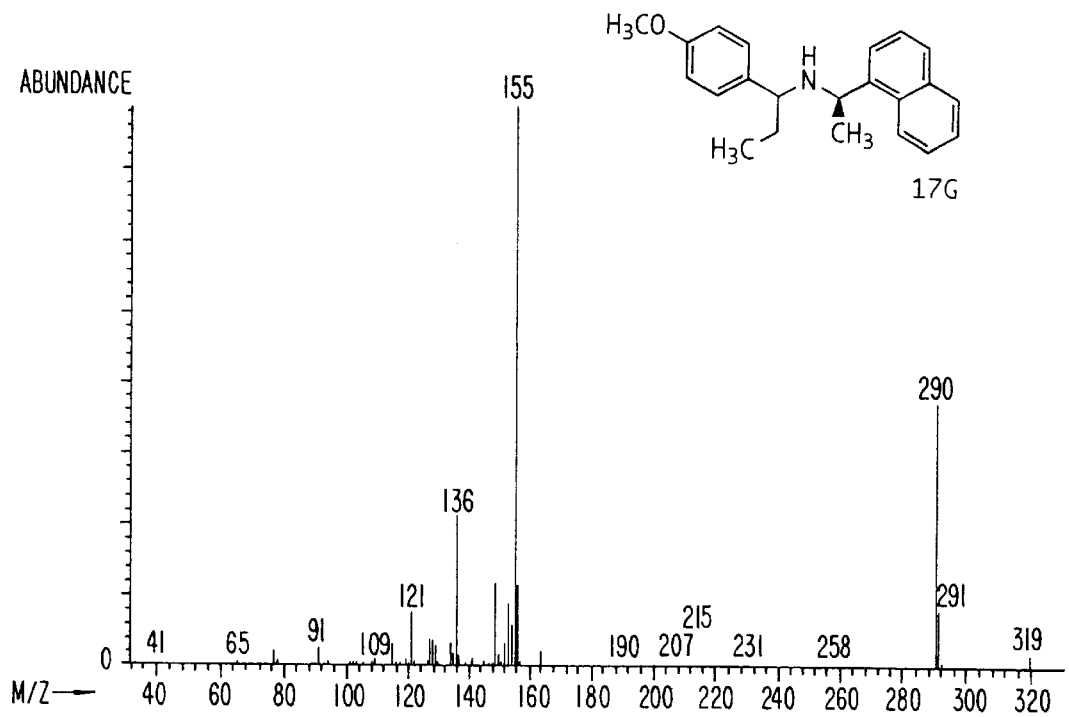
Figure 61:
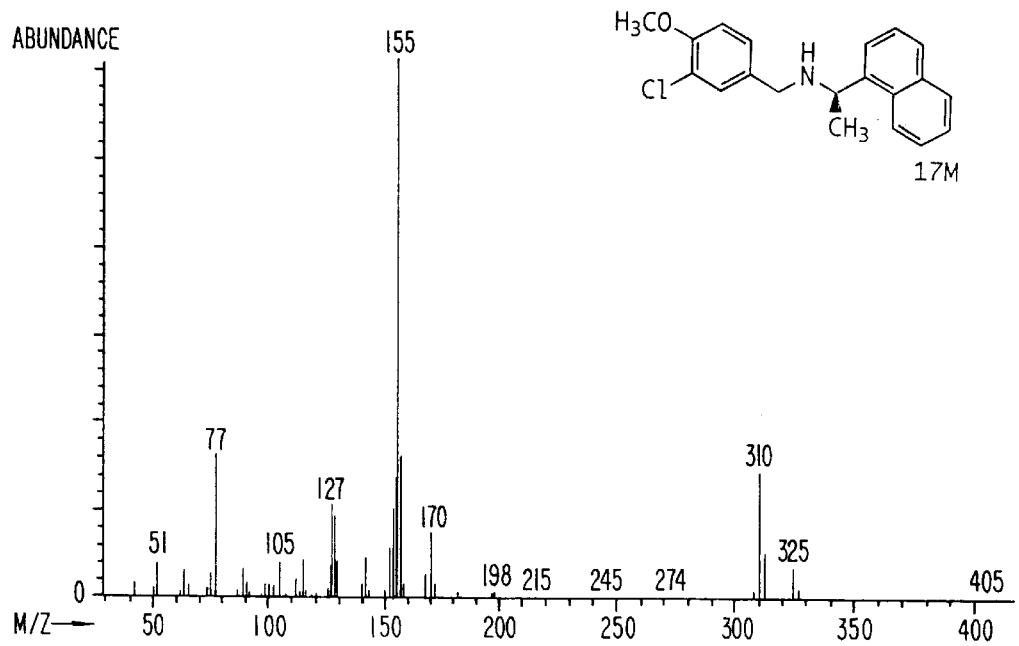
Figure 62:
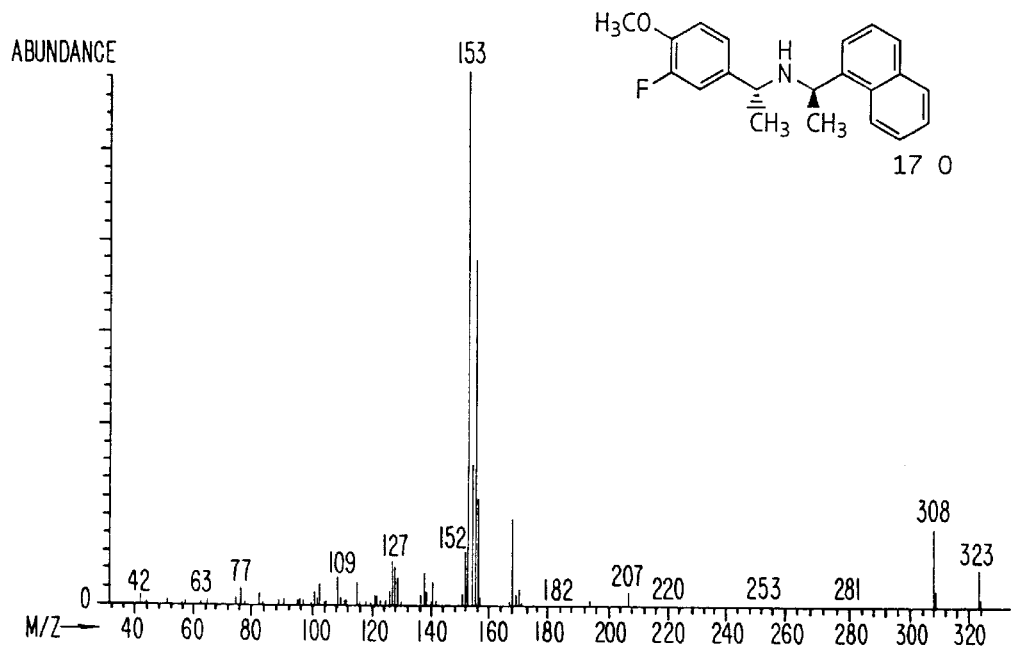
Figure 63:
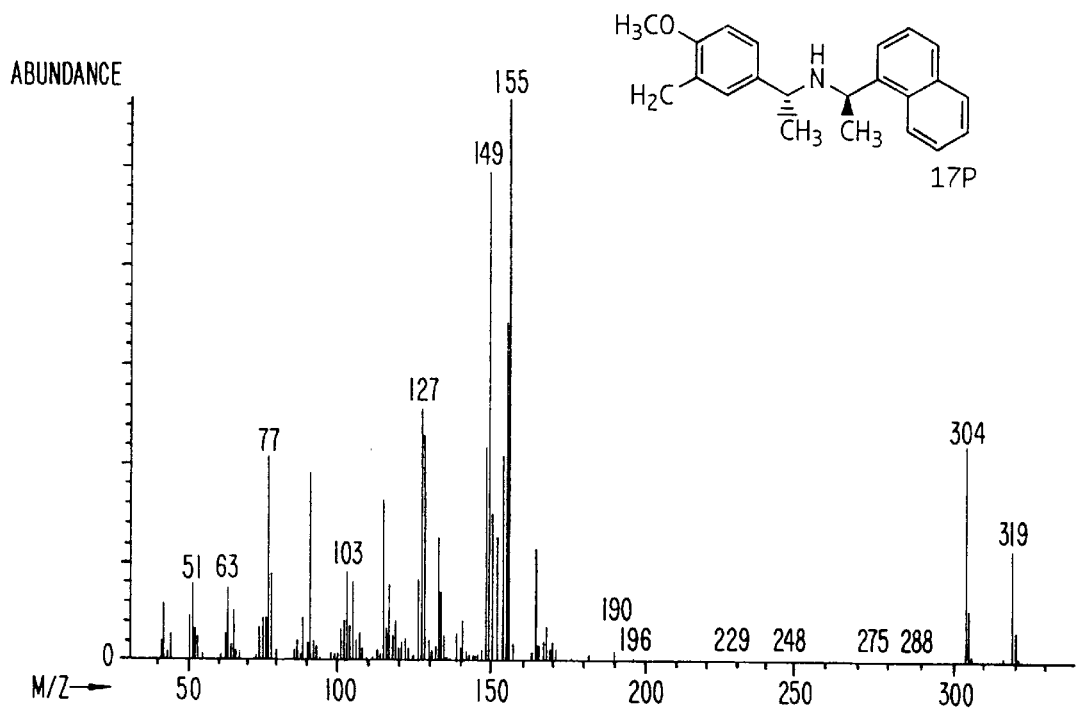
Figure 64:
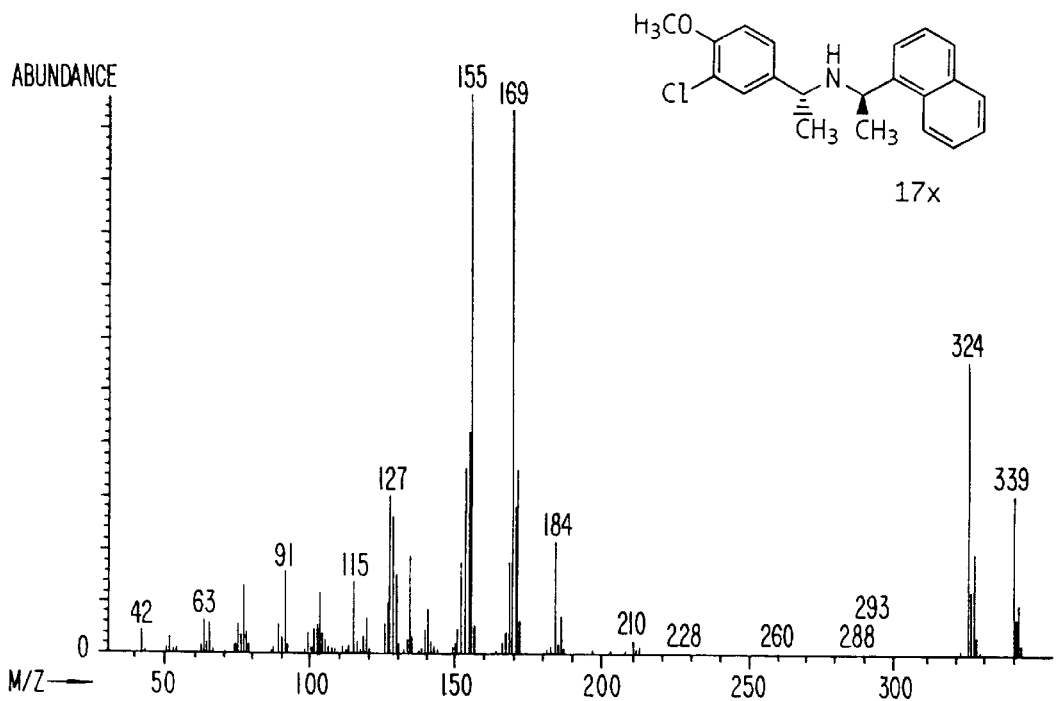
Figure 65:
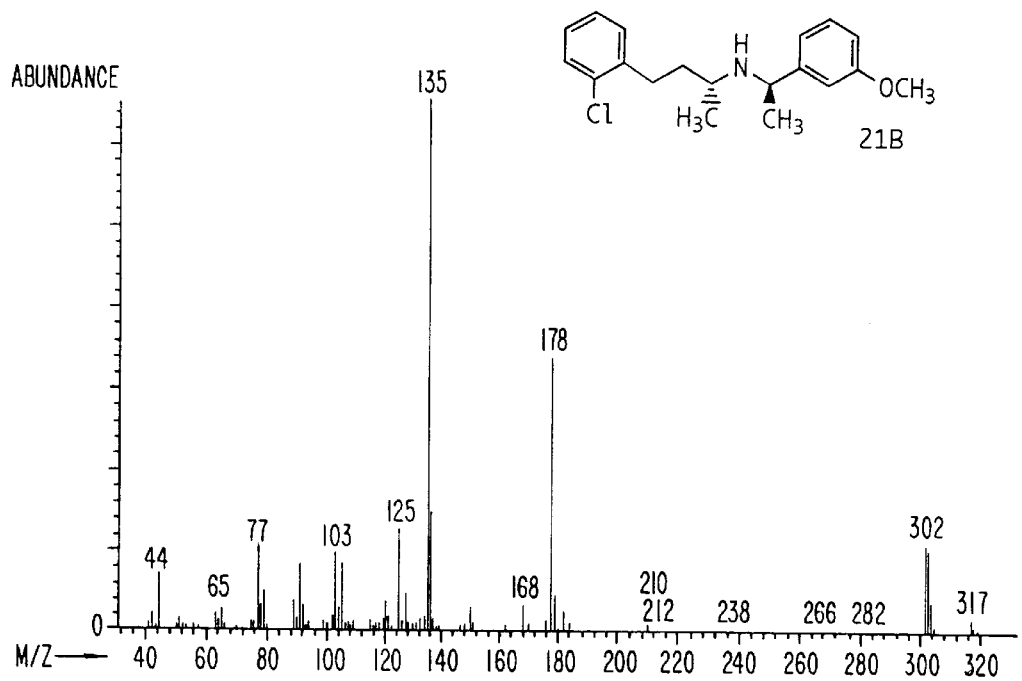
Figure 66:
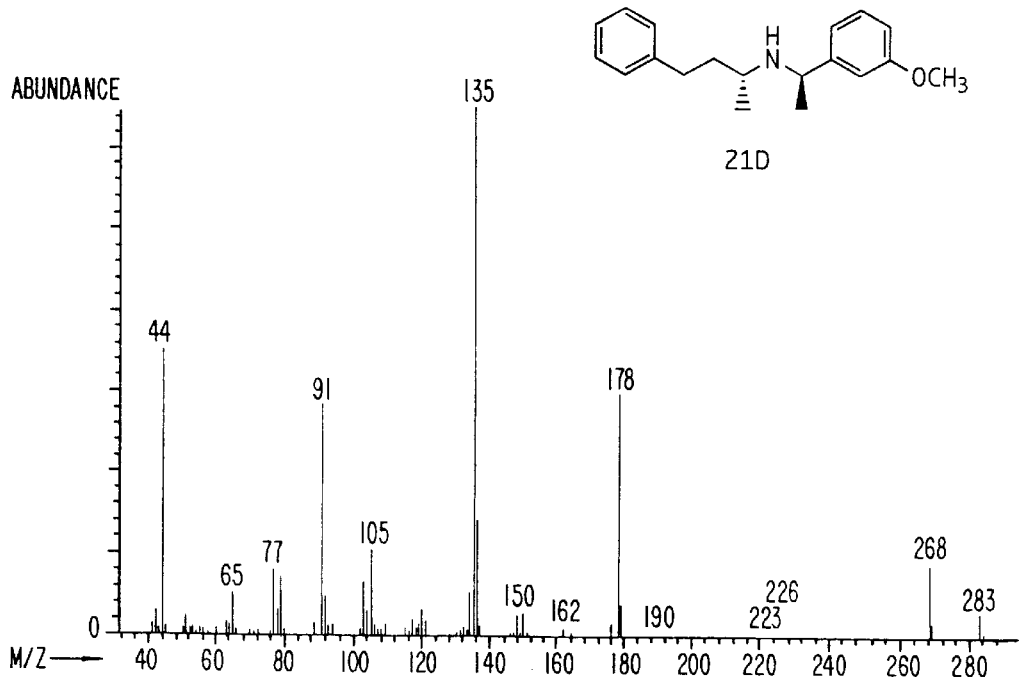
Figure 67:
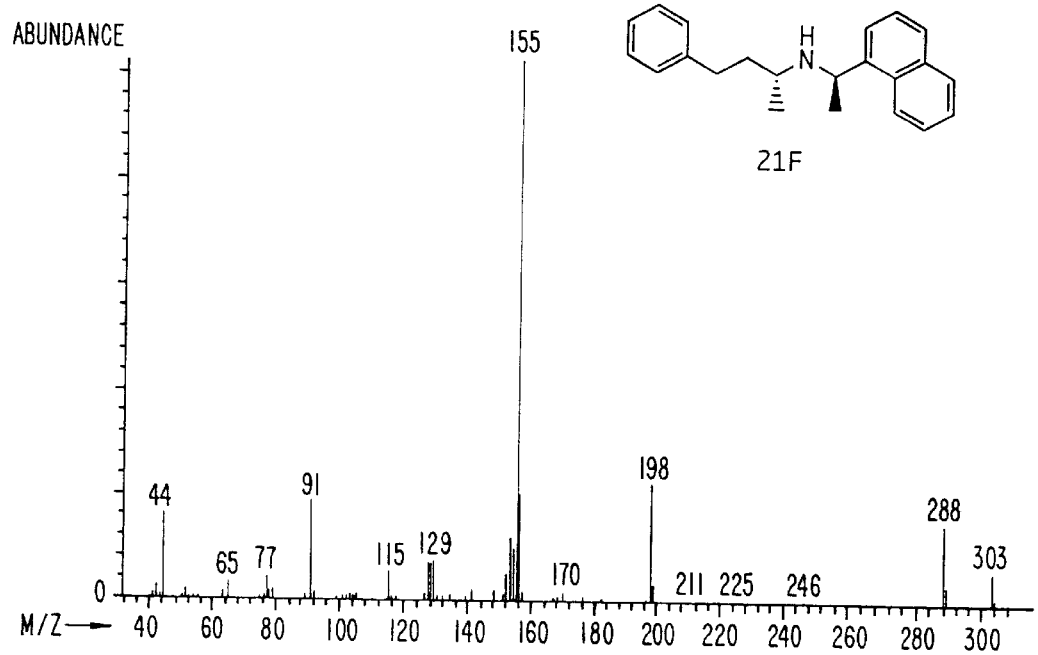
Figure 68:
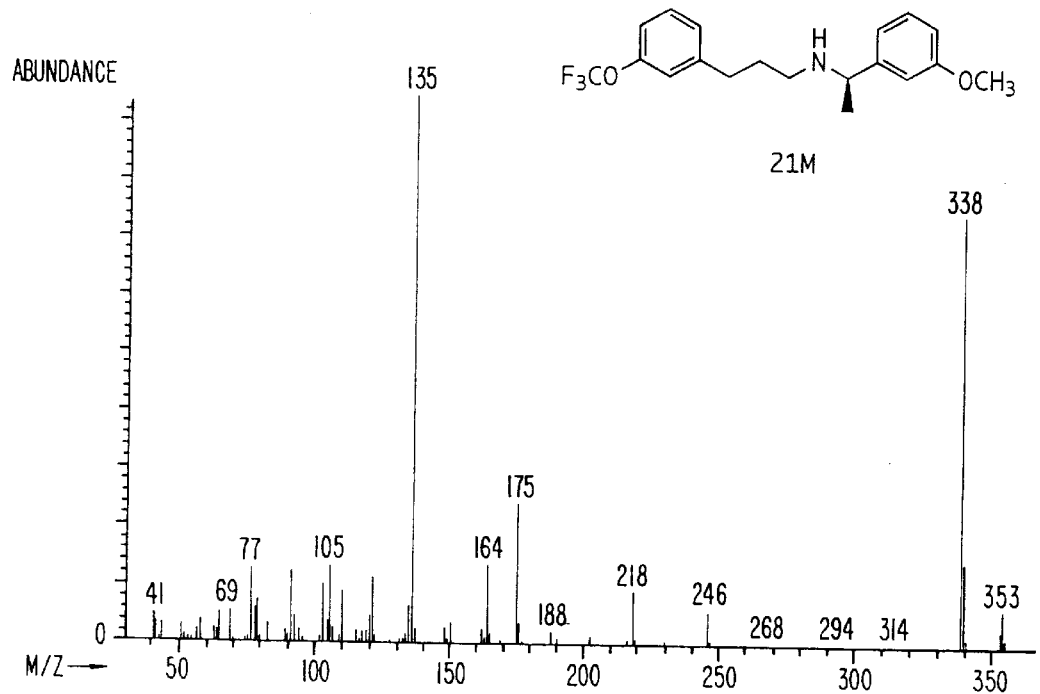
Figure 69:
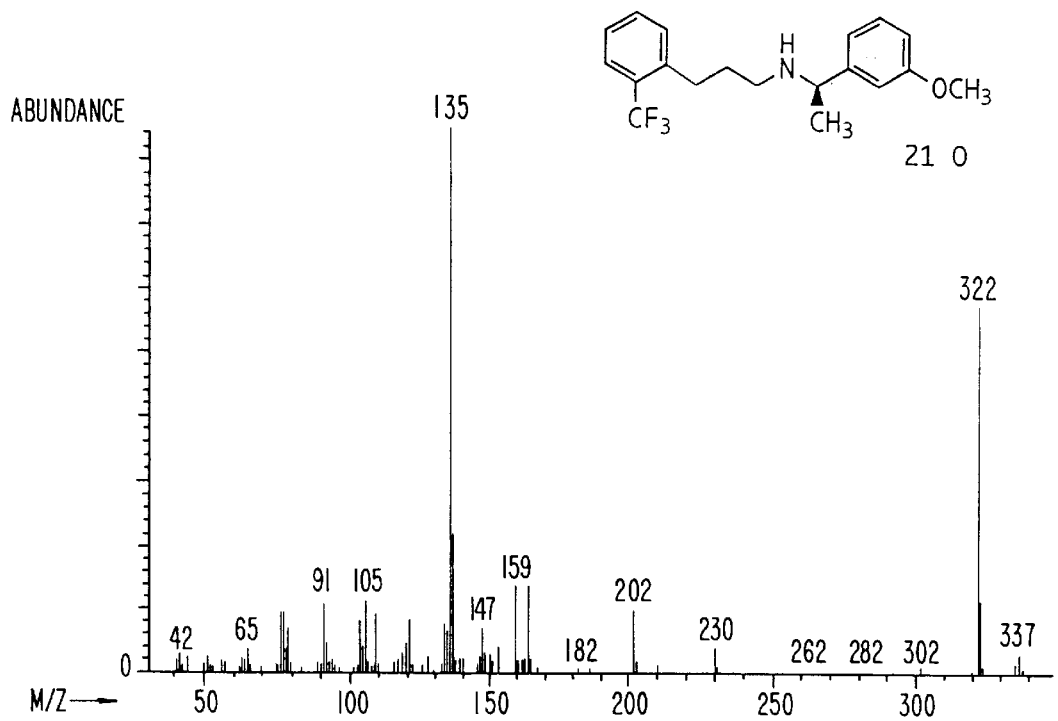
Figure 70:
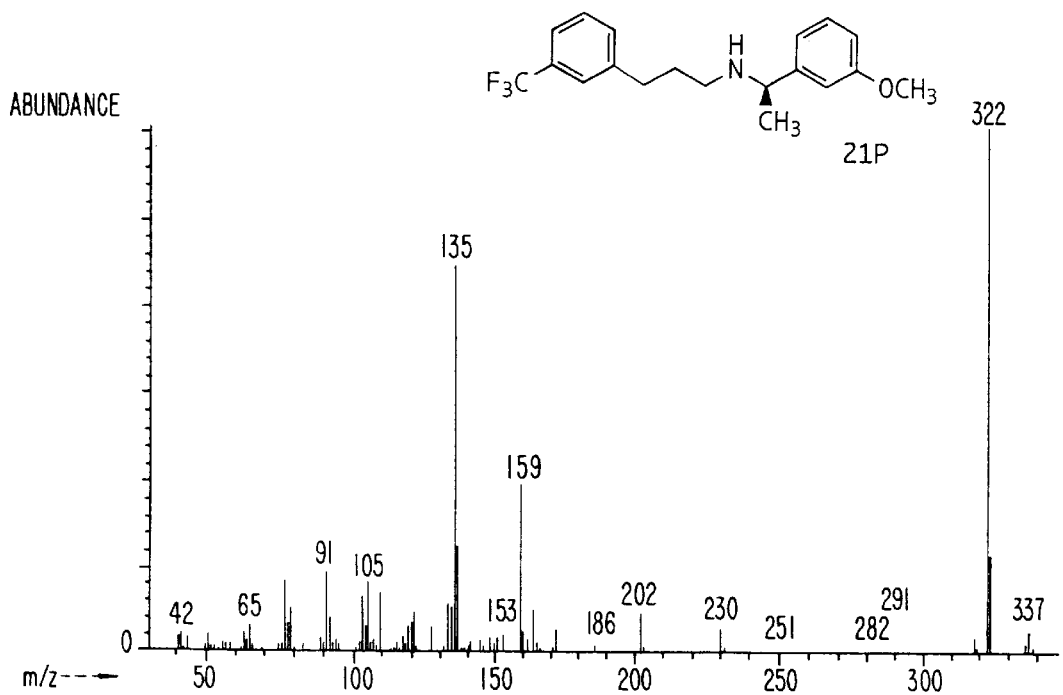
Figure 71:
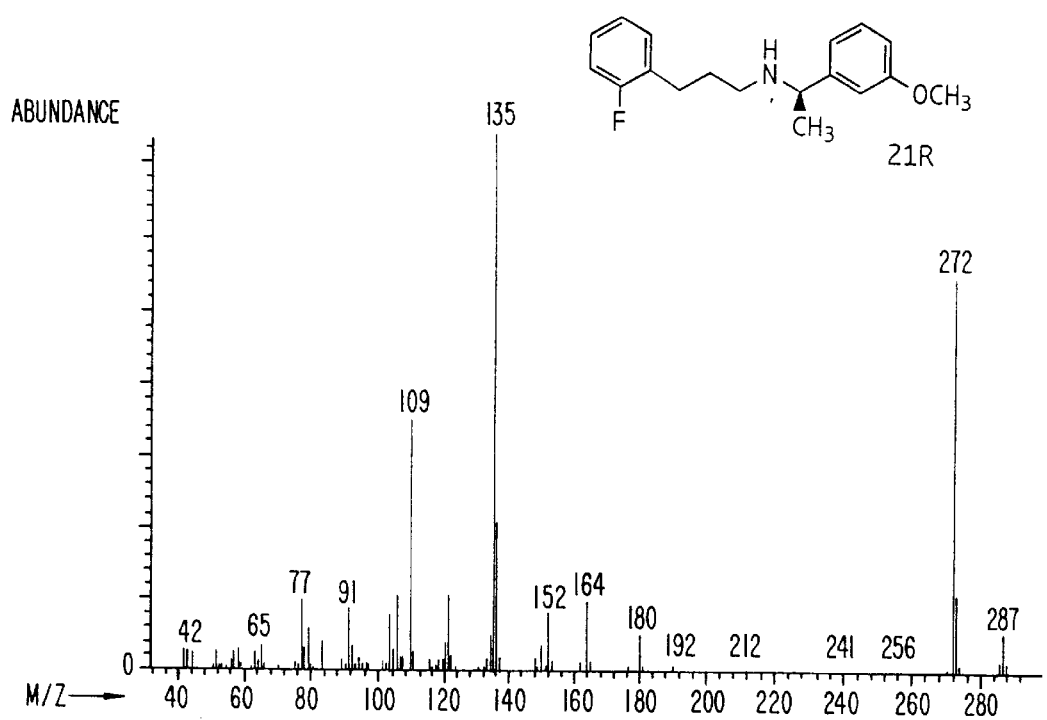
Figure 72:
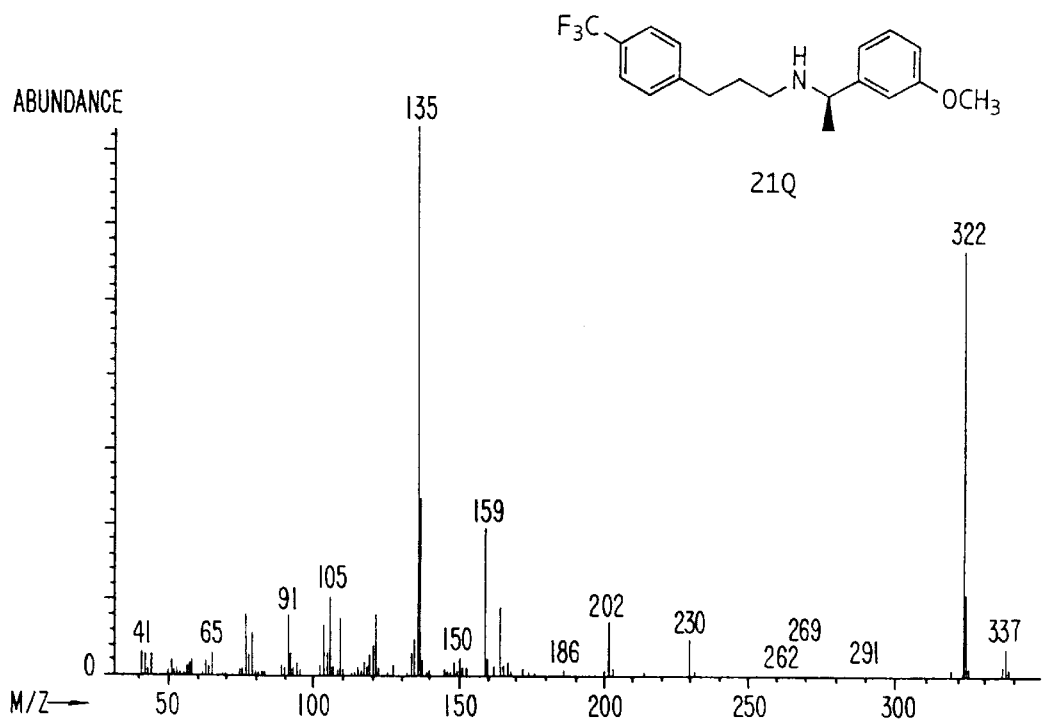
Figure 73:
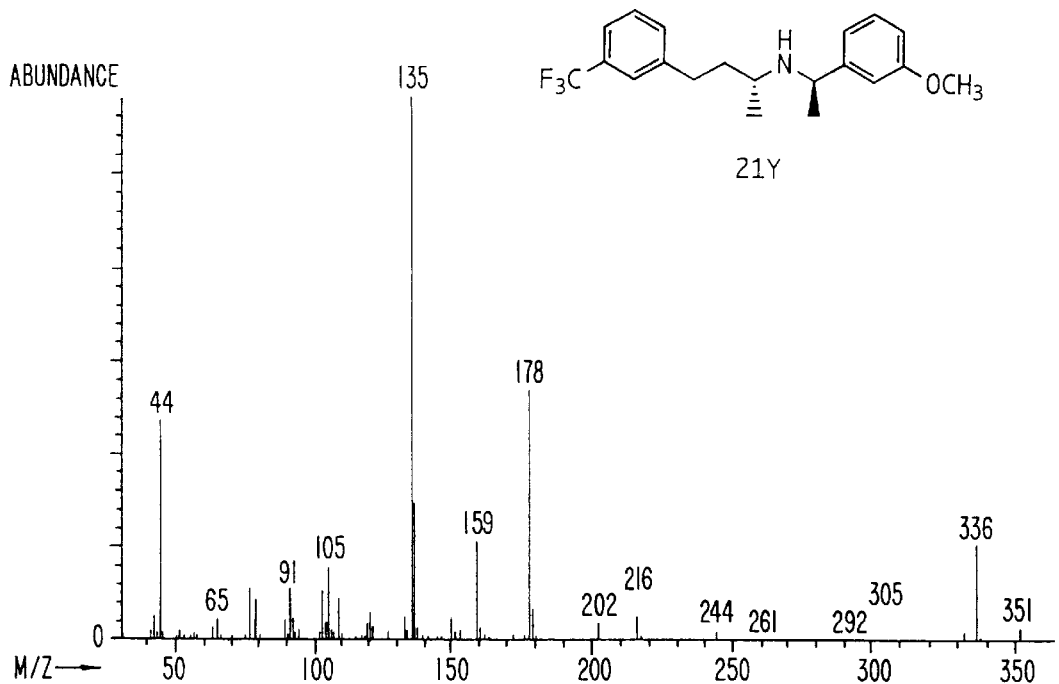
Figure 74:
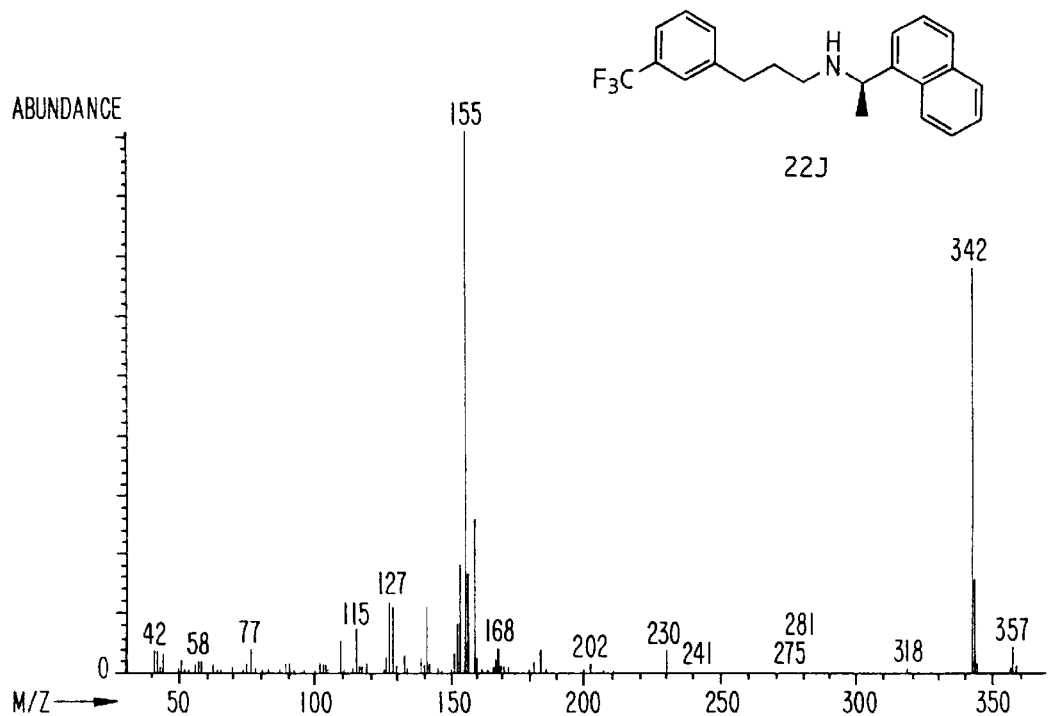
Figure 75:
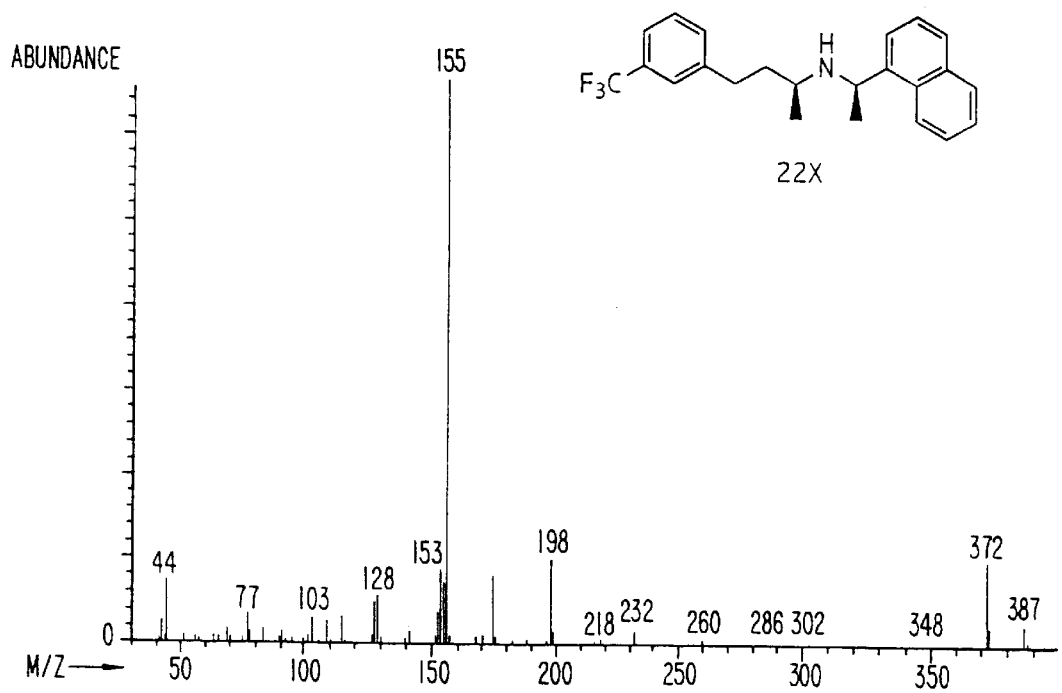
Figure 76:
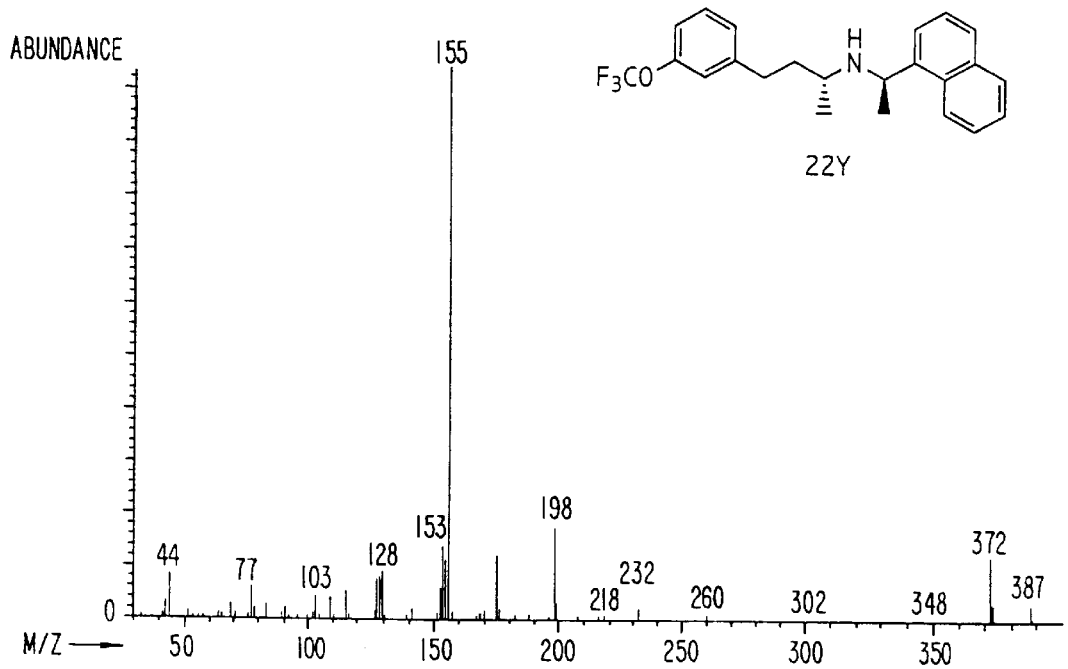
Figure 77:
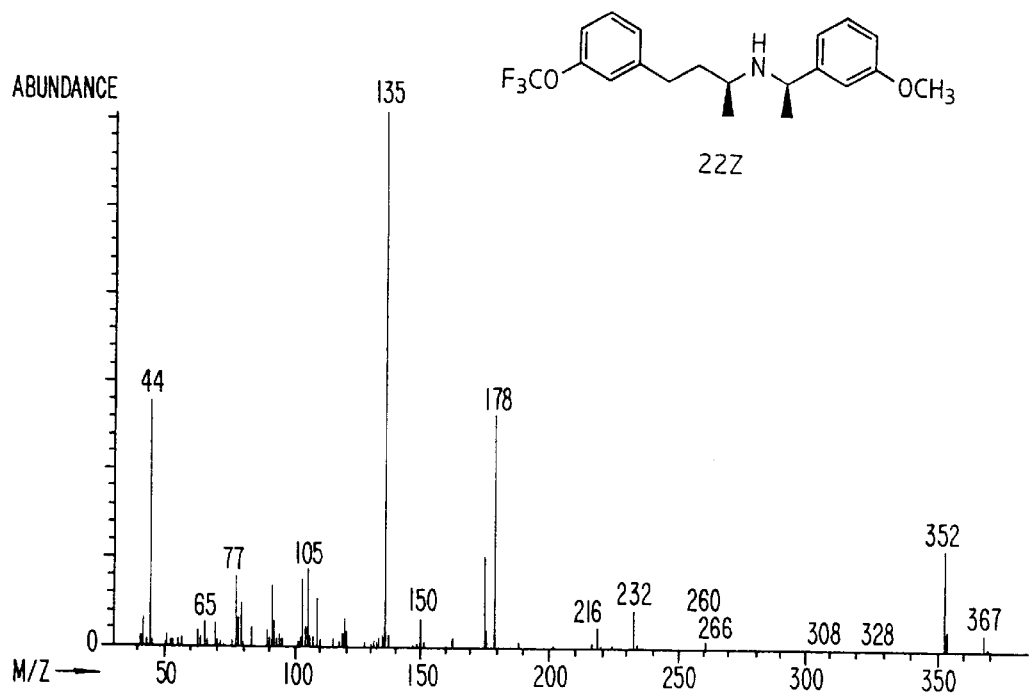
Figure 78:
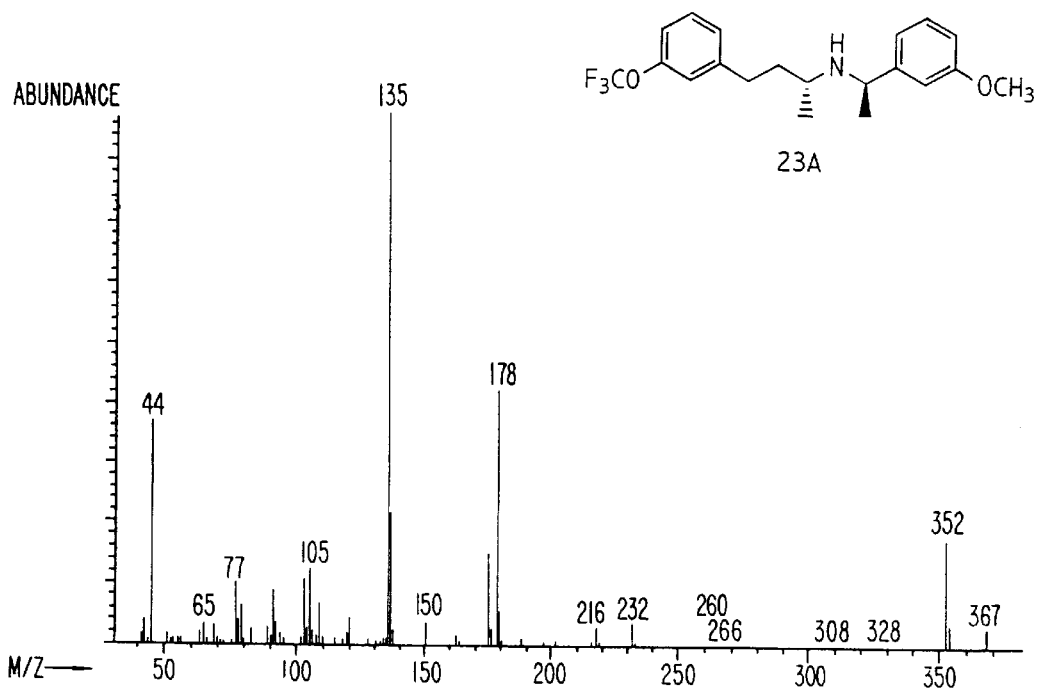
Figure 79:
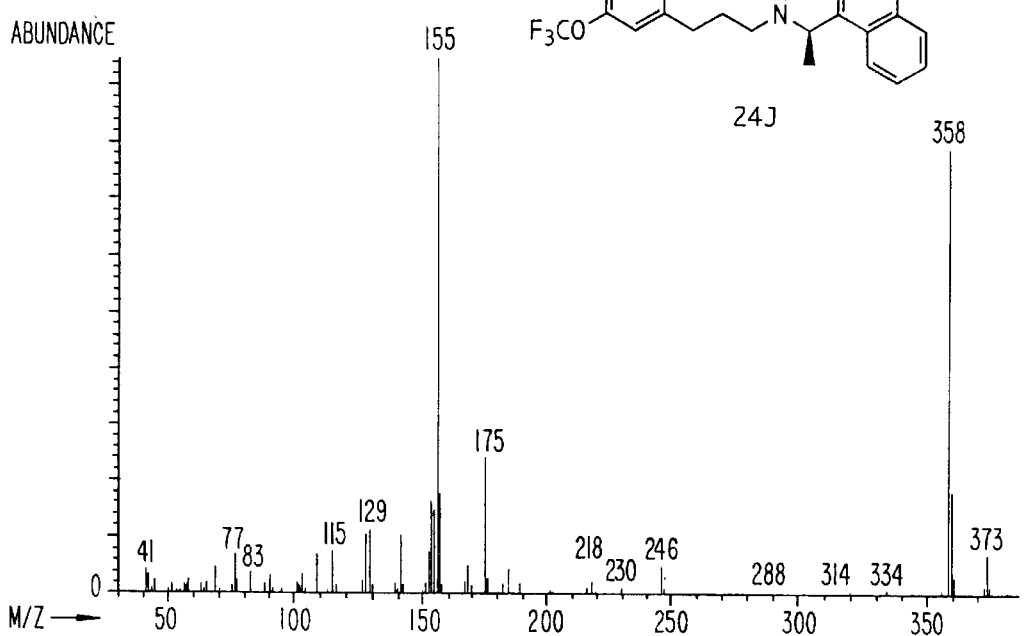
Figure 80:
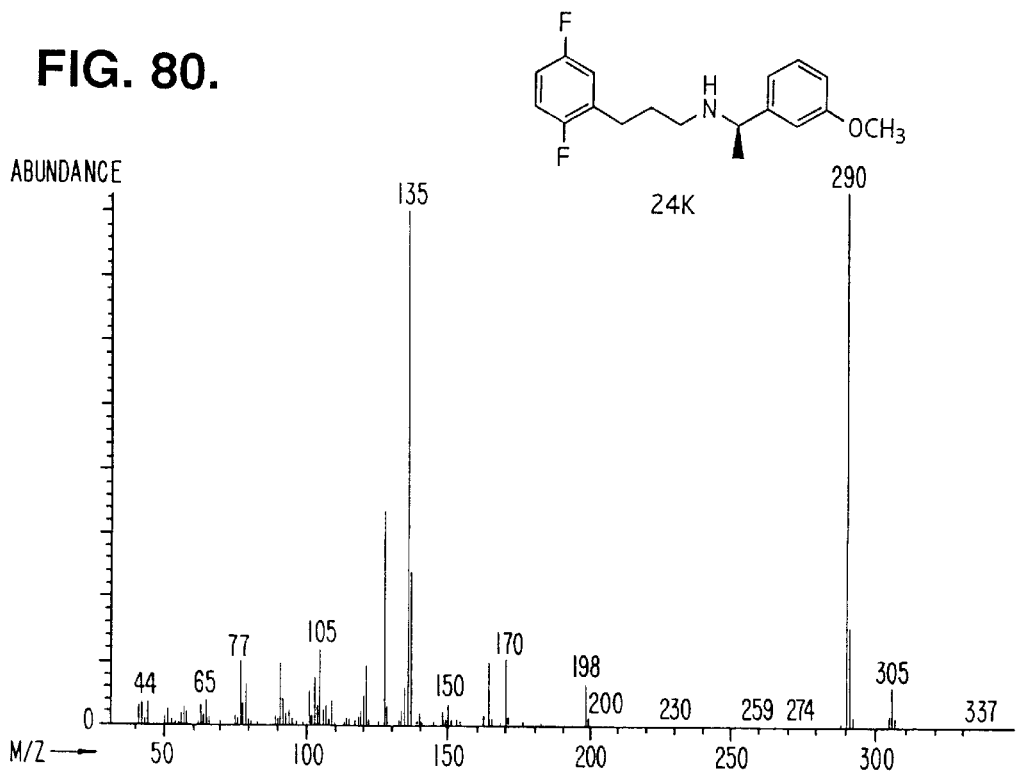
Figure 81:
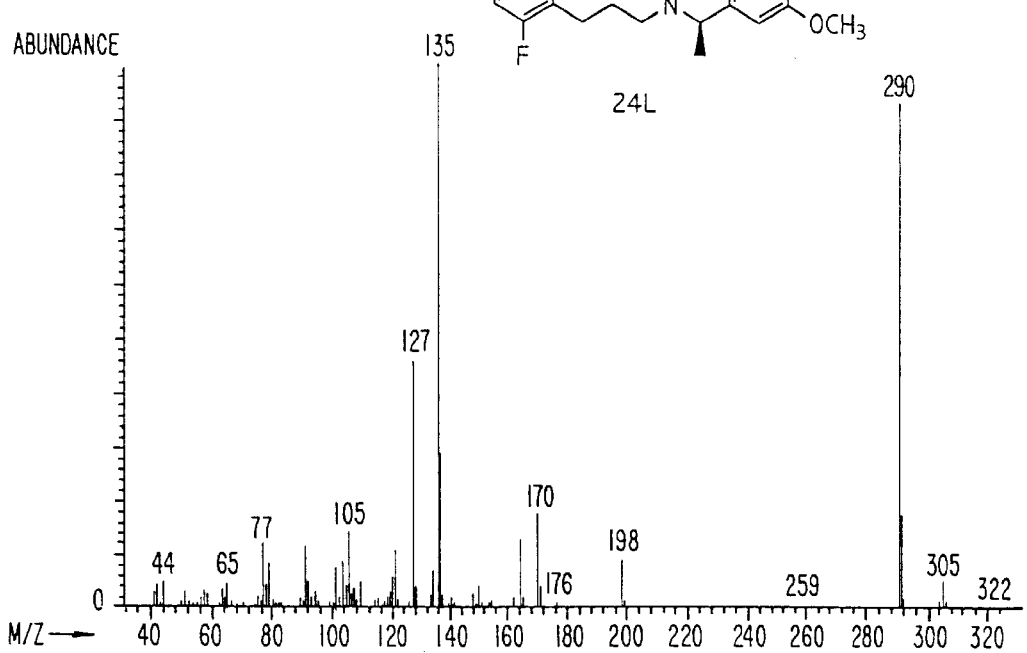
Figure 82:
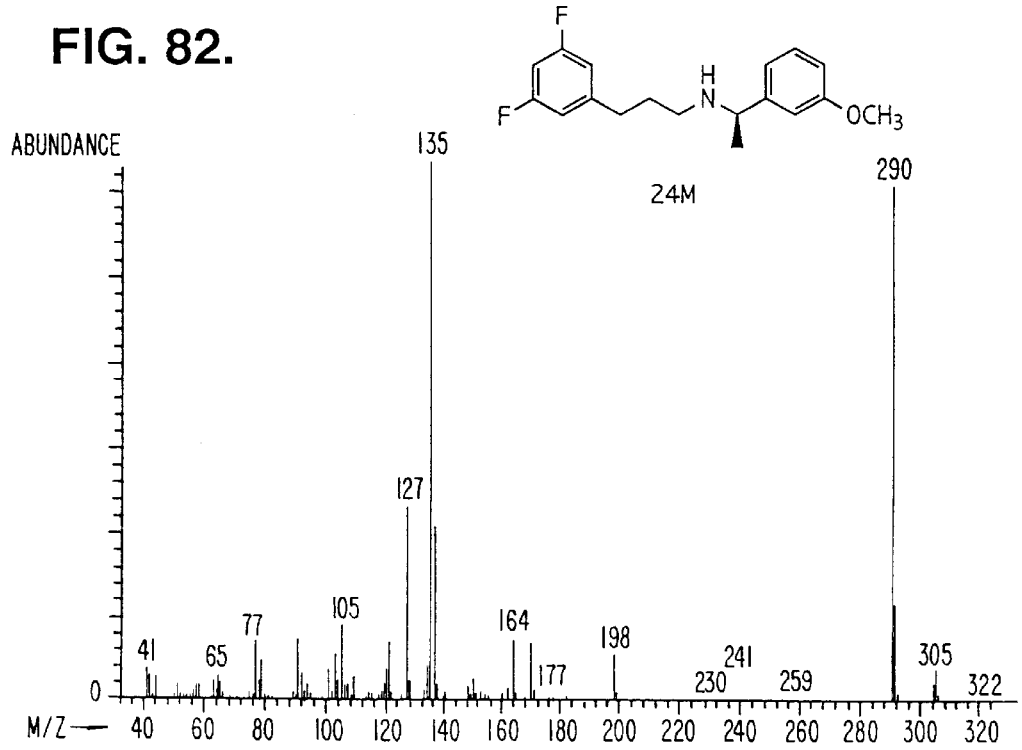
Figure 83:
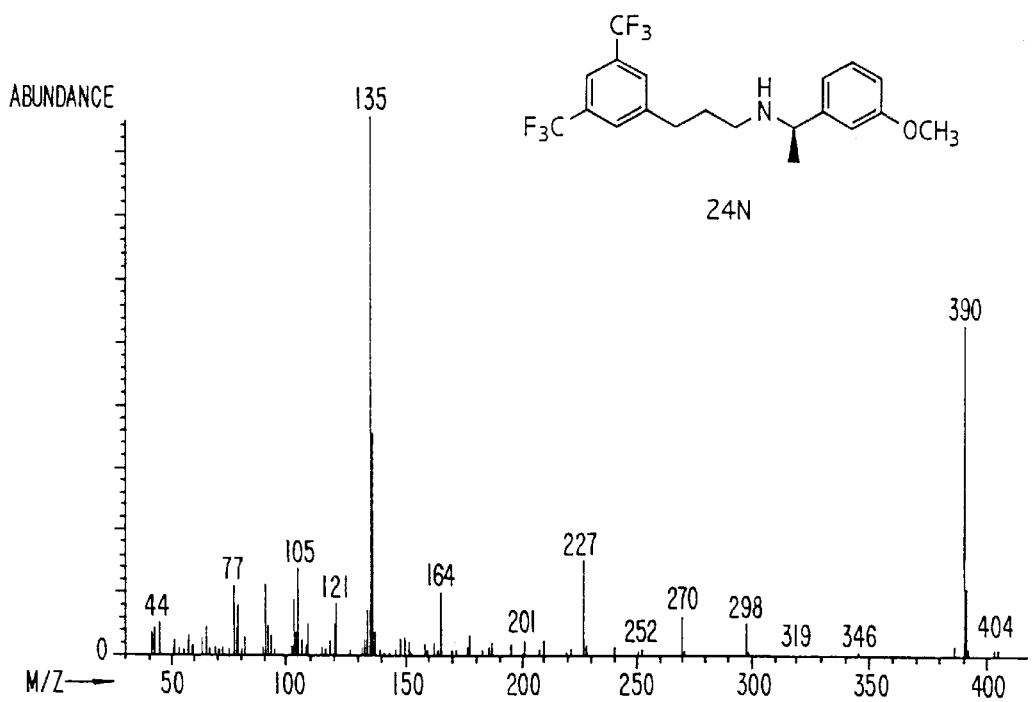
Figure 84:
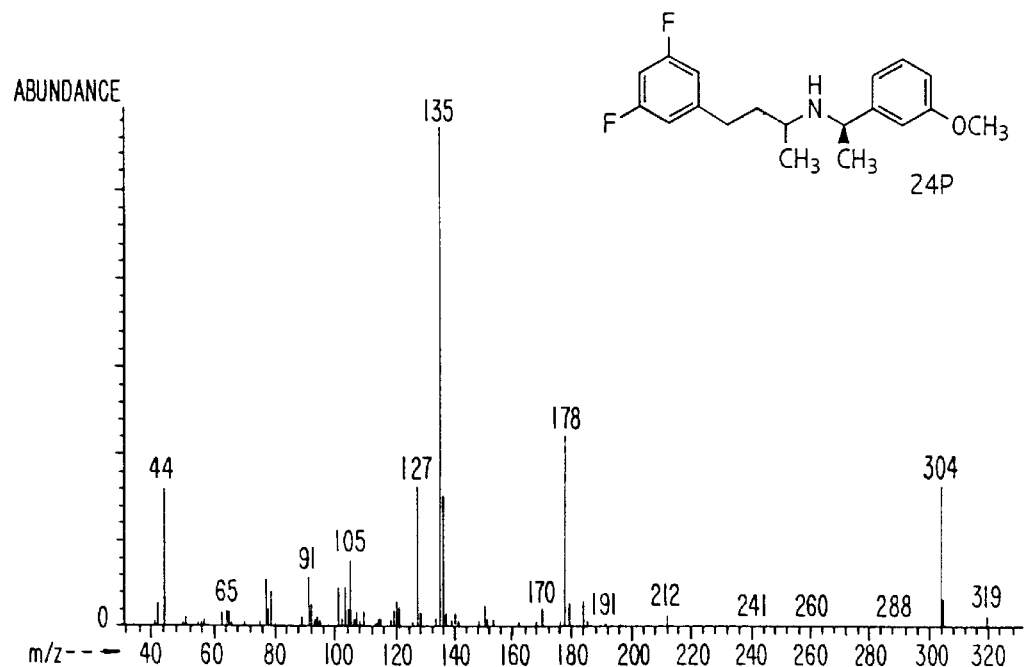
Figure 85:
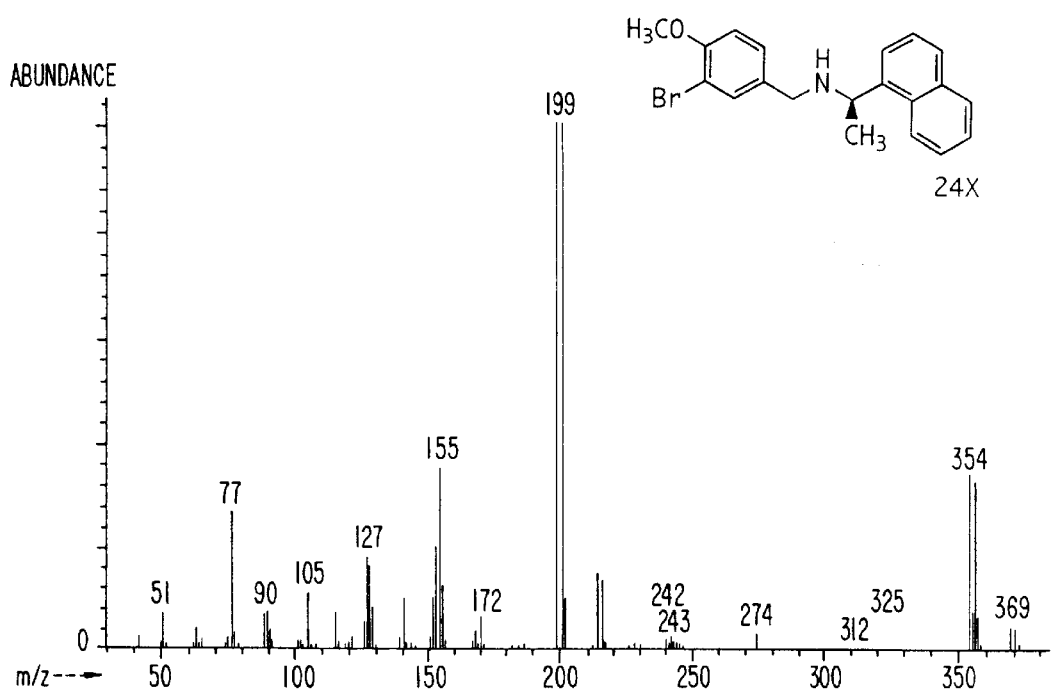
Figure 86:
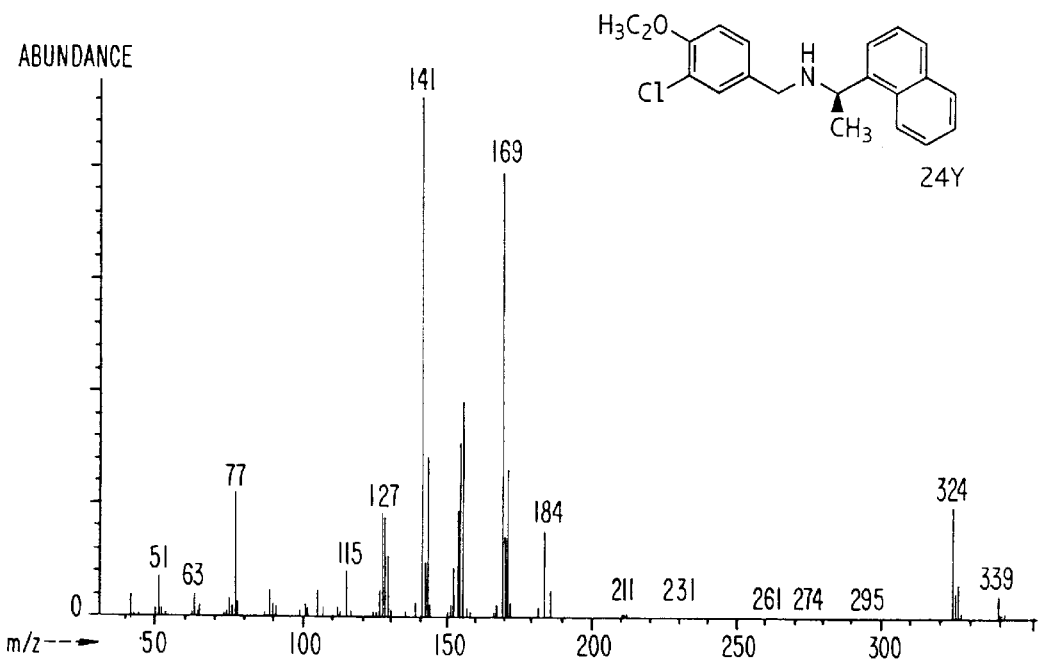
Figure 87:
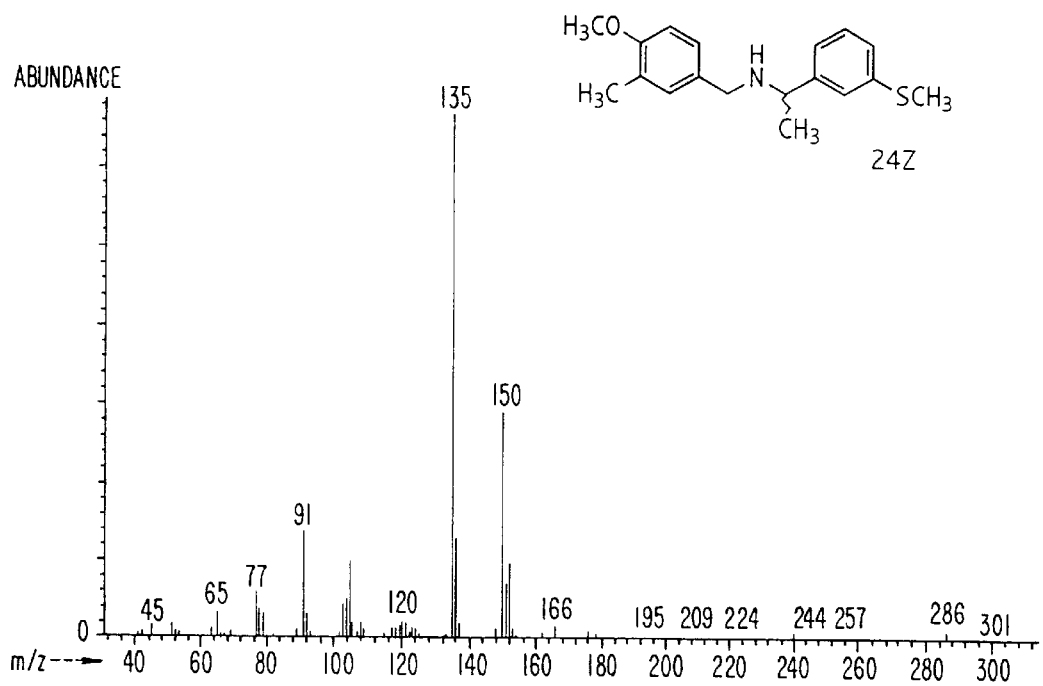
Figure 88:
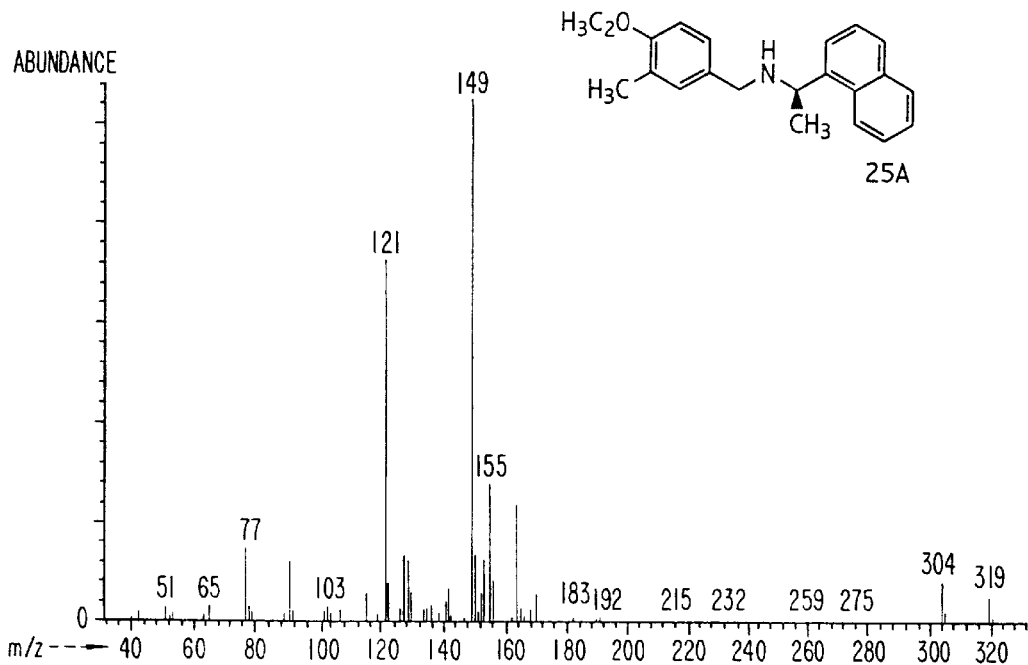
Figure 89:
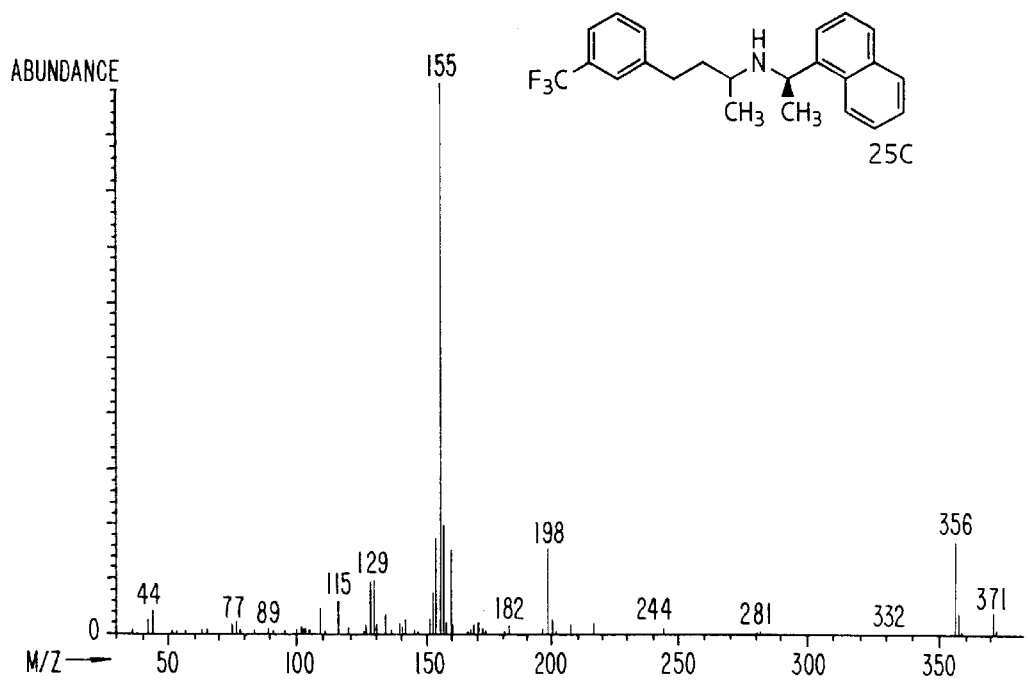
Figure 90:
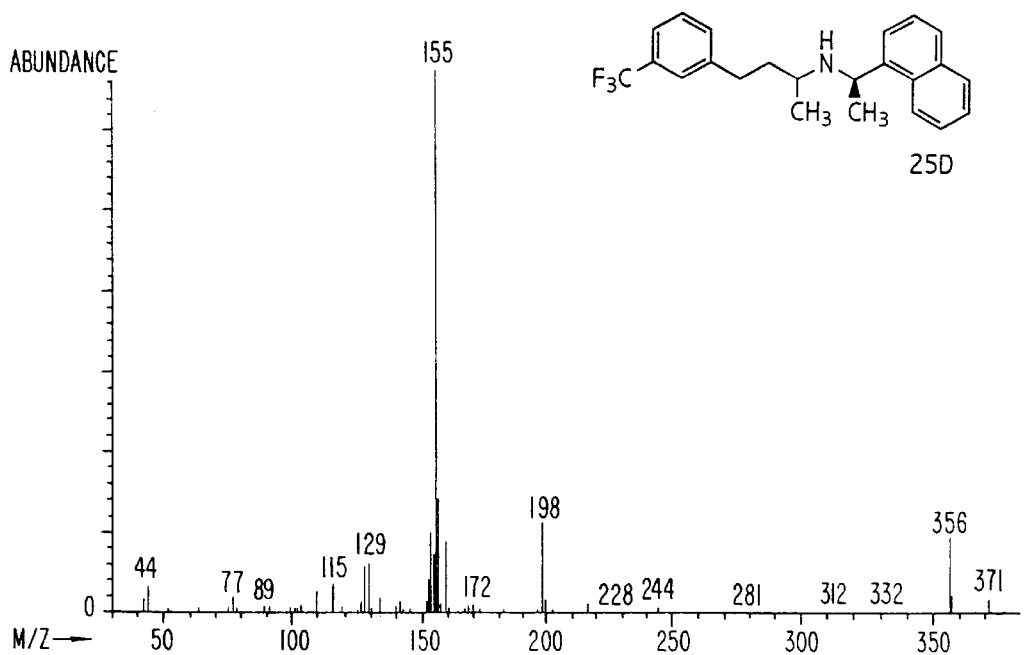
Figure 91:
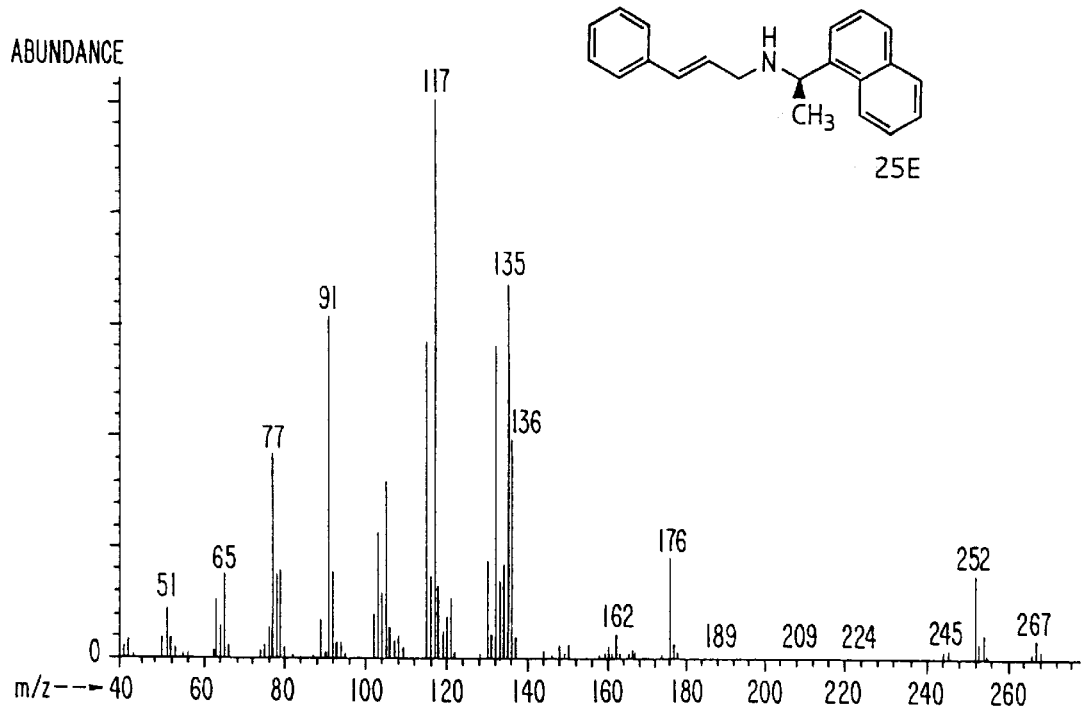
Figure 92:
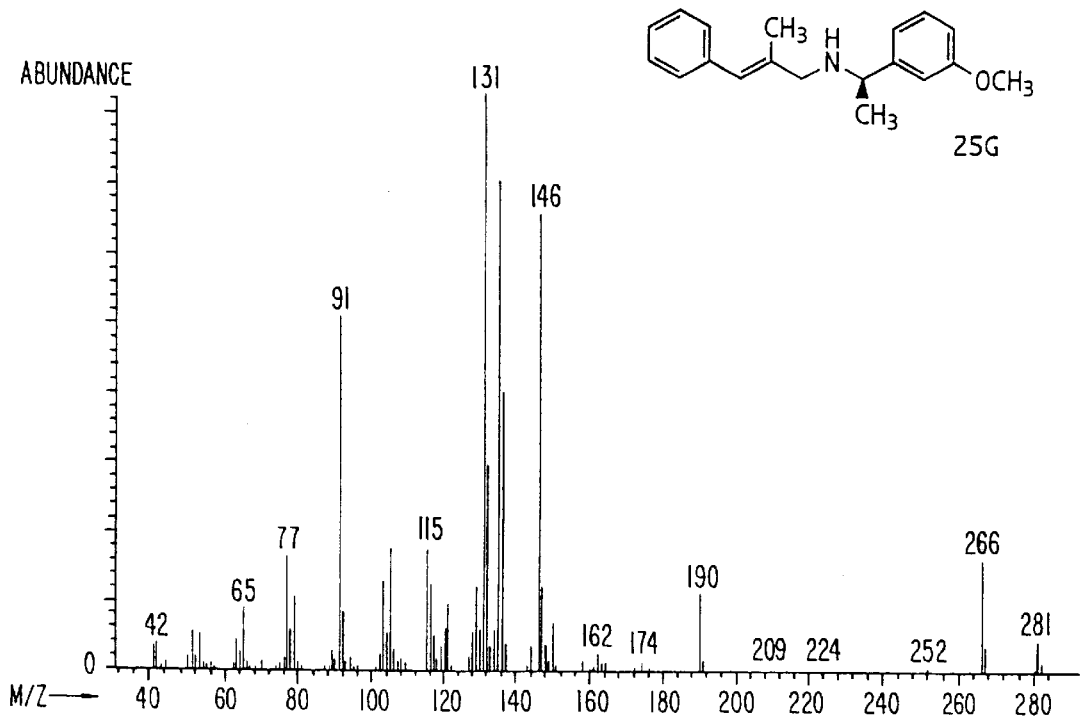
Figure 93:
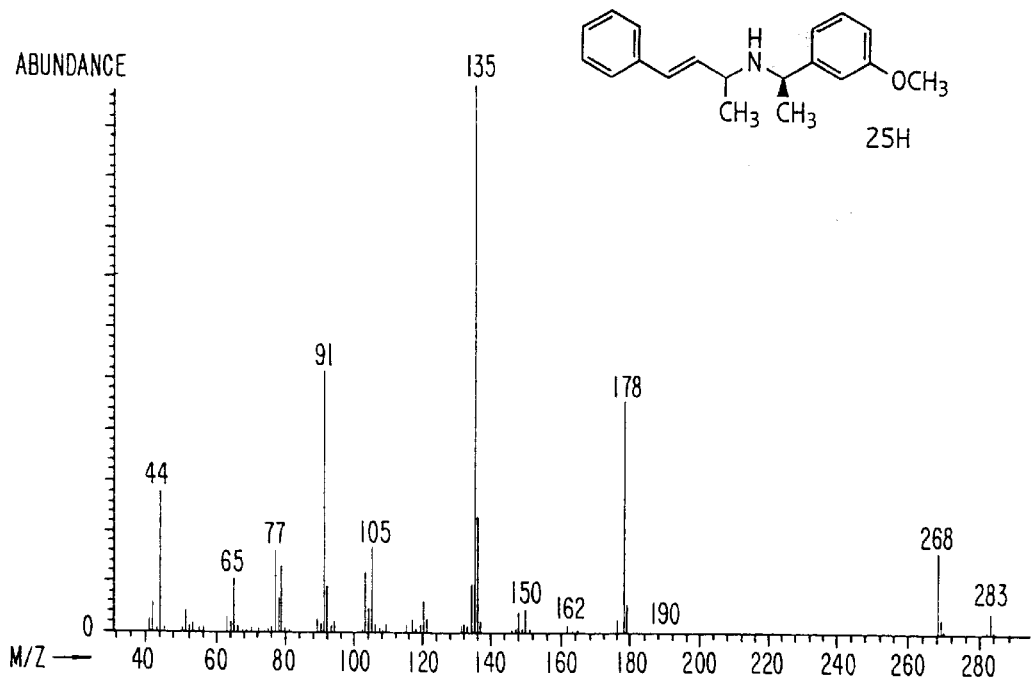
Figure 94:
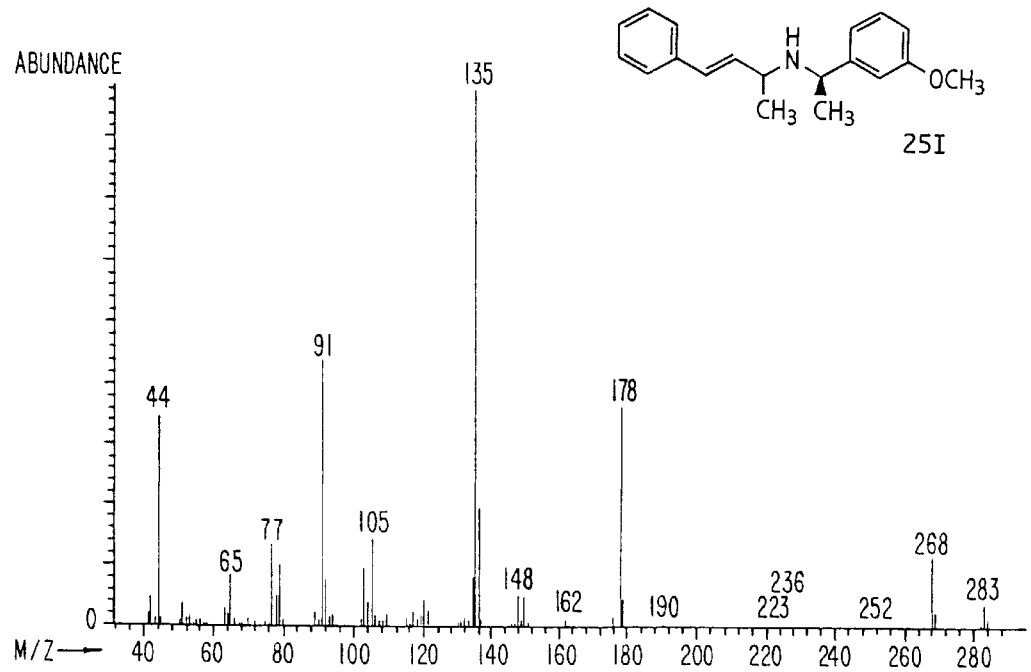
Figure 95:
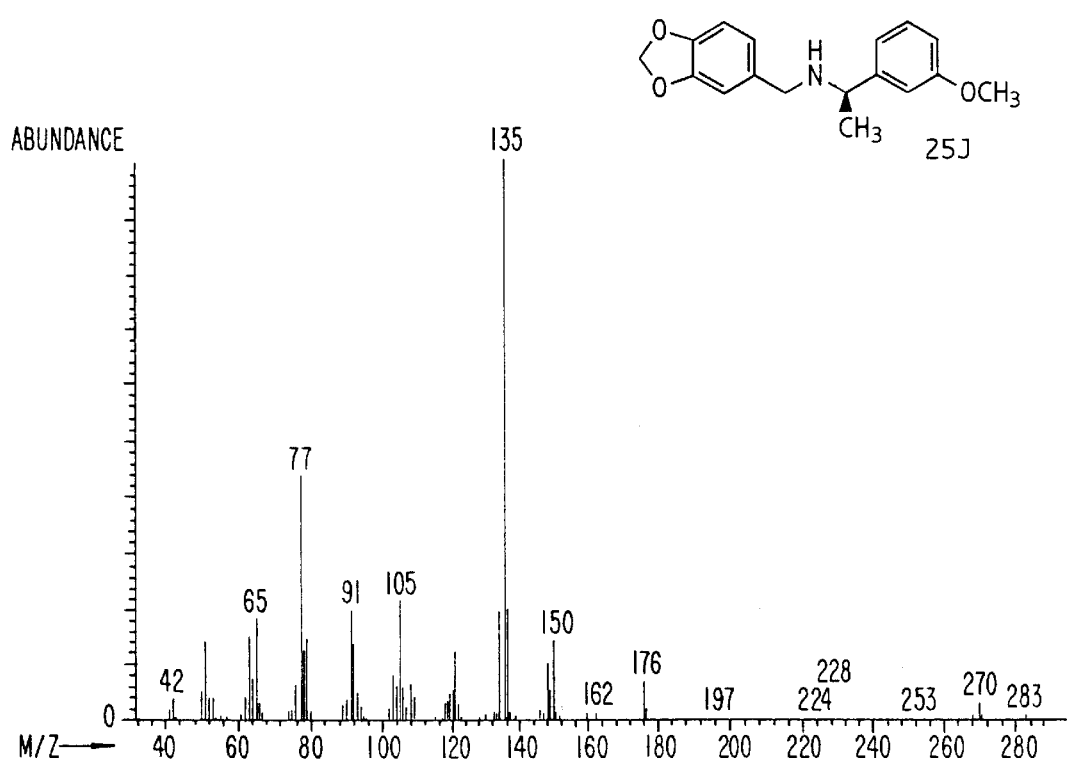
Figure 96:
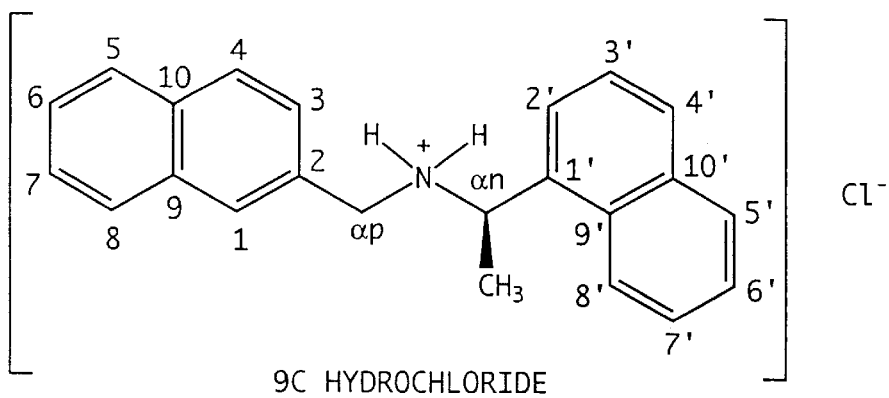
Figure 98:
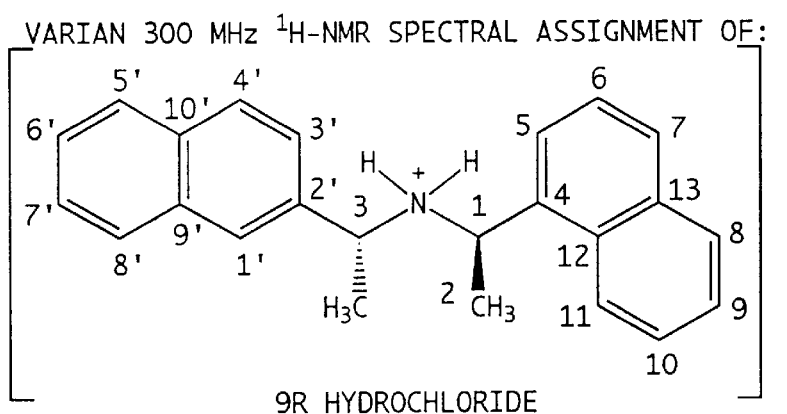
Figure 99:
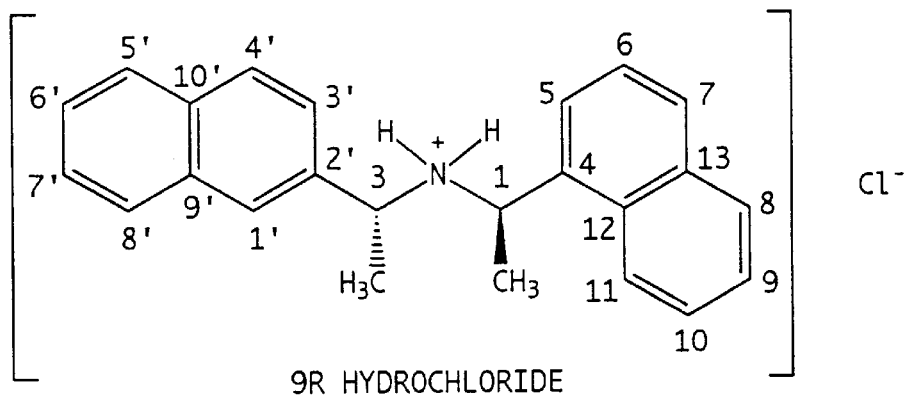
Figure 101:
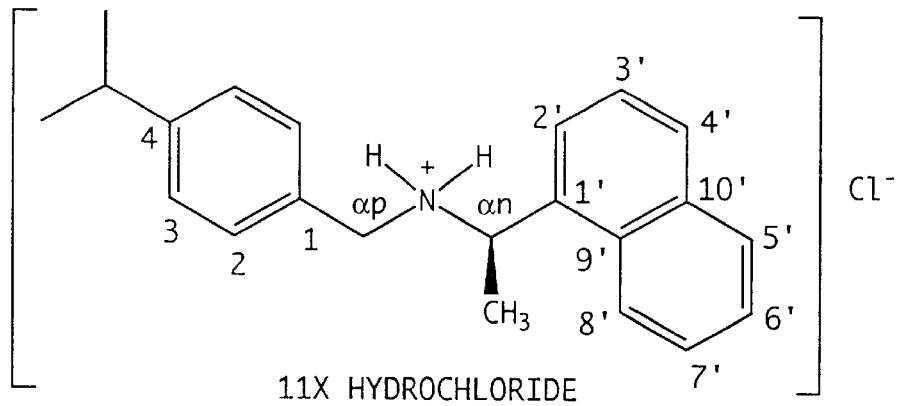
Figure 103:
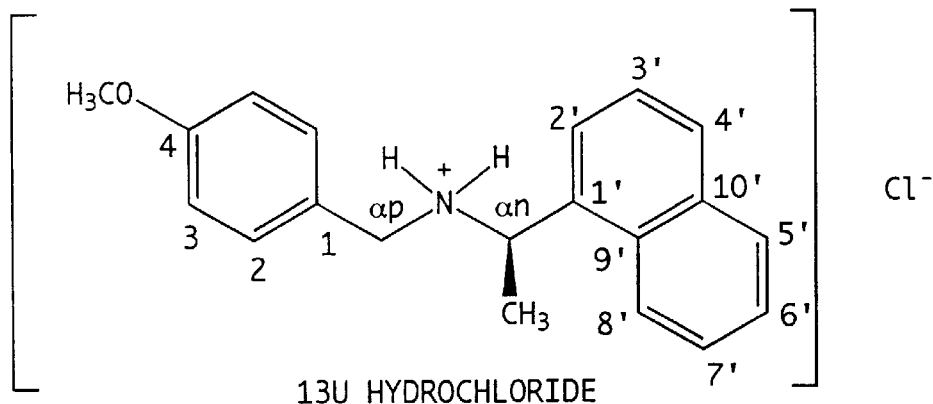
Figure 105:
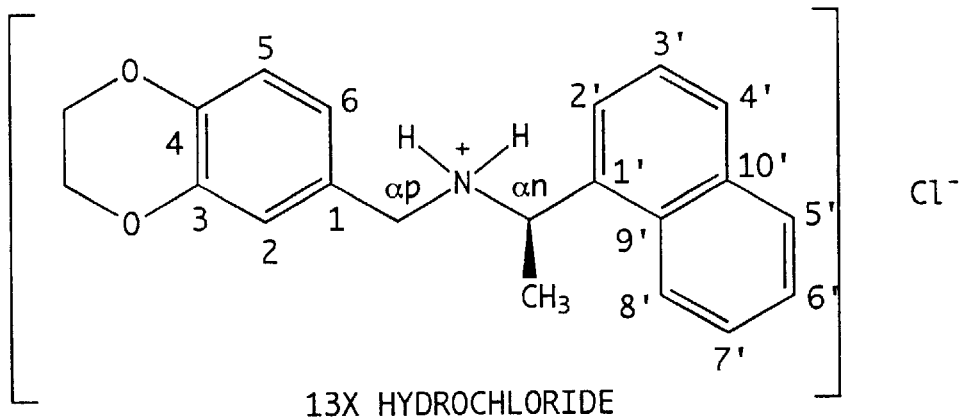
Figure 108:
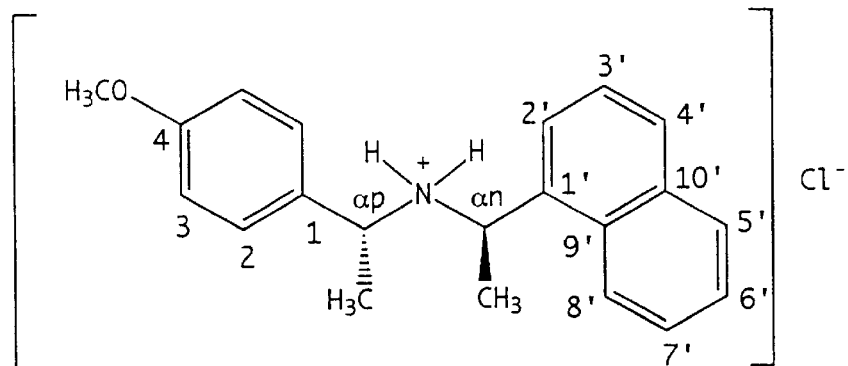
Figure 112:
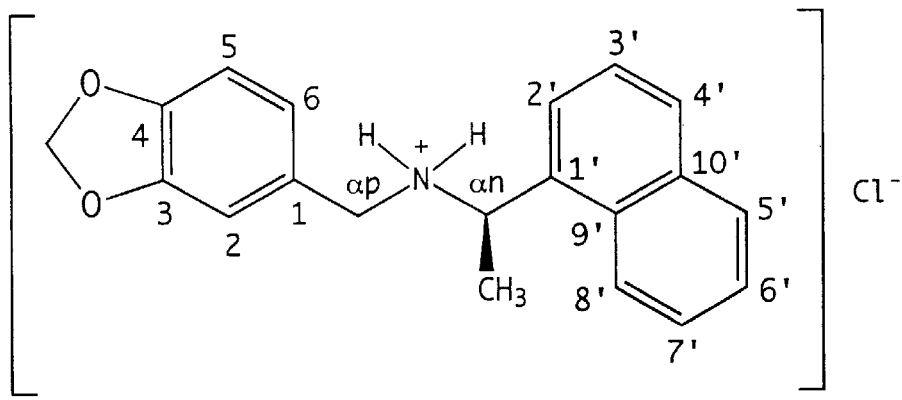
Figure 113:
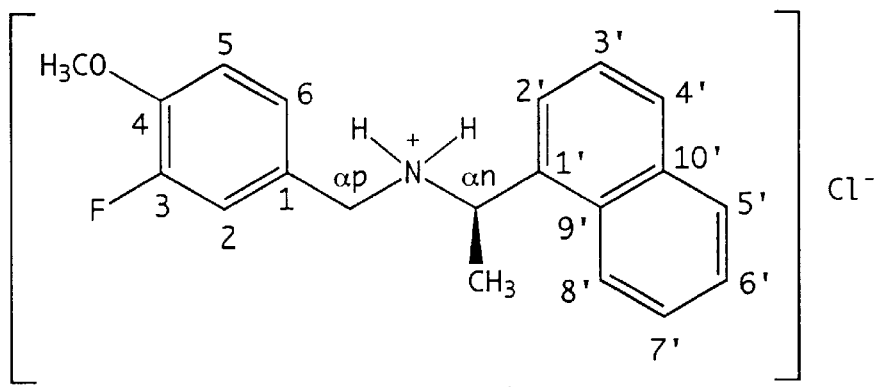
Figure 114:
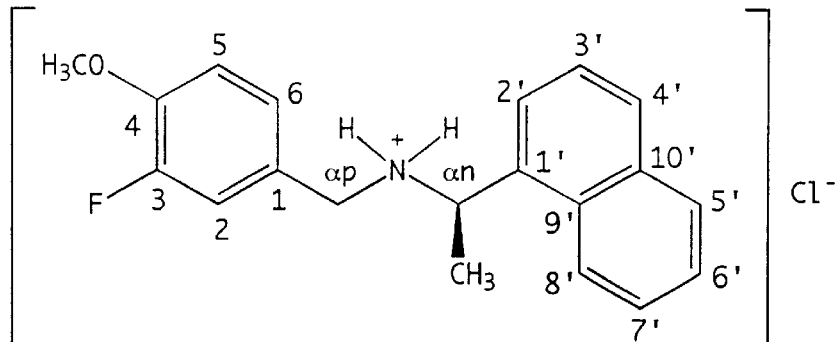
Figure 116:
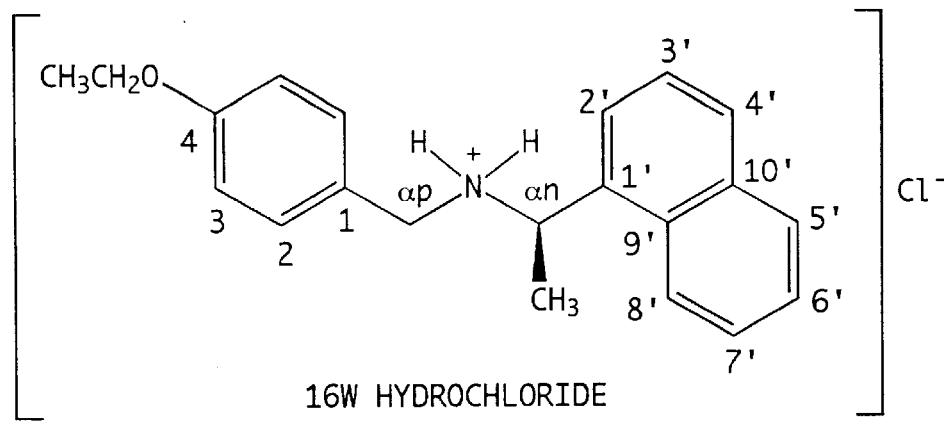
Figure 118:
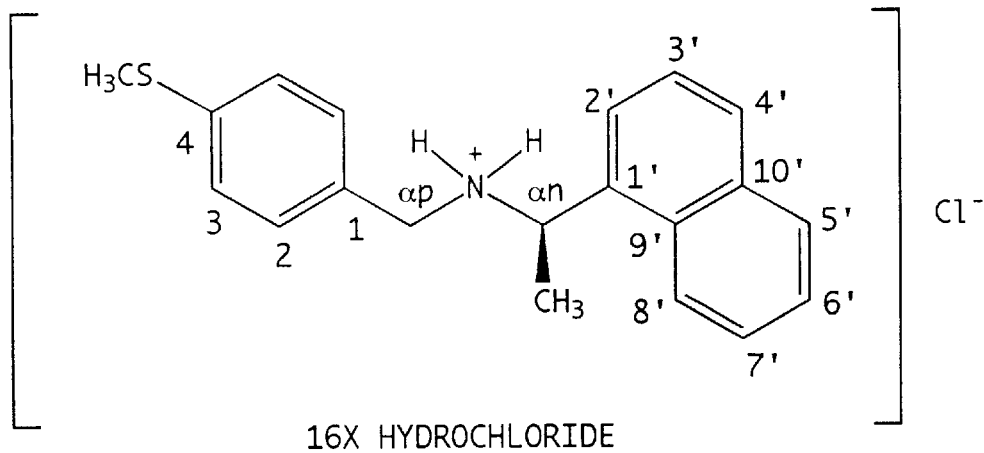
Figure 12O:
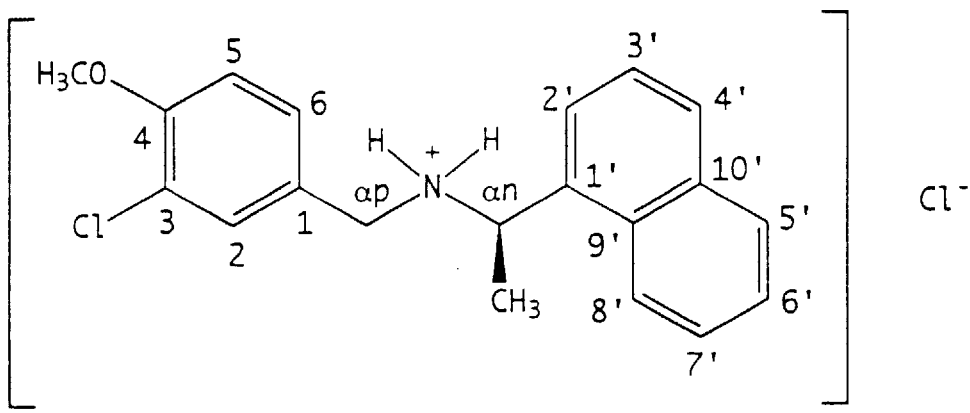
Figure 122:
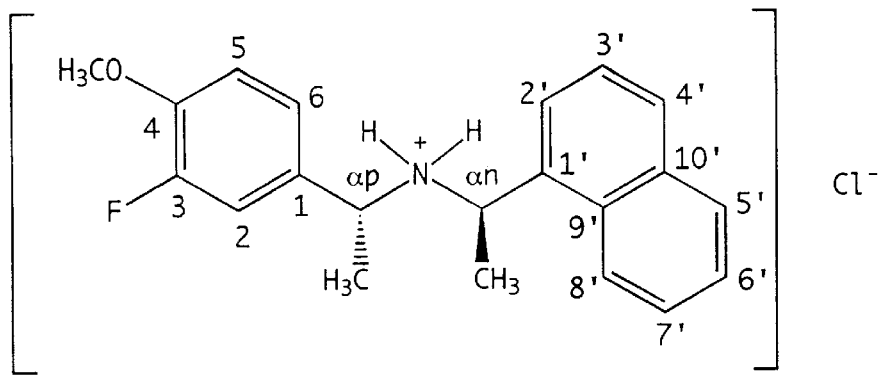
Figure 124:
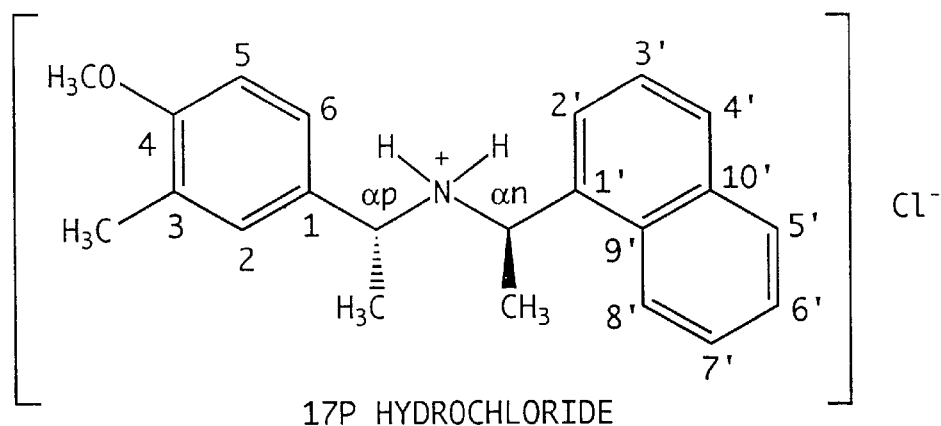
Figure 125:
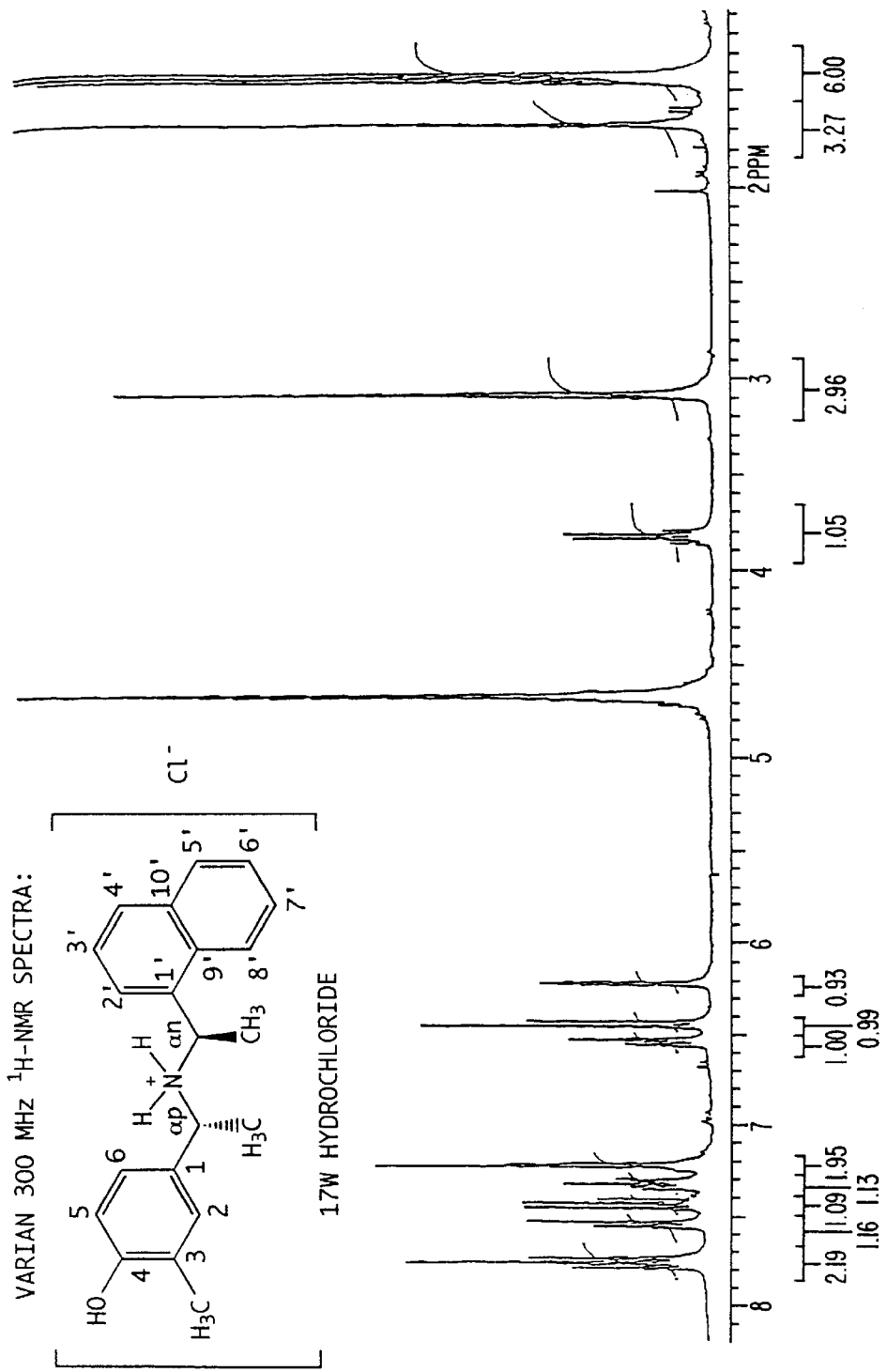
Figure 127:
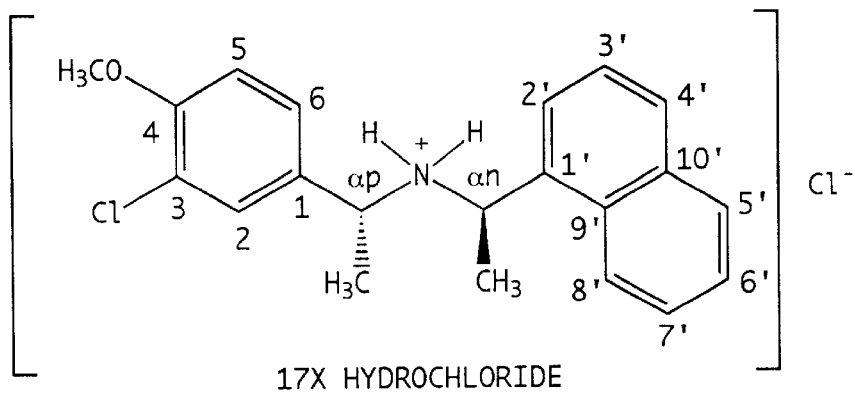
Figure 128:
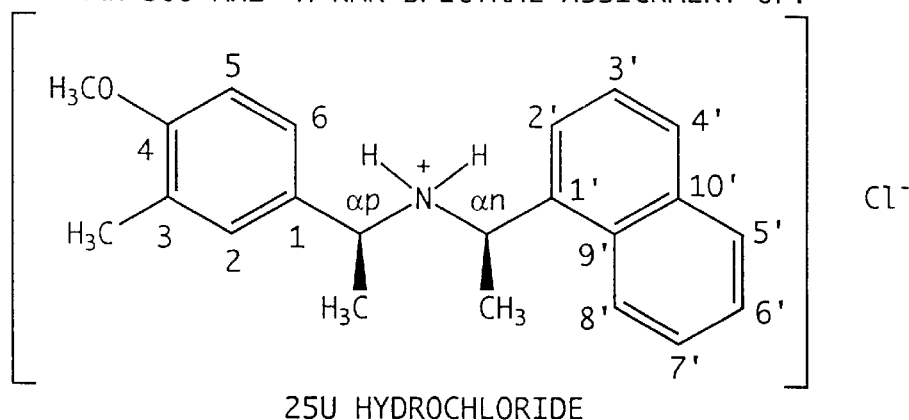
Figure 129:
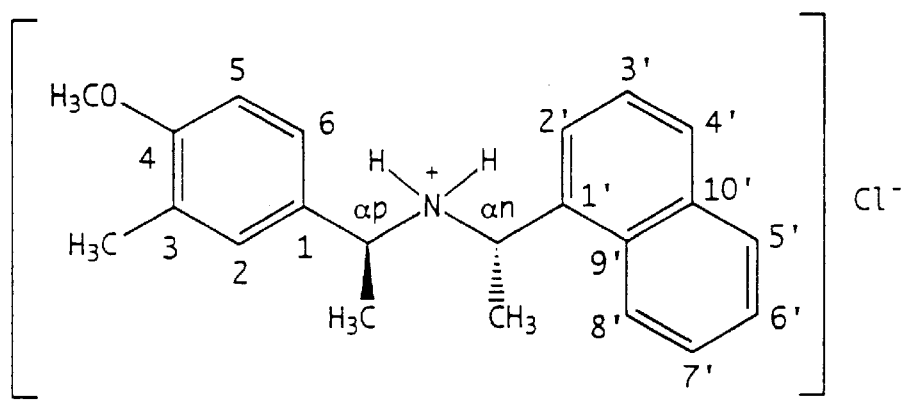
Figure 130:
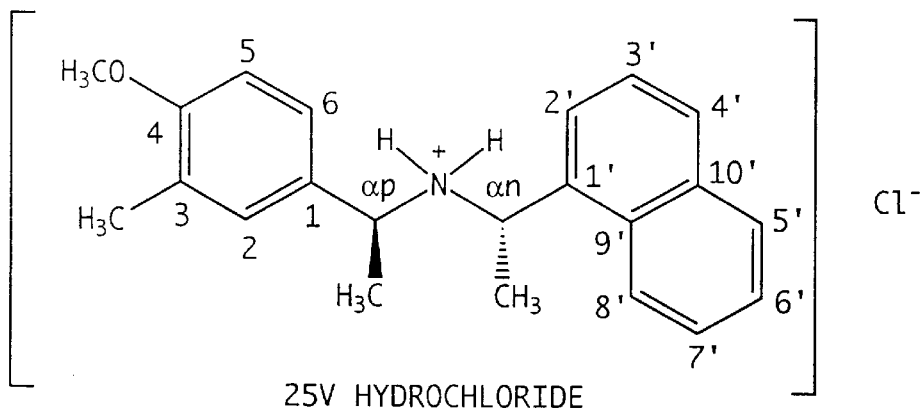
Figure 131:
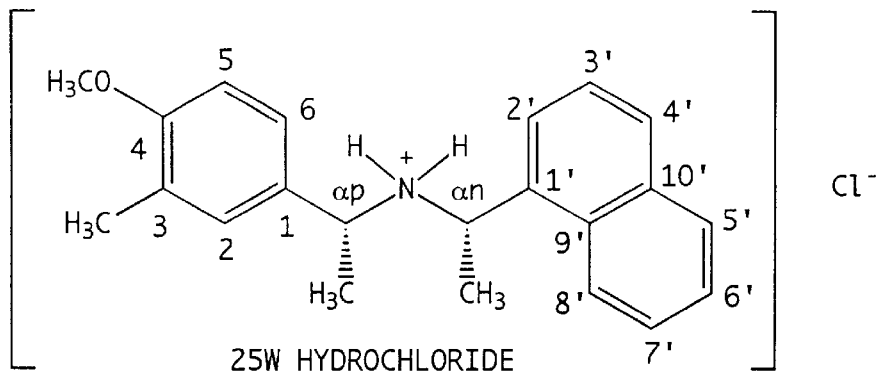

Arylalkylamine Calcimimetics from FIG. 1 Active at the Parathyroid Cell Calcium Receptor In Vitro ($EC_{50} \leq 5$ μM)

| Compound Code (from FIG. 1) | $EC_{50}$ (μM) | Compound Code (from FIG. 1) | $EC_{50}$ (μM) |
|---|---|---|---|
| NPS R-467 | 2.0 | 11X | 0.83 |
| NPS R-568 | 0.60 | 11Y | 2.8 |
| 3U | 0.64 | 12L | 1.7 |
| 3V | 1.8 | 12U | 1.2 |
| 4A | 1.4 | 12V | 0.42 |
| 4B | 2.0 | 12W | 3.2 |
| 4C | 2.0 | 12Y | 2.0 |
| 4D | 4.4 | 12Z | 0.11 |
| 4G | 1.8 | 13Q | ca. 0.8 |
| 4H | $\geq$3.0 | 13R | 0.25 |
| 4J | 2.2 | 13S | <0.13 |
| 4M | 2.1 | 13U | 0.19 |
| 4N | 0.8 | 13X | <0.75 |
| 4P | 1.6 | 14L | 0.26 |
| 4R/6V | 4.2 | 14Q | 0.47 |
| 4S | 3.3 | 14U | 0.13 |
| 4T/4U | 1.6 | 14V | 1.7 |
| 4V | 2.5 | 14Y | 0.38 |
| 4W | 2.3 | 15G | ca. 0.5 |
| 4Y | 1.3 | 16Q | 0.04 |
| 4Z/5A | 4.4 | 16R | 0.36 |
| 5B/5C | 2.8 | 16T | 0.04 |
| 5W/5Y | 3.6 | 16V | <0.13 |
| 6E | 2.7 | 16W | 0.59 |
| 6F(R,R-) | 0.83 | 16X | 0.10 |
| 6R | 3.4 | 17M | 0.15 |
| 6T | 2.9 | 17O | 0.04 |
| 6X | 2.5 | 17P | 0.04 |
| 7W | 3.2 | 17R | 0.39 |
| 7X | 1.1 | 17W | 0.43 |
| 8D | 2.5 | 17X | 0.02 |
| 8J | 0.78 | 20F | <1.0 |
| 8K | 1.3 | 20I | >1.0 |
| 8R | 2.6 | 20J | >3.0 |
| 8S | 1.7 | 20R | 2.4 |
| 8T | 1.8 | 20S | 4.2 |
| 8U | 0.44 | 21D | 3.0 |
| 8X | 0.76 | 21F | 0.38 |
| 8Z | 0.40 | 21G | 1.1 |
| 9C | 0.60 | 21O | 0.26 |
| 9D | 1.4 | 21P | 0.43 |
| 9R | 0.25 | 21Q | 1.4 |
| 9S | 4.8 | 21R | 0.37 |
| 10F | 0.89 | 25C | >2 |
| 11D | 1.8 | 25D | 0.019 |

Examples 6–17

Synthesis of Compounds

The compounds described herein can be synthesized using standard techniques such as those described by Nemeth et al., PCT/US93/01642, International Publication Number WO 94/18959. Examples describing representative syntheses of compounds described in the text are provided below.

Synthesis of compounds 9R, 14U, and 17P were prepared by reductive amination of a commercially available aldehyde or ketone with a primary amine in the presence of sodium cyanoborohydride or sodium triacetoxyborohydride. Compounds 11Y, 12H, 12K, 12M, 14S, 14T, 16L-O, 17E, 17G, 17J, 24X, 24Y, 25A, 25E-25K, and 25O were prepared in a similar manner.

It was found for the syntheses of these three compounds (9R, 14U, and 16P) that sodium triacetoxyborohydride afforded the desired diastereoisomers with greater diastereoselectivity than using sodium cyanoborohydride. The enriched mixtures were further purified to a single diastereomer by normal-phase HPLC or by recystallization from organic solvents.

Compounds 8J, 8U, 11X, 17M, and 25Y were prepared from the condensation of a primary amine with an aldehyde or ketone in the presence of titanium(IV) isopropoxide. The resulting intermediate imines were then reduced in situ by the action of sodium cyanoborohydride, sodium borohydride, or sodium triacetoxyborohydride. The intermediate enamine for the synthesis of compound 8U was catalytically reduced using or palladium dihydroxide on carbon.

Compounds 12U, 12V and 12Z were prepared by a diisobutylaluminum hydride (DIBAL-H) mediated condensation of an amine with a nitrile. The resulting intermediate imine is reduced in situ by the action of sodium cyanoborohydride or sodium borohydride. The intermediate alkenes (compounds 12U and 12V) were reduced by catalytic hydrogenation in EtOH using palladium on carbon. Compounds which were converted to their corresponding hydrochloride were done so by treatment of the free base with ethereal HCl to afford white solids.

The amines in these syntheses were purchased from Aldrich Chemical Co., Milwaukee, Wis., or from Celgene Corp., Warren, N.J., or were prepared synthetically using standard techniques. All other reagent chemicals were purchased from Aldrich Chemical Co.

Example 6

Synthesis of Compound 25Y

N-(3-(2-Phenyl)propyl)-1-(1-naphthyl) ethylamine

A mixture of 3-phenyl-1-propylamine (135 mg, 1 mmol), 1'-acetonaphthone (170 mg, 1 mmol), and titanium (IV) isopropoxide (355 mg, 1.3 mmol) was stirred at room temperature for 1 hour. The reaction was treated with 1 Methanolic sodium cyanoborohydride (1 mL) and stirred at room temperature for 16 hours. The reaction was diluted with ether and treated with water (0.1 mL). The reaction was centrifuged and the ether layer removed and concentrated to a milky oil. A small portion of this material (10 mg) was purified by HPLC (Phenomenex, 1.0×25 cm, 5 μM silica) using a gradient of dichloromethane to 10% methanol in dichloromethane containing 0.1% isopropylamine. This afforded the product (free base) as a single component by GC/El-MS ($R_t$=10.48 min) m/z (rel. int.) 289 ($M^+$,11), 274 (63), 184 (5), 162 (5), 155 (100), 141 (18), 115 (8), 91 (45), 77(5).

Example 7

Synthesis of Compound 8J

N-(3-phenylpropyl)-1-(3-thiomethylphenyl)ethylamine hydrochloride

3'-Aminoacetophenone (2.7 g, 20 mmol) was dissolved in 4 mL of concentrated HCl, 4 g of ice and 8 mL of water. The solution was cooled to 0° C., and sodium nitrite (1.45 g, 21 mmol) dissolved in 3–5 mL of water was added over 5 minutes while maintaining the temperature below 6° C. Sodium thiomethoxide (1.75 g, 25 mmol) was dissolved in 5 mL of water and cooled to 0° C. To this solution was added the diazonium salt over 10 minutes while maintaining the temperature below 10° C. The reaction was stirred for an additional hour while allowing the temperature to rise to ambient. The reaction mixture was partitioned between ether and water. The ether layer was separated and washed with sodium bicarbonate and sodium chloride, and dried over sodium sulfate. The ether was evaporated to give a 74% yield of 3'-thiomethylacetophenone. The crude material was purified by distillation at reduced pressure.

3-Phenylpropylamine (0.13 g, 1 mmol), 3'-thiomethylacetophenone (0.17 g, 1 mmol), and titanium (IV) isopropoxide (0.36 g, 1.25 mmol) were mixed together and allowed to stand for 4 hours. Ethanol (1 mL) and sodium cyanoborohydride (0.063 g, 1 mmol) were added and the reaction was stirred overnight. The reaction was worked up by the addition of 4 mL of ether and 200 μL of water. The mixture was vortexed and then spun in a centrifuge to separate the solids. The ether layer was separated from the precipitate, and the solvent removed in vacuo. The oil was redissolved in dichloromethane and the compound purified by preparative TLC on silica gel eluted with 3% methanol/dichloromethane to yield the title compound as a pure oil: GC/EI-MS($R_t$=7.64 min) m/z (rel. int.)285 ($M^+$, 18), 270 (90), 180(17), 151(100), 136(32), 104(17), 91(54), 77(13).

Example 8

Synthesis of Compound 8U

N-3-(2-methoxyphenyl)-1-propyl-(R)-3-methoxy-α-methylbenzylamine hydrochloride

A mixture of (R)-(+)-3-methoxy-a-methylbenzylamine (3.02 g, 20 mmol), 2-methoxycinnamaldehyde (3.24 g, 20 mmol), and titanium (IV) isopropoxide (8.53 g, 30 mmol, 1.5 Eq.) was stirred 2 hours at room temperature and treated with 1 M (20 mL) ethanolic sodium cyanoborohydride. The reaction was stirred overnight (16 hours), diluted with diethylether, and treated with water (1.44 mL, 80 mmol, 4 Eq.). After mixing for 1 hour the reaction mixture was centrifuged and the ether layer removed and concentrated to an oil. This material was dissolved in glacial acetic acid, shaken with palladium hydroxide and hydrogenated under 60 p.s.i. hydrogen for 2 hours at room temperature. The catalyst was removed by filtration and the resulting solution concentrated to a thick oil. This material was dissolved in dichloromethane and neutralized with 1 N NaOH. The dichloromethane solution was separated from the aqueous phase, dried over anhydrous potassium carbonate and concentrated to an oil. This material was dissolved in ether and treated with 1 M HCl in diethylether. The resulting precipitate (white solid) was collected, washed with diethylether, and air dried. GC/El-MS ($R_t$=9.69 min) of this material (free base) showed a single component: m/z (rel. int.) 299 (M+, 21), 284 (100), 164 (17), 150 (8), 135 (81), 121 (40), 102 (17), 91 (43), 77 (18).

Example 9

Synthesis of Compound 9R (R)-N-(1-(2-naphthyl)ethyl)-(R)-1-(1-naphthyl) ethylamine hydrochloride A mixture of (R)-(+)-1-(1-naphthyl)ethylamine (10.0 g, 58 mmol), 2'-acetonaphthone (9.4 g, 56 mmol), titanium (IV) isopropoxide (20.7 g, 73.0 mmol), and ETOH (abs.) (100 mL) was heated to 60° C. for 3 hours. Sodium cyanoborohydride ($NaCNBH_3$) (3.67 g, 58.4 mmol) was then added. The reaction mixture was stirred at room temperature for 18 hours. Ether (1 L) and $H_2O$ (10 mL) were added to the reaction mixture and the resulting precipitate was then removed by centrifugation. The supernatant was evaporated under vacuum and the crude product was recrystallized four times from hot hexane, to provide 1.5 g of pure (98+%) diastereomer. The free base was dissolved in hexane, filtered, and then ethereal HCl was added to precipitate the product as a white solid (1.1 g, 6% yield), m.p.: softens 200–240° C. (dec.).

Example 10

Synthesis of Compound 11X

N-(4-Isopropylbenzyl)-(R)-1-(1-naphthyl)ethylamine hydrochloride

A mixture of (R)-(+)-1-(1-naphthyl)ethylamine (1.06 g, 6.2 mmol), 4-isopropylbenzaldehyde (0.92 g, 6.2 mmol), and titanium (IV) isopropoxide (2.2 g, 7.7 mmol) was heated to 100° C. for 5 min then allowed to stir at room temperature for 4 hours. Sodium cyanoborohydride ($NaCNBH_3$) (0.39 g, 6.2 mmol) was then added followed by EtOH (1 mL). The reaction mixture was stirred at room temperature for 18 hours. Ether (100 mL) and $H_2O$ (1 mL) were added to the reaction mixture and the resulting precipitate was then removed by centrifugation. The supernatant was evaporated under vacuum and the crude product was chromatographed on silica gel (50 mm×30 cm column) (elution with 1% $MeOH/CHCl_3$). The chromatographed material was then dissolved in hexane and ethereal HCl was added to precipitate the product as a white solid (0.67 g, 35% yield), m.p.; 257–259° C.

Example 11

Synthesis of Compound 12U

N-3-(2-methylphenyl)-1-propyl-(R)-3-methoxy-α-methylbenzyl amine hydrochloride

A solution of 2-methylcinnamonitrile (1.43 g, 10 mmol) in dichloromethane (10 mL) was cooled to 0° C. and treated dropwise (15 minutes) with 1 M diisobutylaluminum hydride (10 mL, dichloromethane). The reaction was stirred at 0° C. for 15 minutes and treated dropwise (15 minutes) with a 1 M solution of (R)-(+)-3-methoxy-α-methylbenzylamine (1.51 g, 10 mmol) in dichloromethane (10 mL). The reaction was stirred 1 hours at 0° C. and poured into a solution of ethanol (100 mL) containing sodium cyanoborohydride (1 g, 16 mmol). The reaction mixture was stirred 48 hour at room temperature. The reaction was diluted with ether and neutralized with 1 N NaOH. The ether layer was removed, dried over anhydrous potassium carbonate and concentrated to an oil. This material was chromatographed through silica using a gradient of dichloromethane to 5% methanol in dichloromethane to afford the unsaturated intermediate, a single component by GC/EI-MS ($R_t$=10.06 min) m/z (rel. int.) 281 (M+, 17), 266 (59), 176 (19), 146 (65), 135 (73), 131 (100), 91 (21), 77 (13).

The unsaturated intermediate in ethanol was hydrogenated (1 atm $H_2$) in the presence of palladium on carbon for 16 hours at room temperature. The product from this reaction was converted to the hydrochloride salt by treatment with 1 M HCl in diethylether. GC/E1-MS ($R_t$=9.31 min) of this material (free base) showed a single component: m/z (rel. int.) 283 (M+, 21), 268 (100), 164 (12), 148 (8), 135 (85), 121 (12), 105 (49), 91 (23), 77 (21).

Example 12

Synthesis of Compound 12V

N-3-(3-methylphenyl)-1-propyl-(R)-3-methoxy-α-methylbenzylamine hydrochloride

The compound was prepared following the procedure described in Example 11, but using 2-methylcinnamonitrile. The unsaturated intermediate was a single component by GC/EI-MS ($R_t$=10.21 min) m/z (rel. int.) 281 (M+, 57), 266 (86), 146 (98), 135 (88), 131 (100), 115 (43), 102 (26), 91 (43), 77 (18). Reduction of this material and hydrochloride formation using the procedure described Example 11 afforded the product. GC/EI-MS ($R_t$=9.18 min) of this material (free base) showed a single component; m/z (rel. int.) 283 (M+, 19), 268 (100), 164 (11), 148 (8), 135 (76), 121 (16), 105 (45), 91 (23), 77 (21).

Example 13

Synthesis of Compound 12Z

N-3-(2-chlorophenyl)-1-propyl -(R)-1-(1-naphthyl) ethylamine hydrochloride

The compound was prepared following the procedures described in Example 11, but using 2-chlorohydrocinnamonitrile and (R)-(+)-1-(1-naphthyl) ethylamine on a 10 mmol scale. Chromatography through silica using a gradient of dichloromethane to 5% methanol in dichloromethane afforded the product as a single component by TLC analysis (5% methanol in dichloromethane). The hydrochloride was prepared by treatment with 1 M HCl in diethylether.

Example 14

Synthesis of Compound 14U (R)-N-(1-(4-methoxyphenyl)ethyl)-(R)-1-(1-naphthyl) ethylamine hydrochloride A mixture of (R)-(+)-1-(1-naphthyl)ethylamine (1.1 g, 6.2 mmol), 4'-methoxyacetophenone (0.93 g, 6.2 mmol), titanium (IV) isopropoxide (2.2 g, 7.7 mmol), and EtOH (abs.) (1 mL) was heated to 60° C. for 3 hours. Sodium cyanoborohydride ($NaCNBH_3$) (0.39 g, 6.2 mmol) was then added, and the reaction mixture was stirred at room temperature for 18 hours. Ether (200 mL) and $H_2O$ (2 mL) were added to the reaction mixture and the resulting precipitate was then removed by centrifugation. The supernatant was evaporated under vacuum and the crude product was chromatographed on silica gel (25 mm×25 cm column) (elution with 1% MeOH/$CHCl_3$). A portion of this material was HPLC chromatographed [Selectosil, 5 µM silica gel; 25 cm×10.0 mm (Phenomenex, Torrance, Calif.), 4 mL per minute; UV det. 275 nM; 12% ethyl acetate-88% hexane (elution time 12.0 min)]. The HPLC purified diastereomer was then dissolved in hexanes and ethereal HCl was added to precipitate the product as a white solid (20 mg), m.p.: 209–210° C. (dec.).

Example 15

Synthesis of Compound 17M

N-(3-chloro-4-methoxybenzyl)-(R)-1-(1-naphthyl) ethylamine hydrochloride

A mixture of (R)-(+)-1-(1-naphthyl)ethylamine (6.6 g, 39 mmol), 3'-chloro-4'-methoxybenzaldehyde (6.6 g, 39 mmol), and titanium (IV) isopropoxide (13.8 g, 48.8 mmol), and EtOH (abs.) (30 mL) was heated to 80° C. for 30 minutes then allowed to stir at room temperature for 3 hours. Sodium cyanoborohydride ($NaCNBH_3$) (2.45 g, 39 mmol) was then added. The reaction mixture was stirred at room temperature for 18 hours. Ether (100 mL) and $H_2O$ (2 mL) were added to the reaction mixture and the resulting precipitate was then removed by centrifugation. The supernatant was evaporated under vacuum and the crude product was chromatographed on silica gel (50 mm×30 cm column) (elution with $CH_2Cl_2$). The chromatographed material was then dissolved in hexane (500 mL), decolorized with Norit® filtered (0.2 µM), and then ethereal HCl was added to precipitate the product as a while solid (10.2 g, 56% yield), m.p.: 241–242° C. (dec.).

Example 16

Synthesis of Compound 17P

4-Methoxy-3-methylacetophenone [17P Precursor]

A mixture of 4'-hydroxy-3'-methylacetophenone (5.0 g, 33.3 mmol), iodomethane (5.7 g, 40.0 mmol), $K_2CO_3$ (granular, anhydrous) (23.0 g, 167 mmol), and acetone (250 mL) was refluxed for 3 hours. The reaction mixture was then cooled to room temperature, filtered to remove the inorganic salts, and evaporated under vacuum. The crude product was dissolved in ether (100 mL) and washed with $H_2O$ (2×20 mL). The organic layer was dried ($Na_2SO_4$) and evaporated to yield 4.5 g, 82.4%. yield. The ketone was used in the following reaction without further purification.

(R)-N-(1-(4-Methoxy-3-methylphenyl)ethyl)-(R)-1-(1-naphthyl)ethylamine hydrochloride [Compound 17P]

A mixture of (R)-(+)-1-(1-naphthyl)ethylamine (4.24 g, 24.8 mmol), 4'-methoxy-3'-methylacetophenone (4.06 g, 24.8 mmol), and titanium (IV) isopropoxide(8.8 g, 30.9 mmol), and EtOH (abs.) (1 mL) was heated to 100° C. for 2 hours. Isopropanol (45 mL) was added and the reaction was then cooled to 10° C. in an ice bath. Sodium triacetoxyborohydride ($NaHB(O_2CCH_3)_3$) (10.5 g, 49.5 mmol) was then added in portions over 15 minutes. The reaction mixture was then heated to 70° C. for 18 hours. The mixture was cooled to room temperature and poured into ether (400 mL).

The suspension was centrifuged, the supernatant was collected and the pellet was washed with ether (400 mL). The combined organic washings were evaporated under vacuum. The residue was dissolved in ether (400 mL) and washed with 1 N NaOH (4×50 mL) and $H_2O$ (2×50 mL). The organic layer was dried ($Na_2SO_4$), filtered and evaporated under vacuum. EtOH (abs.) was added to the wet residue which was then dried thoroughly on a rotary evaporator to provide an oil. The mixture was then chromatographed on silica gel (50 mm×30 cm) [elution with (1% MeOH:1% IPA:$CHCl_3$) to give 4.8 g of an oil].

The desired diastereomer was further purified by HPLC chromatography [SUPELCOSIL™ PLC-Si, 18 μM silica gel; 25 cm×21.2 mm (Supelco, Inc., Bellefonte, Pa.), 7 mL per minute; UV det. 275 nM: 20% EtOAc-80% hexane (elution time 9.5–11.0 min)]. Injections (800 mL aliquots) of the mixture (100 mg/mL solution in eluent) provided 65 mg of the desired isomer. Multiple HPLC injections provided 1.0 g of purified material. The HPLC chromatographed material was dissolved in hexane (50 mL) and the hydrochloride salt was precipitated with ethereal HCl. The salt was collected on fritted glass and washed with hexane to provide 1.0 g of a white solid, mp 204–205° C.

Example 17

Synthesis of Compound 17X

3-Chloro-4-methoxybenzaldehyde

A mixture of 3-chloro-4-hydroxybenzaldehyde (25 g, 160 mmol), iodomethane (27.25 g, 192 mmol), $K_2CO_3$ (granular, anhydrous) (110.6 g, 800 mmol), and acetone (300 mL) was refluxed for 3 hours. The reaction mixture was then cooled to room temperature. Diethyl ether (500 mL) was added and the mixture was filtered through paper to remove the inorganic solids. The filtrate was evaporated under reduced pressure, dissolved in diethyl ether (800 mL), and washed with 0.1 N NaOH (3×100 mL). The organic layer was dried ($Na_2SO_4$) and evaporated under vacuum to yield 24 g, 92t yield of crude product. This material was further purified by chromatography on silica gel (50 mm×30 cm) (elution with hexane-EtOAc, 5:1) to give 15.02 g, 56% yield of a white solid: TLC (hexane-EtOAc, 5:1) $R_f$=0.24; GC $R_t$=4.75 min; MS (EI) m/z 170($M^+$), 172(M+2).

1-Methyl-(3'-chloro-4'-methoxybenzyl) alcohol

A mixture of 3-chloro-4-methoxybenzaldehyde (13 g, 76.5 mmol), methylmagnesium chloride (52 g, 153 mmol), and THF (300 mL) was refluxed for 3 hours. The reaction mixture was cooled to room temperature. $NH_4Cl$ (satd. soln., 6 mL) was added dropwise followed by diethyl ether (500 mL) and the mixture was filtered through paper to remove the inorganic solids. The filtrate was evaporated under reduced pressure and the resulting solid was dissolved in diethyl ether (300 mL) and washed with water (4×25 mL). The organic layer was dried ($Na_2SO_4$) and evaporated under vacuum to yield 11.3 g, 80% yield of crude product. This material was further purified by chromatography on silica gel (50 mm×30 cm) (elution with $CH_2Cl_2$) to yield 11.3 g, 63% yield of an oil; TLC ($CH_2Cl_2$) $R_f$=−0.25; GC $R_t$=5.30 min; MS (EI) m/z 186(M+), 188(M+2)

3'-Chloro-4'-methoxyacetophenone

A mixture of 1-methyl-(3'-Chloro-4'-methoxybenzyl) alcohol (7.6 g, 41 mmol), pyridinium chlorochromate (PCC) (13.16 g, 61.5 mmol), and $CH_2Cl_2$ (300 mL) was allowed to stir at room temperature for 2 hours. Diethyl ether (1000 mL) was added and the resulting mixture was placed on a chromatography column of silica gel (50 mm×30 cm) (elution with diethyl ether) to yield 7.3 g, 97% yield of crude solid product. GC analysis of this material showed it to be 99% pure and it was used in the following reaction without further purification. TLC (diethyl ether) $R_f$=1.0; GC $R_t$=5.3 min; MS (EI) m/z 184($M^+$), 184(M+2).

(R,R)-N-(1-Ethyl-4'-methoxy-3'-chlorophenyl)-1-(1-naphthylethyl) amine

A mixture of 3'-chloro-4'-methoxyacetophenone (5.3 g, 29 mmol), (R)-(+)-1-(1-naphthyl)ethylamine (4.98 g, 29 mmol), titanium (IV) isopropoxide (10.2 g, 36 mmol), and isopropanol (20 mL) was heated to 100° C. for 3 hours. Sodium triacetoxyborohydride (NaB($O_2CCH_3$)$_3$; 12.29 g, 58 mmol) was added in portions over 10 minutes. The reaction mixture was heated to reflux for 30 minutes and was then allowed to stir at room temperature for 18 hours. The mixture was then poured into diethyl ether (500 mL); $H_2O$ (2 mL) was added and the suspension was centrifuged to remove the fine precipitate of titanium salts. The supernatant was collected and the pellet was washed with ether (500 mL). The combined organic layers were dried ($Na_2SO_4$) and evaporated under vacuum to yield 6.81 g, 70% of crude product.

This material was further purified by chromatography on silica gel (50 mm×30 cm) (elution with 3% MeOH-97% $CH_2Cl_2$) to give 2.01 g of an oil. The diastereomer was further purified by recrystallization. The free base (1.98 g) was converted to its HCl salt with ethereal HCl. This salt was dissolved in hot isopropanol (65 mL) and the solution was filtered through paper. The filtrate was evaporated under vacuum and the resulting solid dissolved in isopropanol (30 mL). After standing at room temperature for 18 hours, the crystalline solid was collected, washed with cold isopropanol (20 mL), and dried to yield 0.87 g, 40% (from free base) of the diastereomerically pure hydrochloride salt: mp 236–237° C. (dec); TLC (MeOH-$CH_2Cl_2$[99:1]) $R_f$=0.25; GC $R_t$=11.06 min; FTIR (KBr pellet, $cm^{-1}$) 3433, 2950, 2931, 2853, 2803, 2659, 2608, 2497, 1604, 1595, 1504, 1461, 1444, 1268, 1260, 1067, 1021, 802, 781, 733; MS (EI) m/z 339($M^+$), 341(M+2).

Example 18

Additional Synthesis Protocol

Preparation of 22Z and 23A

A stirred solution of sodium hydride (2.173 g, 60% in oil, 54.325 mmol) in dimethylformamide (100 ml) was treated dropwise with triethyl phosphonoacetate (12.47 g, 55.65 mmol) and stirred 30 min at rt. After this time, a solution of m-trifluoromethoxy benzaldehyde (10.0 g, 52.6 mmol) in dimethylformamide (50 ml) was added dropwise and the solution stirred 30 min at rt and 30 min at 100° C. The reaction was quenched by the addition of water and transferred to a separatory funnel using diethyl ether (500 ml). The ether solution was washed with saturated ammonium chloride (4×500 ml), dried over anhydrous magnesium sulfate, filtered and concentrated to afford ethyl m-trifluoromethoxycinnamate as an oil; m/z (rel. int.) 260 ($M^+$, 19), 232 (16), 215 (100), 187 (21), 101 (28).

The ethyl ester in ethanol (100 ml) was reduced under 60 p.s.i. hydrogen using a catalytic amount (10% by weight) palladium hydroxide. After reduction (2 hr, rt) the reaction was filtered and concentrated to afford ethyl m-trifluoromethoxyhydrocinnamate as an oil; m/z (rel. int.) 262 ($M^+$, 16), 217 (7), 188 (100), 175 (28), 103 (31), 91 (18), 77 (23).

The saturated ethyl ester was hydrolyzed in a solution of ethanol-10 M sodium hydroxide (1:1) for 16 hr at rt. After this time the solution was acidified and the product extracted into diethyl ether. The ether solution was dried over anhydrous magnesium sulfate and concentrated to afford m-trifluoromethoxyhydrocinnamic acid as a solid; m/z (rel. int.) 234 (M$^+$, 46), 188 (100), 174 (65), 103 (27), 91 (12), 77 (17).

The acid, was stirred in excess thionyl chloride for 4 hr at rt. The excess thionyl chloride was evaporated at reduced pressure (100° C.) to afford m-trifluoromethoxyhydrocinnamyl chloride as an oil. The product was used without further purification.

A solution of m-trifluoromethoxyhydrocinnamyl chloride (9.8 g, 39 mmol) in tetrahydrofuran was cooled to −78° C. and treated dropwise with a solution (13 ml of 3 M in tetrahydrofuran) of methylmagnesium bromide (39 mmol). The reaction was stirred 4 hr at −78° C., 8 hr at rt, and quenched with dilute HCl. The reaction mixture was extracted with diethyl ether. The ether was dried over anhydrous magnesium sulfate, filtered and concentrated to an oil. Chromatography of this material through silica using a gradient of hexane to acetone afforded 4-(3-trifluoromethoxyphenyl)-2-butanone as an oil; m/z (rel. int.) 232 (M$^+$, 68), 217 (7), 189 (59), 175 (31), 103 (28), 43 (100).

A solution of 4(3-trifluoromethoxyphenyl)-2-butanone (2.32 g, 10 mmol), (R)-1-(3-methoxyphenyl)ethylamine (1.51 g, 10 mmol), and titanium (IV) isopropoxide (3.55 g, 12.5 mmol) were stirred 4 hr at rt. The reaction mixture was then treated with a solution (10 ml of 1 M) of ethanolic sodium cyanoborohydride (10 mmol) and stirred 16 hr at rt. The reaction was diluted with diethyl ether (50 ml) and treated with water (0.72 ml, 40 mmol). After mixing thoroughly the solution was centrifuged and the ether layer decanted and concentrated to a oily solid. The solid was suspended in diethyl ether, filtered through 0.45 μM CR PTFE Acrodisc and concentrated to give a clear oil. Repetitive preparative thin-layer chromatography using 5% methanol in chloroform afforded the two diasteriomers, (S,R)-N-[4-(3-trifluoromethoxyphenyl)-2-butyl]-1-(3-methoxyphenyl)ethylamIne, 22Z [m/z (rel. int.) 367 (M$^+$, 3), 352 (20), 232 (4), 178 (47), 135 (100), 105 (14), 91 (10), 77 (11)] and (R,R)-N-[4-(3-trifluoromethoxyphenyl)-2-butyl]-1-(3-methoxyphenyl)ethylamine, 23A; m/z (rel. int.) 367 (M$^+$, 3), 352 (19), 232 (7), 178 (43), 135 (100), 105 (19), 91 (10), 77 (11).

Preparation of 22X and 22Y

In a similar fashion an equal molar amount of 4-(3-trifluoromethoxyphenyl)-2-butanone, (R)-1-(1-naphthyl)ethylamine and 1.25 equivalents titanium(IV) isopropoxide were mixed and the intermediate imine reduced with ethanolic sodium cyanoborohydride. Work-up and repetitive preparative thin-layer chromatography using 5% methanol in chloroform afforded (S,R)-N-[4-(3-trifluoromethoxyphenyl)-2-butyl]-1-(1-naphthyl)ethylamine, 22X; m/z (rel. int.) 387 (M$^+$, 3), 372 (15), 198 (15), 176 (12), 155 (100), 128 (8), 115 (6), 109 (4), 103 (5), 77 (8) and (R,R)-N-[4-(3-trifluoromethoxyphenyl)-2-butyl]-1-(1-naphthyl)ethylamine, 22Y; m/z (rel. int.) 387 (M$^+$, 2), 372 (12), 198 (16), 176 (11), 155 (100), 128 (8), 115 (6), 109 (4), 103 (5), 77 (8).

Preparation of 4T

In a similar fashion an equal molar amount of 4-(2-chlorophenyl)-2-butanone, prepared from o-chlorobezaldehyde, (R)-1(3-methoxyphenyl)ethylamine and 1.25 equivalents titanium(IV) isopropoxide were mixed and the intermediate imine reduced with ethanolic sodium cyanoborohydride. Work-up and repetitive preparative thin-layer chromatography using 5% methanol in chloroform afforded (R,R)-N-[4-(2-chlorophenyl)-2-butyl]-1-(3-methoxyphenyl)ethylamine, 4T; m/z (rel. int.) 317 (M$^+$, 3), 302 (16), 178 (62), 135 (100), 125 (15), 105 (10), 91 (6), 77 (8).

Preparation of 21Y

In a similar fashion an equal molar amount of 4-(3-trifluoromethylphenyl)-2-butanone, prepared from m-trifluoromethylbezaldehyde, (R)-1-(3-methoxyphenyl)ethylamine and 1.25 equivalents titanium(IV) isopropoxide were mixed and the intermediate imine reduced with ethanolic sodium cyanoborohydride. Work-up and repetitive preparative thin-layer chromatography using 5% methanol in chloroform afforded (R,R)-N-[4-(3-trifluoromethylphenyl)-2-butyl]-1-(3-methoxyphenyl)ethylamine, 21Y [m/z (rel. int.) 351 (M$^+$, 2), 336 (18), 216 (4), 202 (3), 178 (45), 135 (100), 105 (13), 91(9), 77 (8)] and (S,R-N-[4-(3-trifluoromethylphenyl)-2-butyl]-1-(3-methoxyphenyl)ethylamine, 21X.

Preparation of 25C and 25D.

In a similar fashion an equal molar amount of 4-(3-trifluoromethylphenyl)-2-butanone, (R)-1-(1-naphthyl)ethylamine and 1.25 equivalents titanium(IV) isopropoxide were mixed and the intermediate imine reduced with ethanolic sodium cyanoborohydride. Work-up and repetitive preparative thin-layer chromatography using 5% methanol in chloroform afforded (S,R)-N-[4-(3-trifluoromethylphenyl)-2-butyl]-1-(1-naphthyl)ethylamine, 25C [m/z (rel. int.) 371 (M$^+$, 3), 356 (16), 198 (15), 155 (100), 129 (8),115 (5),109 (3), 77 (2)] and (R,R)-N-[4-(3-trifluoromethylphenyl)-2-butyl]-1-(1-naphthyl)ethylamine, 25D; m/z (rel. int.) 371 (M$^+$, 3), 356 (16), 198 (15), 155 (100), 129 (8), 115 (5), 109 (3), 77 (2).

Preparation of 21D

In a similar fashion an equal molar amount of 4-phenyl-2-butanone (Aldrich Chemical Co.), (R)-1-(3-methoxyphenyl)ethylamine and 1.25 equivalents titanium (IV) isopropoxide were mixed and the intermediate imine reduced with ethanolic sodium cyanoborohydride. Work-up and repetitive preparative thin-layer chromatography using 5% methanol in chloroform afforded (R,R)-N-(4-phenyl-2-butyl)-1-(3-methoxyphenyl)ethylamine, 21D [m/z (rel. int.) 283 (M$^+$, 4), 268 (13), 178 (45), 135 (100), 105 (15), 91 (43), 77 (11)] and (S,R)- N-(4-pbenyl-2-butyl)-1-(3-methoxyphenyl)ethylamine, 21E.

Preparation of 21F

In a similar fashion an equal molar amount of 4-phenyl-2-butanone (Aldrich Chemical Co.), (R)-1-(1-naphthyl)ethylamine and 1.25 equivalents titanium(IV) isopropoxide were mixed and the intermediate imine reduced with ethanolic sodium cyanoborohydride. Work-up and repetitive preparative thin-layer chromatography using 5% methanol in chloroform afforded (R,R)-N-(4-phenyl-2-butyl)-1-(1-naphthyl)etbylamine, 21F; m/z (rel. int.) 303 (M$^+$, 6), 288 (14), 198 (22), 155 (100), 129 (8), 115 (5), 91 (19), 77 (4).

Preparation of 12Z

A stirred solution of 2-chlorohydrocinnamonitrile (Aldrich Chemical Co., 1.66 g, 10 mmol) in dichloromethane (100 ml) was cooled to −78° C. and treated dropwise with diisobutylaluminum hydride (1.42 g, 10 mmol). The reaction was stirred 1 hr at rt, cooled to −78° C. and treated with a solution of 1-(1-naphthyl)ethylamine (1.71 g, 10 mmol) in dichloromethane (25 ml). The reaction was transferred to an ice bath and stirred 2 hr. After this time the reaction was poured directly into a stirred solution of ethanolic sodium borohydride (50 ml of 0.2 M, 10 mmol). The mixture was stirred 30 min at rt and the excess sodium borohydride quenched by the addition of 10% HCl. The solution was then made basic by the addition of 10 N NaOH and transferred to a separatory funnel washing with diethyl ether (300 ml). The aqueous phase was removed and the remaining organic layer washed with 1 N NaOH (3×100 ml). The organic layer was dried over anhydrous magnesium sulfate, and concentrated to an oil. Chromatography of this material through silica gel using a gradient of chloroform to 10% methanol-chloroform afforded 2.34 g (72% yield) of (R)-N-[3-(2-chlorophenyl)propyl]-1-(1-naphthyl)ethylamine, 12Z, as a clear oil; m/z (rel. int.) 323 ($M^+$, 2), 308 (63), 288 (7), 196 (5), 184 (5), 155 (100), 125 (24), 115 (8), 103 (4), 91 (3), 77 (7).

Preparation of 12B

In a similar fashion, 4-methylcinnamonitrile was treated with diisobutyl aluminum hydride and the intermediate aluminum-imine complex treated with (R)-1-(3-methoxyphenyl)ethylamine. The intermediate imine was treated with ethanolic sodium borohydride. Work-up and chromatography yielded (R)-N-[3-(4-methylphenyl)prop-2-enyl]-1-(3-methoxyphenyl)ethylamine, 12B, as a clear, colorless oil; m/z (rel. int.) 281 ($M^+$, 6), 266 (5), 176 (27), 146 (75), 135 (63), 131 (100), 115 (25), 105 (21), 91 (21), 77 (21).

Preparation of 12C

In a similar fashion, 2-methylcinnamonitrile was treated with diisobutyl aluminum hydride and the intermediate aluminum-imine complex treated with (R)-1-(3-methoxyphenyl)ethylamine. The intermediate mine was treated with ethanolic sodium borohydride. Work-up and chromatography yielded (R)-N-[3-(2-methylphenyl)prop-2-enyl]-1-(3-methoxyphenyl)ethylamine, 12C, as a clear, colorless oil; m/z (rel. int.) 281 ($M^+$, 4), 266 (15), 176 (18), 146 (62), 135 (58), 131 (100), 115 (23), 105 (19), 91 (38), 77 (17).

Preparation of 12D

In a similar fashion, 2,4,6-trimethylcinnamonitrile was treated with diisobutyl aluminum hydride and the intermediate aluminum-imine complex treated with (R)-1-(3-methoxyphenyl)ethylamine. The intermediate imine was treated with ethanolic sodium borohydride. Work-up and chromatography yielded (R)-N-[3-(2,4,6-trimethylphenyl)prop-2-enyl]-1-(3-methoxyphenyl)ethylamine, 12D, as a clear, colorless oil; m/z (rel. int.) 309 ($M^+$, 8), 294 (25), 174 (82), 159 (100), 135 (52), 129 (29), 105 (21), 91 (17), 77 (14).

Preparation of 12E

In a similar fashion, 4-isopropylcinnamonitrile was treated with diisobutyl aluminum hydride and the intermediate aluminum-imine complex treated with (R)-1-(3-methoxyphenyl)ethylamine. The intermediate imine was treated with ethanolic sodium borohydride. Work-up and chromatography yielded (R)-N-[3-(4-isopropylphenyl)prop-2-enyl]-1-(3-methoxyphenyl)ethylamine, 12E, as a clear, colorless oil; m/z (rel. int.) 309 ($M^+$, 9), 294 (7), 174 (98), 159 (22), 135 (80), 117 (100), 105 (35), 91 (37), 77 (19).

Preparation of 12F

In a similar fashion, 2,4-dimethylcinnamonitrile was treated with diisobutyl aluminum hydride and the intermediate aluminum-imine complex treated with (R)-1-(3-methoxyphenyl)ethylamine. The intermediate imine was treated with ethanolic sodium borohydride. Work-up and chromatography yielded (R)-N-[3-(2,4-dimethylphenyl)prop-2-enyl]-1-(3-methoxyphenyl)ethylamine, 12F, as a clear, colorless oil; m/z (rel. int.) 295 ($M^+$, 8), 294 (15), 174 (29), 160 (75), 145 (100), 135 (68), 117 (21), 105 (30), 91 (26), 77 (19).

Preparation of 12G

In a similar fashion, 3-methylcinnamonitrile was treated with diisobutyl aluminum hydride and the intermediate aluminum-imine complex treated with (R)-1-(3-methoxyphenyl)ethylamine. The intermediate imine was treated with ethanolic sodium borohydride. Work-up and chromatography yielded (R)-N-[3-(3-methylphenyl)prop-2-enyl]-1-(3-methoxyphenyl)ethylamine, 12G, as a clear, colorless oil; m/z (rel. int.) 281 ($M^+$, 5), 266 (9), 176 (24), 146 (71), 135 (62), 131 (100), 115 (23), 105 (19), 91 (41), 77 (18).

Preparation of 25E

In a similar fashion, cinnamonitrile was treated with diisobutyl aluminum hydride and the intermediate aluminum-imine complex treated with (R)-1-(3-methoxyphenyl)ethylamine. The intermediate imine was treated with ethanolic sodium borohydride. Work-up and chromatography yielded (R)-N-(3-phenylprop-2-enyl)-1-(3-methoxyphenyl)ethylamine, 25E, as a clear colorless oil; m/z (rel. int.) 267 (M+. 3), 252 (14),176 (17), 135 (62),117 (100), 105 (28), 91 (56), 77 (33).

Preparation of 25G

In a similar fashion, α-methylcinnamonitrile was treated with diisobutyl aluminum hydride and the intermediate aluminum-imine complex treated with (R)-1-(3-methoxyphenyl)ethylamine. The intermediate imine was treated with ethanolic sodium borohydride. Work-up and chromatography yielded (R)-N-(2-methyl-3-phenylprop-2-enyl)-1-(3-methoxyphenyl)ethylamine, 25G, as a clear, colorless oil; m/z (rel. int.) 281 ($M^+$, 5), 266 (18), 190 (12), 146 (78), 135 (82), 131 (100), 115 (21), 105 (21), 91 (62), 77 (19).

Preparation of 6X

A stirred solution of sodium hydride (1.8 g, 75 mmol) in dimethylformamide (150 ml) was treated with a solution of diethylcyanomethyl phosphonate (13.3 g, 75 mmol) in dimethylformamide (50 ml). The reaction was stirred 30 min at rt. After this time the reaction was treated with 3-chlorobenzaldehyde (10.54 g, 75 mmol) and stirred 1 hr at rt and 30 min at 60° C. The reaction was then quenched by the addition of water (200 ml). The reaction mixture was transferred to a separatory funnel using diethyl ether (300 ml) and the resulting organic phase washed with water (5×300 ml) and brine. The organic layer was dried over anhydrous potassium carbonate and concentrated to yield 3-chlorocinnamonitrile (11.06 g) as a solid. The solid was dissolved in tetrahydrofuran (50 ml) and treated with excess diborane and stirred 30 min at rt. The reaction was poured over ice/10% HCl. The acidic aqueous phase was washed with diethyl ether (2×200 ml). The aqueous phase was made basic by the addition of 10 N NaOH and extracted with diethyl ether (200 ml). The ether extract was dried over anhydrous potassium carbonate and concentrated to afford 3-(3-chlorophenyl)propylamine as an oil (0.6 g, 3.54 mmol). The 3-(3-chlorophenyl)propylamine (0.60 g, 3.54 mmol), 3'-methoxyacetophenone (0.53 g, 3.54 mmol) and 1.25 molar equivalents titanium(IV) isopropoxide (1.26 g, 4.43 mmol) were mixed 4 hr at rt and the intermediate imine treated with an ethanolic sodium cyanoborohydride (5 ml of 1 M, 5 mmol). The reaction was stirred 16 hr at rt, diluted with diethyl ether (50 ml) and treated with water (0.32 ml, 17.7 mmol). After mixing thoroughly the solution was centrifuged and the ether layer concentrated to a milky solid. This material was suspended in diethyl ether and filtered through a 0.45 µM CR PTFE Acrodisc. The ether wash was concentrated to an oil. Chromatography of this material (silica, preparative thin-layer chromatography) using 3% methanol-dichloromethane (containing 0.1% isopropylamine) afforded N-[3-(3-dichlorophenyl)propyl]-1-(3-methoxyphenyl)ethylamine, 6X; m/z (rel. int.) 303 ($M^+$, 3), 288 (40), 196 (3), 164 (8), 135 (100), 125 (46), 103 (26), 91 (29), 77 (29).

Preparation of 6V

An equal molar amount of 3-(4-chlorophenyl)propylamine (prepared in a similar fashion from 4-chlorobenzaldehyde as above) 3'-methoxyacetophenone and 1.25 molar equivalents titanium(IV) isopropoxide were mixed 4 hr at rt and the intermediate imine treated with an ethanolic sodium cyanoborohydride (5 ml of I M, 5 mmol). Work-up and chromatography afforded N-[3-(4-chlorophenyl)propyl]-1-(3-methoxyphenyl)ethylamine, 6V, as an oil; m/z (rel. int.) 303 ($M^+$, 8), 288 (91), 196 (4), 164 (10), 135 (100), 125 (61), 103 (21), 91 (21), 77 (18).

Preparation of 20A

In a similar fashion, an equal molar amount of 1-(1-methoxyphenyl)ethylamine, 4-t-butylacetophenone and 1.25 molar equivalents titanium(IV) isopropoxide were mixed 4 hr at rt and the intermediate imine treated with an ethanolic sodium cyanoborohydride (5 ml of 1 M, 5 mmol). Work-up and chromatography afforded (R)-N-[1-(4-t-butylphenyl)ethyl]-1-(1-naphthyl)ethylamine, 20A, as an oil; m/z (rel. int.) 331 ($M^+$, 12), 316 (29), 161 (70), 155 (100), 131 (14), 127 (13), 115(10), 105 (6), 91 (10), 77 (7).

Preparation of 25H and 25I

In a similar fashion, an equal molar amount of (R)-1-(3-methoxyphenyl)ethylamine, trans-4-phenyl-3-butene-2-one and 1.25 molar equivalents titanium(IV) isopropoxide were mixed 4 hr at rt and the intermediate imine treated with an ethanolic sodium cyanoborohydride (5 ml of 1 M, 5 mmol). Work-up and chromatography afforded (R,R)-N-(2-methyl-4-phenybut-3-enyl)-1-(3-methoxyphenyl)ethylamine, 25H, as an oil; m/z (rel. int.) 283 ($M^+$, 4), 268 (13), 178 (40), 135 (100), 105 (15), 91 (47), 77 (13) and (S,R)-N-(2-methyl-4-phenybut-3-enyl)-1-(3-methoxyphenyl)ethylamine, 25I, as an oil; m/z (rel. int.) 283 ($M^+$, 4), 268 (13), 178 (40), 135 (100), 105 (15), 91 (47), 77 (13).

Preparation of 16L and 16M

In a similar fashion, an equal molar amount of (R)-1-(3-methoxyphenyl)ethylamine, 3-methoxyacetophenone and 1.25 molar equivalents titanium(IV) isopropoxide were mixed 4 hr at rt and the intermediate imine treated with an ethanolic sodium cyanoborohydride (5 ml of 1 M, 5 mmol). Work-up and chromatography afforded (R,R)-N-[1-(4-methoxyphenyl)ethyl]-1-(3-methoxyphenyl)ethylamine, 16L, as an oil; m/z (rel. int.) 284 (M-1, 1), 270 (85), 150 (83), 135 (100), 120 (12), 105 (28), 91 (25), 77 (23) and (S,R)-N-[1-(4-methoxyphenyl)ethyl]-1-(3-methoxyphenyl)ethylamine, 16M, as an oil; m/z (rel. int.) 284 (M-1, 1), 270 (53), 150 (98),135 (100),120 (11), 105 (33), 91 (25), 77 (23).

Preparation of 5B/5C

In a similar fashion, 4-chloroacetophenone was used to prepare 3-methyl-3-(4-chlorophenyl)cinnamonitrile. The nitrile was catalytically reduced (palladium hydroxide, acetic acid, 60 p.s.i. hydrogen 2 hr) to generate 3-methyl-3-(4-chlorophenyl)propylamine. An equal molar amount of the amine, 3'-methoxyacetophenone and 1.25 molar equivalents titanium(IV) isopropoxide were mixed 4 hr at rt and the intermediate imine treated with an ethanolic sodium cyanoborohydride (5 ml of 1 M, 5 mmol). Work-up and chromatography afforded N-[3-methyl-3-(4-chlorophenyl)propyl]-1-(3-methoxyphenyl)ethylamine, 5B/5C as an oil; m/z (rel. int.) 317 ($M^+$, 12), 302 (74), 210 (2), 182 (4), 164 (12), 135 (100), 121 (25), 103 (40), 91 (19), 77 (28).

Preparation of 4Z/5A

In a similar fashion, 3-chloroacetophenone was used to prepare 3-methyl-3-(3-chlorophenyl)cinnamonitrile. The nitrile was catalytically reduced (palladium hydroxide, acetic acid, 60 p.s.i. hydrogen 2 hr) to generate 3-methyl-3-(3-chlorophenyl)propylamine. An equal molar amount of the amine, 3'-methoxyacetophenone and 1.25 molar equivalents titanium(IV) isopropoxide were mixed 4 hr at rt and the intermediate imine treated with an ethanolic sodium cyanoborohydride (5 ml of 1 M, 5 mmol). Work-up and chromatography afforded N-[3-methyl-3-(3-chlorophenyl)propyl]-1-(3-methoxyphenyl)ethylamine, 4Z/5A, as an oil; m/z (rel. int.) 283 ($M^+$, 17), 268 (71), 164 (13), 135 (100), 121 (21), 105 (27), 91 (26), 77 (14).

Preparation of 4Y

In a similar fashion, 2-chloroacetophenone was used to prepare 3-methyl-3-(2-chlorophenyl)cinnamonitrile. The nitrile was catalytically reduced (palladium hydroxide, acetic acid, 60 p.s.i. hydrogen 2 hr) to generate 3-methyl-3-(2-chlorophenyl)propylamine. An equal molar amount of the amine, 3'-methoxyacetophenone and 1.25 molar equivalents titanium(IV) isopropoxide were mixed 4 hr at rt and the intermediate imine treated with an ethanolic sodium cyanoborohydride (5 ml of 1 M, 5 mmol). Work-up and chromatography afforded N-[3-methyl-3-(2-chlorophenyl)propyl]-1-(3-methoxyphenyl)ethylamine, 4Y, as an oil; m/z (rel. int.) 283 ($M^+$, 17), 268 (71), 164 (13), 135 (100), 121 (21), 105 (27), 91 (26), 77 (14).

Preparation of 6T

A solution of NPS R-568 (30.3 g 100 mmol) in dichloromethane at −78° C. was treated dropwise with borontribromide (50 g, 200 mmol). The reaction 40 was stirred 1 hr at rt and poured over ice. The hydrobromide was extracted from the aqueous phase with chloroform. The chloroform solubles were then washed (4×100 ml) with 50% HCl. The chloroform wash was dried over anhydrous magnesium sulfate and concentrated to afford (R)-N-[3-(2-chlorophenyl)propyl]-1-(3-hydroxyphenyl)ethylamine hydrochloride as a solid. A solution of sodium hydride (0.48 g, 20 mmol) in dimethylformamide was treated with (R)-N-[3-(2-chlorophenyl)propyl]-1-( 3-hydroxyphenyl)ethylamine hydrochloride (3.25 g, 10 mmol) and the reaction stirred 1 hr at rt. The reaction was treated with iodoethane (1.71 g, 11 mmol) and stirred 16 hr at rt. Work-up and chromatography through silica using 3% methanol in chloroform afforded (R)-N-[3-(2-chlorophenyl)propyl]-1-(3-ethoxyphenyl)ethylamine, 6T, as an oil; m/z (rel. int.) 316 ($M^+$, 1), 302 (100), 282 (11), 196 (5), 178 (7), 149 (74), 121 (34), 103 (25), 91 (28), 77 (29).

Preparation of 6R

NPS R-467 was used in a similar fashion to prepare (R)-N-(3-phenylpropyl)-1-(3-ethoxyphenyl)ethylamine, 6R, as an oil; m/z (rel. int.) 283 ($M^+$, 10), 268 (74), 178 (11), 162 (8), 149 (100), 121 (30), 103 (16), 91 (86), 77 (29).

Preparation of 3U

An equal molar mixture of 3,3-diphenylpropylamine (2.11 g, 10 mmol), 1'-acetonaphthone (1.70 g, 10 mmol) and 1.25 equivalents of titanium(IV) isopropoxide (3.55 g, 12.5 mmol) were stirred 4 hr at rt. The reaction mixture was then treated with a 1 M solution of ethanolic sodium cyanoborohydride (12.5 ml, 12.5 mmol) and stirred 16 hr at rt. The reaction was diluted with diethyl ether (50 ml) and treated with water (0.72 ml, 40 mmol). After mixing thoroughly the mixture was centrifuged and the ether layer decanted and concentrated to a milky oil. The oil was suspended in diethyl ether and filtered through a 0.45 $\mu$M CR PTFE Acrodisc. The diethyl ether filtrate was concentrated to afford N-(3,3-diphenylpropyl)-(1-naphthyl)ethylamine, 3U, as a clear, colorless oil; m/z (rel. int.) 365 ($M^+$, 17), 350 (19),181 (23),155 (100), 141 (25), 115 (11), 91 (13), 77 (6).

Preparation of 6F

In a similar fashion equal molar amounts 1-(3-methoxyphenyl)ethylamine (1.51 g, 10 mmol), 2'-acetonaphthone (1.70 g, 10 mmol) and 1.25 equivalents of titanium(IV) isopropoxide (3.55 g, 12.5 mmol) were treated as above. Work-up yielded N-[1-(2-naphthyl)ethyl]-1-(3-methoxyphenyl)ethylamine, 6F, as a clear, colorless oil; m/z (rel. int.) 305 ($M^+$, 1), 290 (35), 170 (49), 155 (100), 135 (55), 115 (8), 105 (10), 91 (9), 77 (10).

Preparation of 4G

In a similar fashion equal molar amounts of (R))-1-phenylethylamine, 1'-acetonaphthone and 1.25 equivalents of titanium(IV) isopropoxide were mixed and the resulting intermediate imine was reduced with ethanolic sodium cyanoborohydride. Work-up and chromatography yielded N-[1-(1-naphthyl)ethyl)-1-phenylethylamine, 4G, as a clear, colorless oil; m/z (rel. int.) 275 ($M^+$, 16), 260 (79), 155 (100), 127 (27), 105 (70), 77 (32).

Preparation of 4H

In a similar fashion equal molar amounts of (R)-1'-phenylethylamine, 2'-acetonaphthone and 1.25 equivalents of titanium(IV) isopropoxide were mixed and the resulting intermediate imine was reduced with ethanolic sodium cyanoborohydride. Work-up and chromatography yielded N-[1-(2-naphthyl)ethyl]-1-phenylethylamine, 4H, as a clear, colorless oil; m/z (rel. int.) 275 ($M^+$, 1), 260 (61), 155 (100), 120 (36), 105 (55), 77 (15).

Preparation of 6E

In a similar fashion equal molar amounts of 1-(3-methoxyphenyl)ethylamine, 1'-acetonaphthone and 1.25 equivalents of titanium(IV) isopropoxide were mixed and the resulting intermediate imine was reduced with ethanolic sodium cyanoborohydride. Work-tip and chromatography yielded N-1-(1-naphthyl)ethyl-1-(3-methoxyphenyl) ethylamine, 6E, as a clear, colorless oil; m/z (rel. int.) 305 ($M^+$, 10), 290 (30), 170 (43), 155 (100), 135 (69), 115 (9), 105 (15), 91 (14), 77 (18).

Example 19

Pharmaceutical Formulation

Preparation of a pharmaceutical formulation suitable for administering a calcimimetic into a human patient is shown in Table 3.

TABLE 3

| Ingredient | mg/capsule | g/representative batch of 5,000 capsules |
|---|---|---|
| NPS R-568 | 56.0 | 280.0 |
| Pregelatinized Starch NF | 134.0 | 670.0 |
| Microcrystalline Cellulose NF | 34.0 | 170.0 |
| Colloidal Silicon Dioxide | 1.0 | 5.0 |
| Total | 225 mg | 1125 g |

Other examples of NPS (R)-568 hydrochloride formulations and dosage forms include those suitable for sustained or extended release, using standard techniques.

Proper dosing can also be carried out using standard techniques. For example, in one set of experiments, 10–400 mg oral doses of NPS (R)-568 hydrochloride showed pharmacological activity in human subjects. Significant levels of the O-glucuronide conjugate of 17Q, a principal metabolite of NPS (R)-568, was observed in human plasma following oral administration of NPS (R)-568 hydrochloride. Thus, the glucuronide conjugate of 17Q may be exerting some beneficial effect.

Using standard techniques other suitable dosage ranges for NPS (R)-568 can be determined.

Suitable dosage ranges, formulations, and dosage forms for other compounds described herein can also be determined by one skilled in art based on the teachings provided in the application.

Other embodiments are within the following claims. Thus, while several embodiments have been shown and described, various modifications may be made, without departing from the spirit and scope of the present invention.

SEQUENCE LISTING (1) GENERAL INFORMATION:

(iii) NUMBER OF SEQUENCES:   2

(2) INFORMATION FOR SEQ ID NO: 1:

(i) SEQUENCE CHARACTERISTICS:
      (A) LENGTH:        5006 base pairs
      (B) TYPE:          nucleic acid
      (C) STRANDEDNESS:  single
      (D) TOPOLOGY:     linear -continued

```
    (ii) MOLECULE TYPE:         cDNA to mRNA (ix) FEATURE:
         (A) NAME/KEY:          CDS
         (B) LOCATION:          436..3699
         (D) OTHER INFORMATION:

(xi) SEQUENCE DESCRIPTION: SEQ ID NO: 1:

GCTGCTGTGG CCGGACCCGA AGGCGGGCGC CGGGAGCGCA GCGAGCCAGA CGCGCCTCTC      60

CAAGACCGTG ACCTTGGCAT AGGGAGCGGG GCTGCGCGCA GTCCTGAGAT CAGACCAGAG     120

CTCATCCTCG TGGAGACCCA CGGCCGAGGG GCCGGAGCTG CCTCTGTGCG AGGGAGCCCT     180

GGCCGCGGCG CAGAAGGCAT CACAGGAGGC CTCTGCATGA TGTGGCTTCC AAAGACTCAA     240

GGACCACCCA CATTACAAGT CTGGATTGAG GAAGGCAGAA ATGGAGATTC AAACACCACG     300

TCTTCTATTA TTTTATTAAT CAATCTGTAG ACATGTGTCC CCACTGCAGG GAGTGAACTG     360

CTCCAAGGGA GAAACTTCTG GGAGCCTCCA AACTCCTAGC TGTCTCATCC CTTGCCCTGG     420

AGAGACGGCA GAACC ATG GCA TTT TAT AGC TGC TGC TGG GTC CTC TTG GCA     471
                 Met Ala Phe Tyr Ser Cys Cys Trp Val Leu Leu Ala
                  1               5                  10

CTC ACC TGG CAC ACC TCT GCC TAC GGG CCA GAC CAG CGA GCC CAA AAG     519
Leu Thr Trp His Thr Ser Ala Tyr Gly Pro Asp Gln Arg Ala Gln Lys
        15                  20                  25

AAG GGG GAC ATT ATC CTT GGG GGG CTC TTT CCT ATT CAT TTT GGA GTA     567
Lys Gly Asp Ile Ile Leu Gly Gly Leu Phe Pro Ile His Phe Gly Val
 30                  35                  40

GCA GCT AAA GAT CAA GAT CTC AAA TCA AGG CCG GAG TCT GTG GAA TGT     615
Ala Ala Lys Asp Gln Asp Leu Lys Ser Arg Pro Glu Ser Val Glu Cys
 45                  50                  55                  60

ATC AGG TAT AAT TTC CGT GGG TTT CGC TGG TTA CAG GCT ATG ATA TTT     663
Ile Arg Tyr Asn Phe Arg Gly Phe Arg Trp Leu Gln Ala Met Ile Phe
                 65                  70                  75

GCC ATA GAG GAG ATA AAC AGC AGC CCA GCC CTT CTT CCC AAC TTG ACG     711
Ala Ile Glu Glu Ile Asn Ser Ser Pro Ala Leu Leu Pro Asn Leu Thr
             80                  85                  90

CTG GGA TAC AGG ATA TTT GAC ACT TGC AAC ACC GTT TCT AAG GCC TTG     759
Leu Gly Tyr Arg Ile Phe Asp Thr Cys Asn Thr Val Ser Lys Ala Leu
         95                 100                 105

GAA GCC ACC CTG AGT TTT GTT GCT CAA AAC AAA ATT GAT TCT TTG AAC     807
Glu Ala Thr Leu Ser Phe Val Ala Gln Asn Lys Ile Asp Ser Leu Asn
     110                 115                 120

CTT GAT GAG TTC TGC AAC TGC TCA GAG CAC ATT CCC TCT ACG ATT GCT     855
Leu Asp Glu Phe Cys Asn Cys Ser Glu His Ile Pro Ser Thr Ile Ala
125                 130                 135                 140

GTG GTG GGA GCA ACT GGC TCA GGC GTC TCC ACG GCA GTG GCA AAT CTG     903
Val Val Gly Ala Thr Gly Ser Gly Val Ser Thr Ala Val Ala Asn Leu
                145                 150                 155

CTG GGG CTC TTC TAC ATT CCC CAG GTC AGT TAT GCC TCC TCC AGC AGA     951
Leu Gly Leu Phe Tyr Ile Pro Gln Val Ser Tyr Ala Ser Ser Ser Arg
            160                 165                 170

CTC CTC AGC AAC AAG AAT CAA TTC AAG TCT TTC CTC CGA ACC ATC CCC     999
Leu Leu Ser Asn Lys Asn Gln Phe Lys Ser Phe Leu Arg Thr Ile Pro
        175                 180                 185

AAT GAT GAG CAC CAG GCC ACT GCC ATG GCA GAC ATC ATC GAG TAT TTC    1047
Asn Asp Glu His Gln Ala Thr Ala Met Ala Asp Ile Ile Glu Tyr Phe
    190                 195                 200

CGC TGG AAC TGG GTG GGC ACA ATT GCA GCT GAT GAC GAC TAT GGG CGG    1095
Arg Trp Asn Trp Val Gly Thr Ile Ala Ala Asp Asp Asp Tyr Gly Arg
205                 210                 215                 220
```

```
CCG GGG ATT GAG AAA TTC CGA GAG GAA GCT GAG GAA AGG GAT ATC TGC    1143
Pro Gly Ile Glu Lys Phe Arg Glu Glu Ala Glu Glu Arg Asp Ile Cys
            225                 230                 235

ATC GAC TTC AGT GAA CTC ATC TCC CAG TAC TCT GAT GAG GAA GAG ATC    1191
Ile Asp Phe Ser Glu Leu Ile Ser Gln Tyr Ser Asp Glu Glu Glu Ile
        240                 245                 250

CAG CAT GTG GTA GAG GTG ATT CAA AAT TCC ACG GCC AAA GTC ATC GTG    1239
Gln His Val Val Glu Val Ile Gln Asn Ser Thr Ala Lys Val Ile Val
            255                 260                 265

GTT TTC TCC AGT GGC CCA GAT CTT GAG CCC CTC ATC AAG GAG ATT GTC    1287
Val Phe Ser Ser Gly Pro Asp Leu Glu Pro Leu Ile Lys Glu Ile Val
        270                 275                 280

CGG CGC AAT ATC ACG GGC AAG ATC TGG CTG GCC AGC GAG GCC TGG GCC    1335
Arg Arg Asn Ile Thr Gly Lys Ile Trp Leu Ala Ser Glu Ala Trp Ala
285                 290                 295                 300

AGC TCC TCC CTG ATC GCC ATG CCT CAG TAC TTC CAC GTG GTT GGC GGC    1383
Ser Ser Ser Leu Ile Ala Met Pro Gln Tyr Phe His Val Val Gly Gly
                305                 310                 315

ACC ATT GGA TTC GCT CTG AAG GCT GGG CAG ATC CCA GGC TTC CGG GAA    1431
Thr Ile Gly Phe Ala Leu Lys Ala Gly Gln Ile Pro Gly Phe Arg Glu
        320                 325                 330

TTC CTG AAG AAG GTC CAT CCC AGG AAG TCT GTC CAC AAT GGT TTT GCC    1479
Phe Leu Lys Lys Val His Pro Arg Lys Ser Val His Asn Gly Phe Ala
            335                 340                 345

AAG GAG TTT TGG GAA GAA ACA TTT AAC TGC CAC CTC CAA GAA GGT GCA    1527
Lys Glu Phe Trp Glu Glu Thr Phe Asn Cys His Leu Gln Glu Gly Ala
        350                 355                 360

AAA GGA CCT TTA CCT GTG GAC ACC TTT CTG AGA GGT CAC GAA GAA AGT    1575
Lys Gly Pro Leu Pro Val Asp Thr Phe Leu Arg Gly His Glu Glu Ser
365                 370                 375                 380

GGC GAC AGG TTT AGC AAC AGC TCG ACA GCC TTC CGA CCC CTC TGT ACA    1623
Gly Asp Arg Phe Ser Asn Ser Ser Thr Ala Phe Arg Pro Leu Cys Thr
                385                 390                 395

GGG GAT GAG AAC ATC AGC AGT GTC GAG ACC CCT TAC ATA GAT TAC ACG    1671
Gly Asp Glu Asn Ile Ser Ser Val Glu Thr Pro Tyr Ile Asp Tyr Thr
        400                 405                 410

CAT TTA CGG ATA TCC TAC AAT GTG TAC TTA GCA GTC TAC TCC ATT GCC    1719
His Leu Arg Ile Ser Tyr Asn Val Tyr Leu Ala Val Tyr Ser Ile Ala
            415                 420                 425

CAC GCC TTG CAA GAT ATA TAT ACC TGC TTA CCT GGG AGA GGG CTC TTC    1767
His Ala Leu Gln Asp Ile Tyr Thr Cys Leu Pro Gly Arg Gly Leu Phe
        430                 435                 440

ACC AAT GGC TCC TGT GCA GAC ATC AAG AAA GTT GAG GCG TGG CAG GTC    1815
Thr Asn Gly Ser Cys Ala Asp Ile Lys Lys Val Glu Ala Trp Gln Val
445                 450                 455                 460

CTG AAG CAC CTA CGG CAT CTA AAC TTT ACA AAC AAT ATG GGG GAG CAG    1863
Leu Lys His Leu Arg His Leu Asn Phe Thr Asn Asn Met Gly Glu Gln
                465                 470                 475

GTG ACC TTT GAT GAG TGT GGT GAC CTG GTG GGG AAC TAT TCC ATC ATC    1911
Val Thr Phe Asp Glu Cys Gly Asp Leu Val Gly Asn Tyr Ser Ile Ile
        480                 485                 490

AAC TGG CAC CTC TCC CCA GAG GAT GGC TCC ATC GTG TTT AAG GAA GTC    1959
Asn Trp His Leu Ser Pro Glu Asp Gly Ser Ile Val Phe Lys Glu Val
            495                 500                 505

GGG TAT TAC AAC GTC TAT GCC AAG AAG GGA GAA AGA CTC TTC ATC AAC    2007
Gly Tyr Tyr Asn Val Tyr Ala Lys Lys Gly Glu Arg Leu Phe Ile Asn
        510                 515                 520

GAG GAG AAA ATC CTG TGG AGT GGG TTC TCC AGG GAG CCA CTC ACC TTT    2055
Glu Glu Lys Ile Leu Trp Ser Gly Phe Ser Arg Glu Pro Leu Thr Phe
525                 530                 535                 540
```

```
GTG CTG TCT GTC CTC CAG GTG CCC TTC TCC AAC TGC AGC CGA GAC TGC      2103
Val Leu Ser Val Leu Gln Val Pro Phe Ser Asn Cys Ser Arg Asp Cys
            545                 550                 555

CTG GCA GGG ACC AGG AAA GGG ATC ATT GAG GGG GAG CCC ACC TGC TGC      2151
Leu Ala Gly Thr Arg Lys Gly Ile Ile Glu Gly Glu Pro Thr Cys Cys
            560                 565                 570

TTT GAG TGT GTG GAG TGT CCT GAT GGG GAG TAT AGT GAT GAG ACA GAT      2199
Phe Glu Cys Val Glu Cys Pro Asp Gly Glu Tyr Ser Asp Glu Thr Asp
        575                 580                 585

GCC AGT GCC TGT AAC AAG TGC CCA GAT GAC TTC TGG TCC AAT GAG AAC      2247
Ala Ser Ala Cys Asn Lys Cys Pro Asp Asp Phe Trp Ser Asn Glu Asn
590                 595                 600

CAC ACC TCC TGC ATT GCC AAG GAG ATC GAG TTT CTG TCG TGG ACG GAG      2295
His Thr Ser Cys Ile Ala Lys Glu Ile Glu Phe Leu Ser Trp Thr Glu
605                 610                 615                 620

CCC TTT GGG ATC GCA CTC ACC CTC TTT GCC GTG CTG GGC ATT TTC CTG      2343
Pro Phe Gly Ile Ala Leu Thr Leu Phe Ala Val Leu Gly Ile Phe Leu
            625                 630                 635

ACA GCC TTT GTG CTG GGT GTG TTT ATC AAG TTC CGC AAC ACA CCC ATT      2391
Thr Ala Phe Val Leu Gly Val Phe Ile Lys Phe Arg Asn Thr Pro Ile
            640                 645                 650

GTC AAG GCC ACC AAC CGA GAG CTC TCC TAC CTC CTC CTC TTC TCC CTG      2439
Val Lys Ala Thr Asn Arg Glu Leu Ser Tyr Leu Leu Leu Phe Ser Leu
            655                 660                 665

CTC TGC TGC TTC TCC AGC TCC CTG TTC TTC ATC GGG GAG CCC CAG GAC      2487
Leu Cys Cys Phe Ser Ser Ser Leu Phe Phe Ile Gly Glu Pro Gln Asp
        670                 675                 680

TGG ACG TGC CGC CTG CGC CAG CCG GCC TTT GGC ATC AGC TTC GTG CTC      2535
Trp Thr Cys Arg Leu Arg Gln Pro Ala Phe Gly Ile Ser Phe Val Leu
685                 690                 695                 700

TGC ATC TCA TGC ATC CTG GTG AAA ACC AAC CGT GTC CTC CTG GTG TTT      2583
Cys Ile Ser Cys Ile Leu Val Lys Thr Asn Arg Val Leu Leu Val Phe
            705                 710                 715

GAG GCC AAG ATC CCC ACC AGC TTC CAC CGC AAG TGG TGG GGG CTC AAC      2631
Glu Ala Lys Ile Pro Thr Ser Phe His Arg Lys Trp Trp Gly Leu Asn
            720                 725                 730

CTG CAG TTC CTG CTG GTT TTC CTC TGC ACC TTC ATG CAG ATT GTC ATC      2679
Leu Gln Phe Leu Leu Val Phe Leu Cys Thr Phe Met Gln Ile Val Ile
            735                 740                 745

TGT GTG ATC TGG CTC TAC ACC GCG CCC CCC TCA AGC TAC CGC AAC CAG      2727
Cys Val Ile Trp Leu Tyr Thr Ala Pro Pro Ser Ser Tyr Arg Asn Gln
750                 755                 760

GAG CTG GAG GAT GAG ATC ATC TTC ATC ACG TGC CAC GAG GGC TCC CTC      2775
Glu Leu Glu Asp Glu Ile Ile Phe Ile Thr Cys His Glu Gly Ser Leu
765                 770                 775                 780

ATG GCC CTG GGC TTC CTG ATC GGC TAC ACC TGC CTG CTG GCT GCC ATC      2823
Met Ala Leu Gly Phe Leu Ile Gly Tyr Thr Cys Leu Leu Ala Ala Ile
            785                 790                 795

TGC TTC TTC TTT GCC TTC AAG TCC CGG AAG CTG CCG GAG AAC TTC AAT      2871
Cys Phe Phe Phe Ala Phe Lys Ser Arg Lys Leu Pro Glu Asn Phe Asn
            800                 805                 810

GAA GCC AAG TTC ATC ACC TTC AGC ATG CTC ATC TTC TTC ATC GTC TGG      2919
Glu Ala Lys Phe Ile Thr Phe Ser Met Leu Ile Phe Phe Ile Val Trp
            815                 820                 825

ATC TCC TTC ATT CCA GCC TAT GCC AGC ACC TAT GGC AAG TTT GTC TCT      2967
Ile Ser Phe Ile Pro Ala Tyr Ala Ser Thr Tyr Gly Lys Phe Val Ser
            830                 835                 840

GCC GTA GAG GTG ATT GCC ATC CTG GCA GCC AGC TTT GGC TTG CTG GCG      3015
Ala Val Glu Val Ile Ala Ile Leu Ala Ala Ser Phe Gly Leu Leu Ala
```

-continued

```
845              850              855              860
TGC ATC TTC TTC AAC AAG ATC TAC ATC ATT CTC TTC AAG CCA TCC CGC        3063
Cys Ile Phe Phe Asn Lys Ile Tyr Ile Ile Leu Phe Lys Pro Ser Arg
                865              870              875

AAC ACC ATC GAG GAG GTG CGT TGC AGC ACC GCA GCT CAC GCT TTC AAG        3111
Asn Thr Ile Glu Glu Val Arg Cys Ser Thr Ala Ala His Ala Phe Lys
                880              885              890

GTG GCT GCC CGG GCC ACG CTG CGC CGC AGC AAC GTC TCC CGC AAG CGG        3159
Val Ala Ala Arg Ala Thr Leu Arg Arg Ser Asn Val Ser Arg Lys Arg
                895              900              905

TCC AGC AGC CTT GGA GGC TCC ACG GGA TCC ACC CCC TCC TCC TCC ATC        3207
Ser Ser Ser Leu Gly Gly Ser Thr Gly Ser Thr Pro Ser Ser Ser Ile
                910              915              920

AGC AGC AAG AGC AAC AGC GAA GAC CCA TTC CCA CGG CCC GAG AGG CAG        3255
Ser Ser Lys Ser Asn Ser Glu Asp Pro Phe Pro Arg Pro Glu Arg Gln
925              930              935              940

AAG CAG CAG CAG CCG CTG GCC CTA ACC CAG CAA GAG CAG CAG CAG CAG        3303
Lys Gln Gln Gln Pro Leu Ala Leu Thr Gln Gln Glu Gln Gln Gln Gln
                945              950              955

CCC CTG ACC CTC CCA CAG CAG CAA CGA TCT CAG CAG CAG CCC AGA TGC        3351
Pro Leu Thr Leu Pro Gln Gln Gln Arg Ser Gln Gln Gln Pro Arg Cys
                960              965              970

AAG CAG AAG GTC ATC TTT GGC AGC GGC ACG GTC ACC TTC TCA CTG AGC        3399
Lys Gln Lys Val Ile Phe Gly Ser Gly Thr Val Thr Phe Ser Leu Ser
                975              980              985

TTT GAT GAG CCT CAG AAG AAC GCC ATG GCC CAC AGG AAT TCT ACG CAC        3447
Phe Asp Glu Pro Gln Lys Asn Ala Met Ala His Arg Asn Ser Thr His
                990              995              1000

CAG AAC TCC CTG GAG GCC CAG AAA AGC AGC GAT ACG CTG ACC CGA CAC        3495
Gln Asn Ser Leu Glu Ala Gln Lys Ser Ser Asp Thr Leu Thr Arg His
1005             1010             1015             1020

CAG CCA TTA CTC CCG CTG CAG TGC GGG GAA ACG GAC TTA GAT CTG ACC        3543
Gln Pro Leu Leu Pro Leu Gln Cys Gly Glu Thr Asp Leu Asp Leu Thr
                1025             1030             1035

GTC CAG GAA ACA GGT CTG CAA GGA CCT GTG GGT GGA GAC CAG CGG CCA        3591
Val Gln Glu Thr Gly Leu Gln Gly Pro Val Gly Gly Asp Gln Arg Pro
                1040             1045             1050

GAG GTG GAG GAC CCT GAA GAG TTG TCC CCA GCA CTT GTA GTG TCC AGT        3639
Glu Val Glu Asp Pro Glu Glu Leu Ser Pro Ala Leu Val Val Ser Ser
                1055             1060             1065

TCA CAG AGC TTT GTC ATC AGT GGT GGA GGC AGC ACT GTT ACA GAA AAC        3687
Ser Gln Ser Phe Val Ile Ser Gly Gly Gly Ser Thr Val Thr Glu Asn
                1070             1075             1080

GTA GTG AAT TCA TAAAATGGAA GGAGAAGACT GGGCTAGGGA GAATGCAGAG            3739
Val Val Asn Ser
1085

AGGTTTCTTG GGGTCCCAGG GATGAGGAAT CGCCCCAGAC TCCTTTCCTC TGAGGAAGAA      3799

GGGATAATAG ACACATCAAA TGCCCCGAAT TTAGTCACAC CATCTTAAAT GACAGTGAAT      3859

TGACCCATGT TCCCTTTAAA ATTAAAAAAA AGAAGAGCCT TGTGTTTCTG TGGTTGCATT      3919

TGTCAAAGCA TTGAGATCTC CACGGTCAGA TTTGCTGTTC ACCCACATCT AATGTCTCTT      3979

CCTCTGTTCT ATCCCACCCA ACAGCTCAGA GATGAAACTA TGGCTTTAAA CTACCCTCCA      4039

GAGTGTGCAG ACTGATGGGA CATCAAATTT GCCACCACTA GAGCTGAGAG TCTGAAAGAC      4099

AGAATGTCAC CAGTCCTGCC CAATGCCTTG ACAACAGACT GAATTTTAAA TGTTCACAAC      4159

ATAAGGAGAA TGTATCTCCT CCTATTTATG AAAACCATAT GATATTTTGT CTCCTACCTG      4219

CTGCTGCTAT TATGTAACAT CCAGAAGGTT TGCACCCCTC CTATACCATA TGTCTGGTTC      4279
```

```
TGTCCAGGAC ATGATACTGA TGCCATGTTT AGATTCCAGG ATCACAAGAA TCACCTCAAA    4339

TTGTTAGGAA GGGACTGCAT AAACCAATGA GCTGTATCTG TAATTAATAT TCCTATATGT    4399

AGCTTTATCC TTAGGAAAAT GCTTCTGTTG TAATAGTCCA TGGACAATAT AAACTGAAAA    4459

ATGTCAGTCT GGTTTATATA AGGCAGTATT ATTGAGCTCT ATTTCCCCAC CCCACTATCC    4519

TCACTCCCAT AAGCTAAGCC TTATGTGAGC CCCTTCAGGG ACTCAAGGGT CCAGAAGTCC    4579

CTCCCATCTC TACCCCAAAG AATTCCTGAA GCCAGATCCA CCCTATCCCT GTACAGAGTA    4639

AGTTCTCAAT TATTGGCCTG CTAATAGCTG CTAGGGTAGG AAAGCGTGGT TCCAAGAAAG    4699

ATCCACCCTC AAATGTCGGA GCTATGTTCC CTCCAGCAGT GGTATTAATA CTGCCGGTCA    4759

CCCAGGCTCT GGAGCCAGAG AGACAGACCG GGGTTCAAGC CATGGCTTCG TCATTTGCAA    4819

GCTGAGTGAC TGTAGGCAGG GAACCTTAAC CTCTCTAAGC CACAGCTTCT TCATCTTTAA    4879

AATAAGGATA ATAATCATTC CTTCCCCTCA GAGCTCTTAT GTGGATTAAA CGAGATAATG    4939

TATATAAAGT ACTTTAGCCT GGTACCTAGC ACACAATAAG CATTCAATAA ATATTAGTTA    4999

ATATTAT                                                               5006

(2) INFORMATION FOR SEQ ID NO: 2:

(i) SEQUENCE CHARACTERISTICS:
        (A) LENGTH:          3809 base pairs
        (B) TYPE:            nucleic acid
        (C) STRANDEDNESS:    single
        (D) TOPOLOGY:        linear (ii) MOLECULE TYPE:      cDNA to mRNA (ix) FEATURE:
        (A) NAME/KEY:        CDS
        (B) LOCATION:        373...3606
        (D) OTHER INFORMATION:

(xi) SEQUENCE DESCRIPTION: SEQ ID NO: 2:

CAACAGGCAC CTGGCTGCAG CCAGGAAGGA CCGCACGCCC TTTCGCGCAG GAGAGTGGAA      60

GGAGGGAGCT GTTTGCCAGC ACCGAGGTCT TGCGGCACAG GCAACGCTTG ACCTGAGTCT     120

TGCAGAATGA AAGGCATCAC AGGAGGCCTC TGCATGATGT GGCTTCCAAA GACTCAAGGA     180

CCACCCACAT TACAAGTCTG GATTGAGGAA GGCAGAAATG GAGATTCAAA CACCACGTCT     240

TCTATTATTT TATTAATCAA TCTGTAGACA TGTGTCCCCA CTGCAGGGAG TGAACTGCTC     300

CAAGGGAGAA ACTTCTGGGA GCCTCCAAAC TCCTAGCTGT CTCATCCCTT GCCCTGGAGA     360

GACGGCAGAA CC ATG GCA TTT TAT AGC TGC TGC TGG GTC CTC TTG GCA          408
              Met Ala Phe Tyr Ser Cys Cys Trp Val Leu Leu Ala
              1               5                   10

CTC ACC TGG CAC ACC TCT GCC TAC GGG CCA GAC CAG CGA GCC CAA AAG        456
Leu Thr Trp His Thr Ser Ala Tyr Gly Pro Asp Gln Arg Ala Gln Lys
         15                  20                  25

AAG GGG GAC ATT ATC CTT GGG GGG CTC TTT CCT ATT CAT TTT GGA GTA        504
Lys Gly Asp Ile Ile Leu Gly Gly Leu Phe Pro Ile His Phe Gly Val
     30                  35                  40

GCA GCT AAA GAT CAA GAT CTC AAA TCA AGG CCG GAG TCT GTG GAA TGT        552
Ala Ala Lys Asp Gln Asp Leu Lys Ser Arg Pro Glu Ser Val Glu Cys
 45                  50                  55                  60

ATC AGG TAT AAT TTC CGT GGG TTT CGC TGG TTA CAG GCT ATG ATA TTT        600
Ile Arg Tyr Asn Phe Arg Gly Phe Arg Trp Leu Gln Ala Met Ile Phe
                 65                  70                  75

GCC ATA GAG GAG ATA AAC AGC AGC CCA GCC CTT CTT CCC AAC TTG ACG        648
Ala Ile Glu Glu Ile Asn Ser Ser Pro Ala Leu Leu Pro Asn Leu Thr
```

```
                    80                  85                    90
CTG GGA TAC AGG ATA TTT GAC ACT TGC AAC ACC GTT TCT AAG GCC TTG          696
Leu Gly Tyr Arg Ile Phe Asp Thr Cys Asn Thr Val Ser Lys Ala Leu
            95                  100                 105

GAA GCC ACC CTG AGT TTT GTT GCT CAA AAC AAA ATT GAT TCT TTG AAC          744
Glu Ala Thr Leu Ser Phe Val Ala Gln Asn Lys Ile Asp Ser Leu Asn
    110                 115                 120

CTT GAT GAG TTC TGC AAC TGC TCA GAG CAC ATT CCC TCT ACG ATT GCT          792
Leu Asp Glu Phe Cys Asn Cys Ser Glu His Ile Pro Ser Thr Ile Ala
125                 130                 135                 140

GTG GTG GGA GCA ACT GGC TCA GGC GTC TCC ACG GCA GTG GCA AAT CTG          840
Val Val Gly Ala Thr Gly Ser Gly Val Ser Thr Ala Val Ala Asn Leu
                145                 150                 155

CTG GGG CTC TTC TAC ATT CCC CAG GTC AGT TAT GCC TCC TCC AGC AGA          888
Leu Gly Leu Phe Tyr Ile Pro Gln Val Ser Tyr Ala Ser Ser Ser Arg
            160                 165                 170

CTC CTC AGC AAC AAG AAT CAA TTC AAG TCT TTC CTC CGA ACC ATC CCC          936
Leu Leu Ser Asn Lys Asn Gln Phe Lys Ser Phe Leu Arg Thr Ile Pro
        175                 180                 185

AAT GAT GAG CAC CAG GCC ACT GCC ATG GCA GAC ATC ATC GAG TAT TTC          984
Asn Asp Glu His Gln Ala Thr Ala Met Ala Asp Ile Ile Glu Tyr Phe
    190                 195                 200

CGC TGG AAC TGG GTG GGC ACA ATT GCA GCT GAT GAC GAC TAT GGG CGG         1032
Arg Trp Asn Trp Val Gly Thr Ile Ala Ala Asp Asp Asp Tyr Gly Arg
205                 210                 215                 220

CCG GGG ATT GAG AAA TTC CGA GAG GAA GCT GAG GAA AGG GAT ATC TGC         1080
Pro Gly Ile Glu Lys Phe Arg Glu Glu Ala Glu Glu Arg Asp Ile Cys
                225                 230                 235

ATC GAC TTC AGT GAA CTC ATC TCC CAG TAC TCT GAT GAG GAA GAG ATC         1128
Ile Asp Phe Ser Glu Leu Ile Ser Gln Tyr Ser Asp Glu Glu Glu Ile
            240                 245                 250

CAG CAT GTG GTA GAG GTG ATT CAA AAT TCC ACG GCC AAA GTC ATC GTG         1176
Gln His Val Val Glu Val Ile Gln Asn Ser Thr Ala Lys Val Ile Val
        255                 260                 265

GTT TTC TCC AGT GGC CCA GAT CTT GAG CCC CTC ATC AAG GAG ATT GTC         1224
Val Phe Ser Ser Gly Pro Asp Leu Glu Pro Leu Ile Lys Glu Ile Val
    270                 275                 280

CGG CGC AAT ATC ACG GGC AAG ATC TGG CTG GCC AGC GAG GCC TGG GCC         1272
Arg Arg Asn Ile Thr Gly Lys Ile Trp Leu Ala Ser Glu Ala Trp Ala
285                 290                 295                 300

AGC TCC TCC CTG ATC GCC ATG CCT CAG TAC TTC CAC GTG GTT GGC GGC         1320
Ser Ser Ser Leu Ile Ala Met Pro Gln Tyr Phe His Val Val Gly Gly
                305                 310                 315

ACC ATT GGA TTC GCT CTG AAG GCT GGG CAG ATC CCA GGC TTC CGG GAA         1368
Thr Ile Gly Phe Ala Leu Lys Ala Gly Gln Ile Pro Gly Phe Arg Glu
            320                 325                 330

TTC CTG AAG AAG GTC CAT CCC AGG AAG TCT GTC CAC AAT GGT TTT GCC         1416
Phe Leu Lys Lys Val His Pro Arg Lys Ser Val His Asn Gly Phe Ala
        335                 340                 345

AAG GAG TTT TGG GAA GAA ACA TTT AAC TGC CAC CTC CAA GAA GGT GCA         1464
Lys Glu Phe Trp Glu Glu Thr Phe Asn Cys His Leu Gln Glu Gly Ala
    350                 355                 360

AAA GGA CCT TTA CCT GTG GAC ACC TTT CTG AGA GGT CAC GAA GAA AGT         1512
Lys Gly Pro Leu Pro Val Asp Thr Phe Leu Arg Gly His Glu Glu Ser
365                 370                 375                 380

GGC GAC AGG TTT AGC AAC AGC TCG ACA GCC TTC CGA CCC CTC TGT ACA         1560
Gly Asp Arg Phe Ser Asn Ser Ser Thr Ala Phe Arg Pro Leu Cys Thr
                385                 390                 395

GGG GAT GAG AAC ATC AGC AGT GTC GAG ACC CCT TAC ATA GAT TAC ACG         1608
Gly Asp Glu Asn Ile Ser Ser Val Glu Thr Pro Tyr Ile Asp Tyr Thr
```

-continued

```
                Gly Asp Glu Asn Ile Ser Ser Val Glu Thr Pro Tyr Ile Asp Tyr Thr
                            400                 405                 410

CAT TTA CGG ATA TCC TAC AAT GTG TAC TTA GCA GTC TAC TCC ATT GCC              1656
His Leu Arg Ile Ser Tyr Asn Val Tyr Leu Ala Val Tyr Ser Ile Ala
        415                 420                 425

CAC GCC TTG CAA GAT ATA TAT ACC TGC TTA CCT GGG AGA GGG CTC TTC              1704
His Ala Leu Gln Asp Ile Tyr Thr Cys Leu Pro Gly Arg Gly Leu Phe
    430                 435                 440

ACC AAT GGC TCC TGT GCA GAC ATC AAG AAA GTT GAG GCG TGG CAG GTC              1752
Thr Asn Gly Ser Cys Ala Asp Ile Lys Lys Val Glu Ala Trp Gln Val
445                 450                 455                 460

CTG AAG CAC CTA CGG CAT CTA AAC TTT ACA AAC AAT ATG GGG GAG CAG              1800
Leu Lys His Leu Arg His Leu Asn Phe Thr Asn Asn Met Gly Glu Gln
                465                 470                 475

GTG ACC TTT GAT GAG TGT GGT GAC CTG GTG GGG AAC TAT TCC ATC ATC              1848
Val Thr Phe Asp Glu Cys Gly Asp Leu Val Gly Asn Tyr Ser Ile Ile
            480                 485                 490

AAC TGG CAC CTC TCC CCA GAG GAT GGC TCC ATC GTG TTT AAG GAA GTC              1896
Asn Trp His Leu Ser Pro Glu Asp Gly Ser Ile Val Phe Lys Glu Val
        495                 500                 505

GGG TAT TAC AAC GTC TAT GCC AAG AAG GGA GAA AGA CTC TTC ATC AAC              1944
Gly Tyr Tyr Asn Val Tyr Ala Lys Lys Gly Glu Arg Leu Phe Ile Asn
    510                 515                 520

GAG GAG AAA ATC CTG TGG AGT GGG TTC TCC AGG GAG GTG CCC TTC TCC              1992
Glu Glu Lys Ile Leu Trp Ser Gly Phe Ser Arg Glu Val Pro Phe Ser
525                 530                 535                 540

AAC TGC AGC CGA GAC TGC CTG GCA GGG ACC AGG AAA GGG ATC ATT GAG              2040
Asn Cys Ser Arg Asp Cys Leu Ala Gly Thr Arg Lys Gly Ile Ile Glu
                545                 550                 555

GGG GAG CCC ACC TGC TGC TTT GAG TGT GTG GAG TGT CCT GAT GGG GAG              2088
Gly Glu Pro Thr Cys Cys Phe Glu Cys Val Glu Cys Pro Asp Gly Glu
            560                 565                 570

TAT AGT GAT GAG ACA GAT GCC AGT GCC TGT AAC AAG TGC CCA GAT GAC              2136
Tyr Ser Asp Glu Thr Asp Ala Ser Ala Cys Asn Lys Cys Pro Asp Asp
        575                 580                 585

TTC TGG TCC AAT GAG AAC CAC ACC TCC TGC ATT GCC AAG GAG ATC GAG              2184
Phe Trp Ser Asn Glu Asn His Thr Ser Cys Ile Ala Lys Glu Ile Glu
    590                 595                 600

TTT CTG TCG TGG ACG GAG CCC TTT GGG ATC GCA CTC ACC CTC TTT GCC              2232
Phe Leu Ser Trp Thr Glu Pro Phe Gly Ile Ala Leu Thr Leu Phe Ala
605                 610                 615                 620

GTG CTG GGC ATT TTC CTG ACA GCC TTT GTG CTG GGT GTG TTT ATC AAG              2280
Val Leu Gly Ile Phe Leu Thr Ala Phe Val Leu Gly Val Phe Ile Lys
                625                 630                 635

TTC CGC AAC ACA CCC ATT GTC AAG GCC ACC AAC CGA GAG CTC TCC TAC              2328
Phe Arg Asn Thr Pro Ile Val Lys Ala Thr Asn Arg Glu Leu Ser Tyr
            640                 645                 650

CTC CTC CTC TTC TCC CTG CTC TGC TGC TTC TCC AGC TCC CTG TTC TTC              2376
Leu Leu Leu Phe Ser Leu Leu Cys Cys Phe Ser Ser Ser Leu Phe Phe
        655                 660                 665

ATC GGG GAG CCC CAG GAC TGG ACG TGC CGC CTG CGC CAG CCG GCC TTT              2424
Ile Gly Glu Pro Gln Asp Trp Thr Cys Arg Leu Arg Gln Pro Ala Phe
    670                 675                 680

GGC ATC AGC TTC GTG CTC TGC ATC TCA TGC ATC CTG GTG AAA ACC AAC              2472
Gly Ile Ser Phe Val Leu Cys Ile Ser Cys Ile Leu Val Lys Thr Asn
685                 690                 695                 700

CGT GTC CTC CTG GTG TTT GAG GCC AAG ATC CCC ACC AGC TTC CAC CGC              2520
Arg Val Leu Leu Val Phe Glu Ala Lys Ile Pro Thr Ser Phe His Arg
                705                 710                 715
```

```
AAG TGG TGG GGG CTC AAC CTG CAG TTC CTG CTG GTT TTC CTC TGC ACC       2568
Lys Trp Trp Gly Leu Asn Leu Gln Phe Leu Leu Val Phe Leu Cys Thr
            720                 725                 730

TTC ATG CAG ATT GTC ATC TGT GTG ATC TGG CTC TAC ACC GCG CCC CCC       2616
Phe Met Gln Ile Val Ile Cys Val Ile Trp Leu Tyr Thr Ala Pro Pro
            735                 740                 745

TCA AGC TAC CGC AAC CAG GAG CTG GAG GAT GAG ATC ATC TTC ATC ACG       2664
Ser Ser Tyr Arg Asn Gln Glu Leu Glu Asp Glu Ile Ile Phe Ile Thr
            750                 755                 760

TGC CAC GAG GGC TCC CTC ATG GCC CTG GGC TTC CTG ATC GGC TAC ACC       2712
Cys His Glu Gly Ser Leu Met Ala Leu Gly Phe Leu Ile Gly Tyr Thr
765                 770                 775                 780

TGC CTG CTG GCT GCC ATC TGC TTC TTC TTT GCC TTC AAG TCC CGG AAG       2760
Cys Leu Leu Ala Ala Ile Cys Phe Phe Phe Ala Phe Lys Ser Arg Lys
                785                 790                 795

CTG CCG GAG AAC TTC AAT GAA GCC AAG TTC ATC ACC TTC AGC ATG CTC       2808
Leu Pro Glu Asn Phe Asn Glu Ala Lys Phe Ile Thr Phe Ser Met Leu
            800                 805                 810

ATC TTC TTC ATC GTC TGG ATC TCC TTC ATT CCA GCC TAT GCC AGC ACC       2856
Ile Phe Phe Ile Val Trp Ile Ser Phe Ile Pro Ala Tyr Ala Ser Thr
            815                 820                 825

TAT GGC AAG TTT GTC TCT GCC GTA GAG GTG ATT GCC ATC CTG GCA GCC       2904
Tyr Gly Lys Phe Val Ser Ala Val Glu Val Ile Ala Ile Leu Ala Ala
            830                 835                 840

AGC TTT GGC TTG CTG GCG TGC ATC TTC TTC AAC AAG ATC TAC ATC ATT       2952
Ser Phe Gly Leu Leu Ala Cys Ile Phe Phe Asn Lys Ile Tyr Ile Ile
845                 850                 855                 860

CTC TTC AAG CCA TCC CGC AAC ACC ATC GAG GAG GTG CGT TGC AGC ACC       3000
Leu Phe Lys Pro Ser Arg Asn Thr Ile Glu Glu Val Arg Cys Ser Thr
                865                 870                 875

GCA GCT CAC GCT TTC AAG GTG GCT GCC CGG GCC ACG CTG CGC CGC AGC       3048
Ala Ala His Ala Phe Lys Val Ala Ala Arg Ala Thr Leu Arg Arg Ser
            880                 885                 890

AAC GTC TCC CGC AAG CGG TCC AGC AGC CTT GGA GGC TCC ACG GGA TCC       3096
Asn Val Ser Arg Lys Arg Ser Ser Ser Leu Gly Gly Ser Thr Gly Ser
            895                 900                 905

ACC CCC TCC TCC TCC ATC AGC AGC AAG AGC AAC AGC GAA GAC CCA TTC       3144
Thr Pro Ser Ser Ser Ile Ser Ser Lys Ser Asn Ser Glu Asp Pro Phe
910                 915                 920

CCA CAG CCC GAG AGG CAG AAG CAG CAG CCG CTG GCC CTA ACC CAG           3192
Pro Gln Pro Glu Arg Gln Lys Gln Gln Pro Leu Ala Leu Thr Gln
925                 930                 935                 940

CAA GAG CAG CAG CAG CAG CCC CTG ACC CTC CCA CAG CAG CAA CGA TCT       3240
Gln Glu Gln Gln Gln Gln Pro Leu Thr Leu Pro Gln Gln Gln Arg Ser
                945                 950                 955

CAG CAG CAG CCC AGA TGC AAG CAG AAG GTC ATC TTT GGC AGC GGC ACG       3288
Gln Gln Gln Pro Arg Cys Lys Gln Lys Val Ile Phe Gly Ser Gly Thr
            960                 965                 970

GTC ACC TTC TCA CTG AGC TTT GAT GAG CCT CAG AAG AAC GCC ATG GCC       3336
Val Thr Phe Ser Leu Ser Phe Asp Glu Pro Gln Lys Asn Ala Met Ala
            975                 980                 985

CAC GGG AAT TCT ACG CAC CAG AAC TCC CTG GAG GCC CAG AAA AGC AGC       3384
His Gly Asn Ser Thr His Gln Asn Ser Leu Glu Ala Gln Lys Ser Ser
            990                 995                 1000

GAT ACG CTG ACC CGA CAC CAG CCA TTA CTC CCG CTG CAG TGC GGG GAA       3432
Asp Thr Leu Thr Arg His Gln Pro Leu Leu Pro Leu Gln Cys Gly Glu
1005                1010                1015                1020

ACG GAC TTA GAT CTG ACC GTC CAG GAA ACA GGT CTG CAA GGA CCT GTG       3480
Thr Asp Leu Asp Leu Thr Val Gln Glu Thr Gly Leu Gln Gly Pro Val
                1025                1030                1035
```

-continued

| | | |
|---|---|---|
| GGT GGA GAC CAG CGG CCA GAG GTG GAG GAC CCT GAA GAG TTG TCC CCA<br>Gly Gly Asp Gln Arg Pro Glu Val Glu Asp Pro Glu Glu Leu Ser Pro<br>                  1040                   1045                1050 | 3528 |
| GCA CTT GTA GTG TCC AGT TCA CAG AGC TTT GTC ATC AGT GGT GGA GGC<br>Ala Leu Val Val Ser Ser Ser Gln Ser Phe Val Ile Ser Gly Gly Gly<br>           1055                    1060                    1065 | 3576 |
| AGC ACT GTT ACA GAA AAC GTA GTG AAT TCA TAAAATGGAA GGAGAAGACT<br>Ser Thr Val Thr Glu Asn Val Val Asn Ser<br>      1070                   1075 | 3626 |
| GGGCTAGGGA GAATGCAGAG AGGTTTCTTG GGGTCCCAGG GATGAGGAAT CGCCCCAGAC | 3686 |
| TCCTTTCCTC TGAGGAAGAA GGGATAATAG ACACATCAAA TGCCCCGAAT TTAGTCACAC | 3746 |
| CATCTTAAAT GACAGTGAAT TGACCCATGT TCCCTTTAAA AAAAAAAAAA AAAAAGCGGC | 3806 |
| CGC | 3809 |

What is claimed is:

1. A compound having the formula:

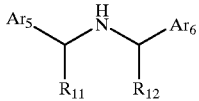

wherein Ar$_5$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, CH$_2$OH, CONH$_2$, CN, acetoxy, benzyl, benzyloxy, α,α-dimethylbenzyl, NO$_2$, CHO, CH$_3$CH(OH), acetyl, ethylene dioxy, and —CH═CH-phenyl;

Ar$_6$ is phenyl substituted with 1 to 5 substituents each independently selected from the group consisting of acetyl, lower alkyl, halogen, lower alkoxy, lower thioalkyl, methylene dioxy, lower haloalkyl, lower haloalkoxy, OH, CH$_2$OH, CONH$_2$, CN, carbomethoxy, OCH$_2$C(O)C$_2$H$_5$ and OCH$_2$C(O)OC$_2$H$_5$ and acetoxy, provided that at least one substituent is OCH$_2$C(O)OC$_2$H$_5$;

R$_{11}$ is hydrogen or methyl; and

R$_{12}$ is hydrogen or methyl;

provided that at least one of R$_{11}$ and R$_{12}$ is methyl; or a pharmaceutically acceptable salt or complex thereof.

2. The compound of claim 1, wherein Ar$_6$ is a substituted phenyl comprising a OCH$_2$C(O)OC$_2$H$_5$ substituent in a meta position.

3. A compound selected from the group consisting of:
- 21S ((R)-N-(3-(2-chlorophenyl)propyl)-1-(3-propoxyphenyl)ethylamine);
- 21T ((R)-N-(3-(2-chlorophenyl)propyl)-1-(3-isopropoxyphenyl)ethylamine);
- 21U ((R)-N-(3-(2-chlorophenyl)propyl)-1-(3-isobutoxyphenyl)ethylamine):
- 21Y ((R,R)-N-(4-(3-(trifluoromethyl)phenyl)-2-butyl)-1-(3-methoxyphenyl)ethylamine);
- 22J ((R)-N-(3-(3-(trifluoromethyl)phenyl)propyl)-1-(1-naphthyl)ethylamine);
- 23A ((R)-N-(4-(3-(trifluoromethoxy)phenyl)-2-butyl)-1-(3-methoxyphenyl)ethylamine):
- 23E ((R)-N-((3-(trifluoromethoxy)phenyl)methyl)-1-(1-naphthyl)ethylamine;
- 24B (N-((3-methyl-4-methoxyohenyl)methyl)-1(2-(trifluoromethyl)phenyl)ethylamine);
- 24J ((R)-N-(3-(3-(trifluoromethoxy)phenyl)proyl)-1-(1-naphthyl)ethylamine;
- 24M ((R)-N-(3-(3,5-difluorophenyl)propyl)-1-(3-methoxyphenyl)ethylamine;
- 24V (N-((3-methyl-4-methoxyphenyl)methyl)-1-(3-(ethylacetoxy)phenyl)ethylamine);
- 24X ((R)-N-((3-bromo-4-methoxyphenyl)methyl)-1-(1-naphthyl)ethylamine);
- 24Y ((R)-N-((3-chloro-4-ethoxyphenyl)methyl)-1-(1-naphthyl)ethylamine;
- 25C ((S,R)-N-(4-(3-trifluoromethyl)phenyl)-2-butyl)-1-(1-naphthyl)ethylamine);
- 25D ((R,R)-N-(4-(3-trifluoromethyl)phenyl)-2-butyl)-1-(1-naphthyl)ethylamine); and
- 25E ((R)-N-(3-phenylprop-2-en-1-yl)-1-(3-methoxyphenyl)ethylamine: or a pharmaceutically acceptable salt or complex thereof.

4. The compound of claim 3, wherein said compound is 21Y ((R,R)-N-(4-(3-(trifluoromethyl)phenyl)-2-butyl)-1-(3-methoxyphenyl)ethylamine) or a pharmaceutically acceptable salt or complex thereof.

5. The compound of claim 3, wherein said compound is 22J ((R)-N-(3-(3-(trifluoromethyl)phenyl)propyl)-1-(1-naphthyl)ethylamine) or a pharmaceutically acceptable salt or complex thereof.

6. The compound of claim 3, wherein said compound is 24V (N-((3-methyl-4-methoxyphenyl)methyl)-1-(3-(ethylacetoxy)phenyl)ethylamine) or a pharmaceutically acceptable salt or complex thereof.

7. The compound of claim 3, wherein said compound is 25D ((R,R)-N-(4-(3-trifluoromethyl)phenyl)-2-butyl)-1-(1-naphthyl)ethylamine) or a pharmaceutically acceptable salt or complex thereof.

8. A method of inhibiting bone resorption in a patient comprising the step of administering to said patient a therapeutically effective amount of a compound selected from the group consisting of:
- 21S ((R)-N-(3-(2-chlorophenyl)propyl)-1-(3-propoxyphenyl)ethylamine);
- 21T ((R)-N-(3-(2-chlorophenyl)propyl)-1-(3-isopropoxyphenyl)ethylamine);

21U ((R)-N-(3-(2-chlorophenyl)propyl)-1-(3-isobutoxyphenyl)ethylamine);

21Y ((R,R)-N-(4-(3-(trifluoromethyl)phenyl)-2-butyl)-1-(3-methoxyphenyl)ethylamine);

22J ((R)-N-(3-(3-(trifluoromethyl)phenyl)propyl)-1-(1-naphthyl)ethylamine);

23A ((R)-N-(4-(3-(trifluoromethoxy)phenyl)-2-butyl)-1-(3-methoxyphenyl)ethylamine);

23E ((R)-N-((3-(trifluoromethoxy)phenyl)methyl)-1-(1-naphthyl)ethylamine;

24B (N-((3-methyl-4-methoxyphenyl)methyl)-1-(2-(trifluoromethyl)phenyl)ethylamine);

24J ((R)-N-(3-(3-(trifluoromethoxy)phenyl)propyl)-1-(1-naphthyl)ethylamine;

24M ((R)-N-(3-(3,5-difluorophenyl)propyl)-1-(3-methoxyphenyl)ethylamine;

24V (N-((3-methyl-4-methoxyphenyl)methyl)-1-(3-(ethylacetoxy)phenyl)ethylamine);

24X ((R)-N-((3-bromo-4-methoxyphenyl)methyl)-1-(1-naphthyl)ethylamine);

24Y ((R)-N-((3-chloro-4-ethoxyphenyl)methyl)-1-(1-naphthyl)ethylamine;

25C ((S,R)-N-(4-(3-trifluoromethyl)phenyl)-2-butyl)-1-(1-naphthyl)ethylamine);

25D ((R,R)-N-(4-(3-trifluoromethyl)phenyl)-2-butyl)-1-(1-naphthyl)ethylamine); and 25E ((R)-N-(3-phenylprop-2-en-1-yl)-1-(3-methoxyphenyl)ethylamine; or a pharmaceutically acceptable salt or complex thereof.

9. A compound having the formula:

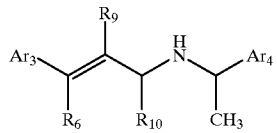

wherein Ar$_3$ is either naphthyl or phenyl optionally substituted with 0 to 5 substituents each independently selected from the group consisting of, lower alkyl, halogen, lower alkoxy, lower thioalkyl, methylene dioxy, lower haloalkyl, lower haloalkoxy, OH, CH$_2$OH, CONH$_2$, CN, acetoxy, benzyl, benzyloxy, dimethylbenzyl, NO$_2$, CHO, CH$_3$CH(OH), N(CH$_3$)$_2$, acetyl, and ethylene dioxy;

Ar$_4$ is either naphthyl or phenyl optionally substituted with 0 to 5 substituents each independently selected from the group consisting of lower alkyl, halogen, lower alkoxy, lower thioalkyl, methylene dioxy, lower haloalkyl, lower haloalkoxy, OH, CH$_2$OH, CONH$_2$, CN, and acetoxy;

provided that if Ar$_4$ is 3-methoxyphenyl, then Ar$_3$ is a substituted phenyl that is not 2-methoxy, 3-methyl, 2-methyl, 4-methyl, 2,4-dimethyl, 2,4,6-trimethyl, or 4-isopropyl; and if Ar$_4$ is unsubstituted phenyl, then Ar$_3$ is a substituted phenyl that is not 2-nitrophenyl, 4-nitrophenyl, or 4-dimethylaminophenyl;

R$_8$ is either hydrogen or phenyl;

R$_9$ is either hydrogen or methyl; and

R$_{10}$ is either hydrogen, methyl, or phenyl;

or a pharmaceutically acceptable salt or complex thereof.

10. The compound of claim 3, wherein said compound is 21S ((R)-N-(3-(2-chlorophenyl)propyl)-1-(3-propoxyphenyl)ethylamine) or a pharmaceutically acceptable salt or complex thereof.

11. The compound of claim 3, wherein said compound is 21T ((R)-N-(3-(2-chlorophenyl)propyl)-1-(3-isopropoxyphenyl)ethylamine) or a pharmaceutically acceptable salt or complex thereof.

12. The compound of claim 3, wherein said compound is 21U ((R)-N-(3-(2-chlorophenyl)propyl)-1-(3-isobutoxyphenyl)ethylamine) or a pharmaceutically acceptable salt or complex thereof.

13. The compound of claim 3, wherein said compound is 23A ((R)-N-(4-(3-(trifluoromethoxy)phenyl)-2-butyl)-1-(3-methoxyphenyl)ethylamine) or a pharmaceutically acceptable salt or complex thereof.

14. The compound of claim 3, wherein said compound is 24B (N-((3-methyl-4-methoxyphenyl)methyl)-1-(2-(trifluoromethyl)phenyl)ethylamine) or a pharmaceutically acceptable salt or complex thereof.

15. The compound of claim 3, wherein said compound is 23E ((R)-N-((3-(trifluoromethoxy)phenyl)methyl)-1(1-naphthyl)ethylamine or a pharmaceutically acceptable salt or complex thereof.

16. The compound of claim 3, wherein said compound is 24J ((R)-N-(3-(3-(trifluoromethoxy)phenyl)propyl)-1-(1-naphthyl)ethylamine or a pharmaceutically acceptable salt or complex thereof.

17. The compound of claim 3, wherein said compound is 24M ((R)-N-(3-(3,5-difluorophenyl)propyl)-1-(3-methoxyphenyl)ethylamine or a pharmaceutically acceptable salt or complex thereof.

18. The compound of claim 3, wherein said compound is 24X ((R)-N-((3-bromo-4-methoxyphenyl)methyl)-1-(1-naphthyl)ethylamine)) or a pharmaceutically acceptable salt or complex thereof.

19. The compound of claim 3, wherein said compound is 24Y ((R)-N-((3-chloro-4-ethoxyphenyl)methyl)-1-(1-naphthyl)ethylamine or a pharmaceutically acceptable salt or complex thereof.

20. The compound of claim 3, wherein said compound is 25E ((R)-N-(3-phenylprop-2-en-1-yl)-1-(3-methoxyphenyl)ethylamine or a pharmaceutically acceptable salt or complex thereof.

21. A method of decreasing parathyroid hormone level in a patent to achieve a beneficial effect comprising the step of administering to said patient an effective amount of a compound selected from the group consisting of:

21S ((R)-N-(3-(2-chlorophenyl)propyl)-1-(3-propoxyphenyl)ethylamine);

21T ((R)-N-(3-(2-chlorophenyl)propyl)-1-(3-isopropoxyphenyl)ethylamine);

21U ((R)-N-(3-(2-chlorophenyl)propyl)-1(3-isobutoxyphenyl)ethylamine);

21Y ((R,R)-N-(4-(3-(trifluoromethyl)phenyl)-2-butyl)-1-(3-methoxyphenyl)ethylamine);

22J ((R)-N-(3-(3-(trifluoromethyl)phenyl)propyl)-1-(1-naphthyl)ethylamine);

23A ((R)-N-(4-(3-(trifluoromethoxy)phenyl)-2-butyl)-1-(3-methoxyphenyl)ethylamine);

23E ((R)-N-((3-(trifluoromethoxy)phenyl)methyl)-1-(1-naphthyl)ethylamine;

24B (N-((3-methyl-4-methoxyphenyl)methyl)-1-(2-(trifluoromethyl)phenyl)ethylamine);

24J ((R)-N-(3-(3-(trifluoromethoxy)phenyl)propyl)-1-(1-naphthyl)ethylamine;

24M ((R)-N-(3-(3,5-difluorophenyl)propyl)-1-(3-methoxyphenyl)ethylamine;

24V (N-((3-methyl-4-methoxyphenyl)methyl)-1(3-(ethylacetoxy)phenyl)ethylamine);

24X ((R)-N-((3-bromo-4-methoxyphenyl)methyl)-1-(1-naphthyl)ethylamine);

24Y ((R)-N-((3-chloro-4-ethoxyphenyl)methyl)-1-(1-naphthyl)ethylamine;

25C ((S,R)-N-(4-(3-trifluoromethyl)phenyl)-2-butyl)-1-(1-naphthyl)ethylamine); and 25D ((R,R)-N-(4-(3-trifluoromethyl)phenyl)-2-butyl)-1-(1-naphthyl)ethylamine);

25E ((R)-N-(3-phenylprop-2-en-1-yl)-1-(3-methoxyphenyl)ethylamine or a pharmaceutically acceptable salt or complex thereof.

22. The method of claim 21, wherein said compound is 21S (R)-N-(3-(2-chlorophenyl)propyl)-1-(3-propoxyphenyl)ethylamine) or a pharmaceutically acceptable salt or complex thereof.

23. The method of claim 21, wherein said compound is 21T ((R)-N-(3-(2-chlorophenyl)propyl)-1-(3-isopropoxyphenyl)ethylamine) or a pharmaceutically acceptable salt or complex thereof.

24. The method of claim 21, wherein said compound is 21U ((R)-N-(3-(2-chlorophenyl)propyl)-1-(3-isobutoxyphenyl)ethylamine) or a pharmaceutically acceptable salt or complex thereof.

25. The method of claim 21, wherein said compound is 21Y ((R,R)-N-(4-(3-(trifluoromethyl)phenyl)-2-butyl)-1-(3-methoxyphenyl)ethylamine) or a pharmaceutically acceptable salt or complex thereof.

26. The method of claim 21, wherein said compound is 22J ((R)-N-(3-(3-(trifluoromethyl)phenyl)propyl)-1-(1-naphthyl)ethylamine) or a pharmaceutically acceptable salt or complex thereof.

27. The method of claim 21, wherein said compound is 23A ((R)-N-(4-(3-(trifluoromethoxy)phenyl)-2-butyl)-1-(3-methoxyphenyl)ethylamine) or a pharmaceutically acceptable salt or complex thereof.

28. The method of claim 21, wherein said compound is 23E ((R)-N-((3-(trifluoromethoxy)phenyl)methyl)-1-(1-naphthyl)ethylamine or a pharmaceutically acceptable salt or complex thereof.

29. The method of claim 21, wherein said compound is 24B (N-((3-methyl-4-methoxyphenyl)methyl)-1-(2-(trifluoromethyl)phenyl)ethylamine) or a pharmaceutically acceptable salt or complex thereof.

30. A method of treating a patient having a disease selected from the group consisting of hyperparathyroidism, Paget's disease, a hypercalcemic disorder, osteoporosis, hypertension, and renal osteodystrophy, comprising the step of administering to said patient an effective amount of the compound of any of claims 1, 2, 3, 4, 5, 6, 7, 10, 11, 12, 13 14, 15, 16, 17, 18 or 19 or 20.

31. The method of claim 30, wherein said disease is hyperparathyroidism.

32. The method of claim 30, wherein said disease is Paget's disease.

33. The method of claim 30, wherein said disease is osteoporosis.

34. The method of claim 30, wherein said disease is hypertension.

35. The method of claim 30, wherein said disease is renal osteodystrophy.

36. The method of claim 21, wherein said compound is 24J ((R)-N-(3-(3-(trifluoromethoxy)phenyl)propyl)-1-(1-naphthyl)ethylamine or a pharmaceutically acceptable salt or complex thereof.

37. The method of claim 21, wherein said compound is 24M ((R)-N-(3-(3,5-difluorophenyl)propyl)-1-(3-methoxyphenyl)ethylamine or a pharmaceutically acceptable salt or complex thereof.

38. The method of claim 21, wherein said compound is 24V (N-((3-methyl-4-methoxyphenyl)methyl)-1-(3-(ethylacetoxy)phenyl)ethylamine) or a pharmaceutically acceptable salt or complex thereof.

39. The method of claim 21, wherein said compound is 24X ((R)-N-((3-bromo-4-methoxyphenyl)methyl)-1-(1-naphthyl)ethylamine) or a pharmaceutically acceptable salt or complex thereof.

40. The method of claim 21, wherein said compound is 24Y ((R)-N-((3-chloro-4-ethoxyphenyl)methyl)-1-(1-naphthyl)ethylamine or a pharmaceutically acceptable salt or complex thereof.

41. The method of claim 21, wherein said compound is 25C ((S,R)-N-(4-(3-trifluoromethyl)phenyl)-2-butyl)-1-(1-naphthyl)ethylamine) or a pharmaceutically acceptable salt or complex thereof.

42. The method of claim 21, wherein said compound is 25D ((R,R)-N-(4-(3-trifluoromethyl)phenyl)-2-butyl)-1-(1-naphthyl)ethylamine) or a pharmaceutically acceptable salt or complex thereof.

43. The method of claim 21, wherein said compound is 25E ((R)-N-(3-phenylprop-2-en-1-yl)-1-(3-methoxyphenyl)ethylamine or a pharmaceutically acceptable salt or complex thereof.

44. A pharmaceutical composition comprising a therapeutically effective amount of the compound of any of claims 1, 2, 3, 4, 5, 6, 7, 10, 11, 12, 13, 14, 15, 16, 17, 18, or 20 and a pharmaceutically acceptable carrier.

45. A method of treating a patient having a disease or disorder characterized by abnormal bone and mineral homeostasis comprising the step of administering to said patient a therapeutically effective amount of the compound of any of claims 1, 2, 3, 4, 5, 6, 7, 10, 11, 12, 13, 14, 15, 16, 17, 18, 19, or 20.

46. The compound of claim 9, wherein $Ar_3$ is either naphthyl optionally substituted with 0–5 substituents or phenyl optionally substituted with 1 to 5 substituents each independently selected from the group consisting of halogen, lower alkoxy, lower thioalkyl, methylene dioxy, lower haloalkyl, lower haloalkoxy, OH, $CH_2OH$, $CONH_2$, CN, acetoxy, benzyl, benzyloxy, dimethylbenzyl, $NO_2$, CHO, $CH_3CH(OH)$, $N(CH_3)_2$, acetyl, and ethylene dioxy.

* * * * *